(12) United States Patent
Nakashima et al.

(10) Patent No.: US 8,178,885 B2
(45) Date of Patent: May 15, 2012

(54) AROMATIC AMINE COMPOUND, AND LIGHT EMITTING ELEMENT, LIGHT EMITTING DEVICE, AND ELECTRONIC DEVICE USING AROMATIC AMINE COMPOUND

(75) Inventors: Harue Nakashima, Atsugi (JP); Sachiko Kawakami, Isehara (JP); Satoko Shitagaki, Atsugi (JP); Satoshi Seo, Kawasaki (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

(21) Appl. No.: 12/858,761

(22) Filed: Aug. 18, 2010

(65) Prior Publication Data

US 2010/0308319 A1 Dec. 9, 2010

Related U.S. Application Data

(60) Continuation of application No. 12/219,786, filed on Jul. 29, 2008, now Pat. No. 7,795,449, which is a division of application No. 11/581,086, filed on Oct. 16, 2006, now Pat. No. 7,442,803.

(30) Foreign Application Priority Data

Oct. 18, 2005 (JP) ................................ 2005-302853

(51) Int. Cl.
*H01L 27/28* (2006.01)
*C07D 209/86* (2006.01)
(52) U.S. Cl. .......................................... 257/82; 548/442
(58) Field of Classification Search .................... 257/82
See application file for complete search history.

(56) References Cited

U.S. PATENT DOCUMENTS

| | | | |
|---|---|---|---|
| 2,862,932 A | 12/1958 | Schmidt-Nickels et al. | |
| 5,508,136 A | 4/1996 | Shirota et al. | |

FOREIGN PATENT DOCUMENTS

| | | |
|---|---|---|
| JP | 2000-063335 | 2/2000 |
| JP | 3419534 | 6/2003 |
| JP | 2004-087395 | 3/2004 |

OTHER PUBLICATIONS

International Search Report (Application No. PCT/JP2006/320889) dated Dec. 26, 2006.
Written Opinion (Application No. PCT/JP2006/320889) dated Dec. 26, 2006.
Ishii, et al., Document No. 140:278200, retrieved from CAPLUS on Dec. 6, 2009.

*Primary Examiner* — Shawquia Young
(74) *Attorney, Agent, or Firm* — Eric J. Robinson; Robinson Intellectual Property Law Office, P.C.

(57) ABSTRACT

An object is to provide an aromatic amine compound with excellent heat resistance. Another object is to provide a light emitting element, a light emitting device, and an electronic device with excellent heat resistance. An aromatic amine compound represented by General Formula (1) is provided. The aromatic amine compound represented by General Formula (1) has a high glass transition point and excellent heat resistance. By using the aromatic amine compound represented by General Formula (1) for a light emitting element, a light emitting device, and an electronic device, a light emitting element, a light emitting device, and an electronic device with excellent heat resistance can be obtained.

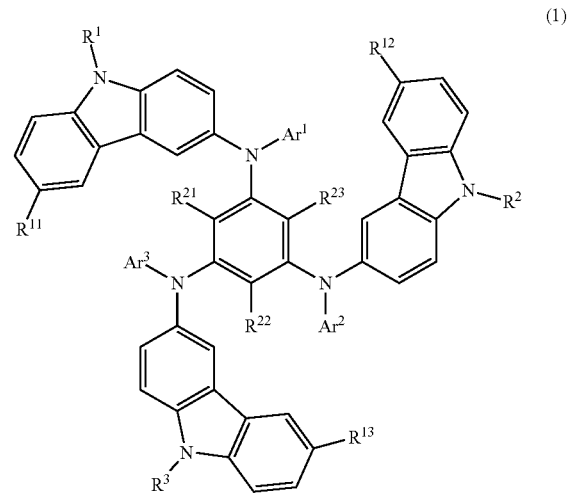

18 Claims, 37 Drawing Sheets

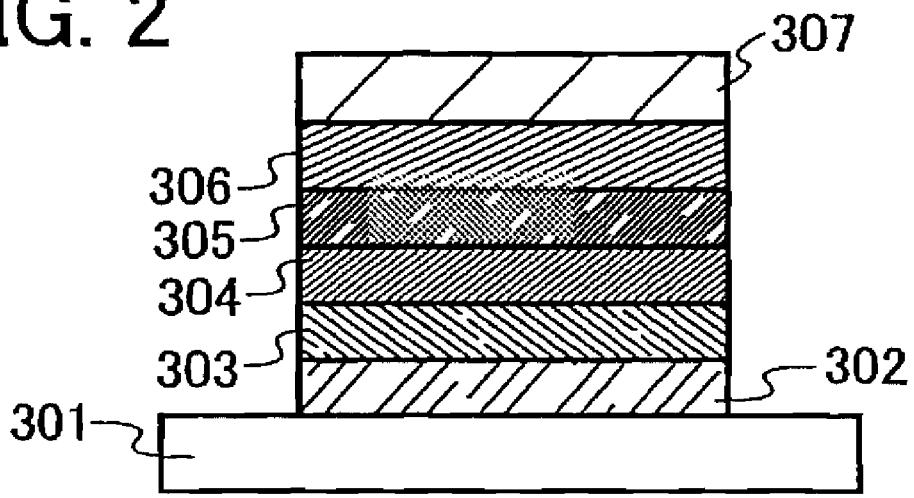

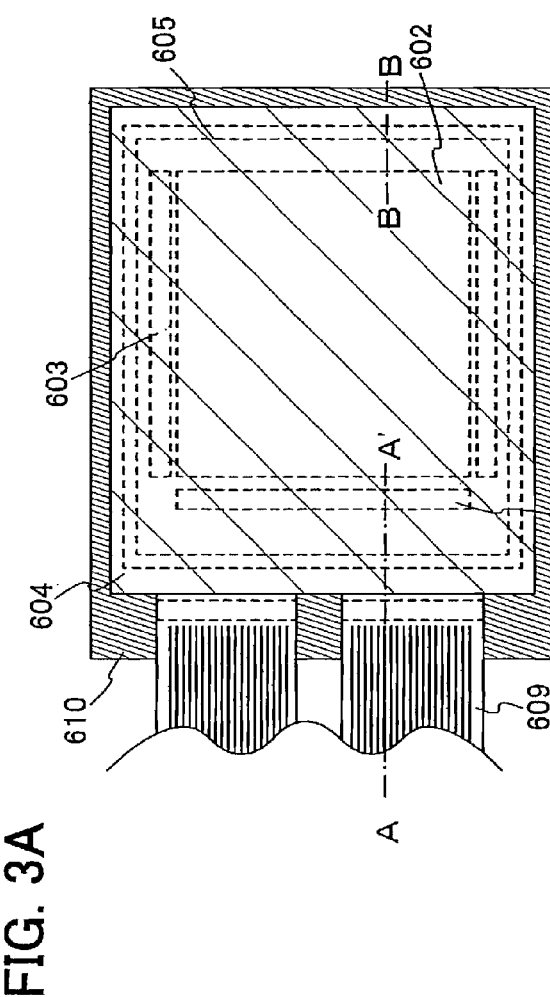
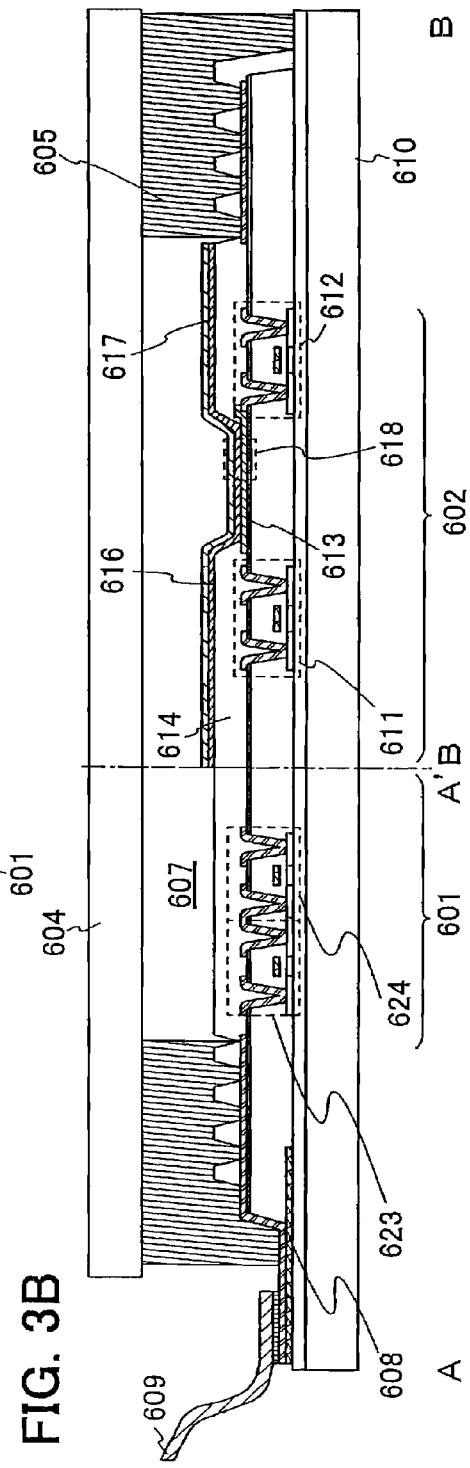
FIG. 3A
FIG. 3B

AROMATIC AMINE COMPOUND, AND LIGHT EMITTING ELEMENT, LIGHT EMITTING DEVICE, AND ELECTRONIC DEVICE USING AROMATIC AMINE COMPOUND

TECHNICAL FIELD

The present invention relates to an aromatic amine compound, and a light emitting element, a light emitting device, and an electronic device using the aromatic amine compound.

BACKGROUND ART

In recent years, a light emitting element using a light emitting organic compound has been actively researched and developed. A basic structure of this light emitting element is that which is formed by sandwiching a layer containing a light emitting organic compound between a pair of electrodes. By applying a voltage to this element, electrons and holes are separately injected from the pair of electrodes into the layer containing a light emitting organic compound, and current flows. Then, recombination of these carriers (the electrons and holes) causes the light emitting organic compound to form an excited state and to emit light when the excited state returns to a ground state. Owing to such a mechanism, such a light emitting element is referred to as a current-excitation light emitting element.

Note that excited states an organic compound forms can be a singlet excited state or a triplet excited state. Light emission from the singlet excited state is referred to as fluorescence, and light emission from the triplet excited state is referred to as phosphorescence.

A great advantage of such a light emitting element is that the light emitting element can be manufactured to be thin and lightweight because the light emitting element is formed of an organic thin film with, for example, a thickness of approximately 0.1 μm. In addition, extremely high response speed is another advantage, because time between carrier injection and light emission is approximately 1 μsec or less. These characteristics are considered suitable for a flat panel display element.

Such a light emitting element is formed in a film shape. Thus, surface emission can be easily obtained by forming a large-area element. This characteristic is hard to be obtained by a point light source typified by an incandescent lamp or an LED or a line light source typified by a fluorescent lamp. Therefore, the above described light emitting element also has a high utility value as a surface light source which is applicable to lighting or the like.

Such a light emitting element has many material-dependent problems in improving its element characteristics, and improvement in an element structure, development of materials, and the like are conducted to overcome the problems.

As one of the causes of deterioration of the current-excitation light emitting element, deterioration of a material contained in a layer containing a light emitting substance formed between a pair of electrodes is given. Due to current flow in the layer containing a light emitting substance in the current-excitation light emitting element, the material contained in the layer containing a light emitting substance is repeatedly subjected to oxidation reaction and reduction reaction. When a material which is easily decomposed by oxidation reaction and reduction reaction is contained in the layer containing a light emitting substance, the material is gradually deteriorated by the repeated oxidation reaction and reduction reaction and the light emitting element itself is also deteriorated. Thus, development of an electrochemically stable substance is demanded.

Reference 1 discloses trisarylaminobenzene as a substance with few electrochemical changes (Reference 1: Japanese Patent No. 3419534). However, characteristics such as heat resistance are not sufficient yet, and development of an organic compound with better heat resistance is demanded.

DISCLOSURE OF INVENTION

In view of the above problems, it is an object of the present invention to provide an aromatic amine compound with excellent heat resistance.

It is another object to provide a light emitting element, a light emitting device, and an electronic device with excellent heat resistance.

One aspect of the present invention is an aromatic amine compound represented by General Formula (1).

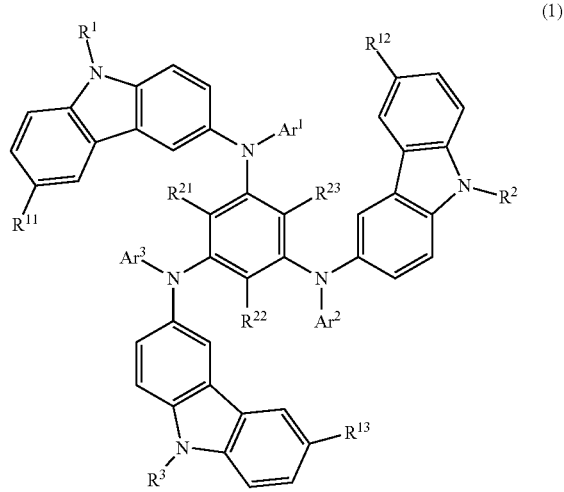

(where each of $Ar^1$ to $Ar^3$ represents an aryl group having 6 to 12 carbon atoms or a heteroaromatic group having 4 to 9 carbon atoms; each of $R^1$ to $R^3$ represents an alkyl group having 1 to 4 carbon atoms or an aryl group having 6 to 25 carbon atoms; each of $R^{11}$ to $R^{13}$ represents a hydrogen atom, an alkyl group having 1 to 4 carbon atoms, or an aryl group having 6 to 25 carbon atoms; and each of $R^{21}$ to $R^{23}$ represents a hydrogen atom, a methyl group, or a methoxy group.)

The aromatic amine compound represented by General Formula (1) is preferably an aromatic amine compound represented by General Formula (2).

(2)

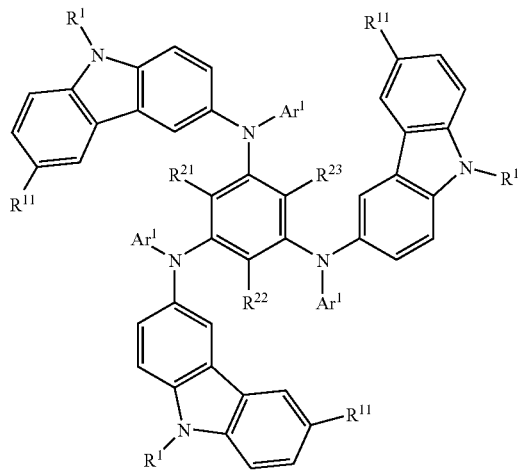

(where Ar¹ represents an aryl group having 6 to 12 carbon atoms or a heteroaromatic group having 4 to 9 carbon atoms; R¹ represents an alkyl group having 1 to 4 carbon atoms or an aryl group having 6 to 25 carbon atoms; R¹¹ represents a hydrogen atom, an alkyl group having 1 to 4 carbon atoms, or an aryl group having 6 to 25 carbon atoms; and each of R²¹ to R²³ represents a hydrogen atom, a methyl group, or a methoxy group.)

The aromatic amine compound represented by General Formula (1) is more preferably an aromatic amine compound represented by General Formula (3).

(3)

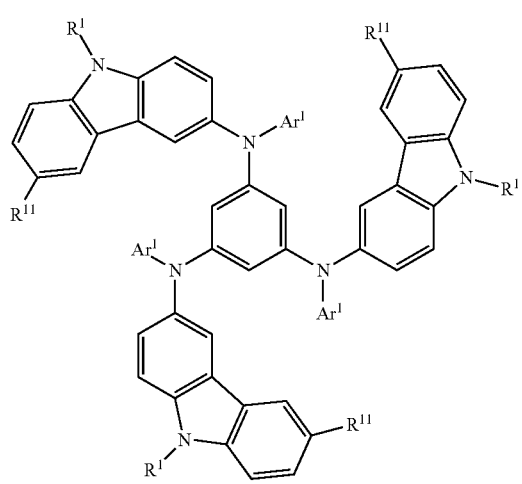

(where Ar¹ represents an aryl group having 6 to 12 carbon atoms or a heteroaromatic group having 4 to 9 carbon atoms; R¹ represents an alkyl group having 1 to 4 carbon atoms or an aryl group having 6 to 25 carbon atoms; and R¹¹ represents a hydrogen atom, an alkyl group having 1 to 4 carbon atoms, or an aryl group having 6 to 25 carbon atoms.)

An aromatic amine compound represented by Structural Formula (21) is more preferable.

(21)

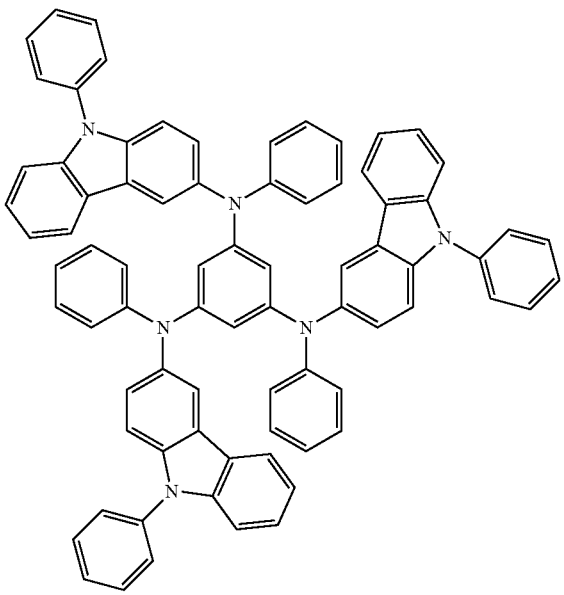

One aspect of the present invention is an aromatic amine compound represented by General Formula (4).

(4)

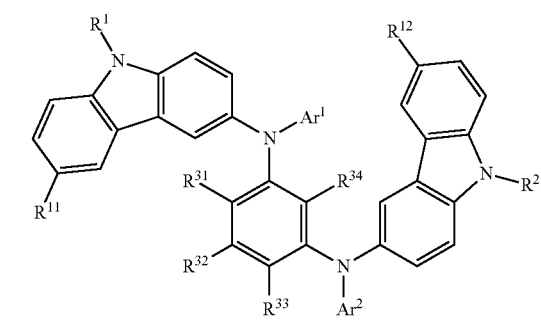

(where each of Ar¹ and Ar² represents an aryl group having 6 to 12 carbon atoms or a heteroaromatic group having 4 to 9 carbon atoms; each of R¹ and R² represents an alkyl group having 1 to 4 carbon atoms or an aryl group having 6 to 25 carbon atoms; each of R¹¹ and R¹² represents a hydrogen atom, an alkyl group having 1 to 4 carbon atoms, or an aryl group having 6 to 25 carbon atoms; and each of R³¹ to R³⁴ represents a hydrogen atom, a methyl group, or a silyl group having a substituent.)

The aromatic amine compound represented by General Formula (4) is preferably an aromatic amine compound represented by General Formula (5).

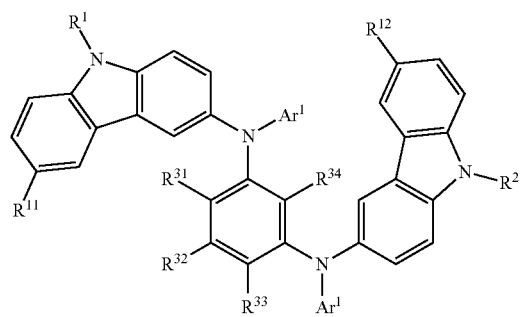

(5)

(where Ar¹ represents an aryl group having 6 to 12 carbon atoms or a heteroaromatic group having 4 to 9 carbon atoms; R¹ represents an alkyl group having 1 to 4 carbon atoms or an aryl group having 6 to 25 carbon atoms; $R^{11}$ represents a hydrogen atom, an alkyl group having 1 to 4 carbon atoms, or an aryl group having 6 to 25 carbon atoms; and each of $R^{31}$ to $R^{34}$ represents a hydrogen atom, a methyl group, or a silyl group having a substituent.)

The aromatic amine compound represented by General Formula (4) is preferably an aromatic amine compound represented by General Formula (6).

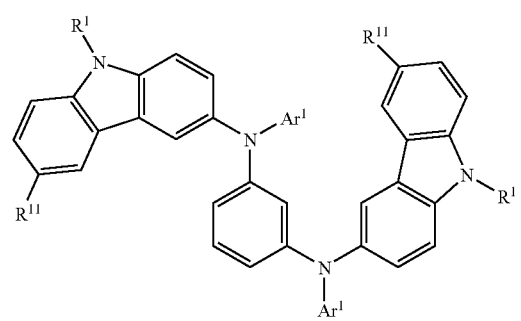

(6)

(where Ar¹ represents an aryl group having 6 to 12 carbon atoms or a heteroaromatic group having 4 to 9 carbon atoms; R¹ represents an alkyl group having 1 to 4 carbon atoms or an aryl group having 6 to 25 carbon atoms; and $R^{11}$ represents a hydrogen atom, an alkyl group having 1 to 4 carbon atoms, or an aryl group having 6 to 25 carbon atoms.)

An aromatic amine compound represented by Structural Formula (51) is more preferable.

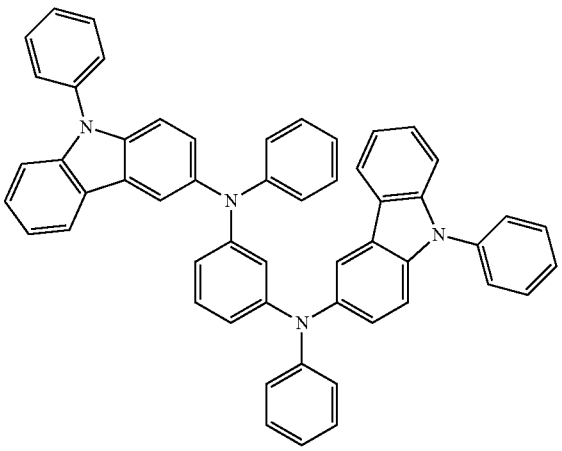

(51)

One of the present invention is an aromatic amine compound represented by General Formula (7).

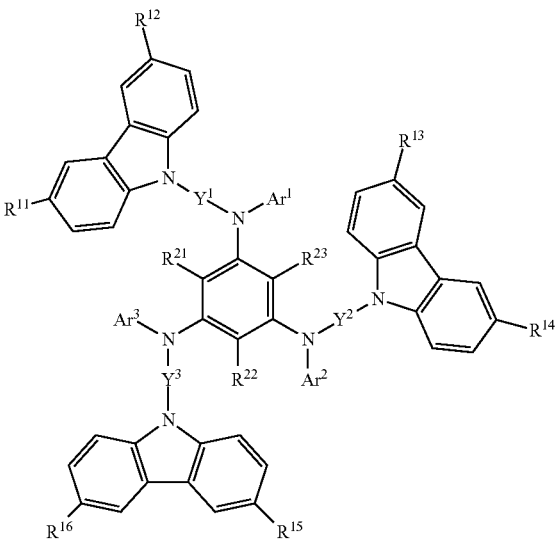

(7)

(where each of Ar¹ to Ar³ represents an aryl group having 6 to 12 carbon atoms or a heteroaromatic group having 4 to 9 carbon atoms; each of Y¹ to Y³ represents an arylene group having 6 to 25 carbon atoms; each of $R^{11}$ to $R^{16}$ represents a hydrogen atom, an alkyl group having 1 to 4 carbon atoms, or an aryl group having 6 to 25 carbon atoms; and each of $R^{21}$ to $R^{23}$ represents a hydrogen atom, a methyl group, or a methoxy group.)

The aromatic amine compound represented by General Formula (7) is preferably an aromatic amine compound represented by General Formula (8).

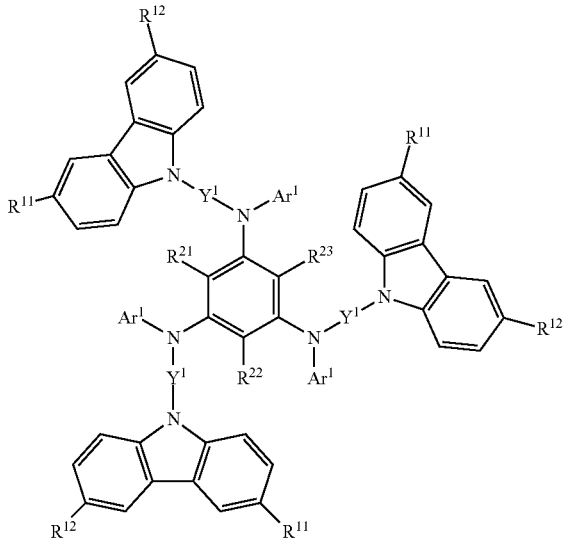

(8)

(where $Ar^1$ represents an aryl group having 6 to 12 carbon atoms or a heteroaromatic group having 4 to 9 carbon atoms; $Y^1$ represents an arylene group having 6 to 25 carbon atoms; each of $R^{11}$ and $R^{12}$ represents a hydrogen atom, an alkyl group having 1 to 4 carbon atoms, or an aryl group having 6 to 25 carbon atoms; and each of $R^{21}$ to $R^{23}$ represents a hydrogen atom, a methyl group, or a methoxy group.)

The aromatic amine compound represented by General Formula (7) is more preferably an aromatic amine compound represented by General Formula (9).

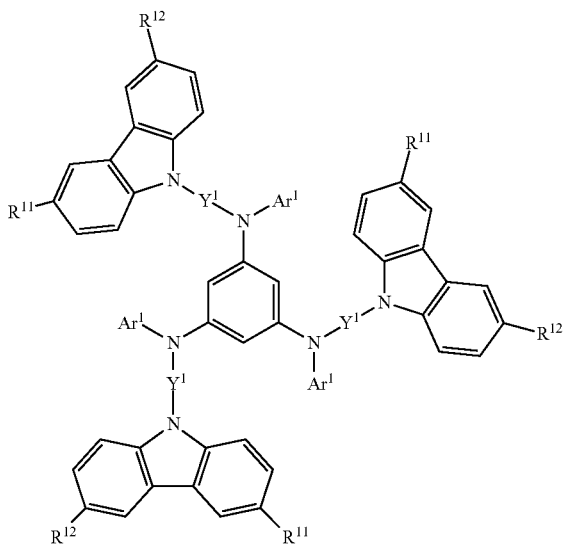

(9)

(where $Ar^1$ represents an aryl group having 6 to 12 carbon atoms or a heteroaromatic group having 4 to 9 carbon atoms; $Y^1$ represents an arylene group having 6 to 25 carbon atoms; and each of $R^{11}$ and $R^{12}$ represents a hydrogen atom, an alkyl group having 1 to 4 carbon atoms, or an aryl group having 6 to 25 carbon atoms.)

An aromatic amine compound represented by Structural Formula (81) is more preferable.

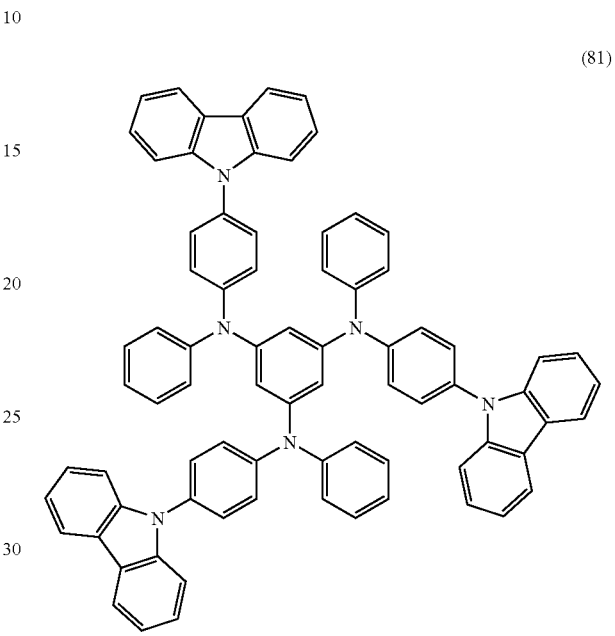

(81)

One aspect of the present invention is an aromatic amine compound represented by General Formula (10).

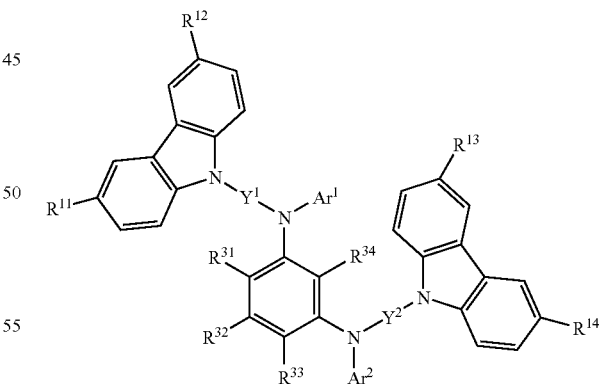

(10)

(where each of $Ar^1$ and $Ar^2$ represents an aryl group having 6 to 12 carbon atoms or a heteroaromatic group having 4 to 9 carbon atoms; each of $Y^1$ and $Y^2$ represents an arylene group having 6 to 25 carbon atoms; each of $R^{11}$ to $R^{14}$ represents a hydrogen atom, an alkyl group having 1 to 4 carbon atoms, or an aryl group having 6 to 25 carbon atoms; and each of $R^{31}$ to $R^{34}$ represents a hydrogen atom, a methyl group, or a silyl group having a substituent.)

The aromatic amine compound represented by General Formula (10) is preferably an aromatic amine compound represented by General Formula (11).

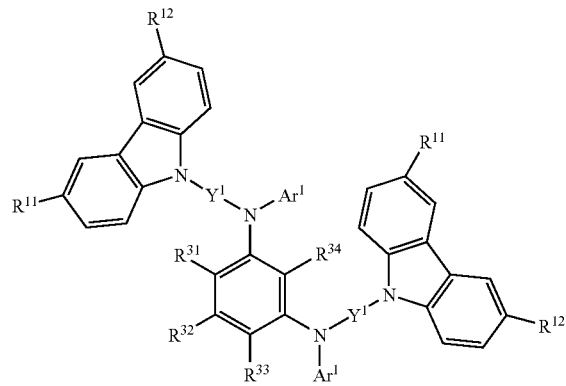

(11)

(where Ar$^1$ represents an aryl group having 6 to 12 carbon atoms or a heteroaromatic group having 4 to 9 carbon atoms; Y$^1$ represents an arylene group having 6 to 25 carbon atoms; each of R$^{11}$ and R$^{12}$ represents a hydrogen atom, an alkyl group having 1 to 4 carbon atoms, or an aryl group having 6 to 25 carbon atoms; and each of R$^{31}$ to R$^{34}$ represents a hydrogen atom, a methyl group, or a silyl group having a substituent.)

The aromatic amine compound represented by General Formula (10) is preferably an aromatic amine compound represented by General Formula (12).

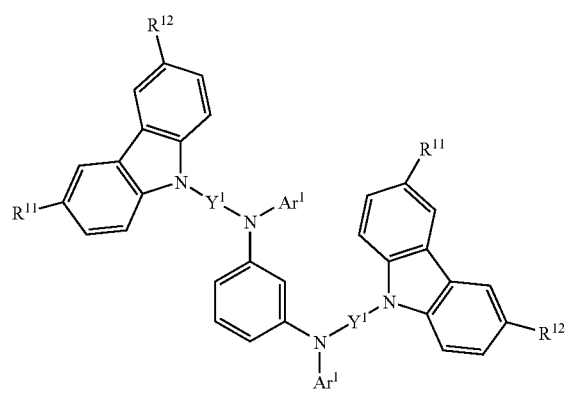

(12)

(where Ar$^1$ represents an aryl group having 6 to 12 carbon atoms or a heteroaromatic group having 4 to 9 carbon atoms; Y$^1$ represents an arylene group having 6 to 25 carbon atoms; and each of R$^{11}$ and R$^{12}$ represents a hydrogen atom, an alkyl group having 1 to 4 carbon atoms, or an aryl group having 6 to 25 carbon atoms.)

An aromatic amine compound represented by Structure Formula (111) is more preferable.

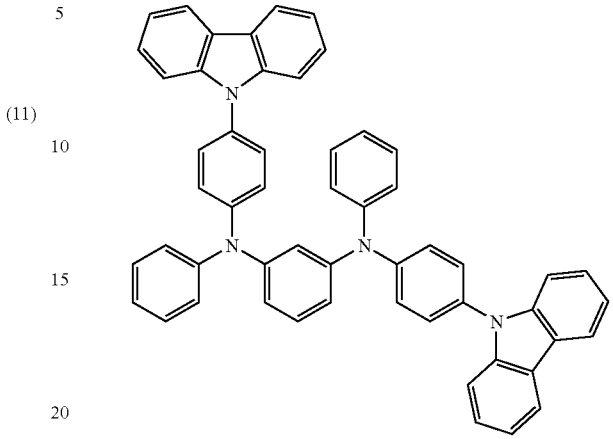

(111)

One aspect of the present invention is a light emitting element including a layer containing a light emitting substance between a pair of electrodes, in which the layer containing a light emitting substance contains the above aromatic amine compound.

Another aspect of the present invention is a light emitting element including a layer containing a light emitting substance between a first electrode and a second electrode, in which the layer containing a light emitting substance includes a light emitting layer and a layer containing the aromatic amine compound on a side closer to the first electrode from the light emitting layer, and the light emitting substance emits light when a voltage is applied so that a potential of the first electrode becomes higher than that of the second electrode.

Another aspect of the present invention is a light emitting element including a layer containing a light emitting substance between a pair of electrodes, in which the layer containing a light emitting substance includes a light emitting layer, and the light emitting layer contains the above-described aromatic amine compound.

One feature of a light emitting device of the present invention is to include a light emitting element in which a layer containing a light emitting substance is included between a pair of electrodes, in which the layer containing a light emitting substance contains the above-described aromatic amine compound, and a control means of controlling light emission of the light emitting element. Note that the light emitting device in this specification refers to an image display device, a light emitting device, or a light source (including a lighting system). Further, the light emitting device could be any of the following modules: a module having a panel provided with a connector such as an FPC (Flexible Printed Circuit), a TAB (Tape Automated Bonding) tape, or a TCP (Tape Carrier Package); a module having a TAB tape or a TCP provided with a printed wiring board at the end thereof; and a module having an IC (Integrated Circuit) directly mounted on a light emitting element by a COG (Chip On Glass) method.

The present invention also includes in its scope an electronic device using the light emitting element of the present invention for a display portion. Therefore, one feature of an electronic device of the present invention is to include a display portion, in which the display portion has a control means to control the above-described light emitting element and light emission of the light emitting element.

The aromatic amine compounds of the present invention have a high glass transition point and excellent heat resistance.

By using the aromatic amine compound of the present invention for a light emitting element, a light emitting device, and an electronic device, a light emitting element, a light emitting device, and an electronic device with excellent heat resistance can be obtained.

BRIEF DESCRIPTION OF DRAWINGS

FIG. 2 is a diagram for explaining a light emitting element of the present invention.

FIGS. 3A and 3B are diagrams for explaining a light emitting device of the present invention.

BEST MODE FOR CARRYING OUT THE INVENTION

Figure 1A:
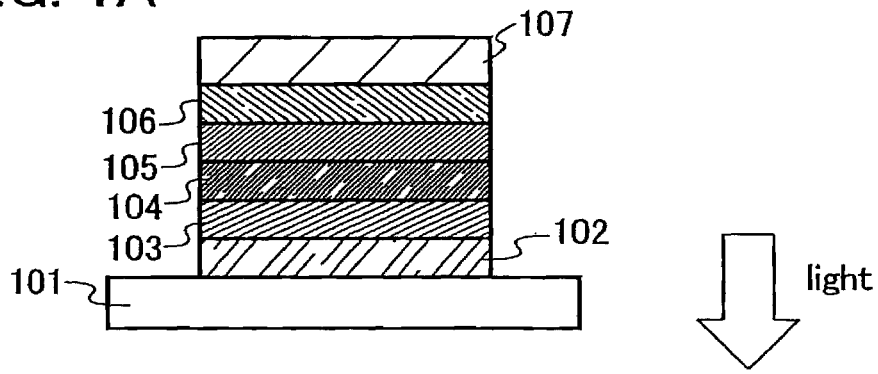
FIGS. 1A to 1C are diagrams for explaining a light emitting element of the present invention.

Embodiments and examples of the present invention will be hereinafter described with reference to the accompanying drawings. However, the present invention is not limited to the following explanation. As is easily known to a person skilled in the art, the mode and the detail of the invention can be variously changed without departing from the spirit and the scope of the present invention. Therefore, the present invention is not interpreted as being limited to the following description of the embodiments and the examples.

Embodiment 1

The present invention is an aromatic amine compound represented by General Formula (1).

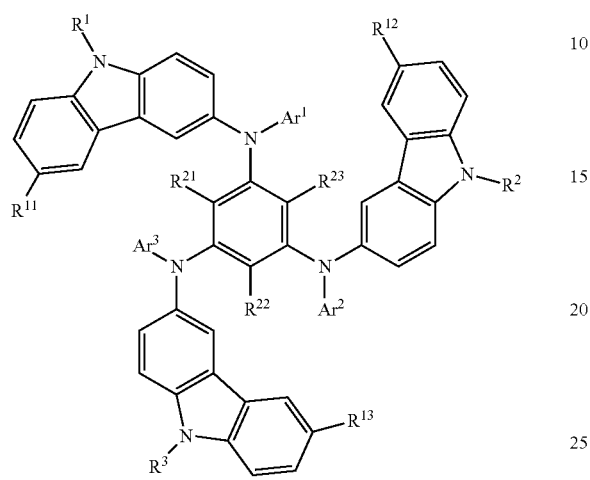

(1)

(where each of Ar¹ to Ar³ represents an aryl group having 6 to 12 carbon atoms or a heteroaromatic group having 4 to 9 carbon atoms; each of $R^1$ to $R^3$ represents an alkyl group having 1 to 4 carbon atoms or an aryl group having 6 to 25 carbon atoms; each of $R^{11}$ to $R^{13}$ represents a hydrogen atom, an alkyl group having 1 to 4 carbon atoms, or an aryl group having 6 to 25 carbon atoms; and each of $R^{21}$ to $R^{23}$ represents a hydrogen atom, a methyl group, or a methoxy group.)

In General Formula (1), each of Ar¹ to Ar³ represents an aryl group having 6 to 12 carbon atoms or a heteroaromatic group having 4 to 9 carbon atoms. Specifically, substituents represented by Structural Formulas (13-1) to (13-17) are given. Preferably, each of Ar¹ to Ar³ is an aryl group having 6 to 12 carbon atoms.

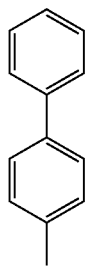

(13-1)

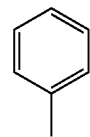

(13-2)

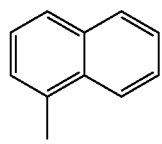

(13-3)

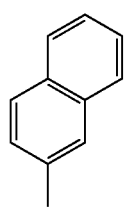

(13-4)

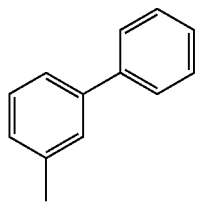

(13-5)

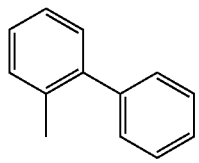

(13-6)

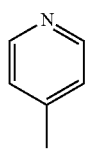

(13-7)

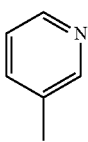

(13-8)

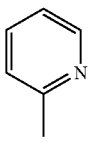

(13-9)

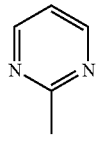

(13-10)

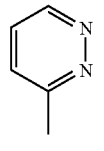

(13-11)

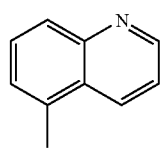

(13-12)

(13-13) 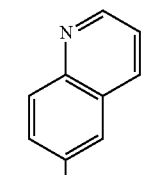
(13-14) 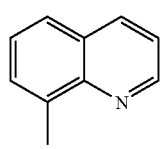
(13-15) 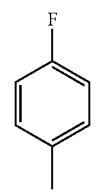
(13-16) 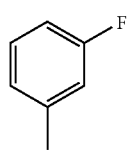
(13-17) 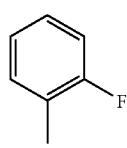
In General Formula (1), each of $R^1$ to $R^3$ represents an alkyl group having 1 to 4 carbon atoms or an aryl group having 6 to 25 carbon atoms. Specifically, substituents represented by Structural Formulas (14-1) to (14-16) are given.
(14-1) 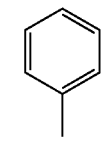
(14-2) 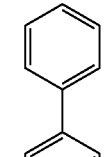
(14-3) 
(14-4) 
CH₃
(14-5) 
CH₃
CH₂
(14-6) 
CH₃
CH₂
CH₂
(14-7) 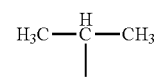
H₃C—CH—CH₃
(14-8) 
CH₃
CH₂
CH₂
CH₂
(14-9)
H₃C—C(CH₃)₂—CH₃
(14-10) 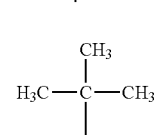
CH₃
HC—CH₃
CH₂
(14-11)
CH₃
CH₂
HC—CH₃
(14-12) 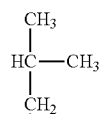
(14-13) 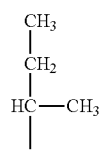

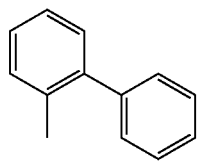
(14-14)
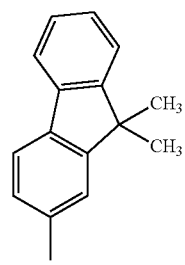
(14-15)
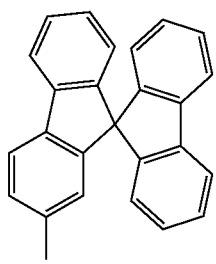
(14-16)
In General Formula (1), each of $R^{11}$ to $R^{13}$ represents a hydrogen atom, an alkyl group having 1 to 4 carbon atoms, or an aryl group having 6 to 25 carbon atoms. Specifically, substituents represented by Structural Formulas (15-1) to (15-17) are given.
(15-1) H—
(15-2) 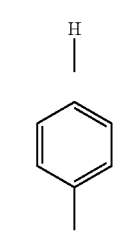
(15-3) 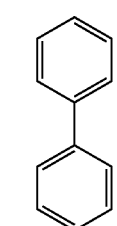
(15-4) 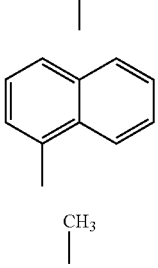
(15-5) CH₃—
(15-6) CH₃—CH₂—
(15-7) CH₃—CH₂—CH₂—
(15-8) H₃C—CH—CH₃
(15-9) CH₃—CH₂—CH₂—CH₂—
(15-10) H₃C—C(CH₃)—CH₃
(15-11) (CH₃)₂CH—CH₂—
(15-12) CH₃—CH₂—CH(CH₃)—
(15-13) 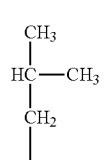
(15-14) 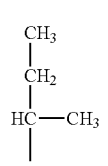
(15-15) 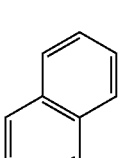

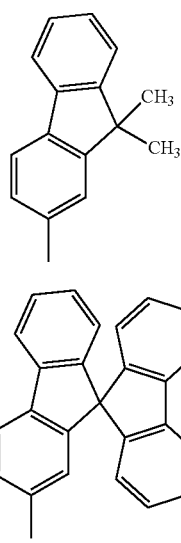

(15-16)

(15-17)

In General Formula (1), $Ar^1$, $Ar^2$, and $Ar^3$ are preferably the same substituents.

In General Formula (1), $R^1$, $R^2$, and $R^3$ are preferably the same substituents.

In General Formula (1), $R^{11}$, $R^{12}$, and $R^{13}$ are preferably the same substituents.

When $Ar^1$, $Ar^2$, and $Ar^3$ are the same substituents, $R^1$, $R^2$, and $R^3$ are the same substituents, and $R^{11}$, $R^{12}$, and $R^{13}$ are the same substituents, synthesis becomes easier. In other words, by reacting the same three secondary amines with 1,3,5-trihalogenated benzene, the aromatic amine compound of the present invention can be obtained.

In other words, an aromatic amine compound represented by General Formula (2) is preferable.

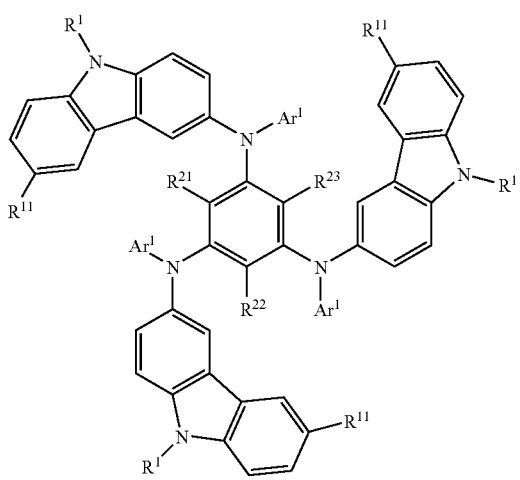

(2)

(where $Ar^1$ represents an aryl group having 6 to 12 carbon atoms or a heteroaromatic group having 4 to 9 carbon atoms; $R^1$ represents an alkyl group having 1 to 4 carbon atoms or an aryl group having 6 to 25 carbon atoms; $R^{11}$ represents a hydrogen atom, an alkyl group having 1 to 4 carbon atoms, or an aryl group having 6 to 25 carbon atoms; and each of $R^{21}$ to $R^{23}$ represents a hydrogen atom, a methyl group, or a methoxy group.)

In General Formulas (1) and (2), each of $R^{21}$ to $R^{23}$ is preferably a hydrogen atom. When each of $R^{21}$ to $R^{23}$ is a hydrogen atom, synthesis becomes easier.

In other words, an aromatic amine compound represented by General Formula (3) is preferable.

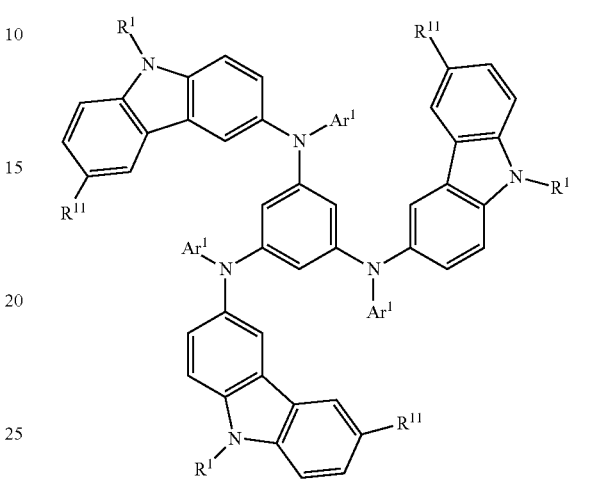

(3)

(where $Ar^1$ represents an aryl group having 6 to 12 carbon atoms or a heteroaromatic group having 4 to 9 carbon atoms; $R^1$ represents an alkyl group having 1 to 4 carbon atoms or an aryl group having 6 to 25 carbon atoms; and $R^{11}$ represents a hydrogen atom, an alkyl group having 1 to 4 carbon atoms, or an aryl group having 6 to 25 carbon atoms.)

In addition, one aspect of the present invention is an aromatic amine compound represented by General Formula (4).

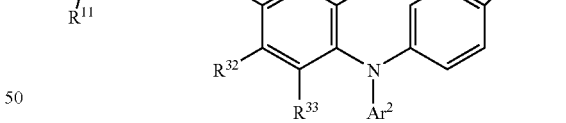

(4)

(where each of $Ar^1$ and $Ar^2$ represents an aryl group having 6 to 12 carbon atoms or a heteroaromatic group having 4 to 9 carbon atoms; each of $R^1$ and $R^2$ represents an alkyl group having 1 to 4 carbon atoms or an aryl group having 6 to 25 carbon atoms; each of $R^{11}$ and $R^{12}$ represents a hydrogen atom, an alkyl group having 1 to 4 carbon atoms, or an aryl group having 6 to 25 carbon atoms; and each of $R^{31}$ to $R^{34}$ represents a hydrogen atom, a methyl group, or a silyl group having a substituent.)

In General Formula (4), each of $Ar^1$ and $Ar^2$ represents an aryl group having 6 to 12 carbon atoms or a heteroaromatic group having 4 to 9 carbon atoms. Specifically, the substituents represented by Structural Formulas (13-1) to (13-17) are given. Preferably, each of $Ar^1$ and $Ar^2$ is an aryl group having 6 to 12 carbon atoms.

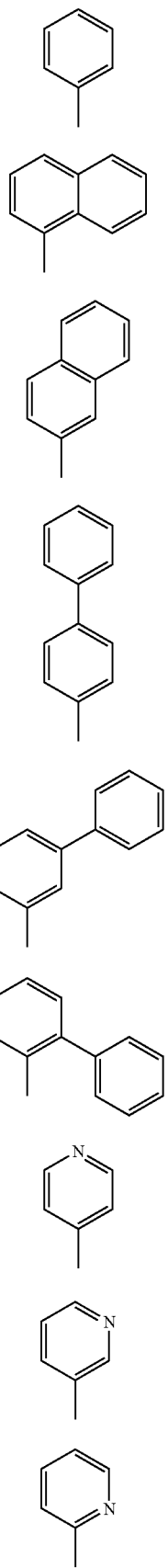
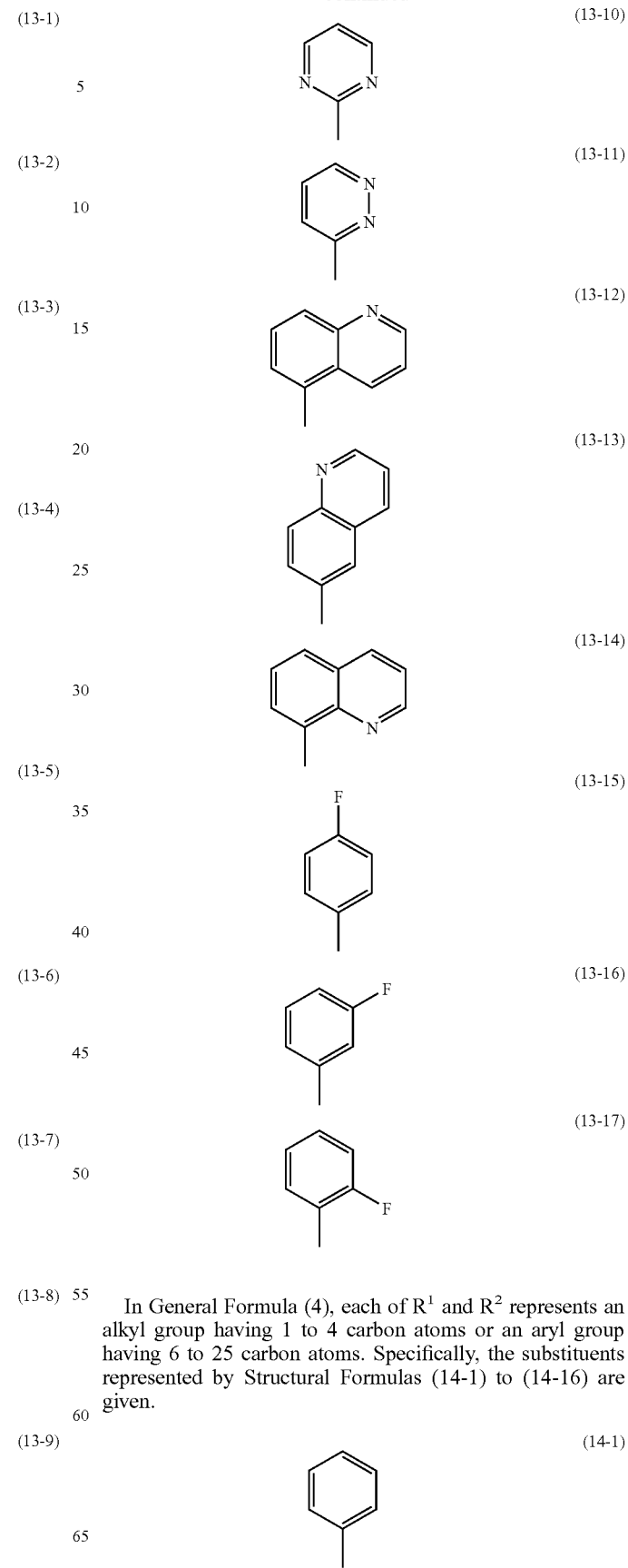
In General Formula (4), each of $R^1$ and $R^2$ represents an alkyl group having 1 to 4 carbon atoms or an aryl group having 6 to 25 carbon atoms. Specifically, the substituents represented by Structural Formulas (14-1) to (14-16) are given.

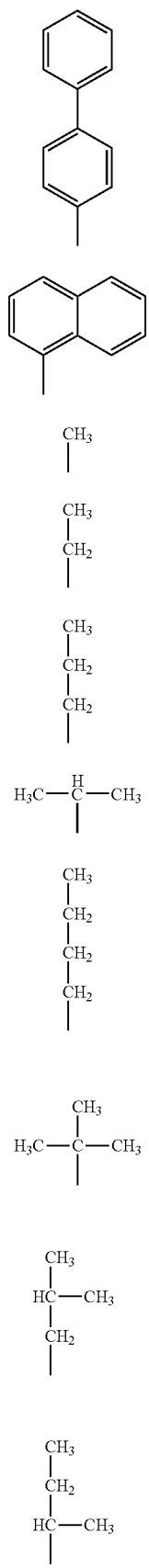
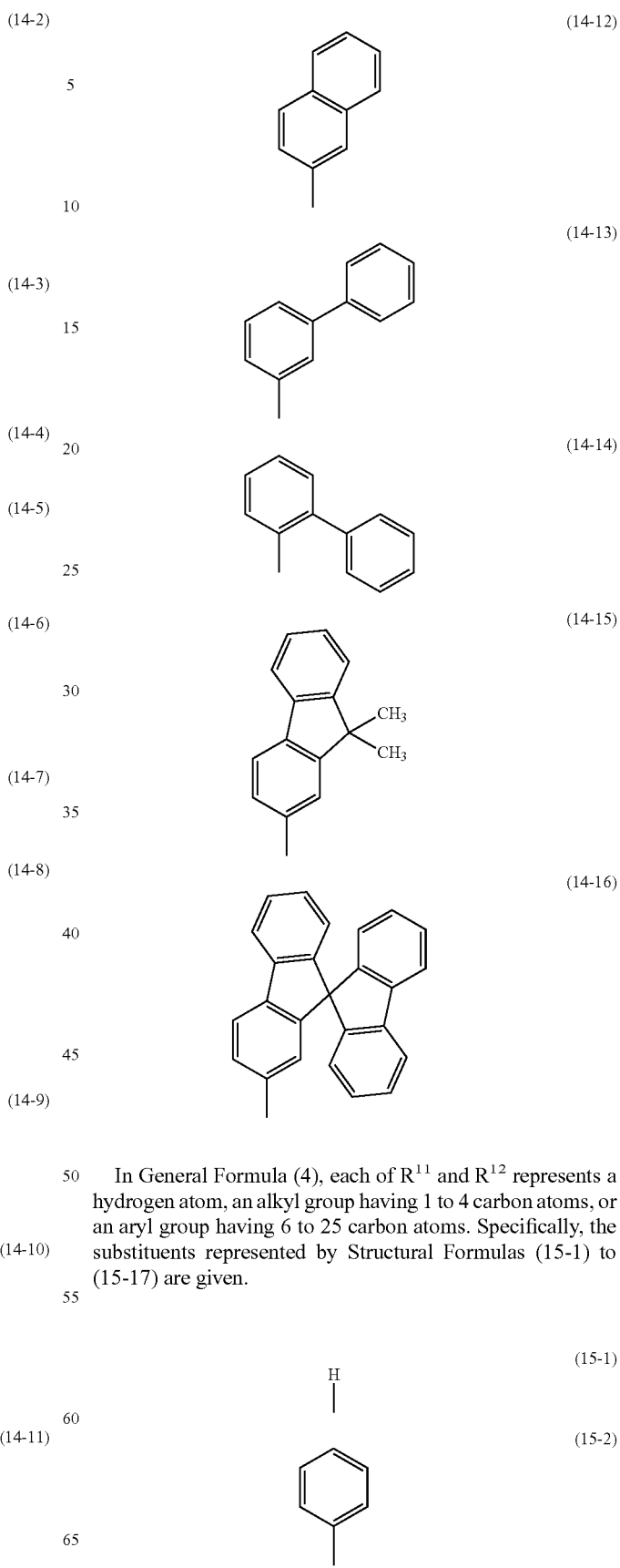
In General Formula (4), each of $R^{11}$ and $R^{12}$ represents a hydrogen atom, an alkyl group having 1 to 4 carbon atoms, or an aryl group having 6 to 25 carbon atoms. Specifically, the substituents represented by Structural Formulas (15-1) to (15-17) are given.

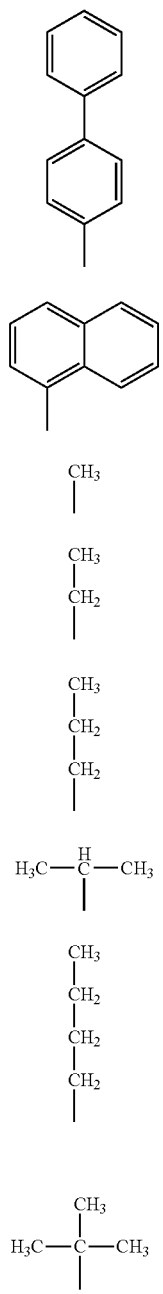

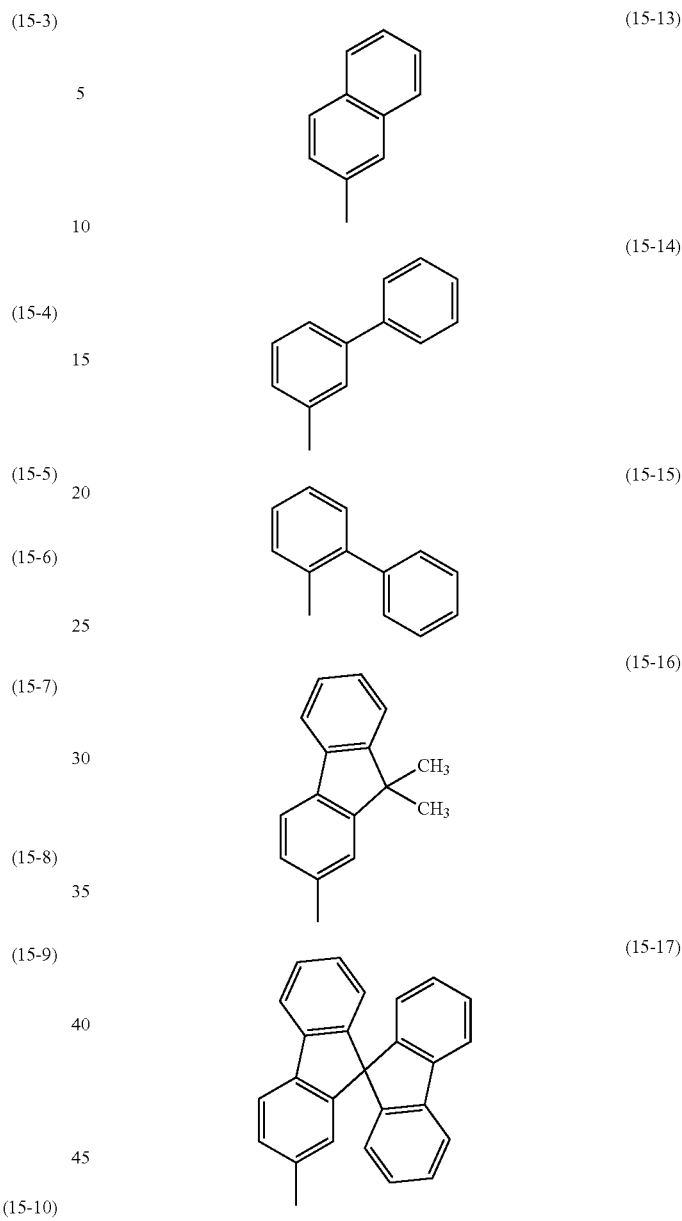

In General Formula (4), $Ar^1$ and $Ar^2$ are preferably the same substituents.

In General Formula (4), $R^1$ and $R^2$ are preferably the same substituents.

In General Formula (4), $R^{11}$ and $R^{12}$ are preferably the same substituents.

When $Ar^1$ and $Ar^2$ are the same substituents, $R^1$ and $R^2$ are the same substituents, and $R^{11}$ and $R^{12}$ are the same substituents, synthesis becomes easier. In other words, by reacting the same two secondary amines with 1,3-dihalogenated benzene, the aromatic amine compound of the present invention can be obtained.

In other words, an aromatic amine compound represented by General Formula (5) is preferable.

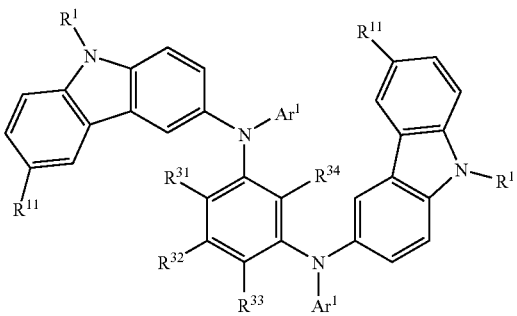

(5)

(where $Ar^1$ represents an aryl group having 6 to 12 carbon atoms or a heteroaromatic group having 4 to 9 carbon atoms; $R^1$ represents an alkyl group having 1 to 4 carbon atoms or an aryl group having 6 to 25 carbon atoms; $R^{11}$ represents a hydrogen atom, an alkyl group having 1 to 4 carbon atoms, or an aryl group having 6 to 25 carbon atoms; and each of $R^{31}$ to $R^{34}$ represents a hydrogen atom, a methyl group, or a silyl group having a substituent.)

In General Formulas (4) and (5), each of $R^{31}$ to $R^{34}$ is preferably a hydrogen atom. When each of $R^{31}$ to $R^{34}$ is a hydrogen atom, synthesis becomes easier.

In other words, an aromatic amine compound represented by General Formula (6) is preferable.

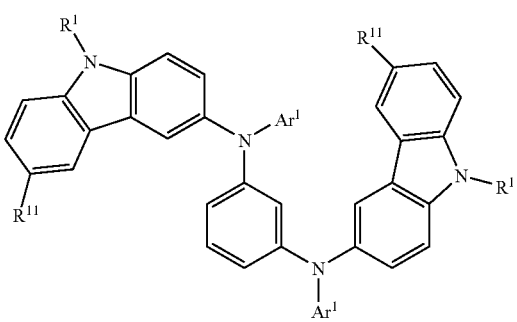

(6)

(where $Ar^1$ represents an aryl group having 6 to 12 carbon atoms or a heteroaromatic group having 4 to 9 carbon atoms; $R^1$ represents an alkyl group having 1 to 4 carbon atoms or an aryl group having 6 to 25 carbon atoms; and $R^{11}$ represents a hydrogen atom, an alkyl group having 1 to 4 carbon atoms, or an aryl group having 6 to 25 carbon atoms.)

In addition, one aspect of the present invention is an aromatic amine compound represented by General Formula (7).

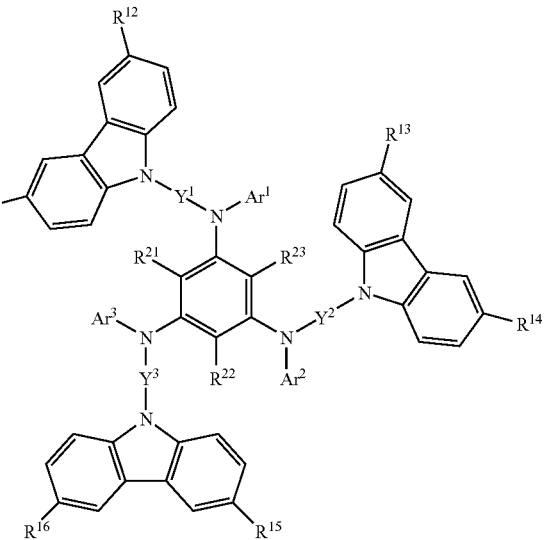

(7)

(where each of $Ar^1$ to $Ar^3$ represents an aryl group having 6 to 12 carbon atoms or a heteroaromatic group having 4 to 9 carbon atoms; each of $Y^1$ to $Y^3$ represents an arylene group having 6 to 25 carbon atoms; each of $R^{11}$ to $R^{16}$ represents a hydrogen atom, an alkyl group having 1 to 4 carbon atoms, or an aryl group having 6 to 25 carbon atoms; and each of $R^{21}$ to $R^{23}$ represents a hydrogen atom, a methyl group, or a methoxy group.)

In General Formula (7), each of $Ar^1$ to $Ar^3$ represents an aryl group having 6 to 12 carbon atoms or a heteroaromatic group having 4 to 9 carbon atoms. Specifically, substituents represented by Structural Formulas (16-1) to (16-17) are given. Preferably, each of $Ar^1$ to $Ar^3$ is an aryl group having 6 to 12 carbon atoms.

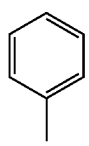

(16-1)

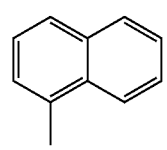

(16-2)

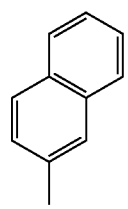

(16-3)

-continued
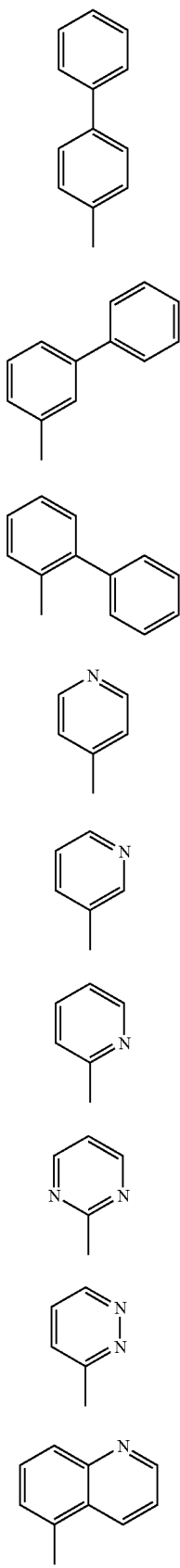
(16-4)
(16-5)
(16-6)
(16-7)
(16-8)
(16-9)
(16-10)
(16-11)
(16-12)
-continued
(16-13) 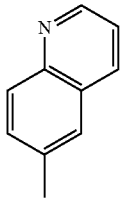
(16-14) 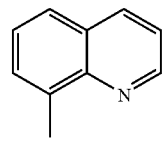
(16-15) 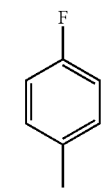
(16-16) 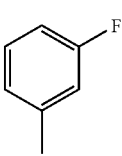
(16-17) 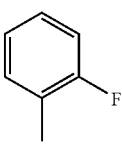
In General Formula (7), each of $Y^1$ to $Y^3$ represents an arylene group having 6 to 25 carbon atoms. Specifically, substituents represented by Structural Formulas (17-1) to (17-7) are given.
(17-1) 
(17-2) 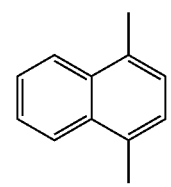

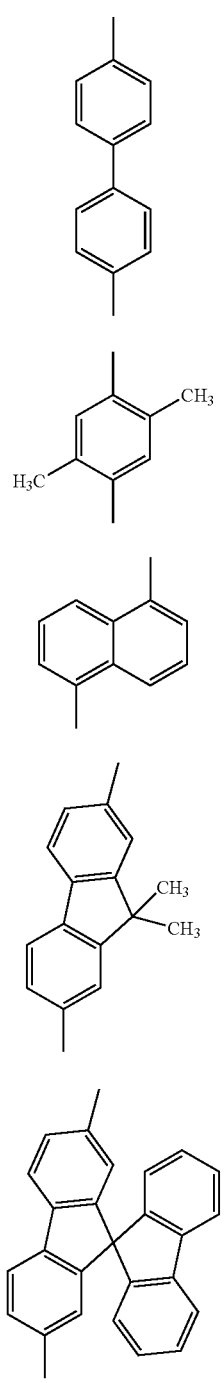
In General Formula (7), each of $R^{11}$ to $R^{16}$ represents a hydrogen atom, an alkyl group having 1 to 4 carbon atoms, or an aryl group having 6 to 25 carbon atoms. Specifically, substituents represented by Structural Formulas (18-1) to (18-17) are given.
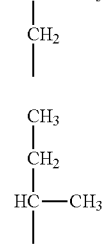

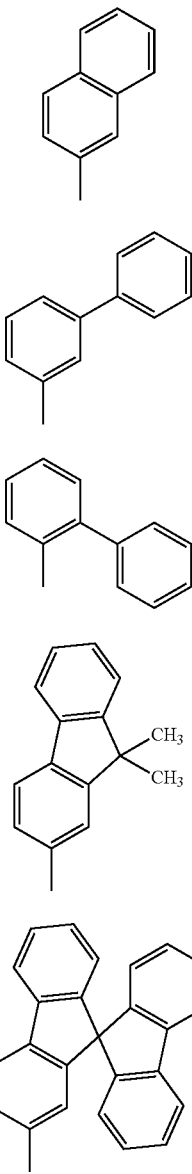

(18-13)

(18-14)

(18-15)

(18-16)

(18-17)

In General Formula (7), $Ar^1$, $Ar^2$, and $Ar^3$ are preferably the same substituents.

In General Formula (7), $Y^1$, $Y^2$, and $Y^3$ are preferably the same substituents.

In General Formula (7), $R^{11}$, $R^{13}$, and $R^{15}$ are preferably the same substituents.

In General Formula (7), $R^{12}$, $R^{14}$, and $R^{16}$ are preferably the same substituents.

When $Ar^1$, $Ar^2$, and $Ar^3$ are the same substituents, $Y^1$, $Y^2$, and $Y^3$ are the same substituents, $R^{11}$, $R^{13}$, and $R^{15}$ are the same substituents, and $R^{12}$, $R^{14}$, and $R^{16}$ are the same substituents, synthesis becomes easier. In other words, by reacting the same three secondary amines with 1,3,5-trihalogenated benzene, the aromatic amine compound of the present invention can be obtained.

In other words, an aromatic amine compound represented by General Formula (8) is preferable.

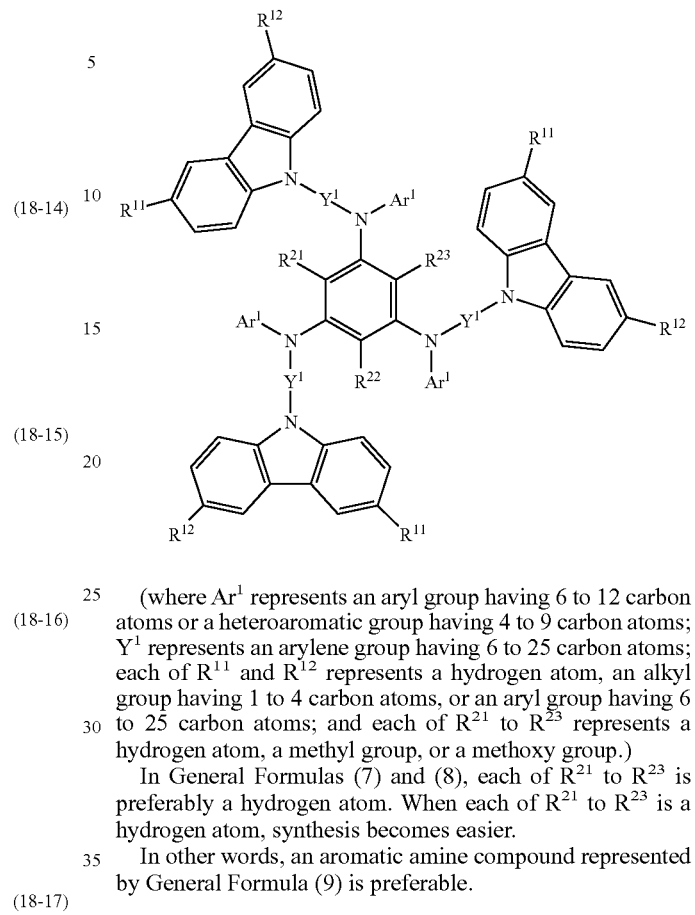

(8)

(where $Ar^1$ represents an aryl group having 6 to 12 carbon atoms or a heteroaromatic group having 4 to 9 carbon atoms; $Y^1$ represents an arylene group having 6 to 25 carbon atoms; each of $R^{11}$ and $R^{12}$ represents a hydrogen atom, an alkyl group having 1 to 4 carbon atoms, or an aryl group having 6 to 25 carbon atoms; and each of $R^{21}$ to $R^{23}$ represents a hydrogen atom, a methyl group, or a methoxy group.)

In General Formulas (7) and (8), each of $R^{21}$ to $R^{23}$ is preferably a hydrogen atom. When each of $R^{21}$ to $R^{23}$ is a hydrogen atom, synthesis becomes easier.

In other words, an aromatic amine compound represented by General Formula (9) is preferable.

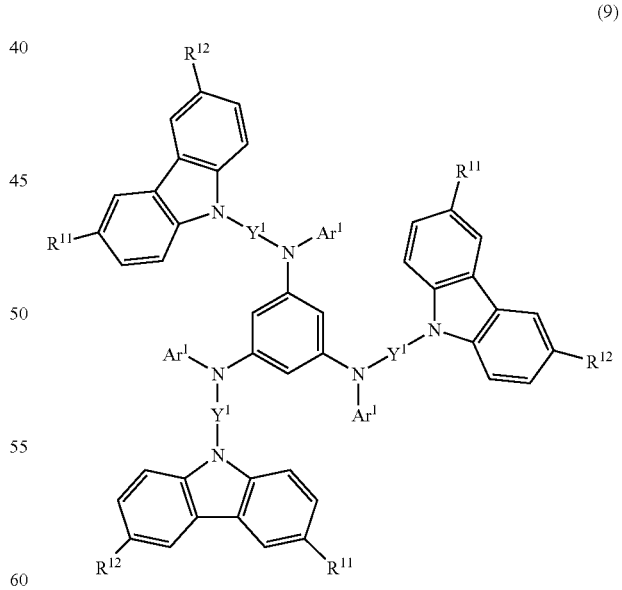

(9)

(where $Ar^1$ represents an aryl group having 6 to 12 carbon atoms or a heteroaromatic group having 4 to 9 carbon atoms; $Y^1$ represents an arylene group having 6 to 25 carbon atoms; and each of $R^{11}$ and $R^{12}$ represents a hydrogen atom, an alkyl group having 1 to 4 carbon atoms, or an aryl group having 6 to 25 carbon atoms.)

In addition, one aspect of the present invention is an aromatic amine compound represented by General Formula (10).

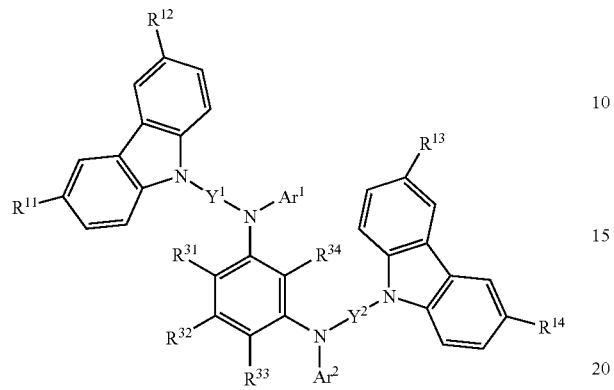

(10)

(where each of Ar¹ and Ar² represents an aryl group having 6 to 12 carbon atoms or a heteroaromatic group having 4 to 9 carbon atoms; each of Y¹ and Y² represents an arylene group having 6 to 25 carbon atoms; each of $R^{11}$ to $R^{14}$ represents a hydrogen atom, an alkyl group having 1 to 4 carbon atoms, or an aryl group having 6 to 25 carbon atoms; and each of $R^{31}$ to $R^{34}$ represents a hydrogen atom, a methyl group, or a silyl group having a substituent.)

In General Formula (10), each of Ar¹ and Ar² represents an aryl group having 6 to 12 carbon atoms or a heteroaromatic group having 4 to 9 carbon atoms. Specifically, the substituents represented by Structural Formulas (16-1) to (16-17) are given. Preferably, each of Ar¹ to Ar³ is an aryl group having 6 to 12 carbon atoms.

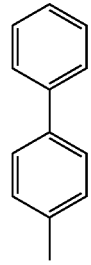

(16-1)

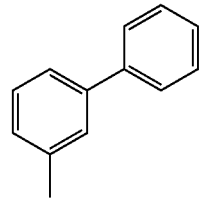

(16-2)

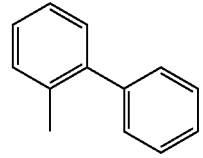

(16-3)

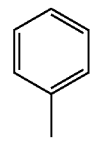

(16-4)

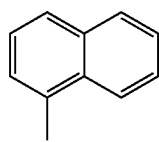

(16-5)

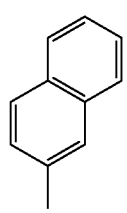

(16-6)

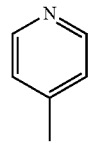

(16-7)

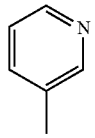

(16-8)

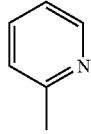

(16-9)

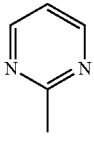

(16-10)

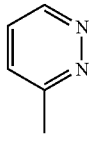

(16-11)

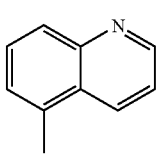

(16-12)

(16-13)
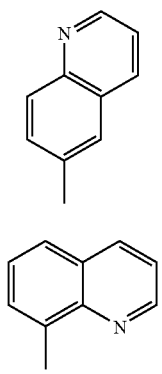

(16-14)

(16-15)
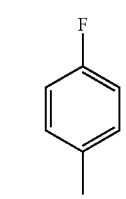

(16-16)
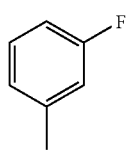

(16-17)
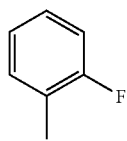

In General Formula (10), each of $Y^1$ and $Y^2$ represents an arylene group having 6 to 25 carbon atoms. Specifically, the substituents represented by Structural Formulas (17-1) to (17-7) are given.

(17-1)
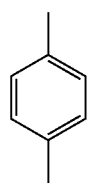

(17-2)
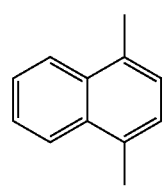

(17-3)
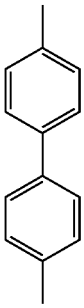

(17-4)
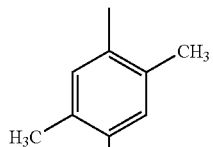

(17-5)
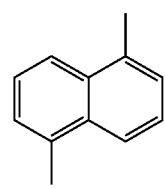

(17-6)
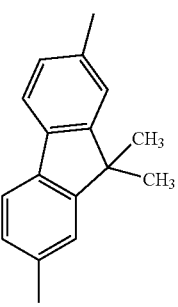

(17-7)
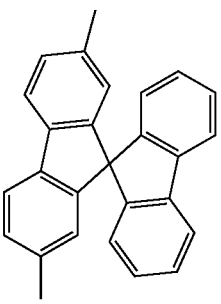

In General Formula (10), each of $R^{11}$ to $R^{14}$ represents a hydrogen atom, an alkyl group having 1 to 4 carbon atoms, or an aryl group having 6 to 25 carbon atoms. Specifically, the substituents represented by Structural Formulas (18-1) to (18-17) are given.

(18-1)
H

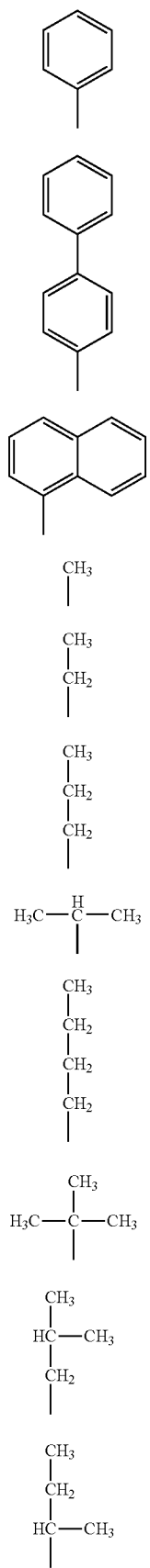

(18-2)
(18-3)
(18-4)
(18-5)
(18-6)
(18-7)
(18-8)
(18-9)
(18-10)
(18-11)
(18-12)

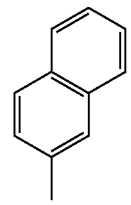

(18-13)

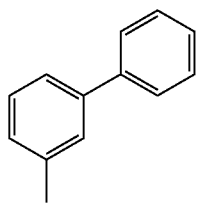

(18-14)

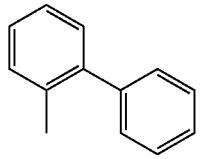

(18-15)

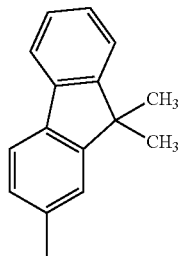

(18-16)

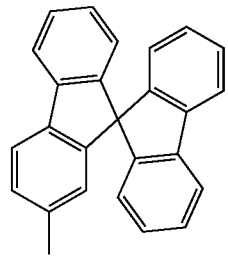

(18-17)

In General Formula (10), $Ar^1$ and $Ar^2$ are preferably the same substituents.

In General Formula (10), $Y^1$ and $Y^2$ are preferably the same substituents.

In General Formula (10), $R^{11}$ and $R^{1a}$ are preferably the same substituents.

In General Formula (10), $R^{12}$ and $R^{14}$ are preferably the same substituents.

When $Ar^1$ and $Ar^2$ are the same substituents, $Y^1$ and $Y^2$ are the same substituents, $R^{11}$ and $R^{13}$ are the same substituents, and $R^{12}$ and $R^{14}$ are the same substituents, synthesis becomes easier. In other words, by reacting the same two secondary amines with 1,3-dihalogenated benzene, the aromatic amine compound of the present invention can be obtained.

In other words, an aromatic amine compound represented by General Formula (11) is preferable.

In other words, an aromatic amine compound represented by General Formula (12) is preferable.

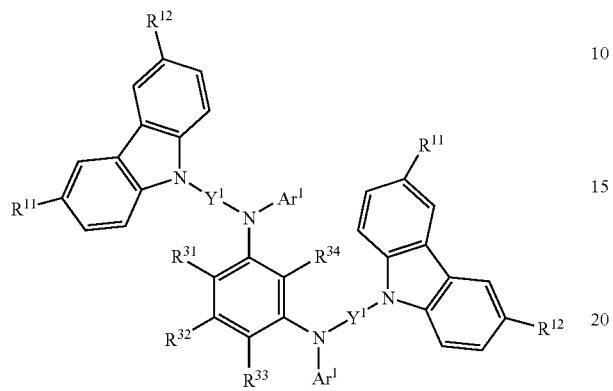

(11)

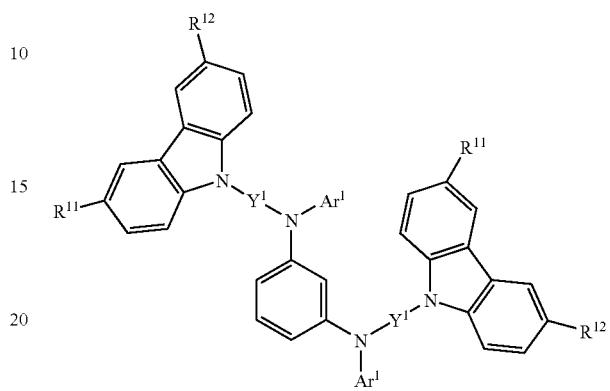

(12)

(where $Ar^1$ represents an aryl group having 6 to 12 carbon atoms or a heteroaromatic group having 4 to 9 carbon atoms; $Y^1$ represents an arylene group having 6 to 25 carbon atoms; each of $R^{11}$ and $R^{12}$ represents a hydrogen atom, an alkyl group having 1 to 4 carbon atoms, or an aryl group having 6 to 25 carbon atoms; and each of $R^{31}$ to $R^{34}$ represents a hydrogen atom, a methyl group, or a silyl group having a substituent.)

In General Formulas (10) and (11), each of $R^{31}$ to $R^{34}$ is preferably a hydrogen atom. When each of $R^{31}$ to $R^{34}$ is a hydrogen atom, synthesis becomes easier.

(where $Ar^1$ represents an aryl group having 6 to 12 carbon atoms or a heteroaromatic group having 4 to 9 carbon atoms; $Y^1$ represents an arylene group having 6 to 25 carbon atoms; and each of $R^{11}$ and $R^{12}$ represents a hydrogen atom, an alkyl group having 1 to 4 carbon atoms, or an aryl group having 6 to 25 carbon atoms.)

As specific examples of the aromatic amine compound of the present invention, aromatic amine compounds represented by Structural Formulas (21) to (142) are given. However, the present invention is not limited to these.

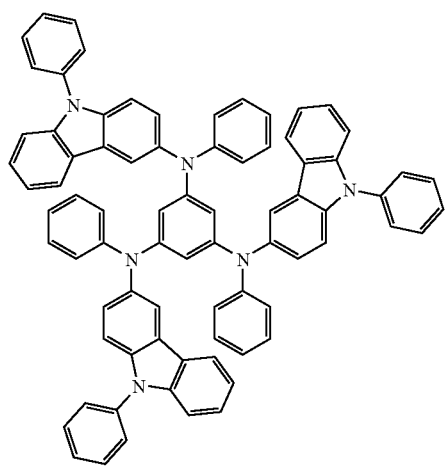

(21)

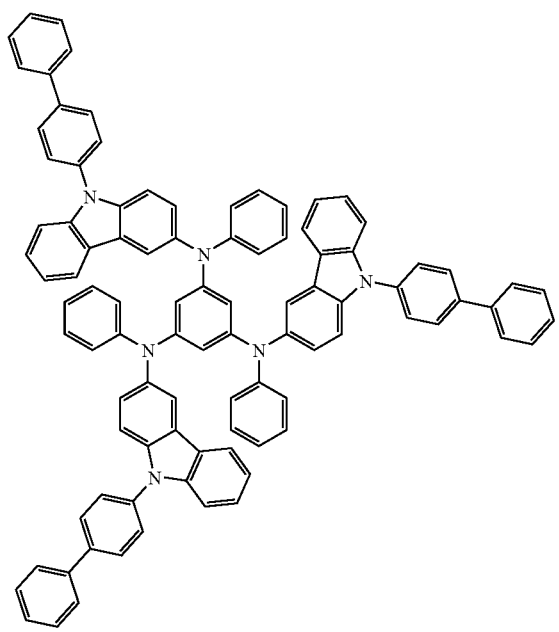

(22)

(23)
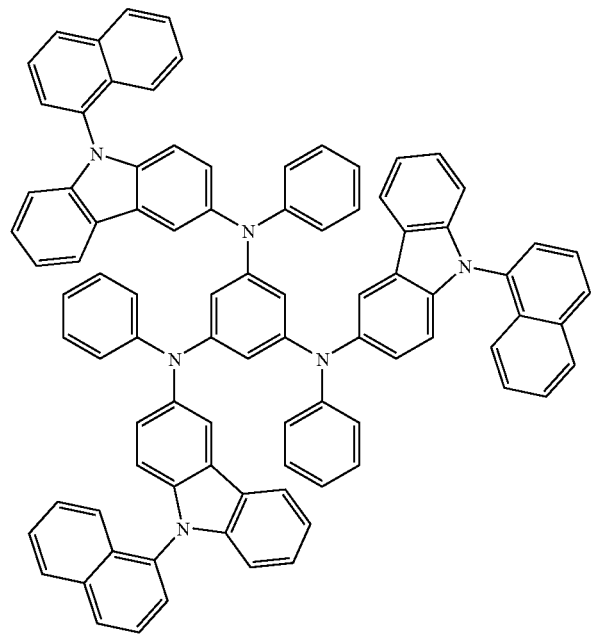
(24)
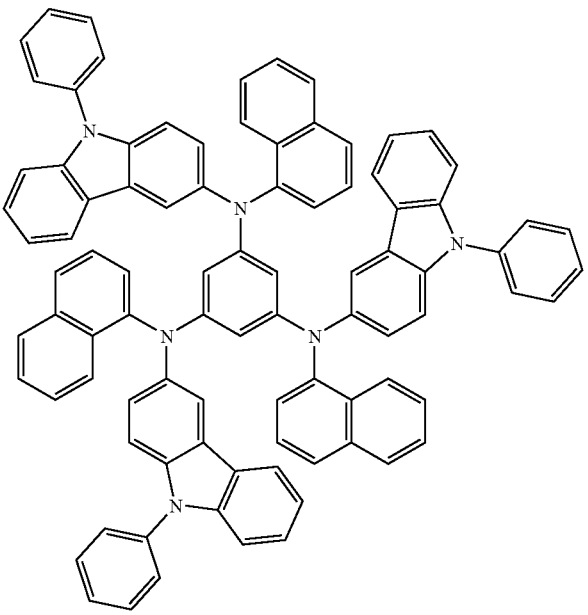
(25)
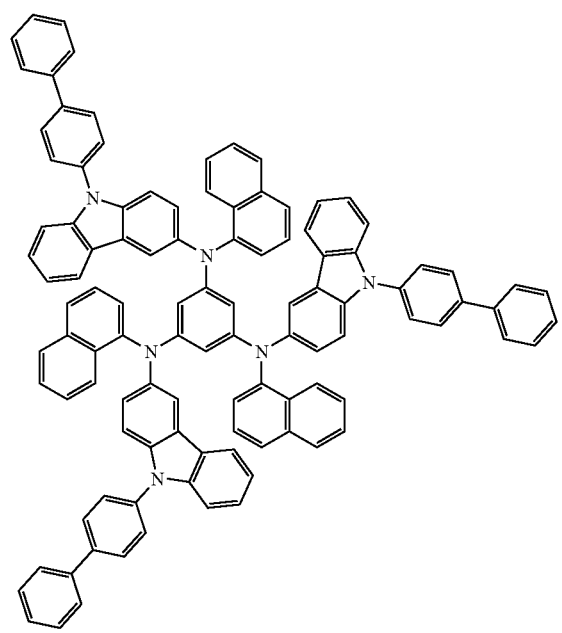
(26)
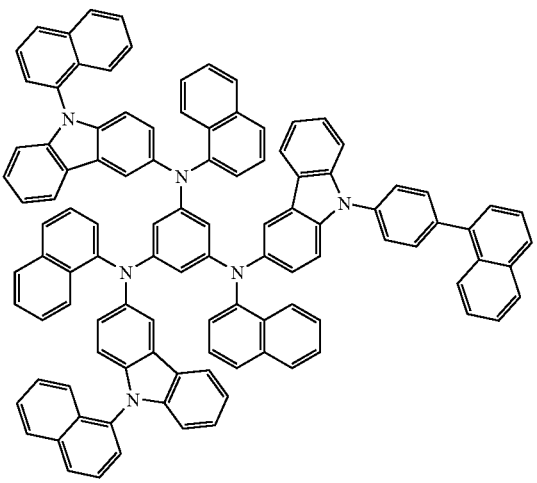

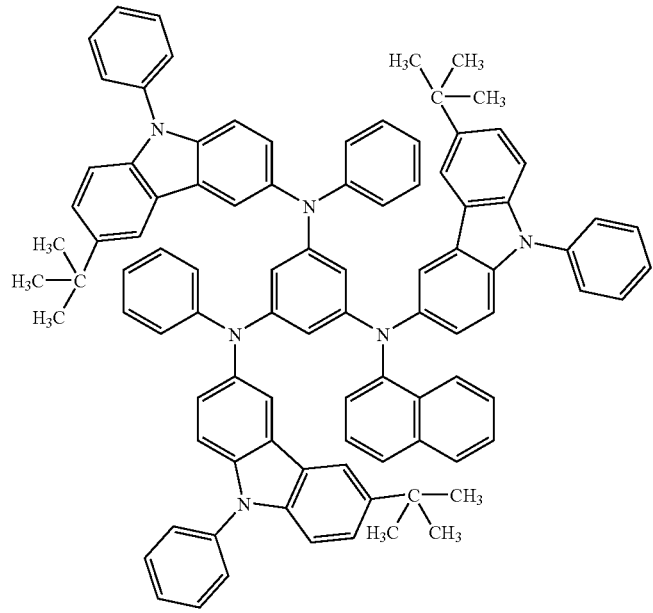
(27)
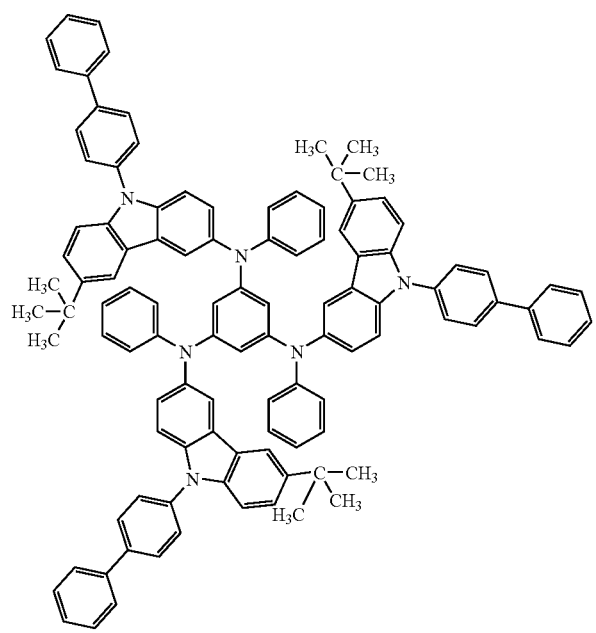
(28)
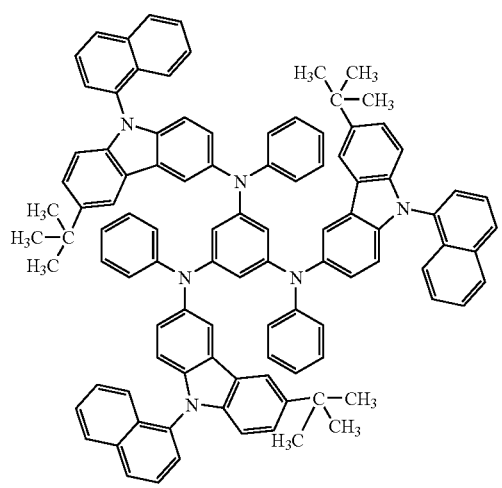
(29)

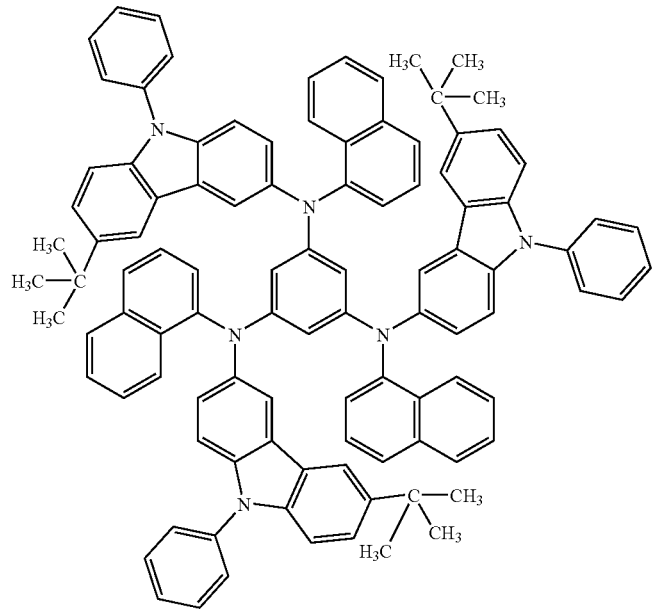
(30)
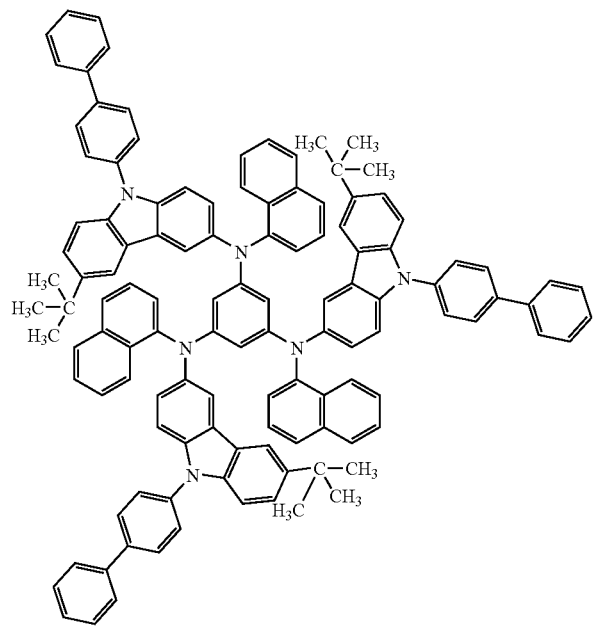
(31)
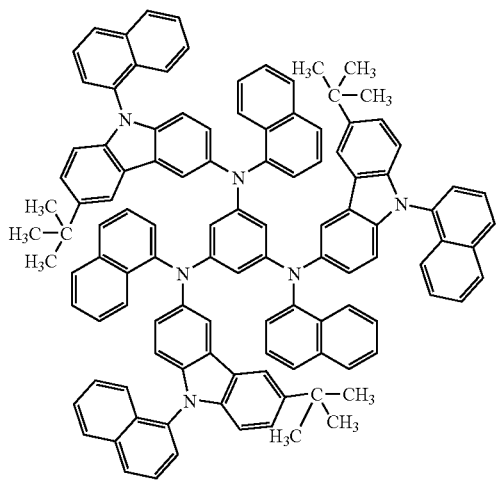
(32)

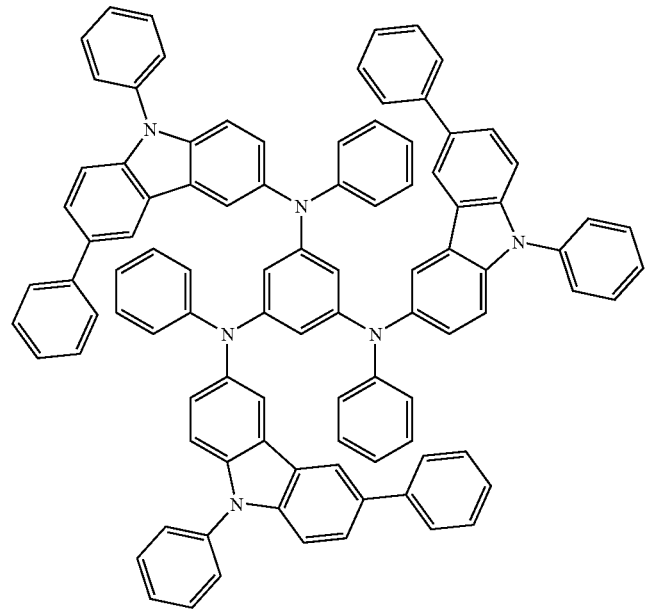
(33)
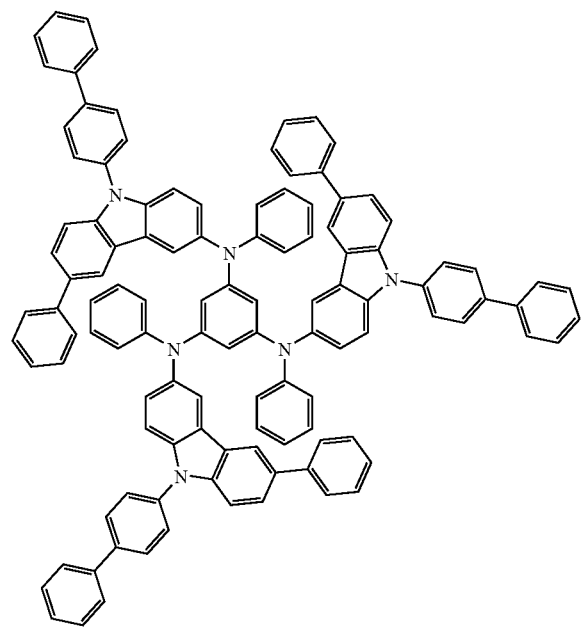
(34)
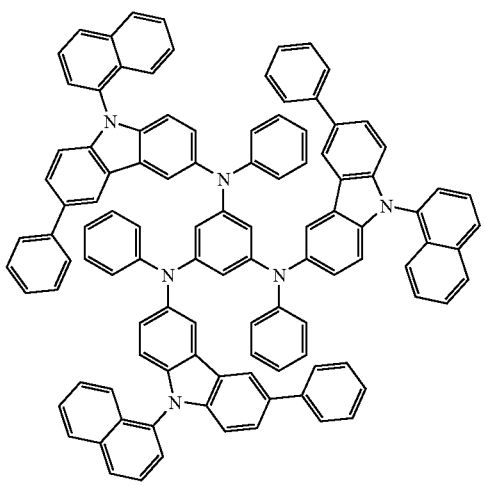
(35)

-continued
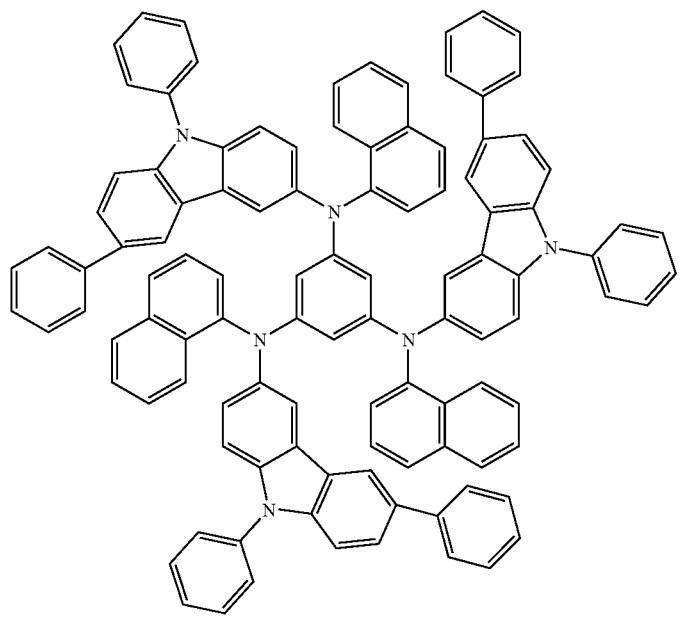
(36)
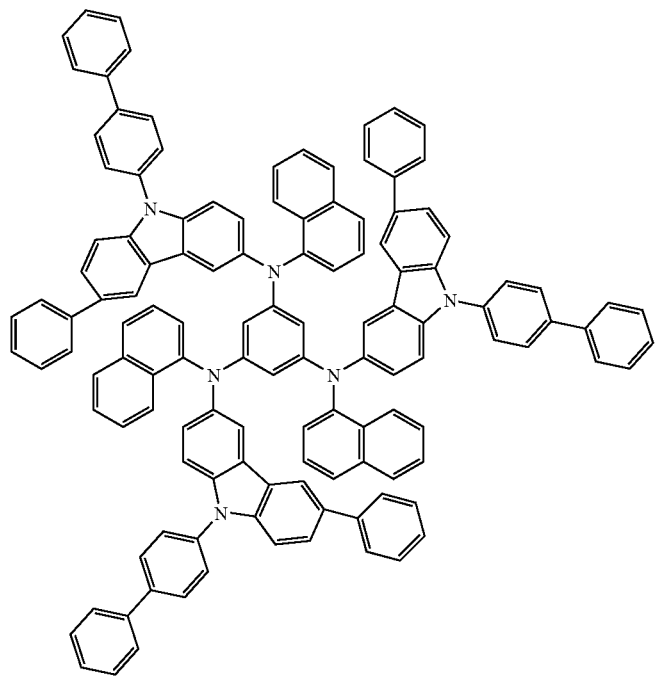
(37)

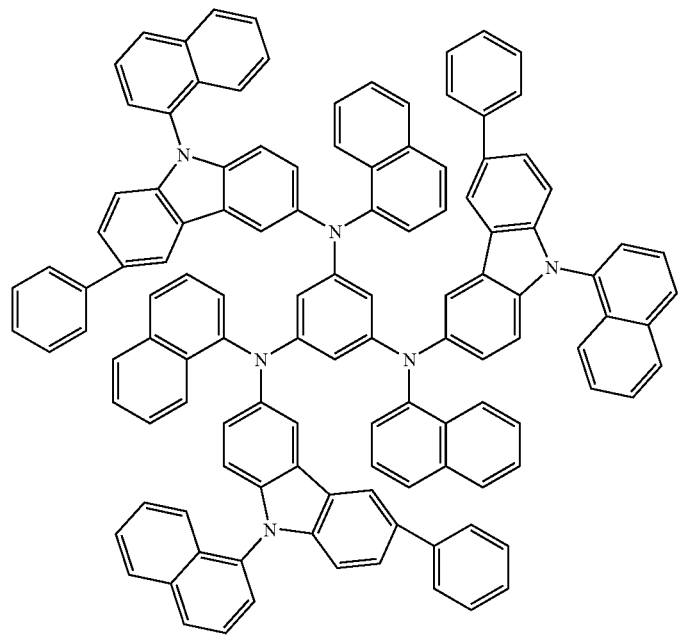
(38)
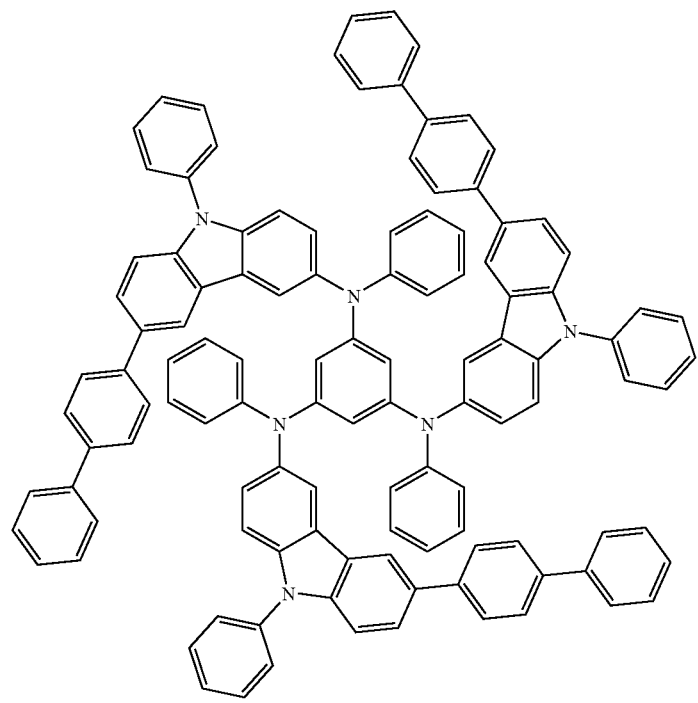
(39)

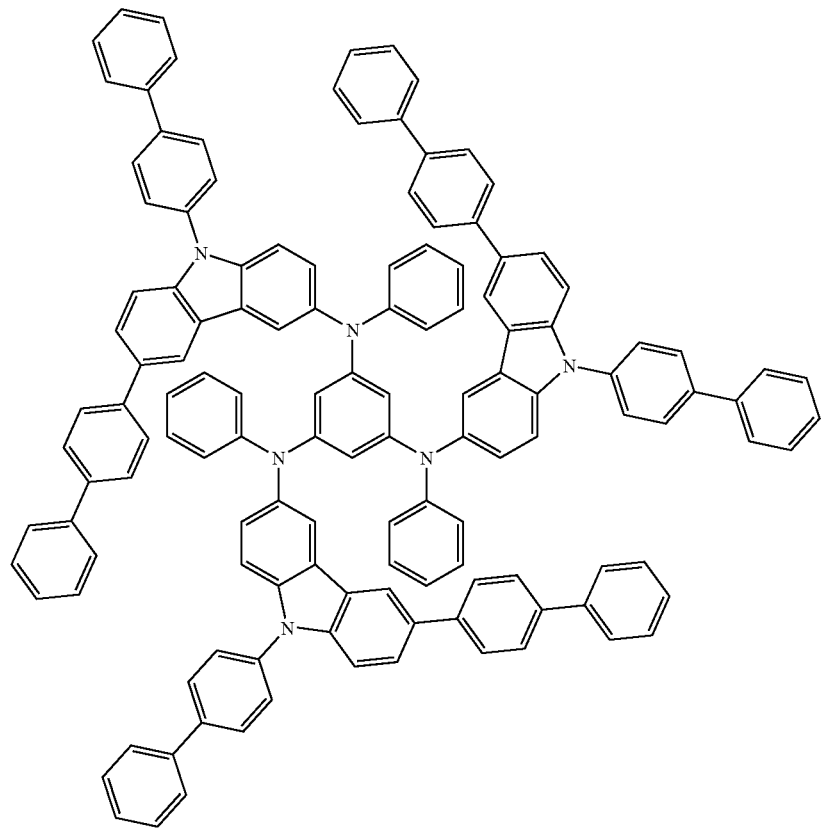
(40)
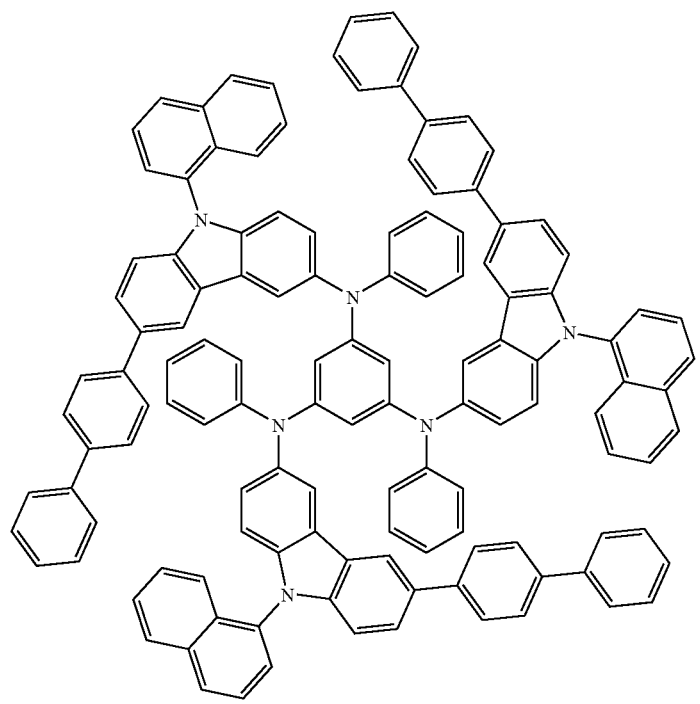
(41)

(42)
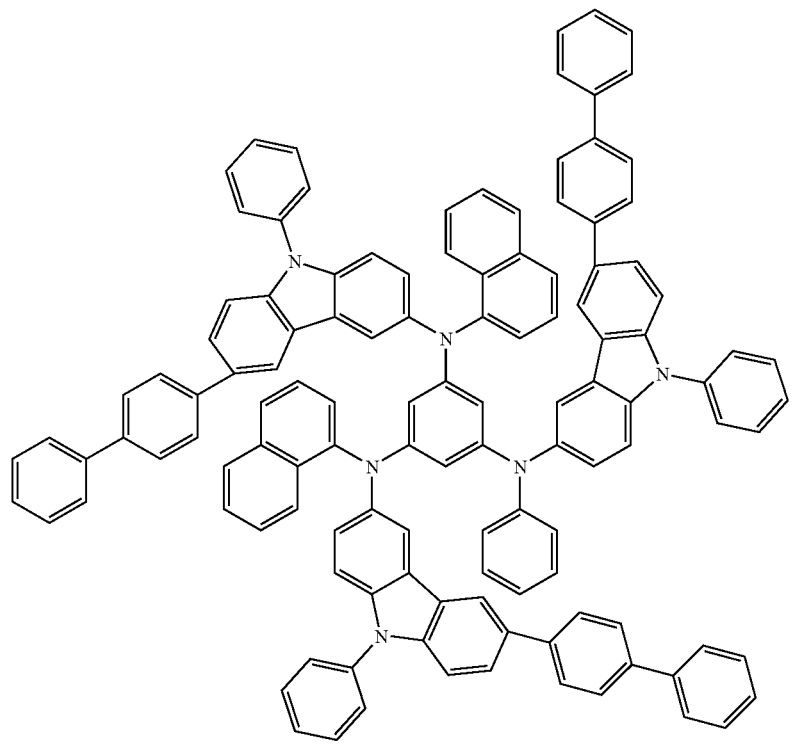
(43)
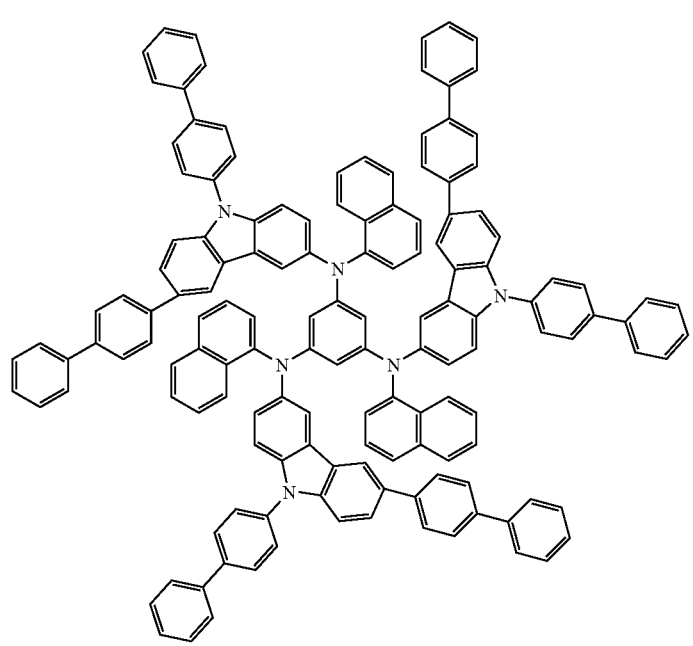

(44)
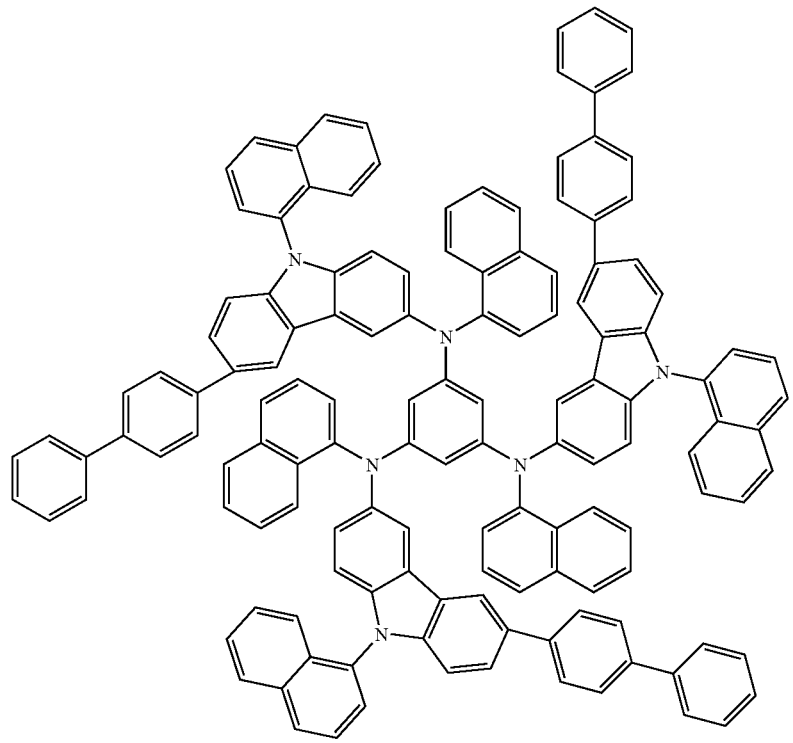
(45)
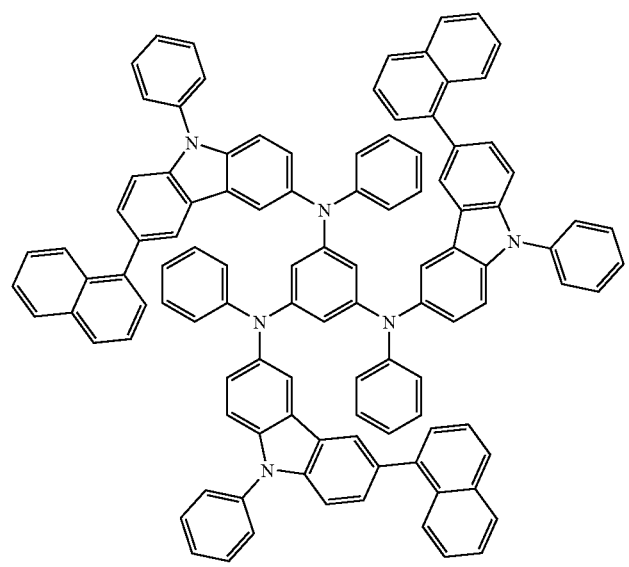

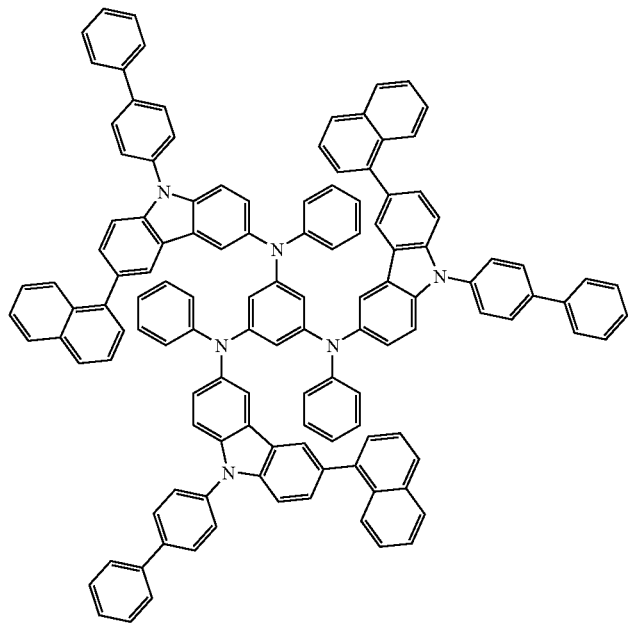
(46)
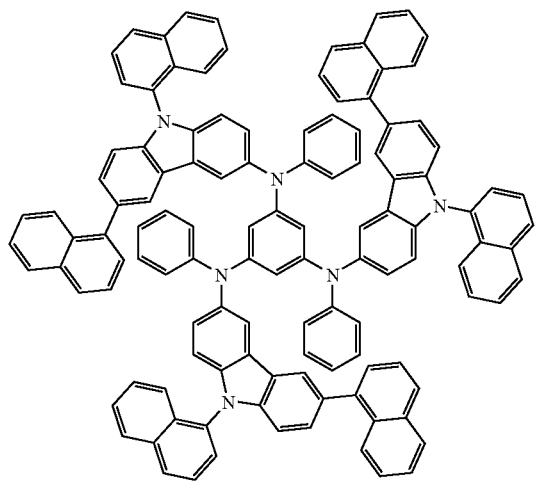
(47)
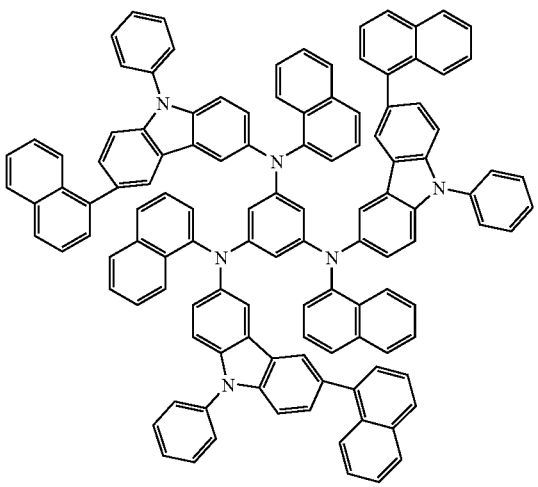
(48)

(49)
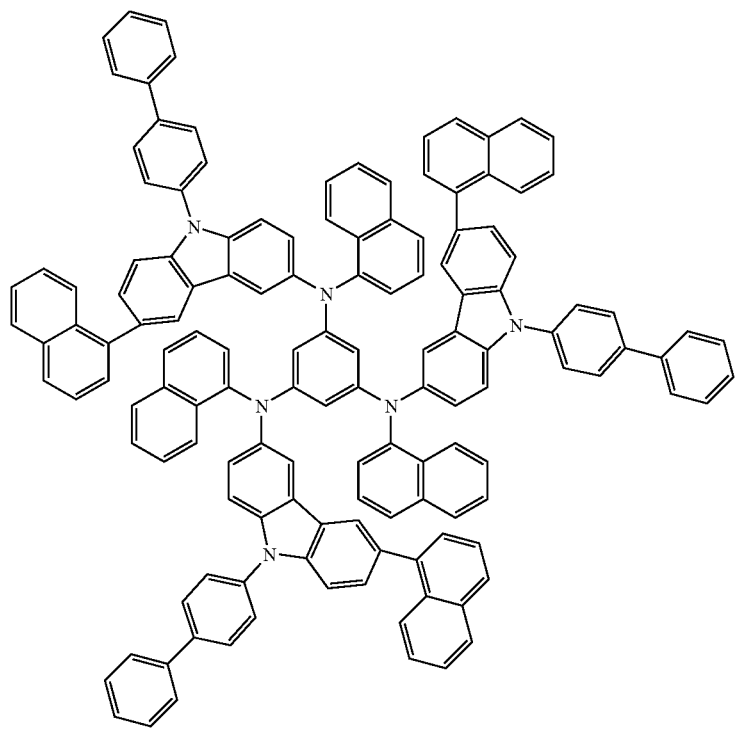
(50)
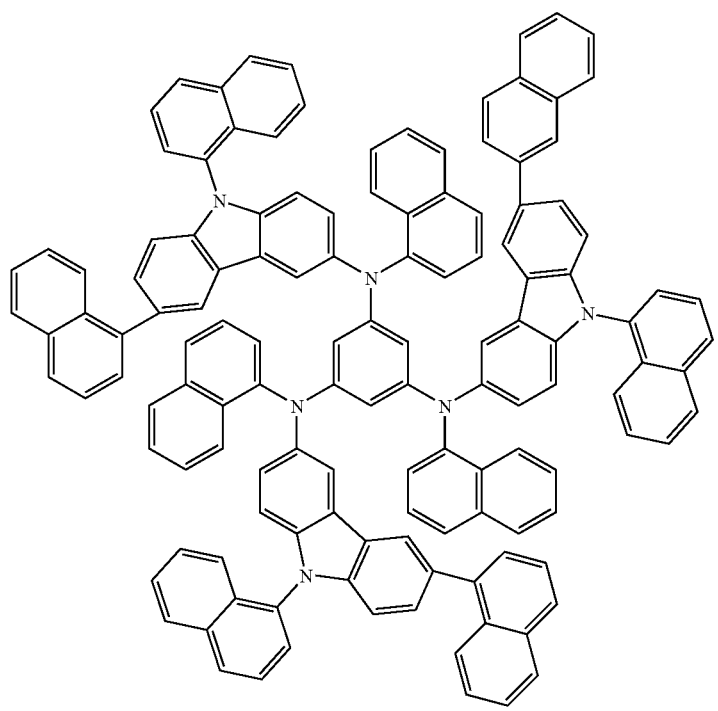

-continued
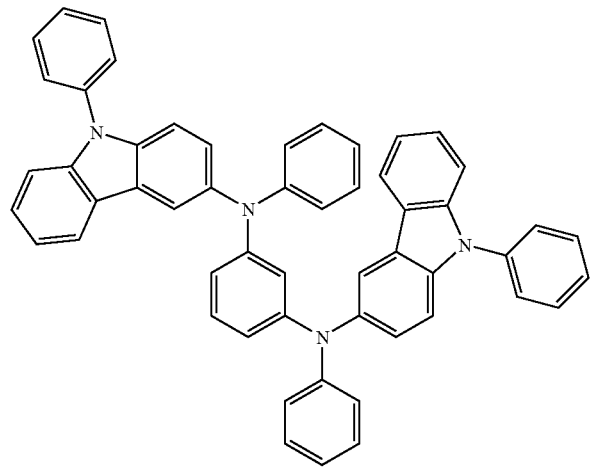
(51)
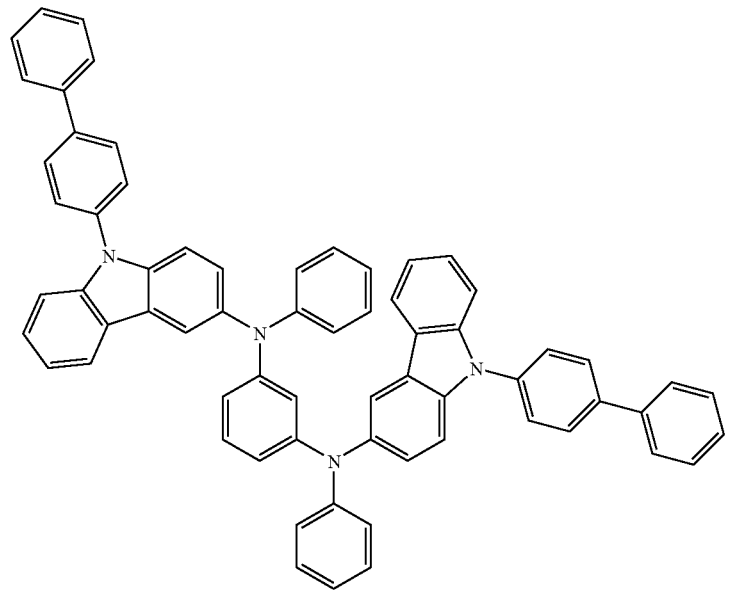
(52)
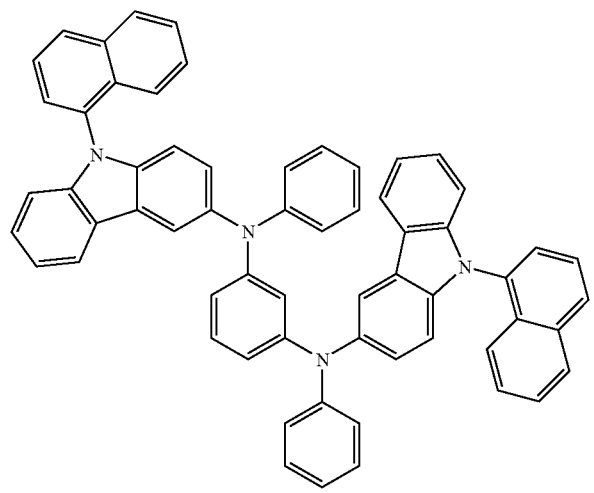
(53)
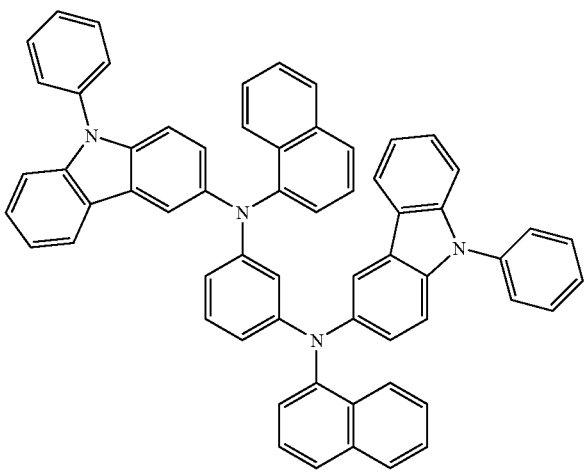
(54)

-continued
(55)
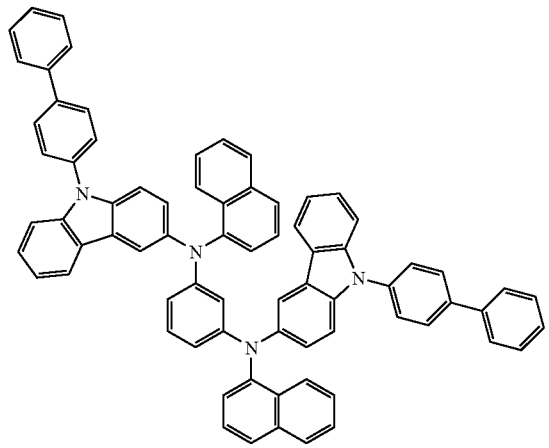
(56)
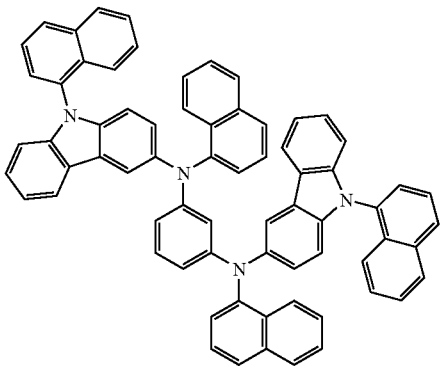
(57)
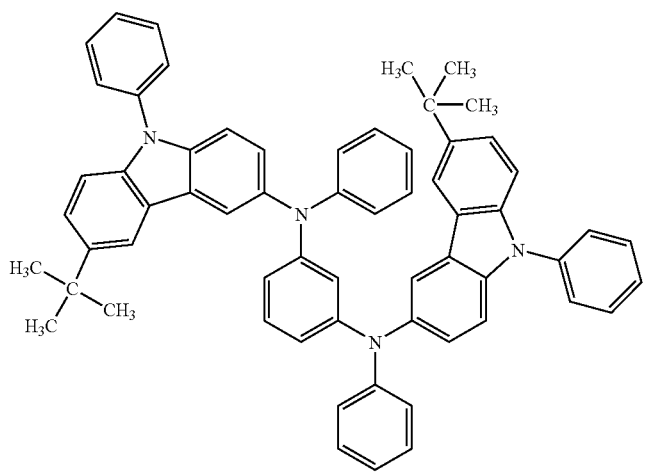
(58)
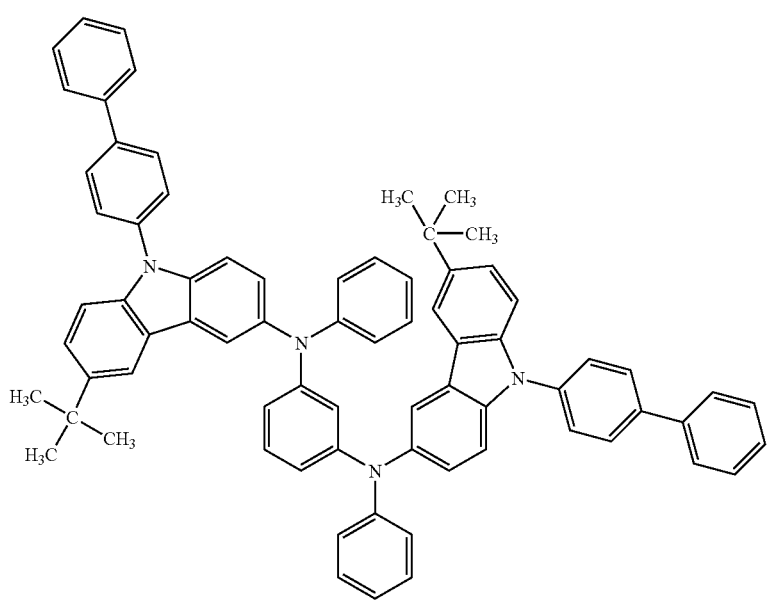

-continued
(59)
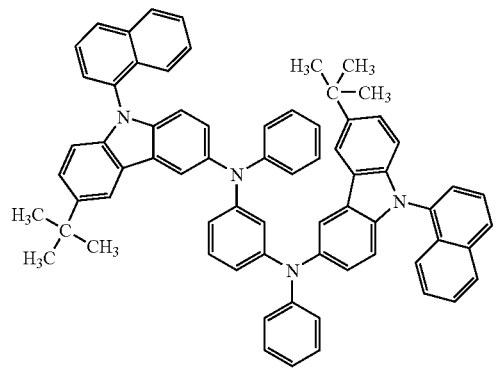
(60)
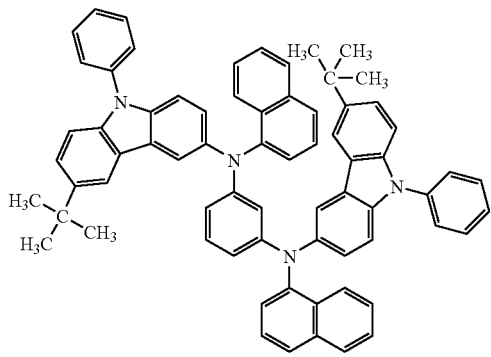
(61)
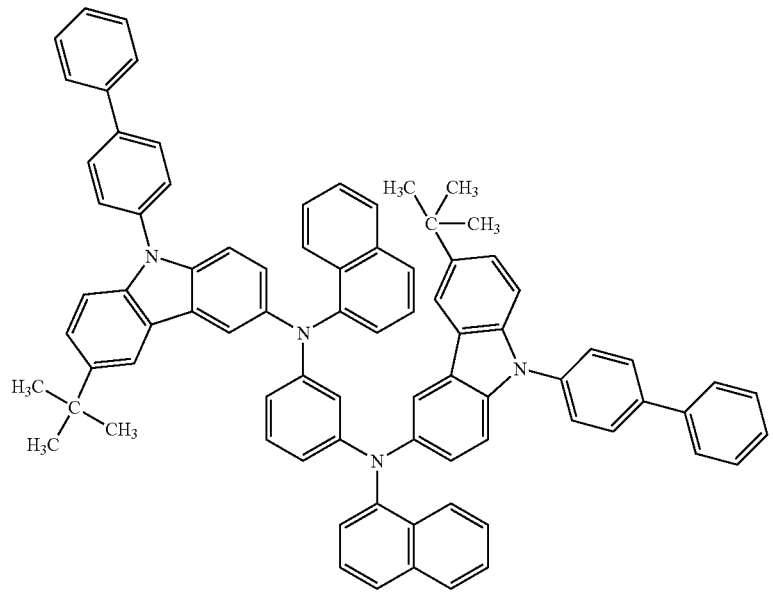
(62)
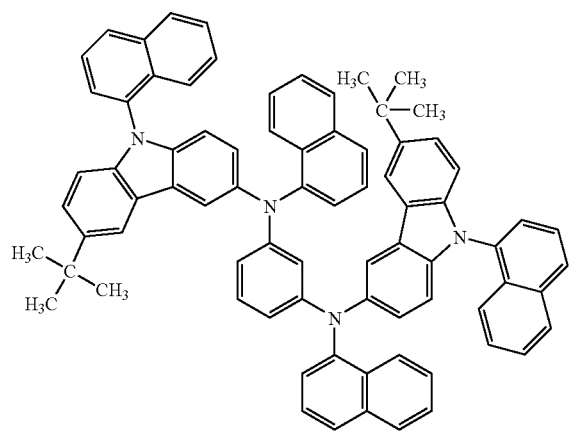
(63)
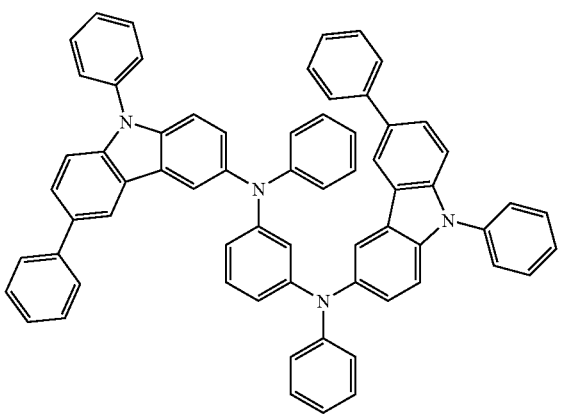

(64)
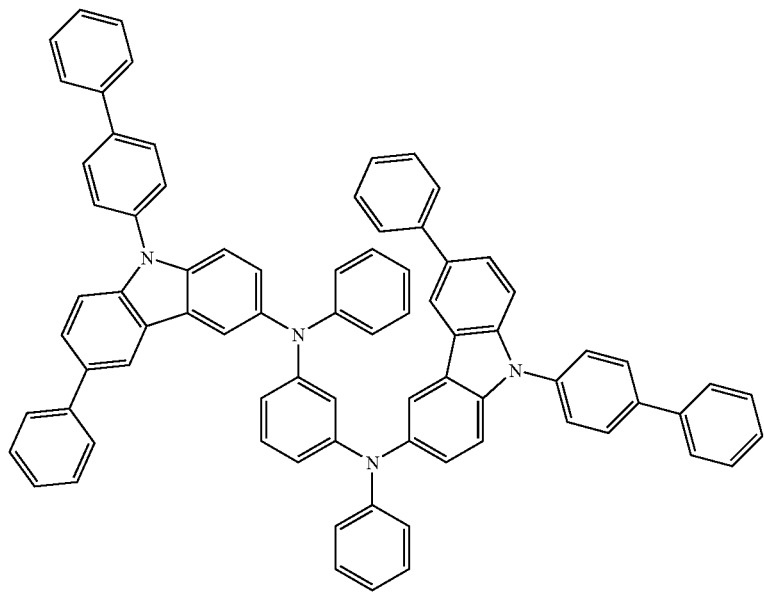
(65)
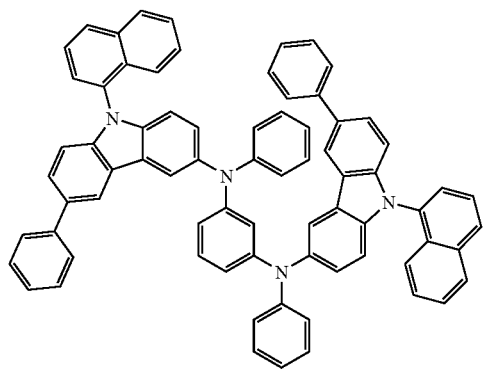
(66)
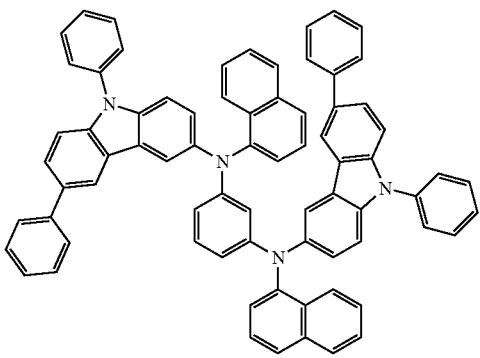
(67)
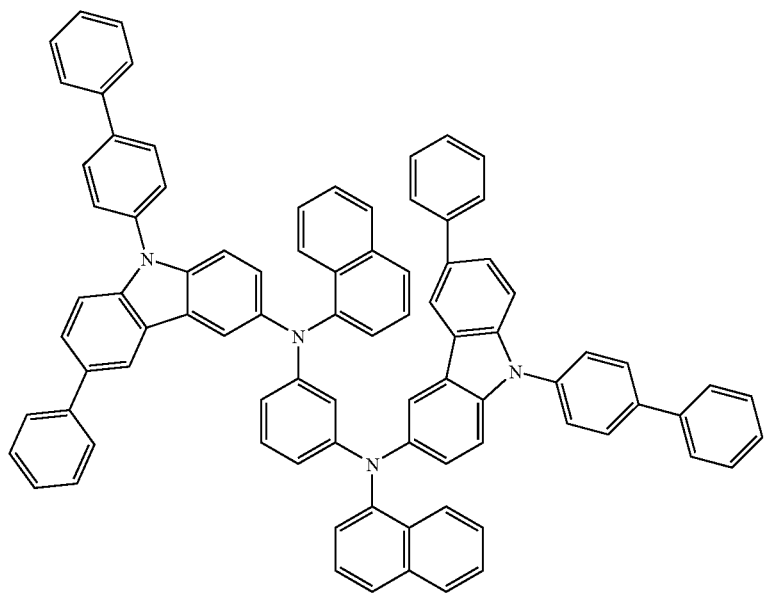

(68)
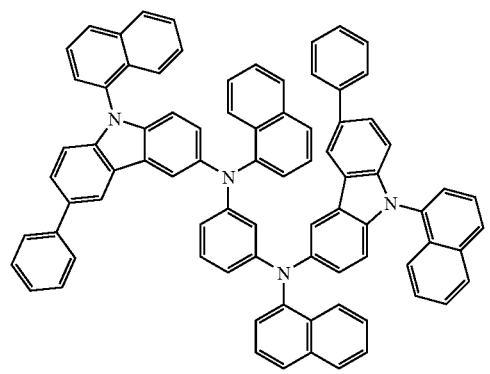
(69)
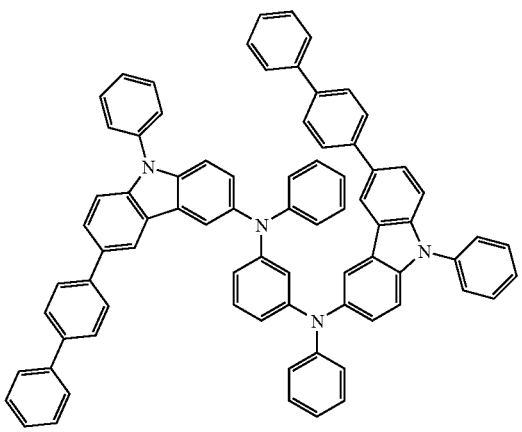
(70)
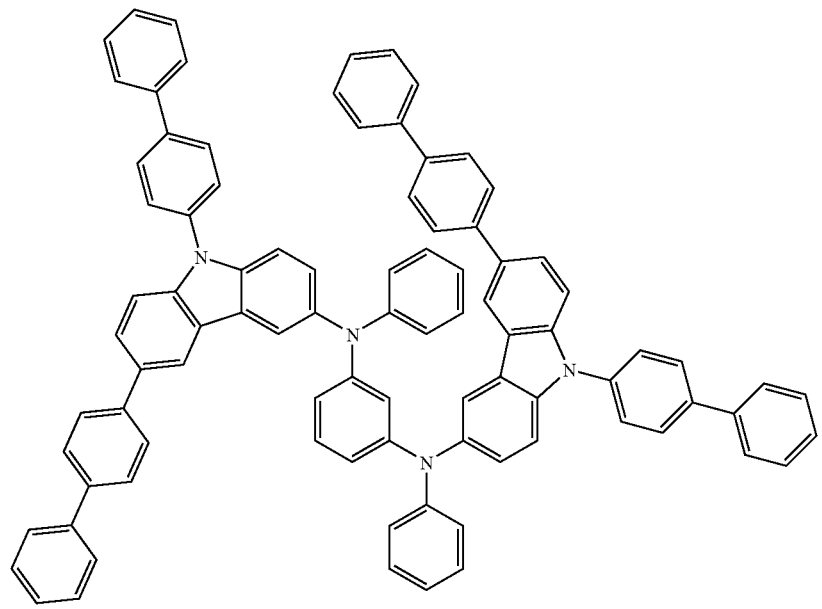
(71)
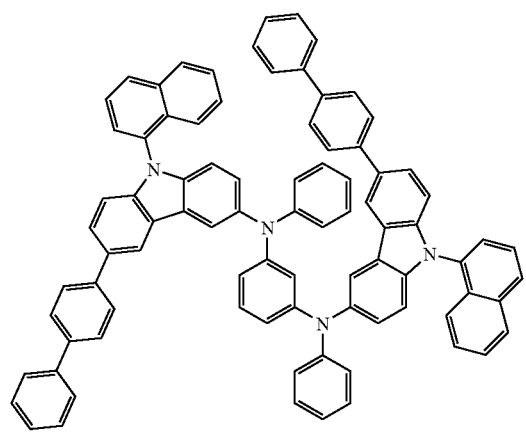
(72)
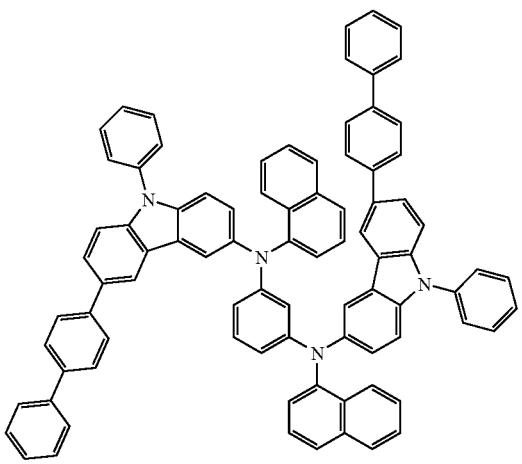

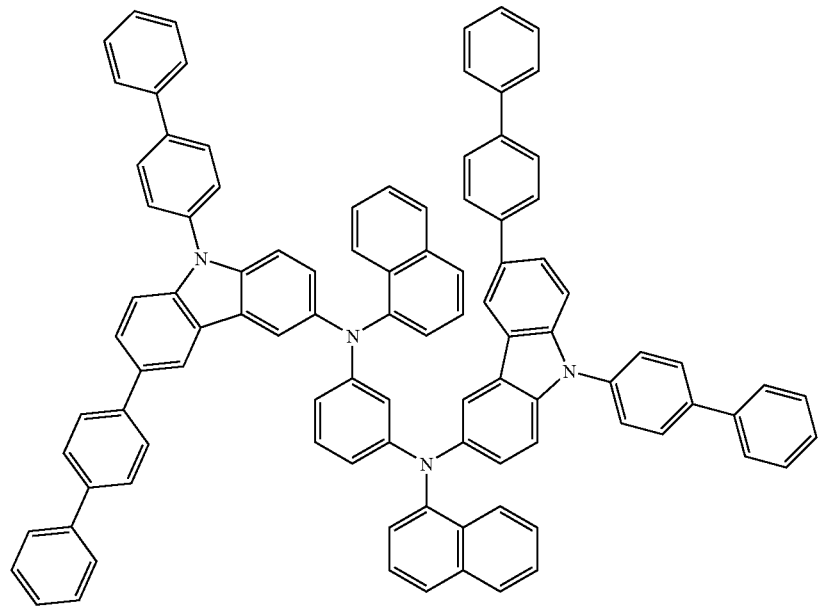
(73)
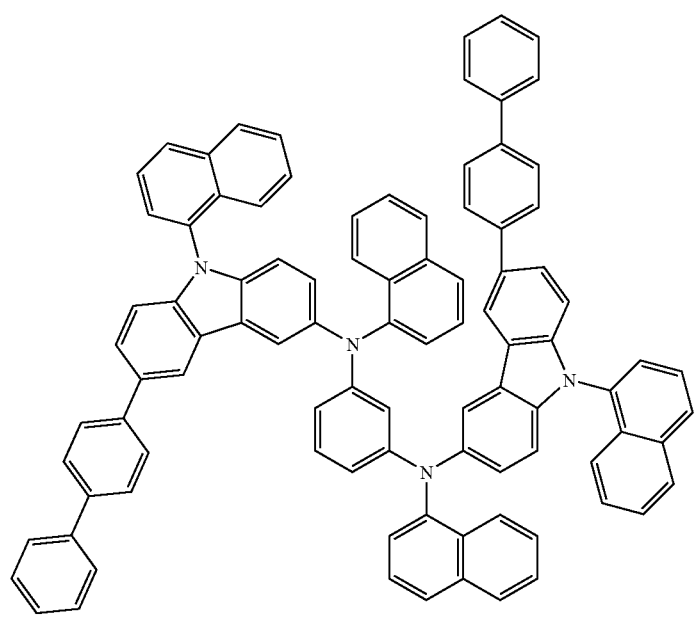
(74)

(75)
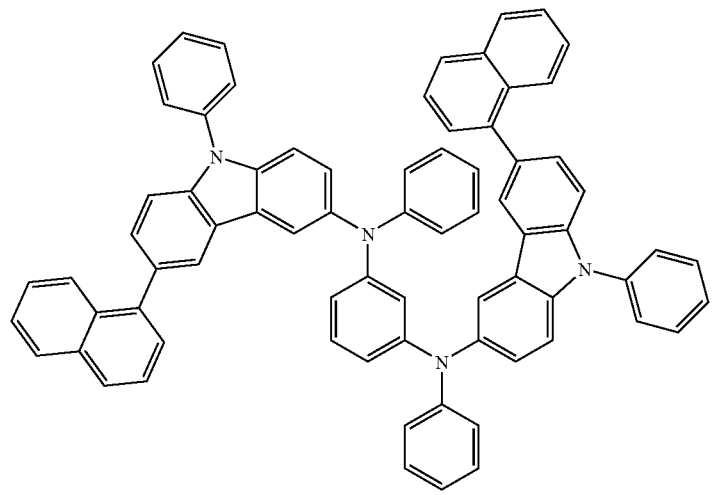
(76)
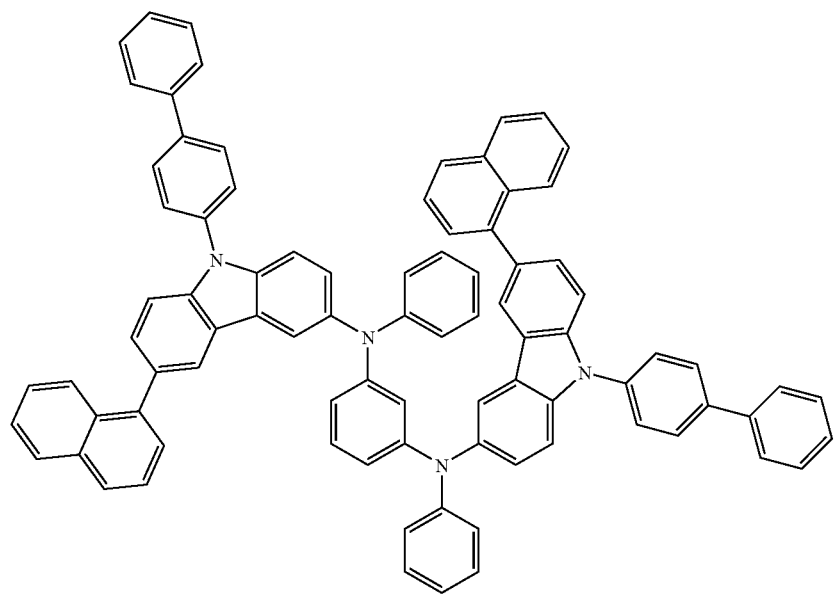
(77)
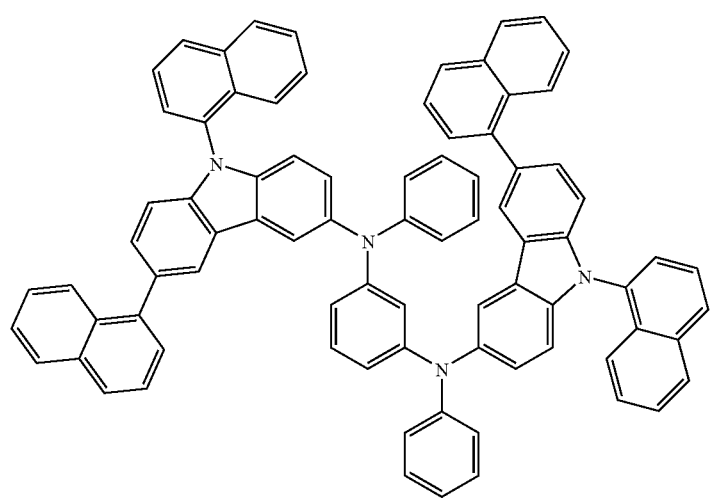

(78)
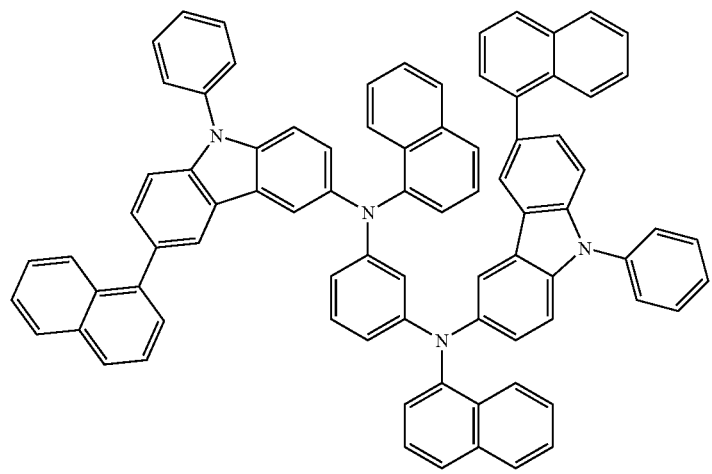
(79)
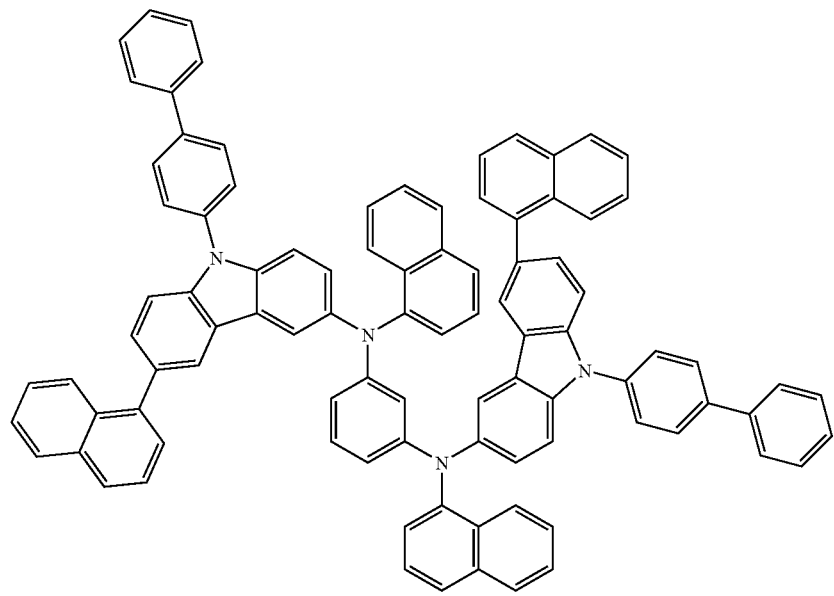
(80)
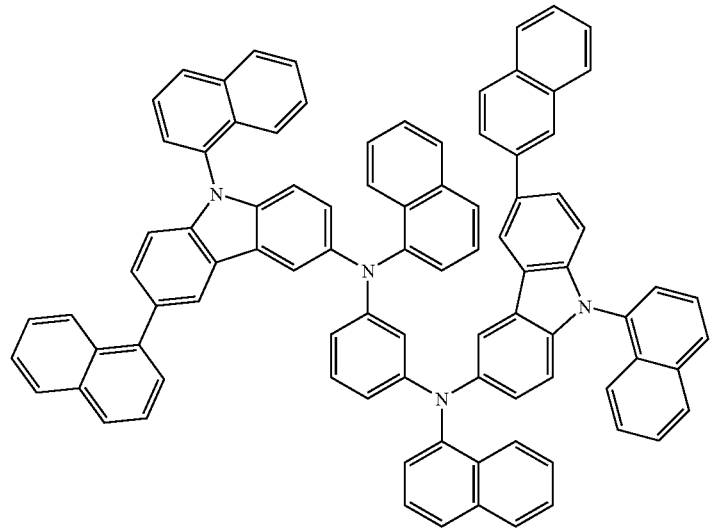

(81)
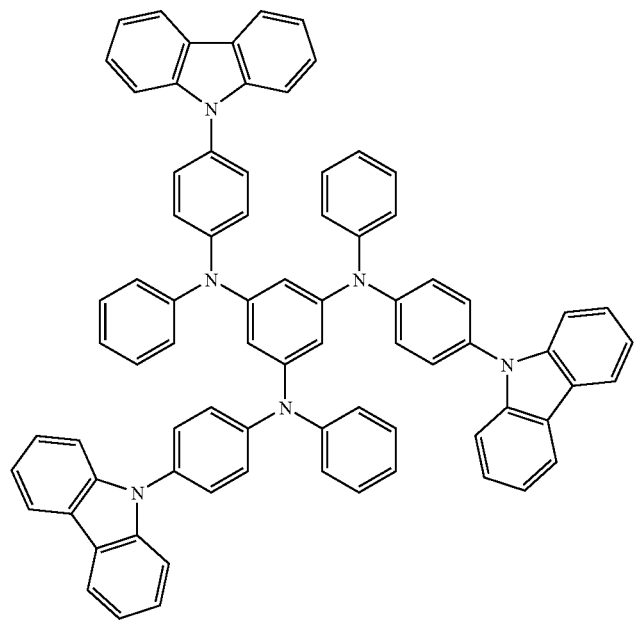
(82)
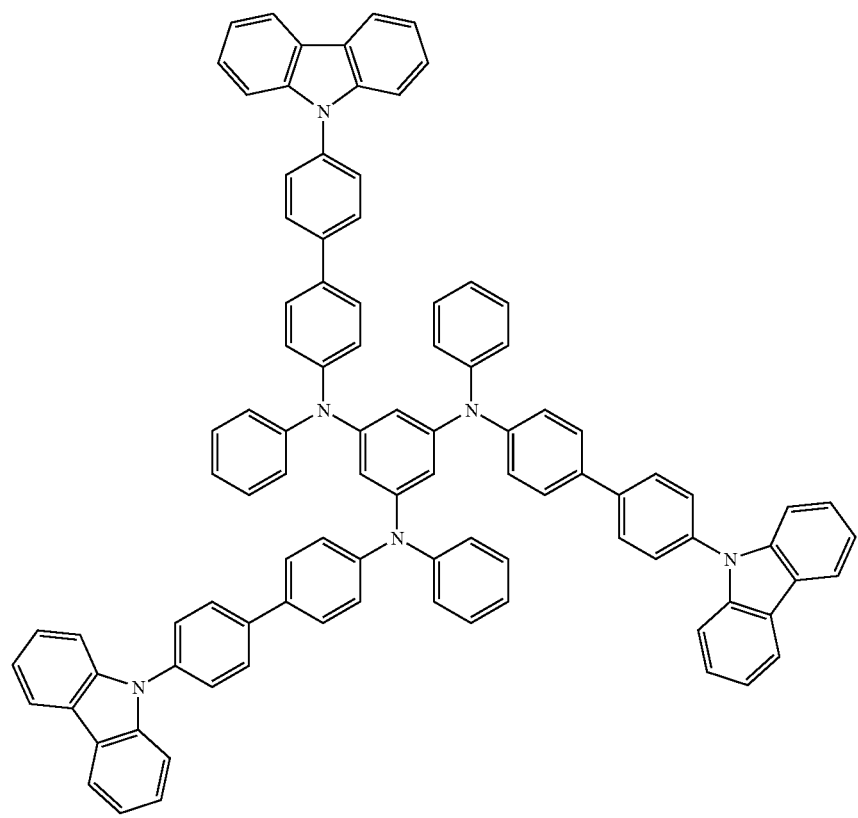

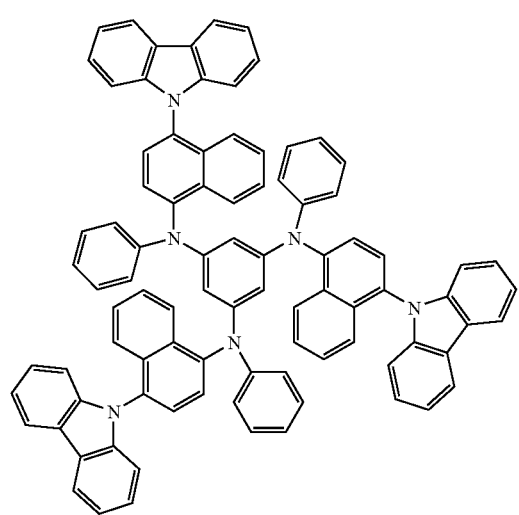
(83)
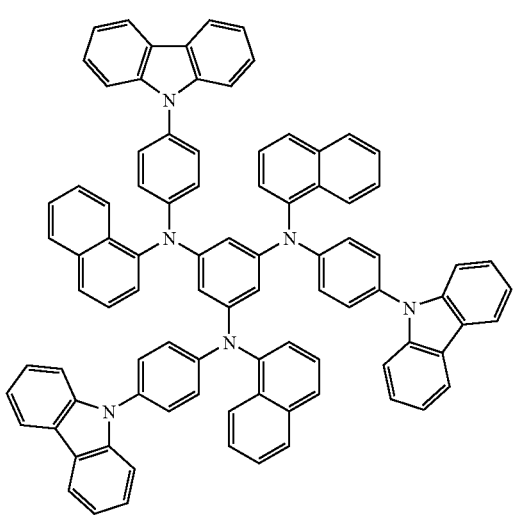
(84)
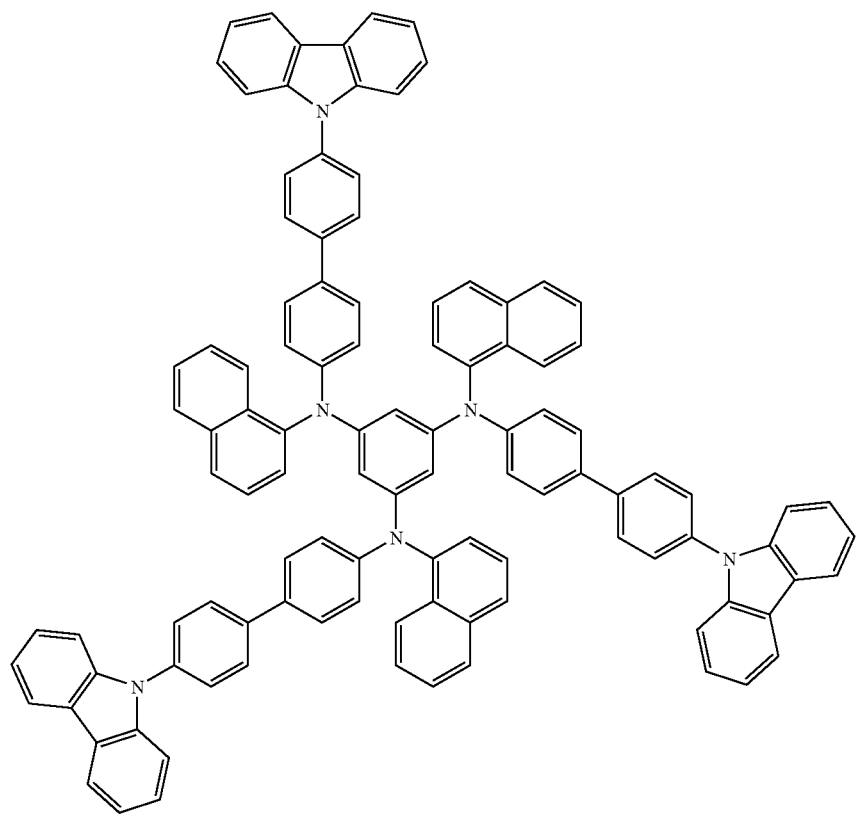
(85)

(86)
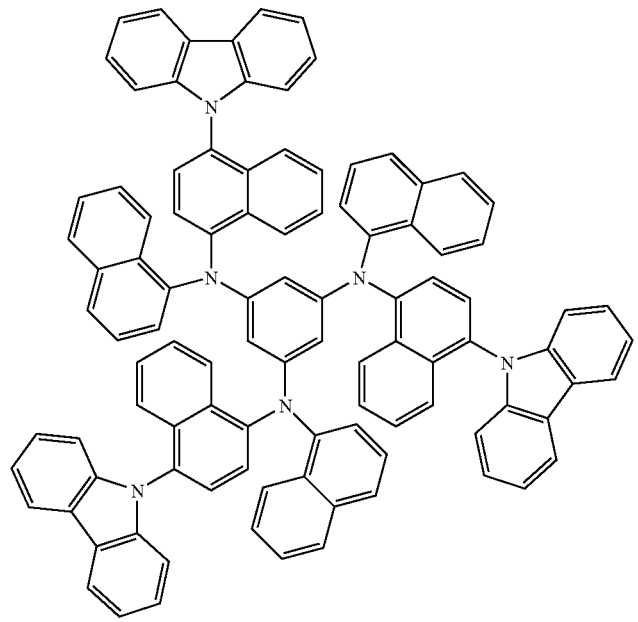
(87)
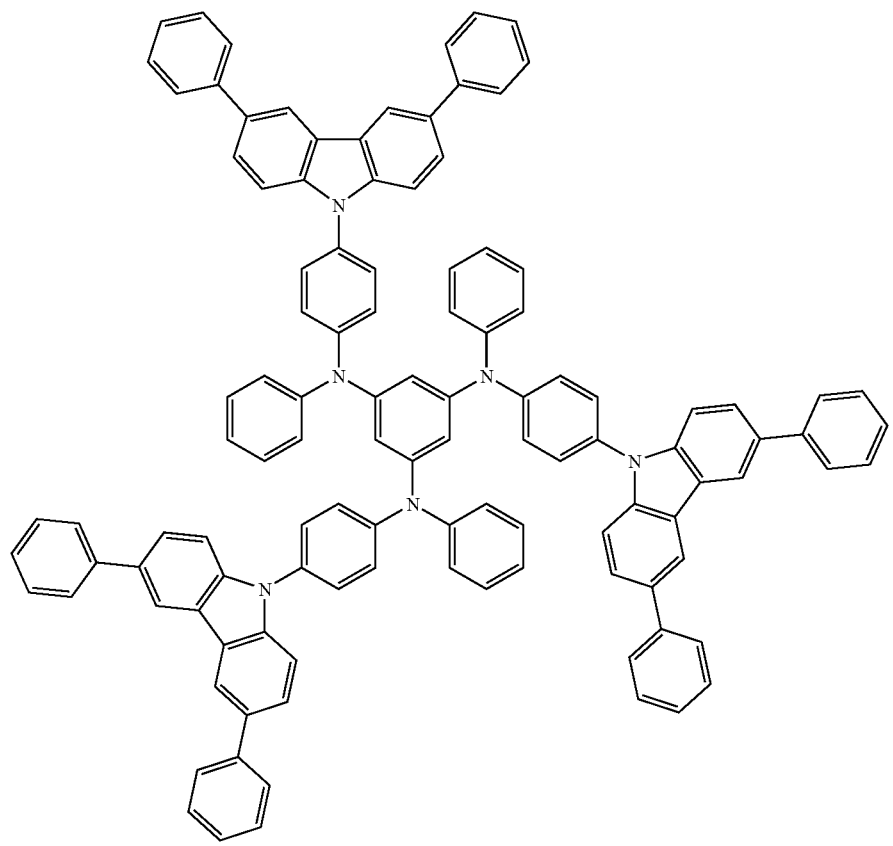

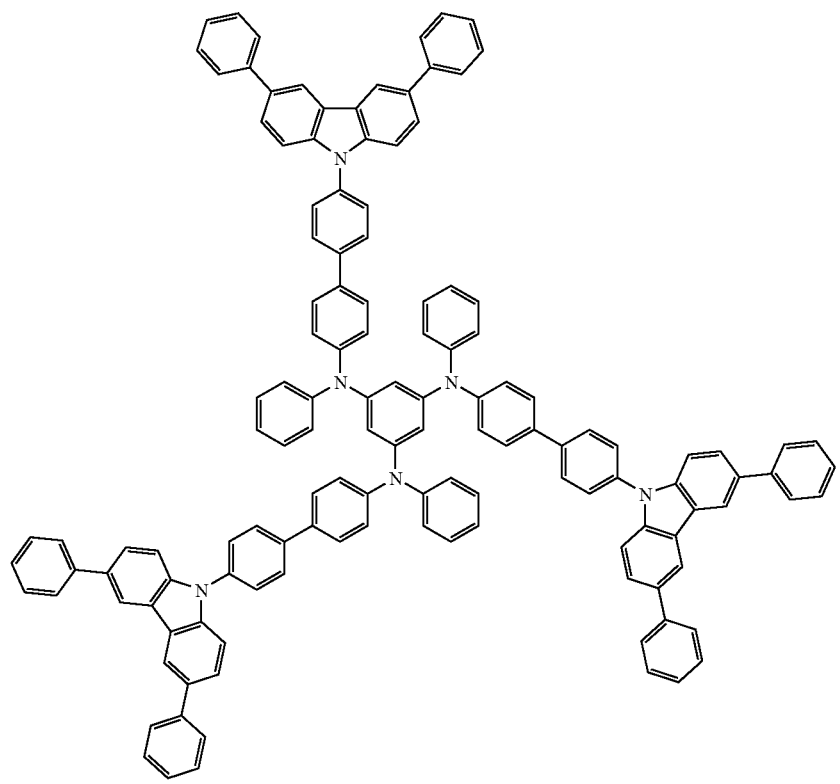
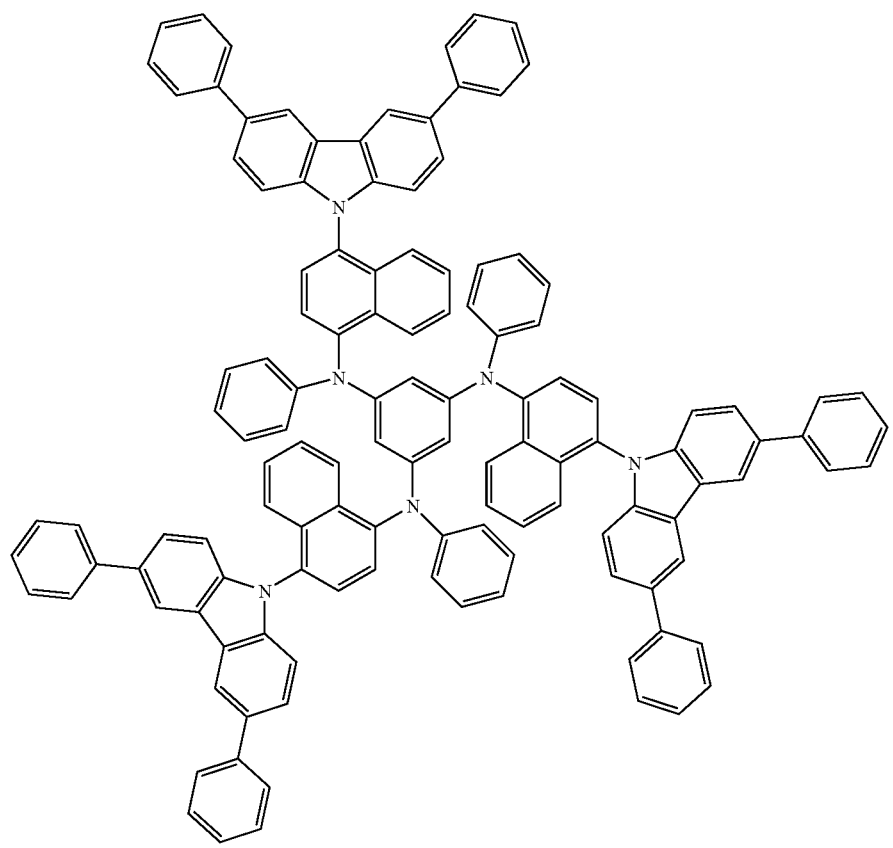
(89)

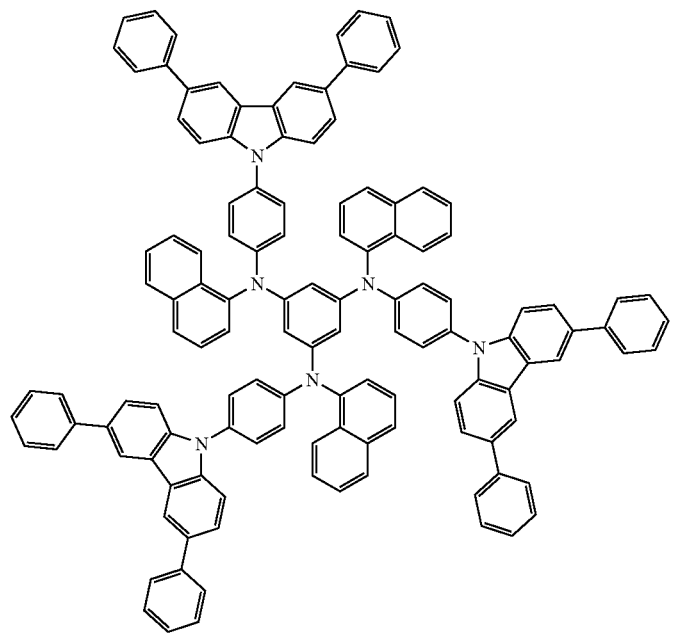
(90)
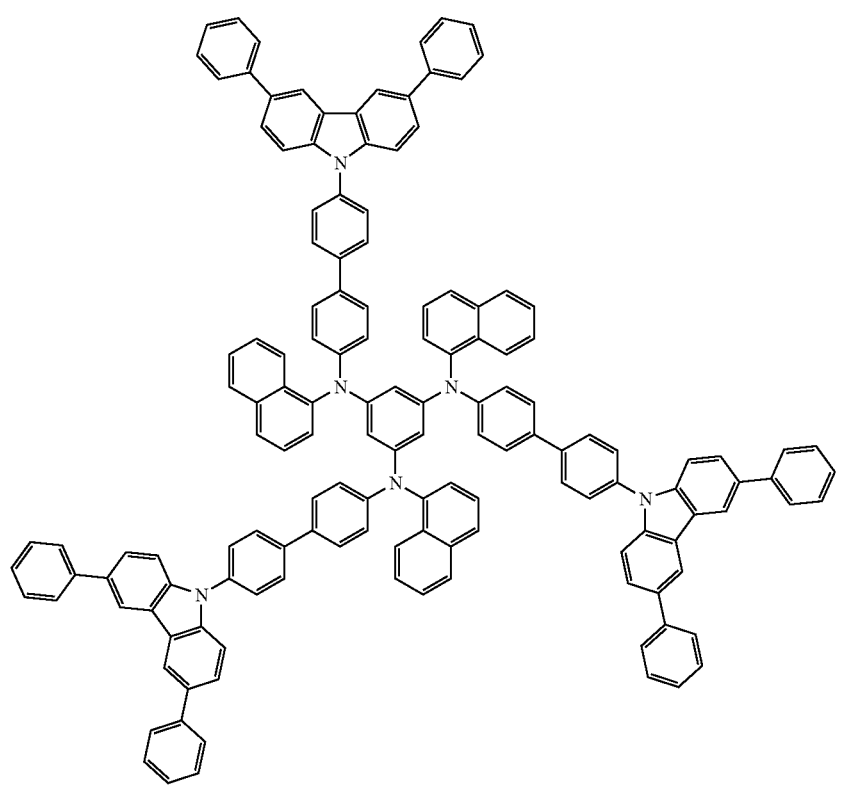
(91)

(92)
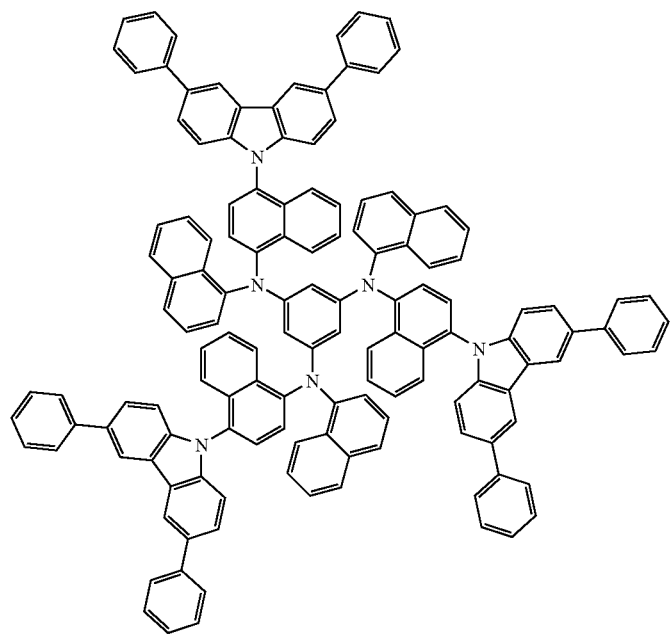
(93)
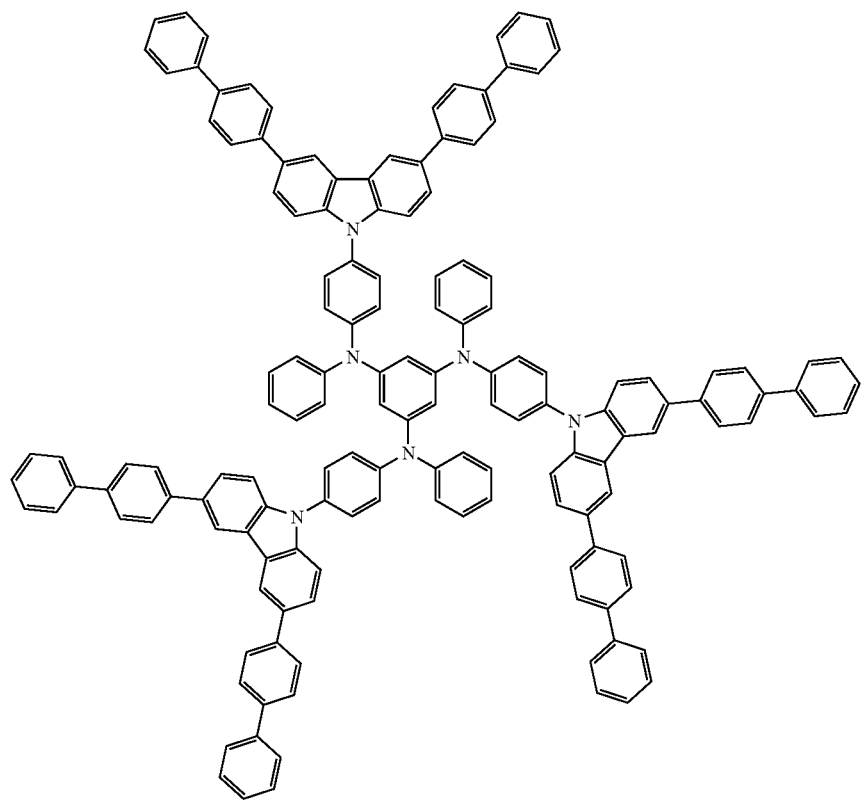

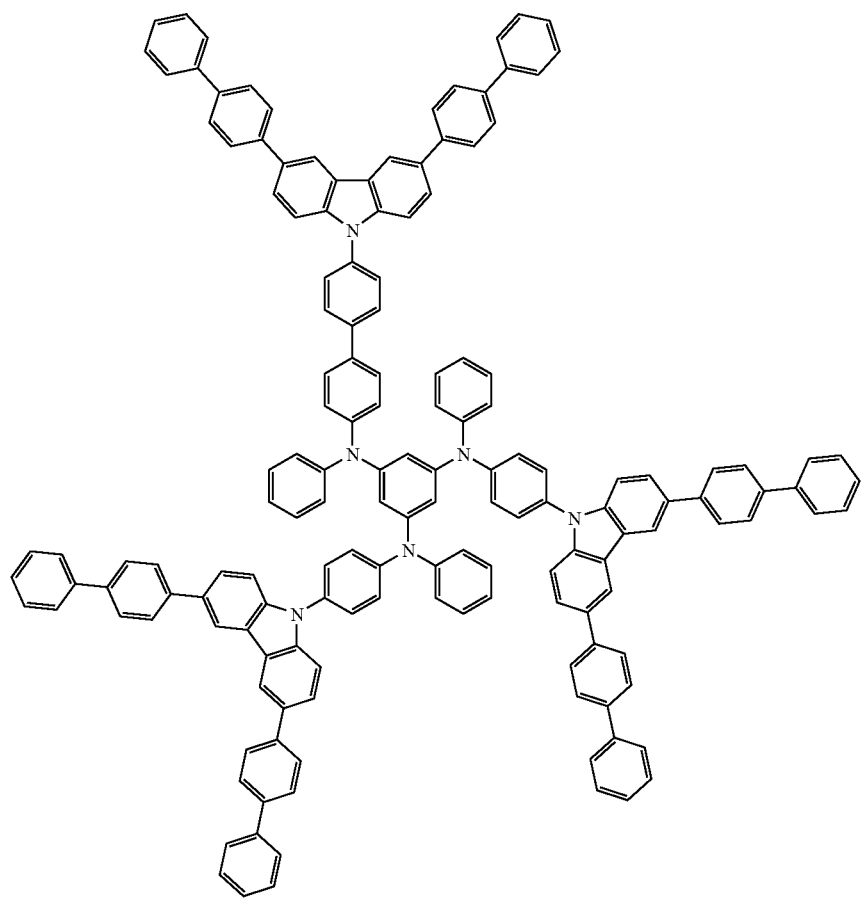
(94)
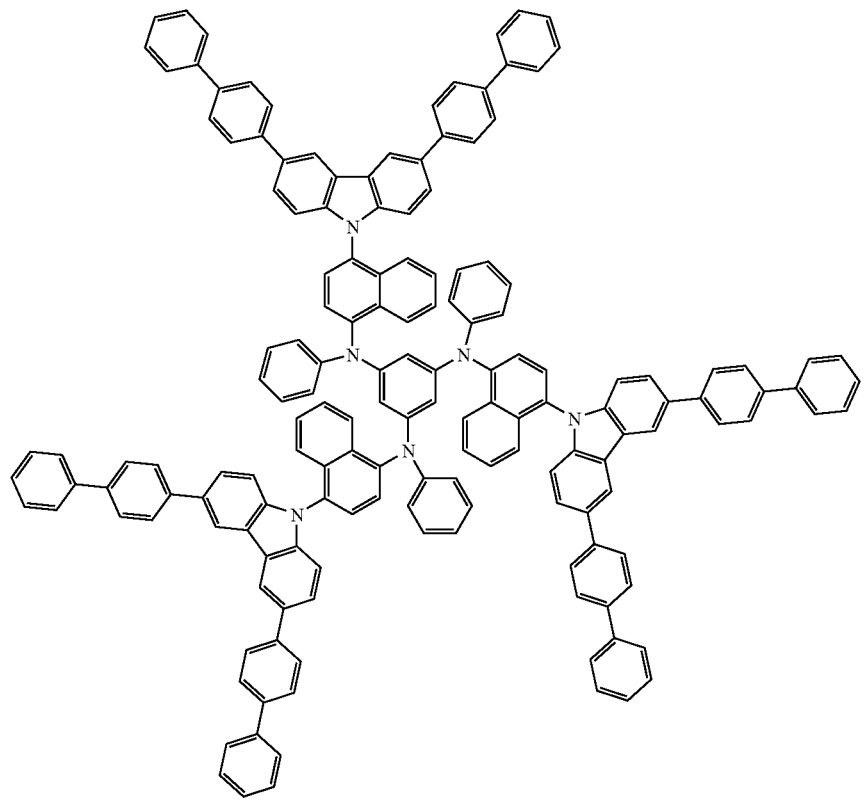
(95)

(96)
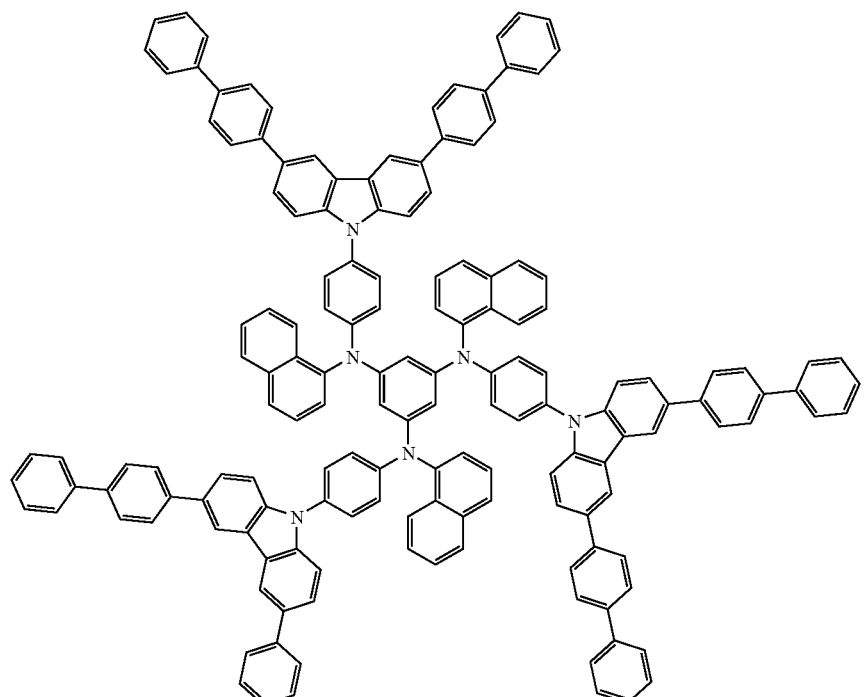
(97)
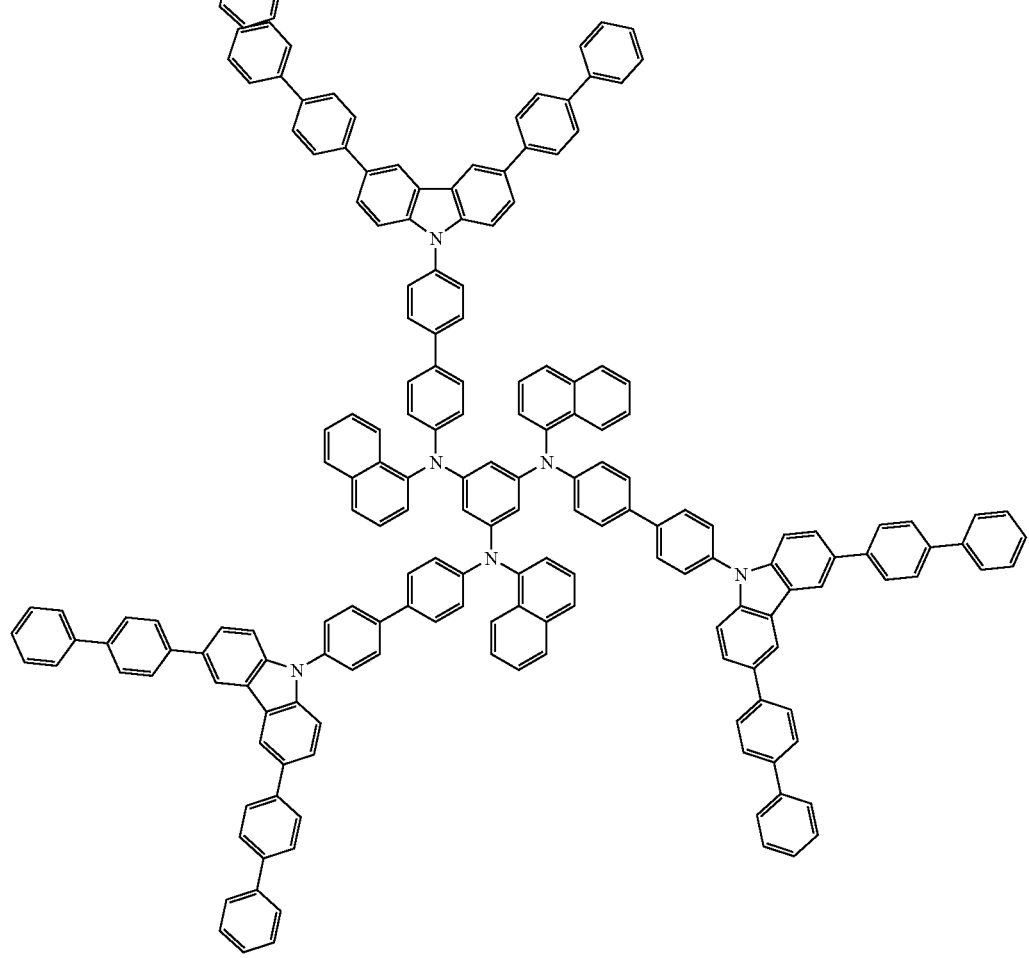

(98)
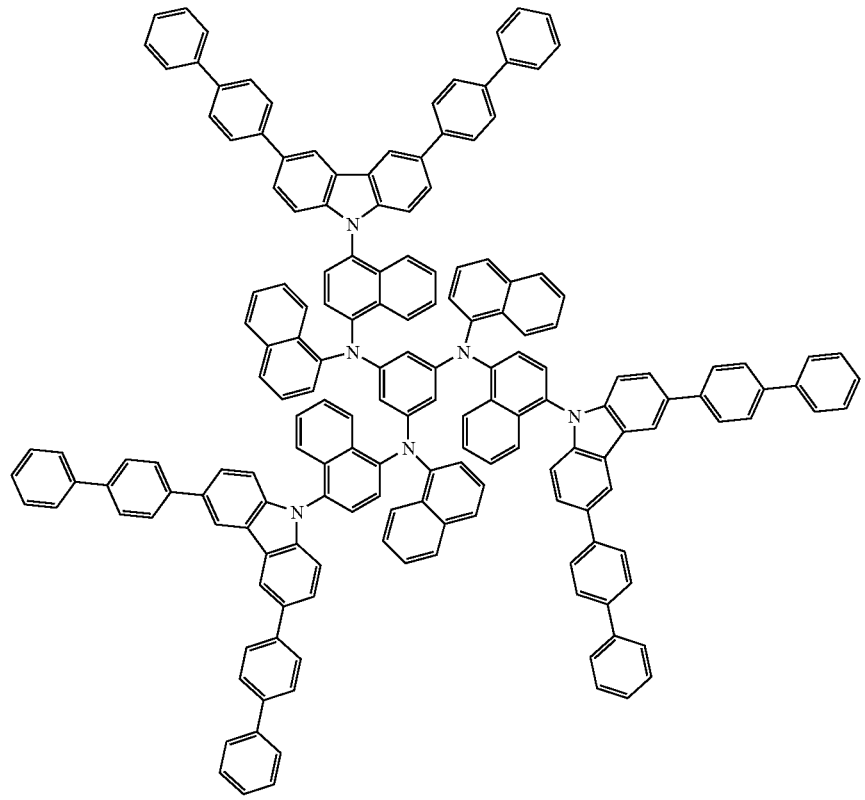
(99)
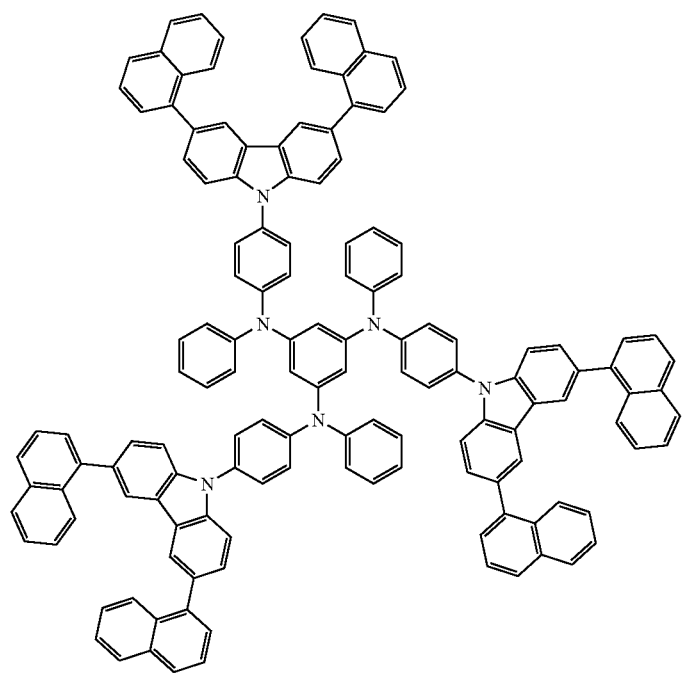

(100)
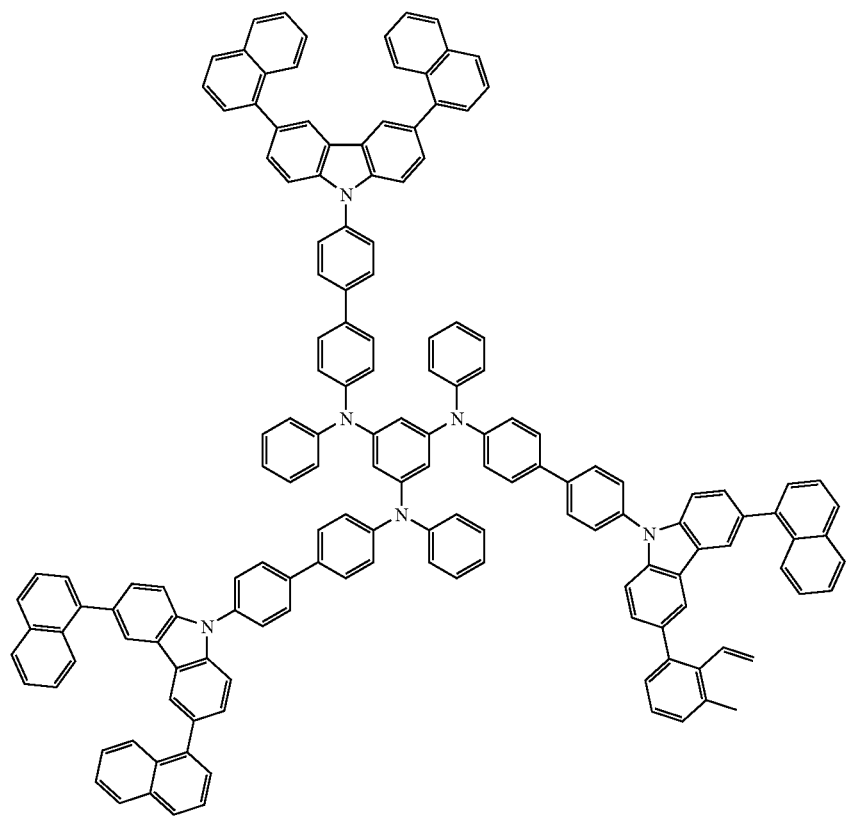
(101)
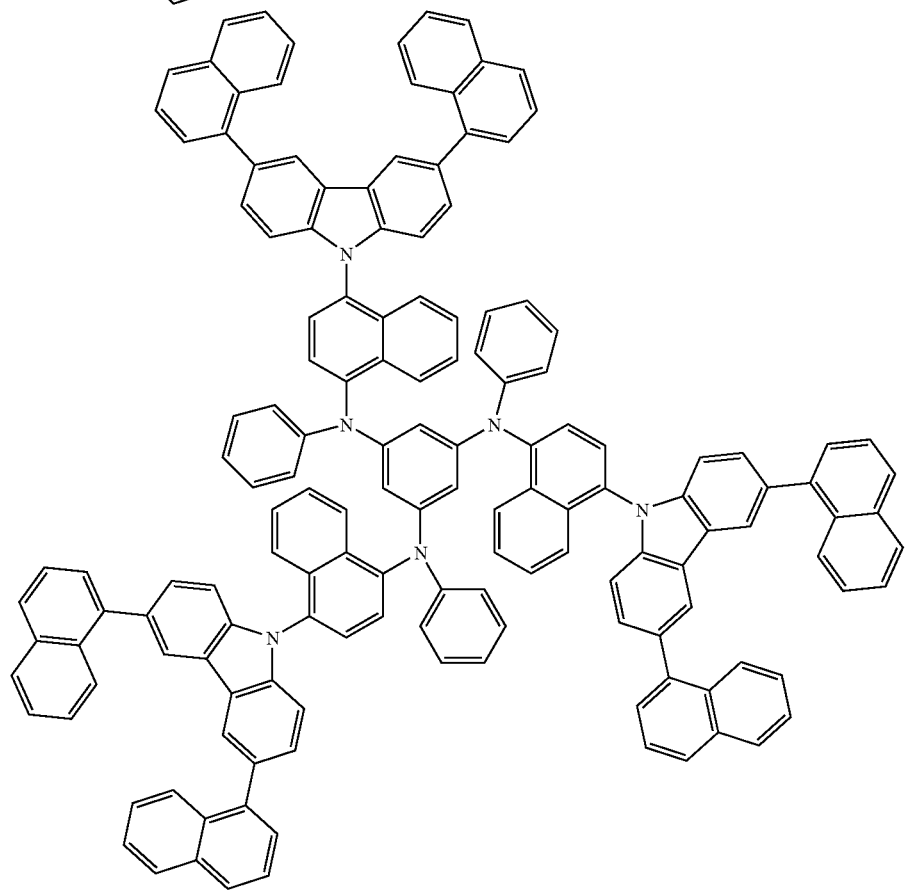

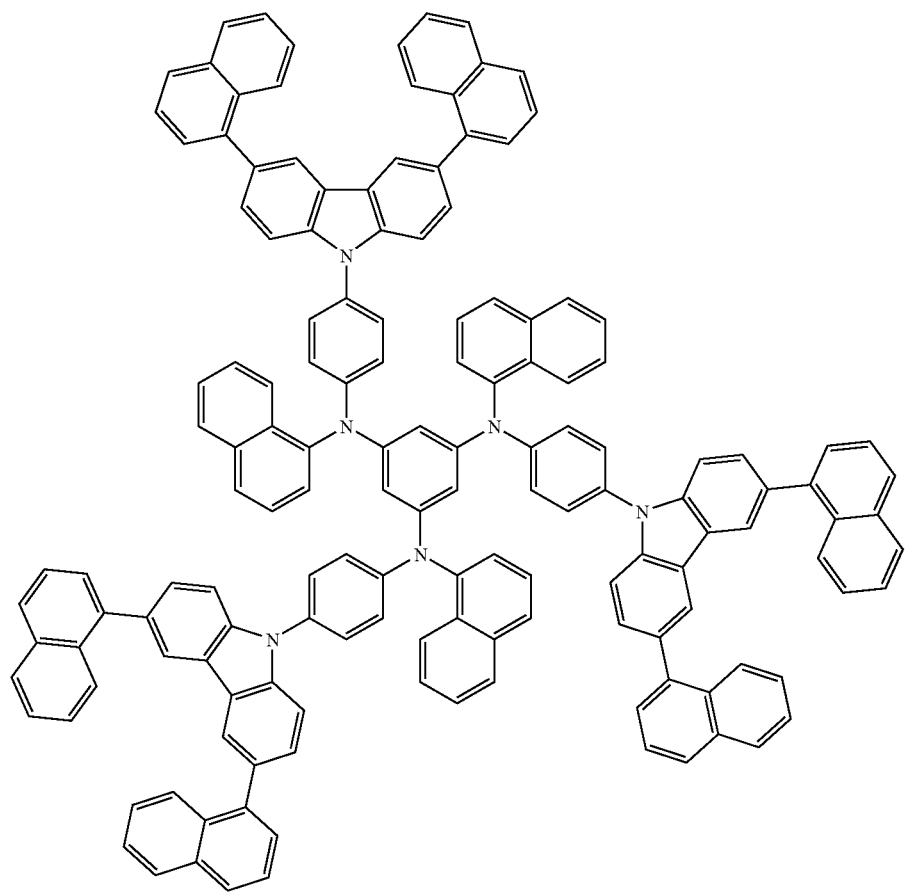
(102)

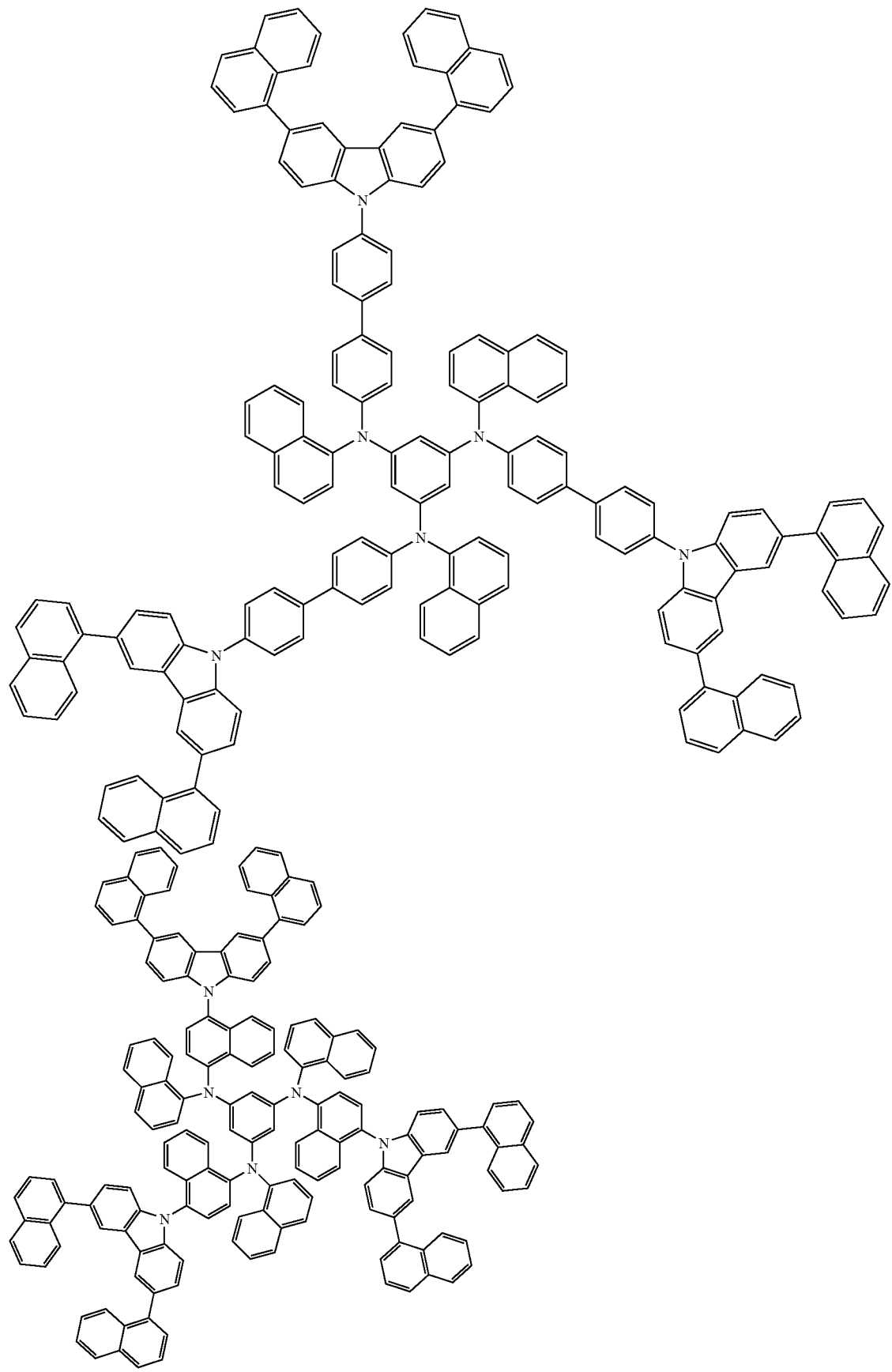

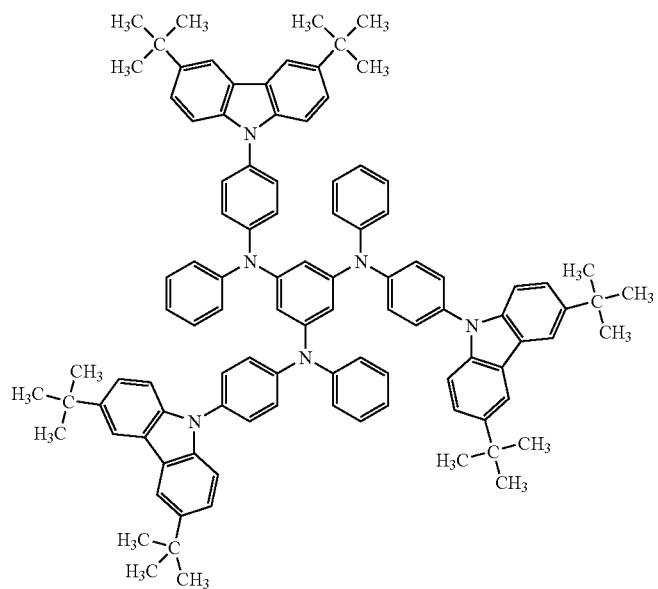
(105)
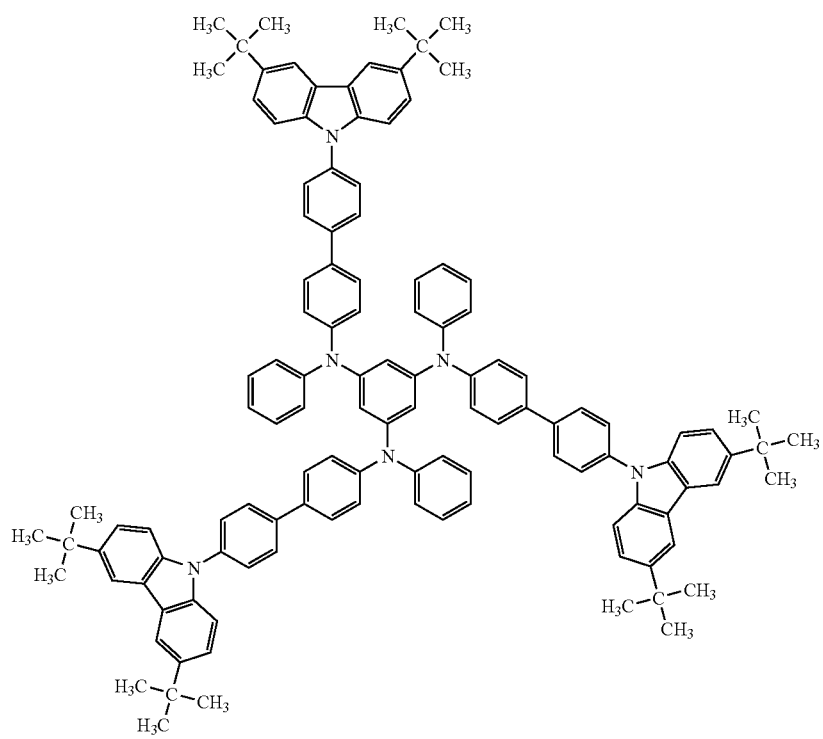
(106)

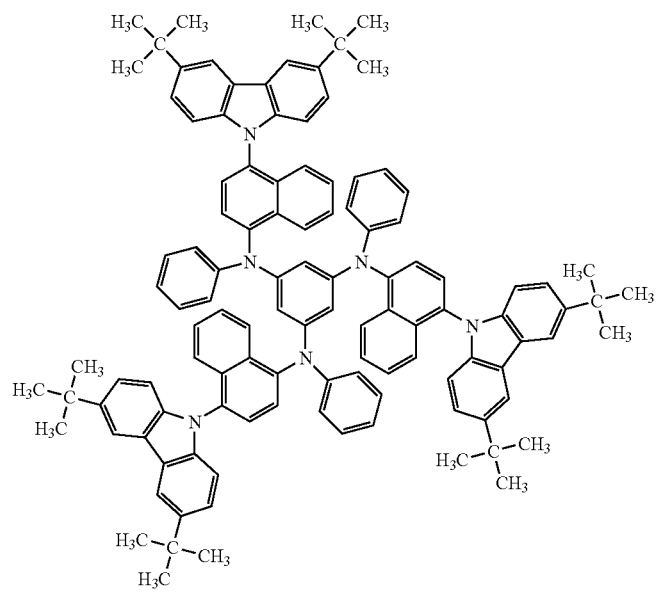
(107)
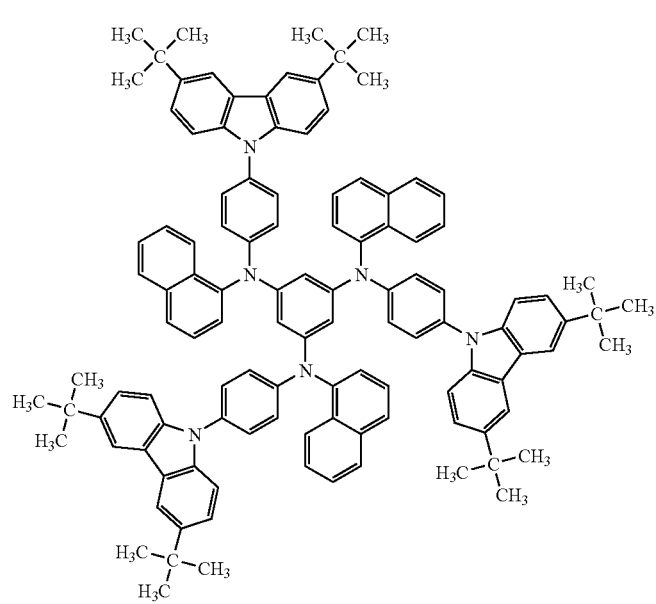
(108)

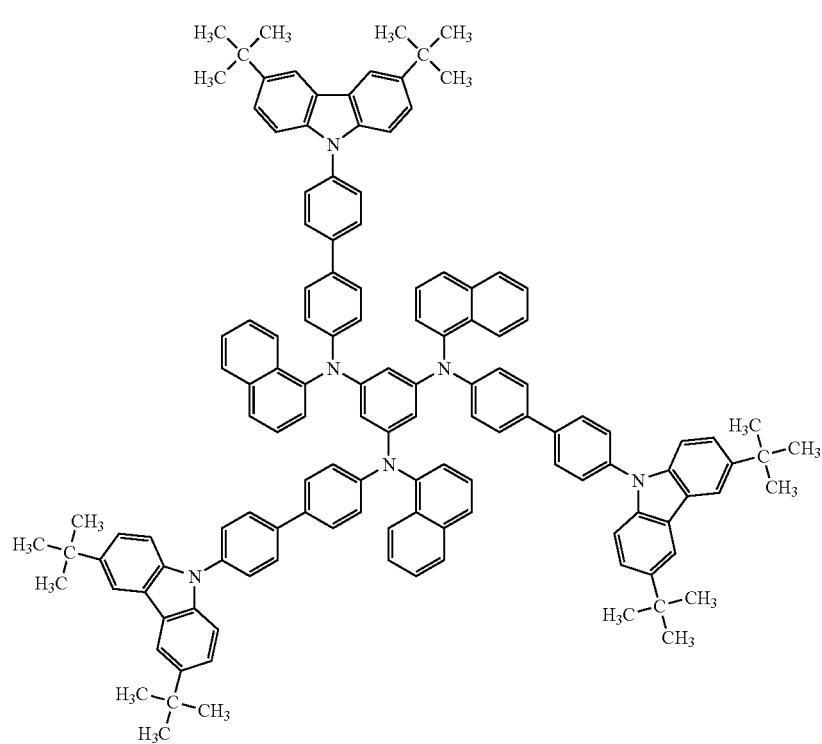
(109)
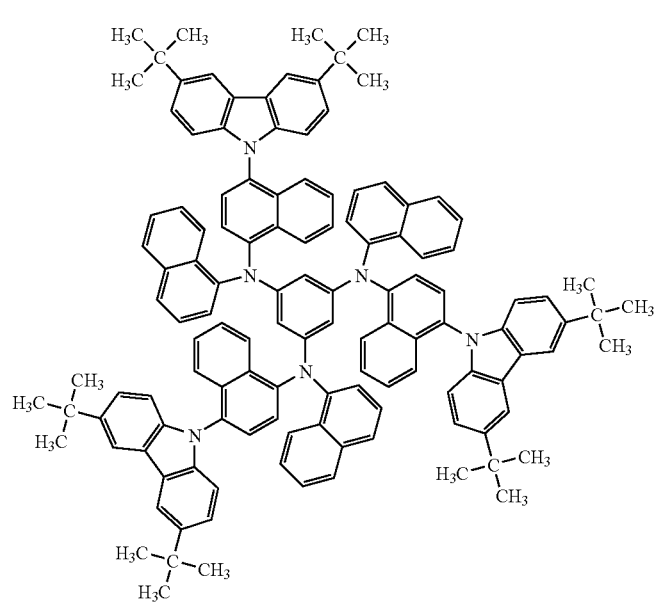
(110)

(111)
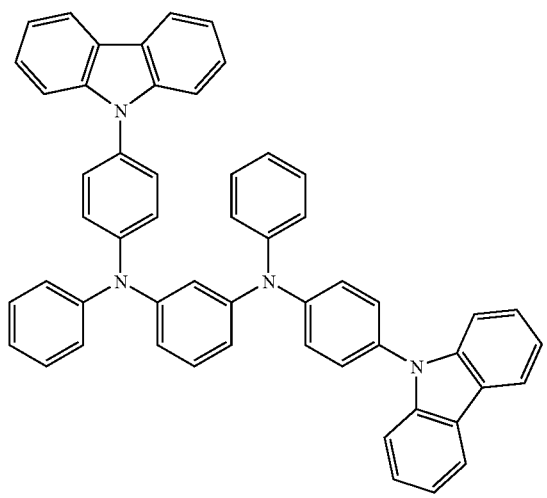
(112)
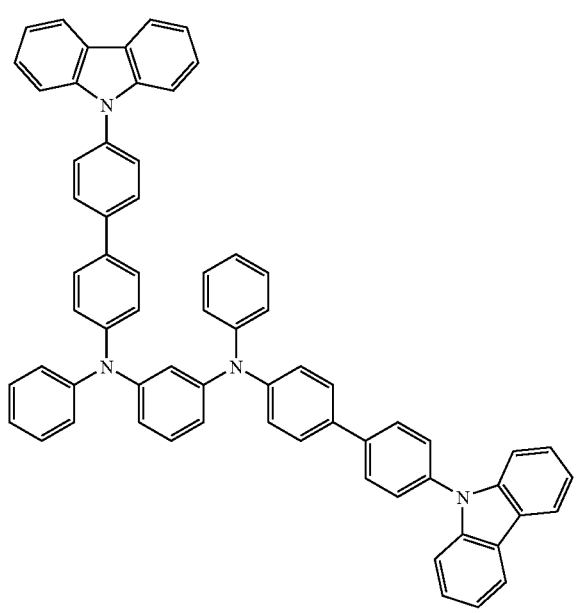
(113)
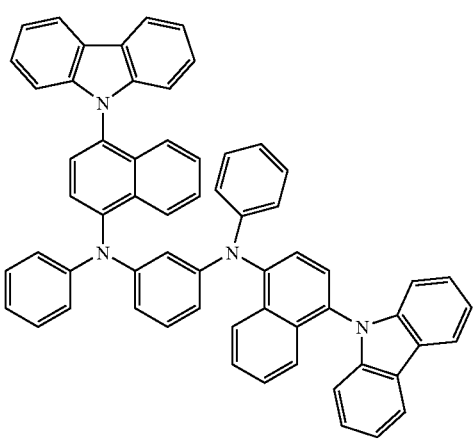
(114)
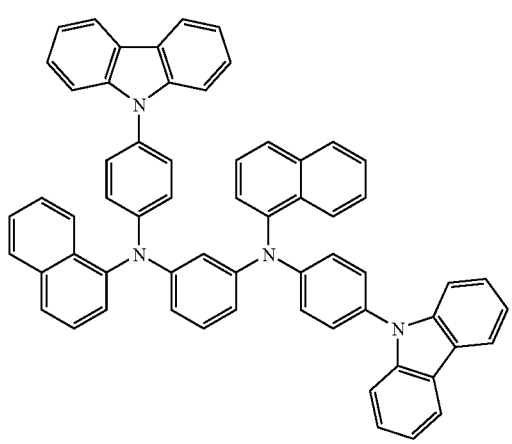

(115)
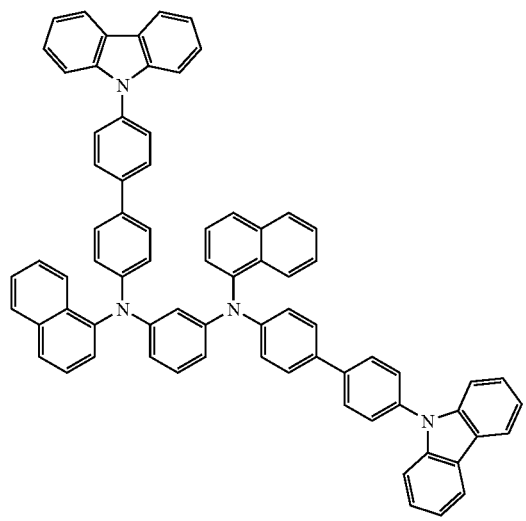
(116)
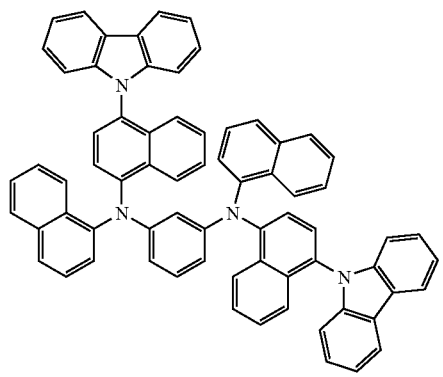
(117)
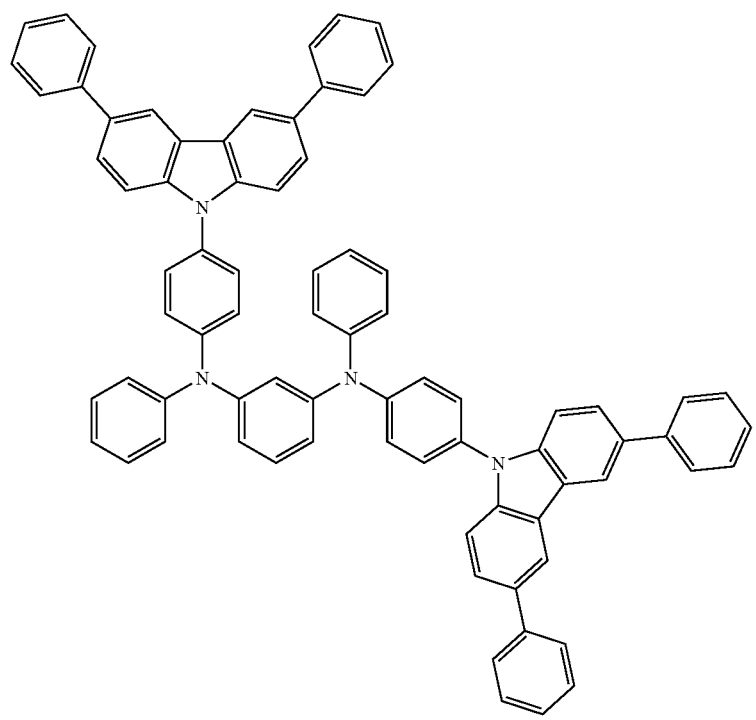

(118)
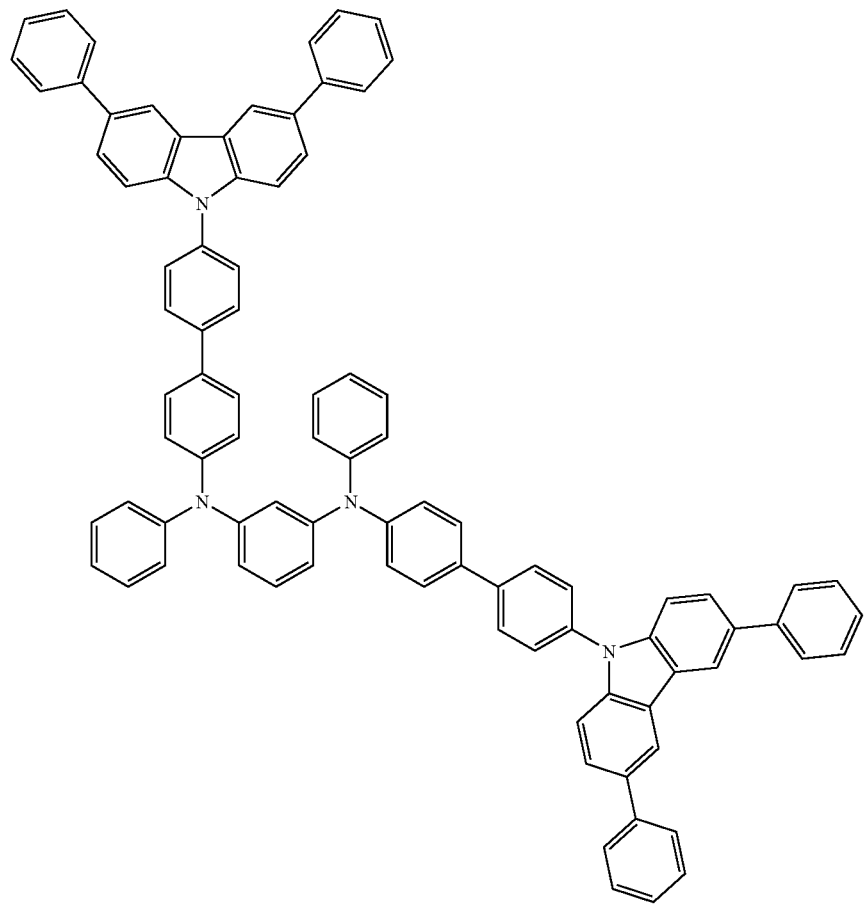
(119)
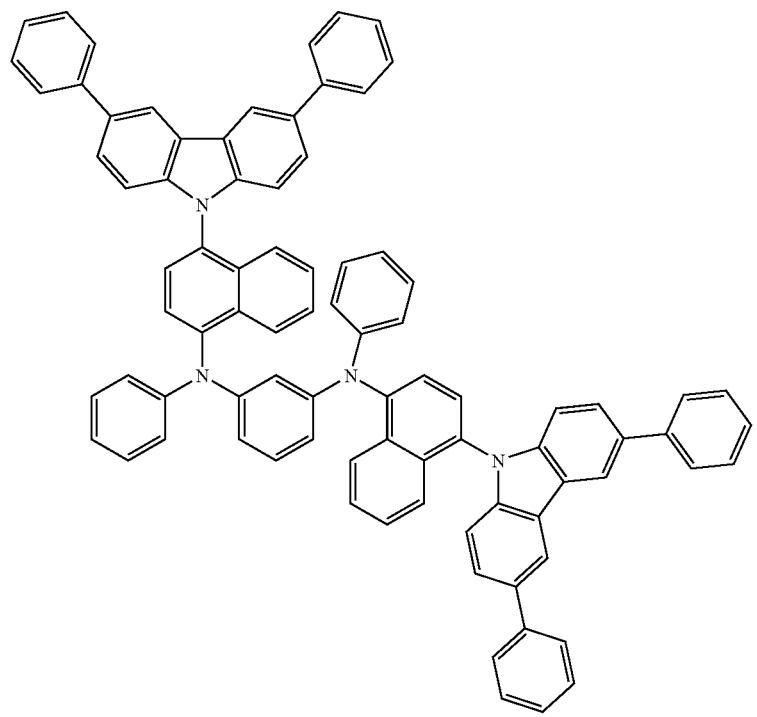

(120)
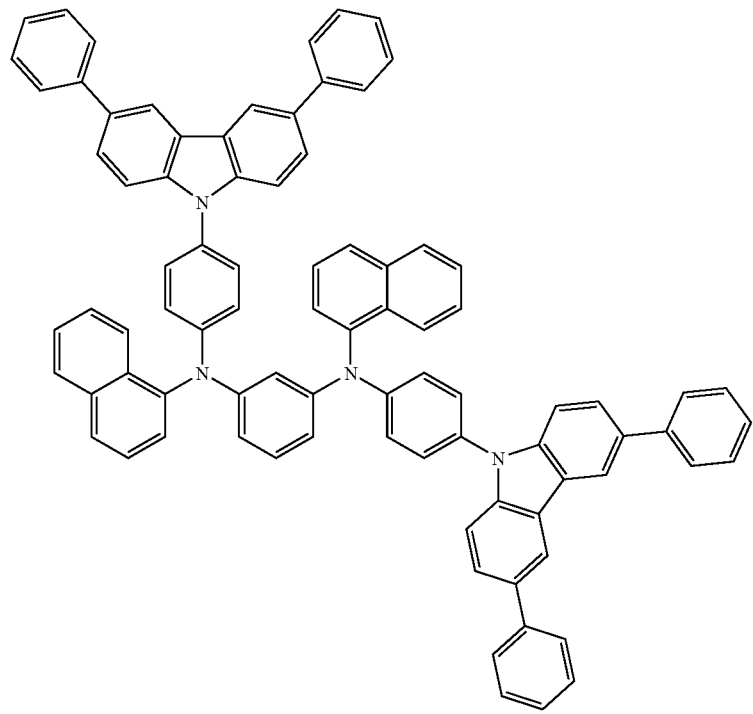
(121)
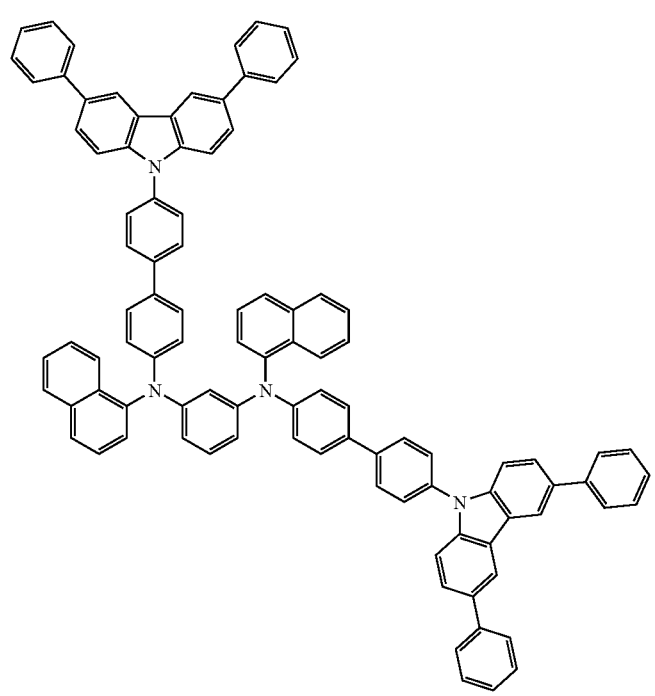

(122)
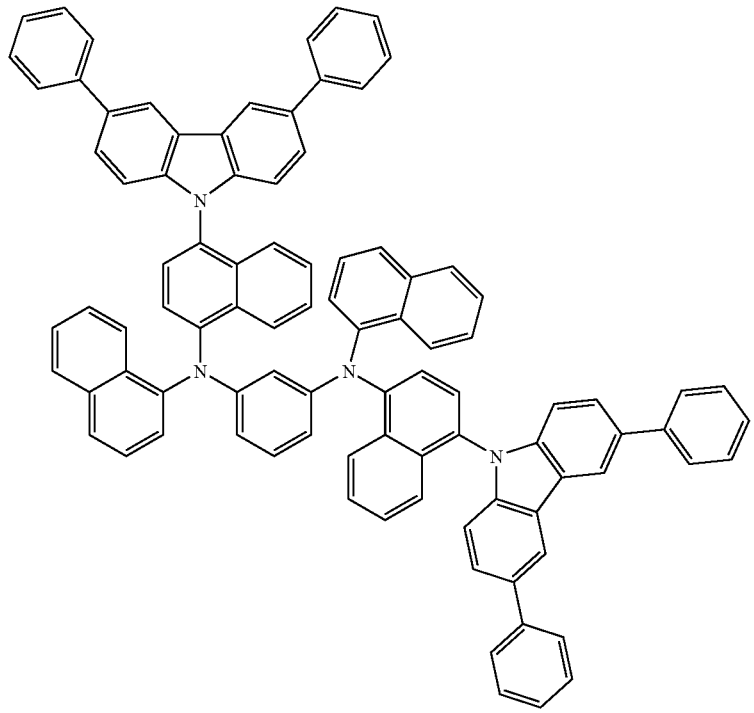
(123)
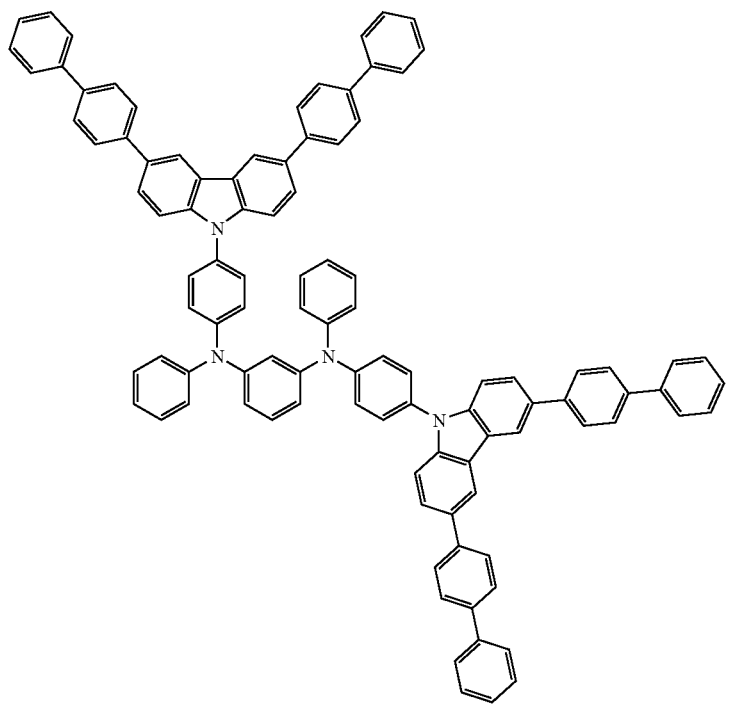

(124)
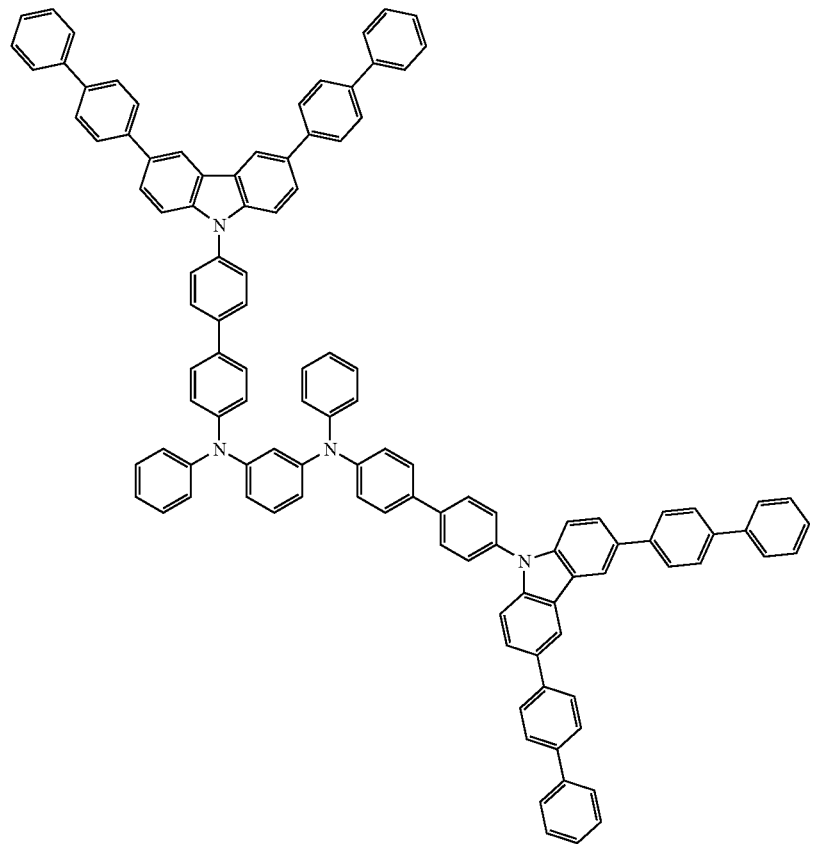
(125)
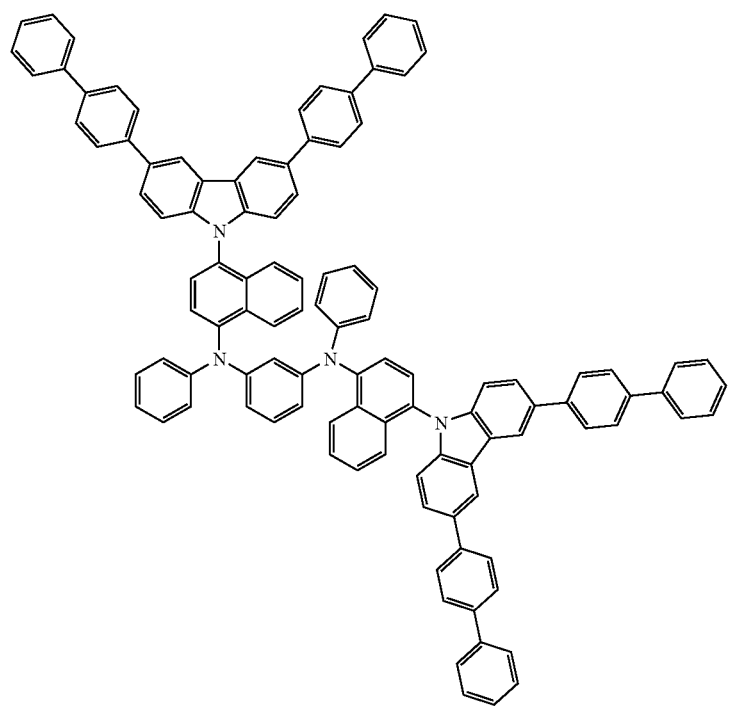

(126)
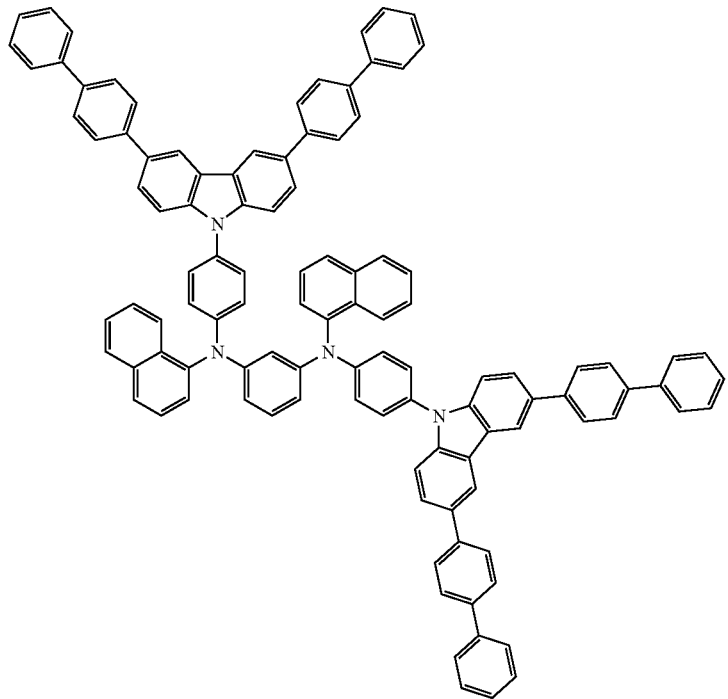
(127)
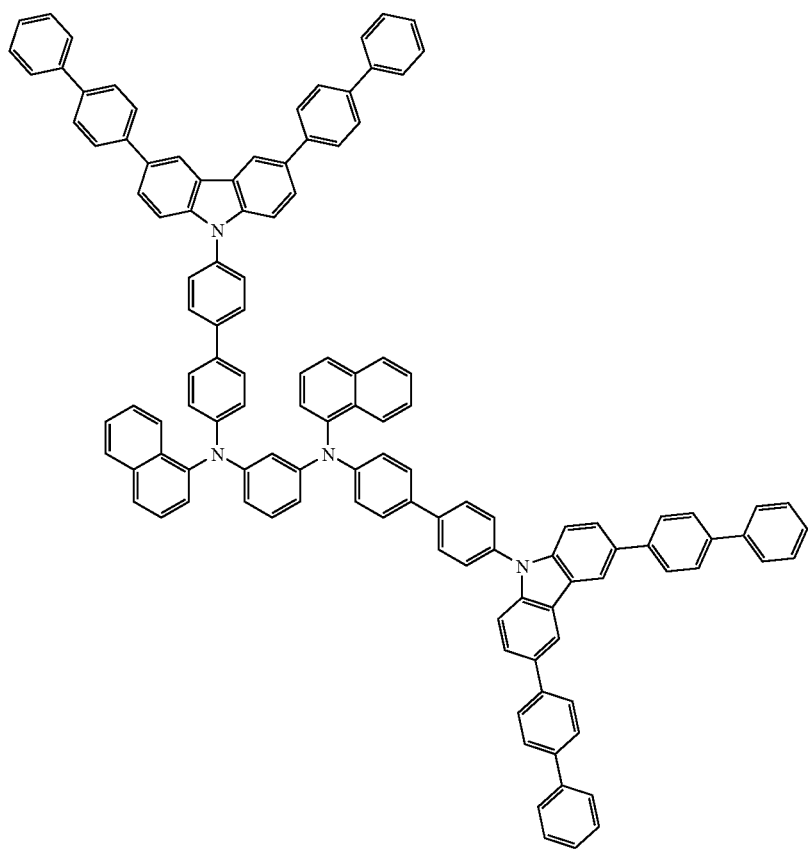

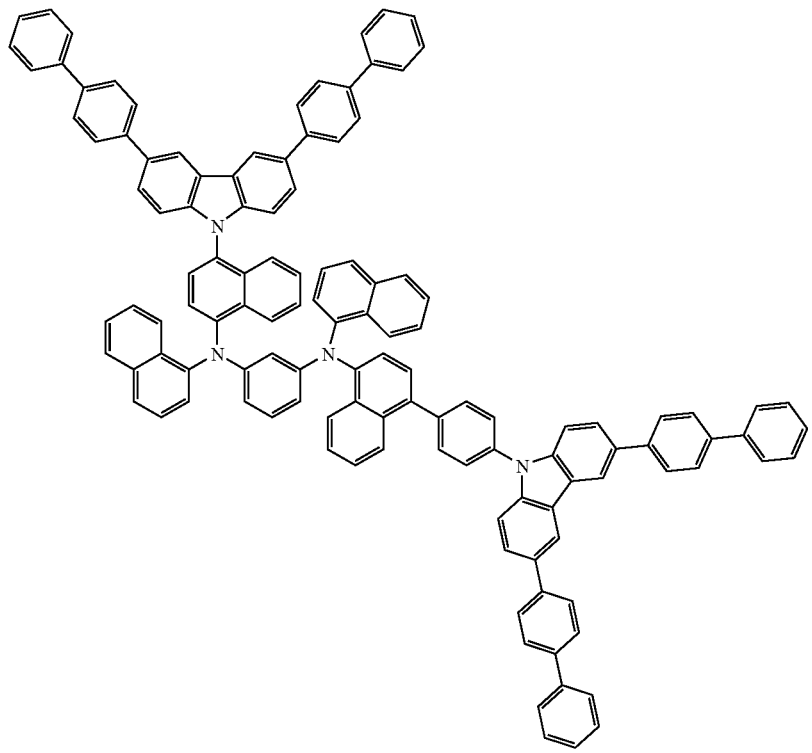
(128)
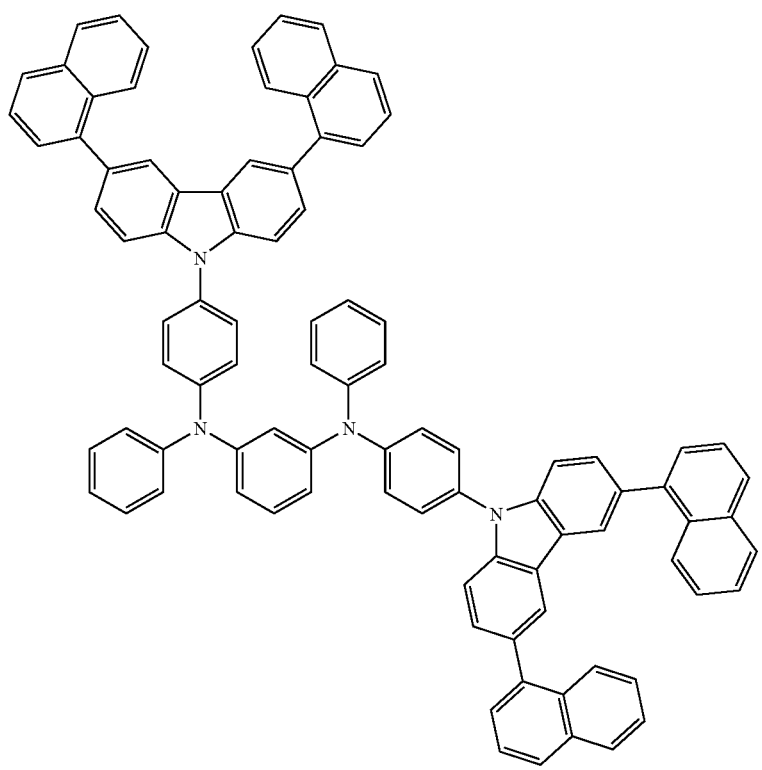
(129)

(130)
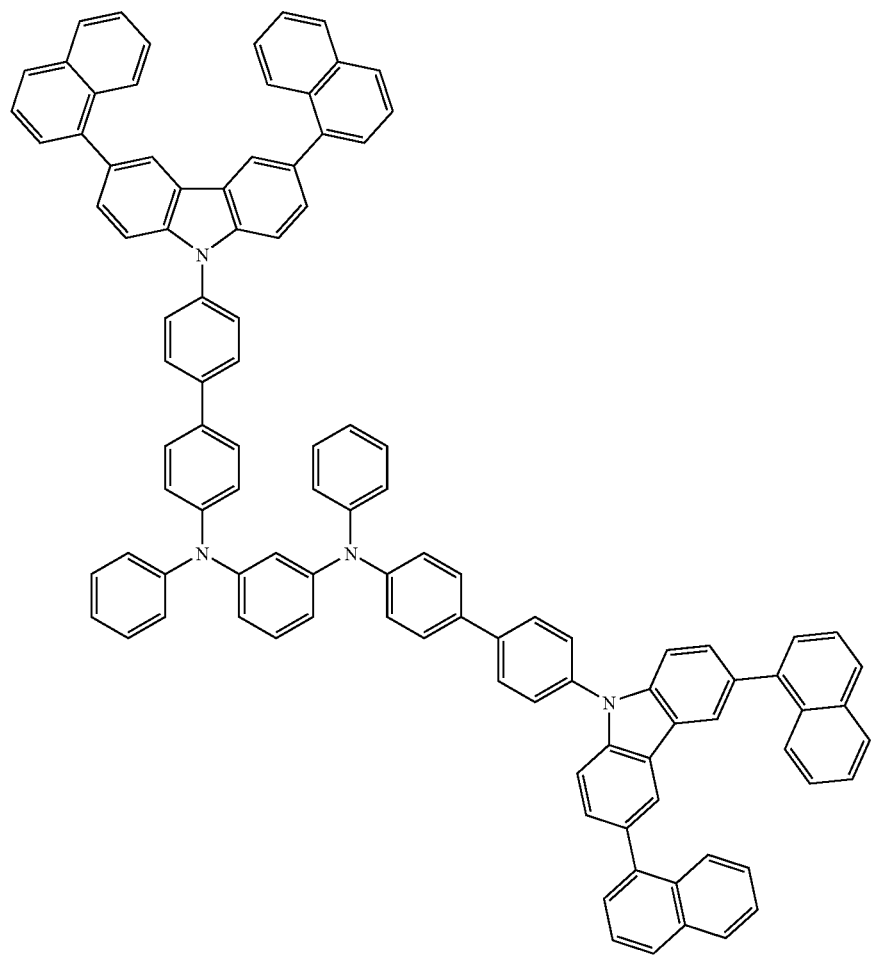
(131)
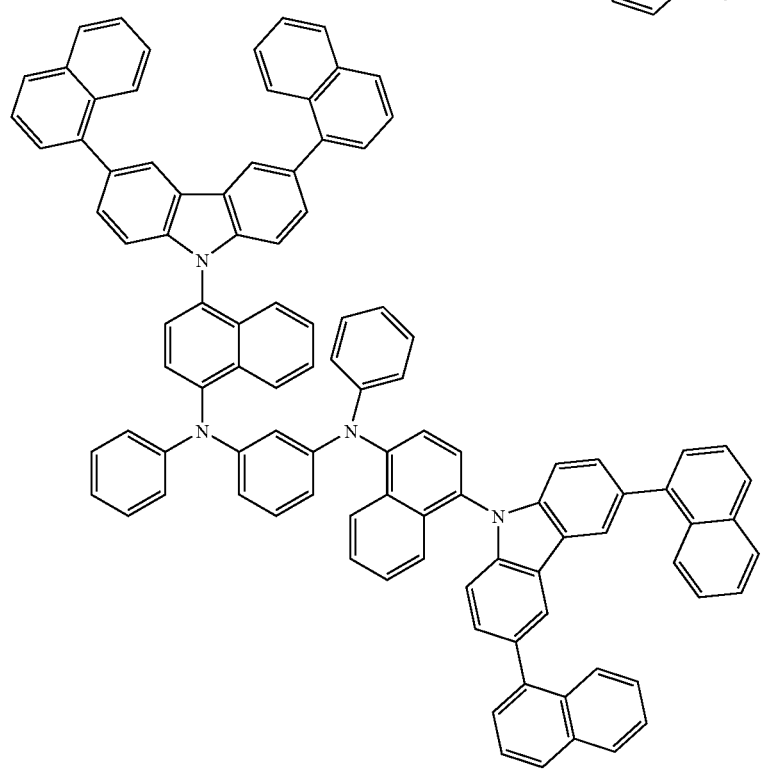

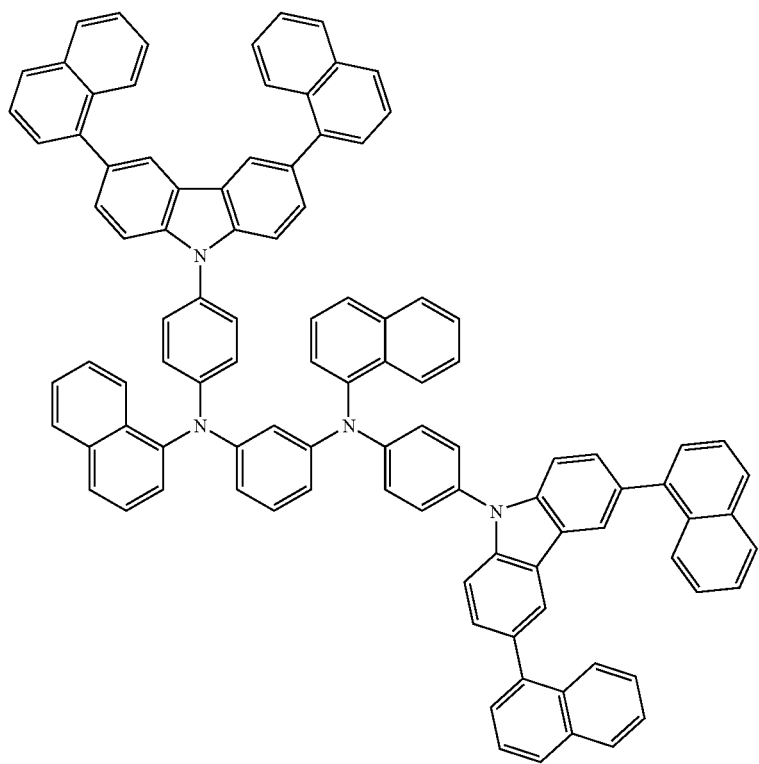
(132)
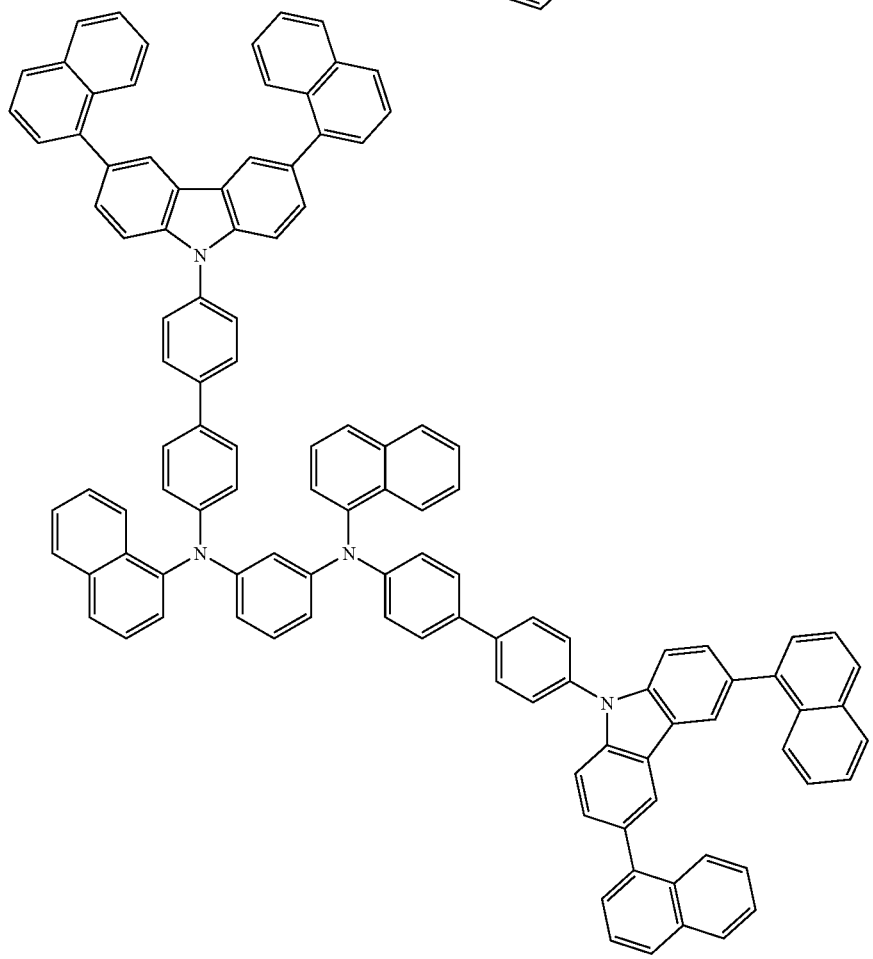
(133)

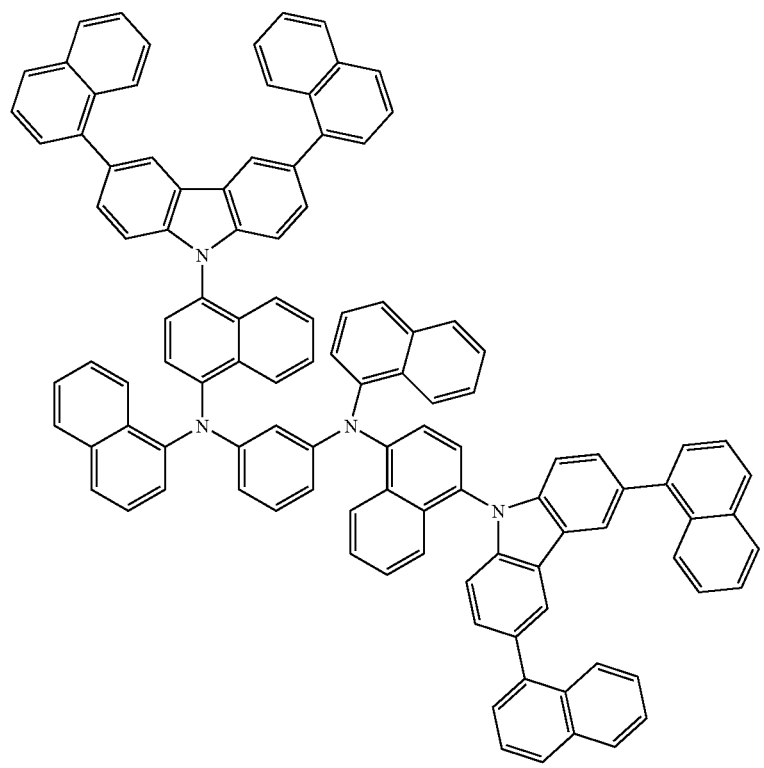
(134)
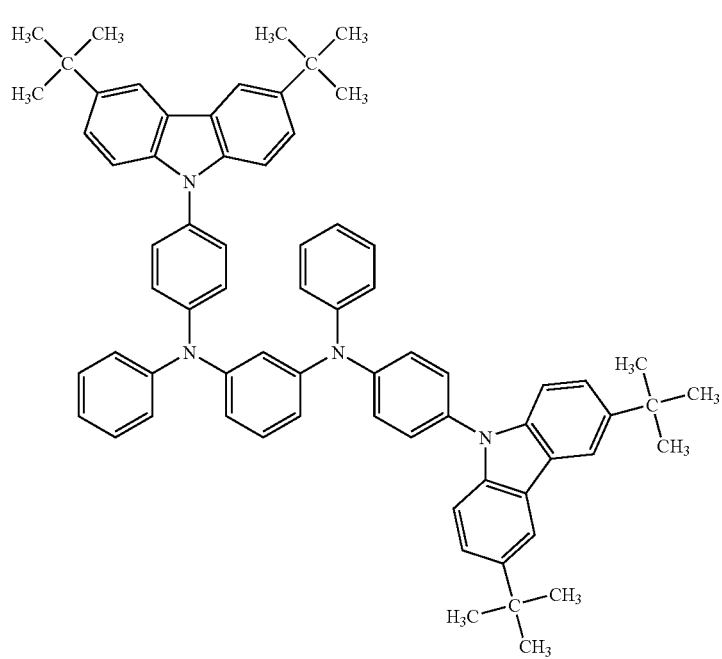
(135)

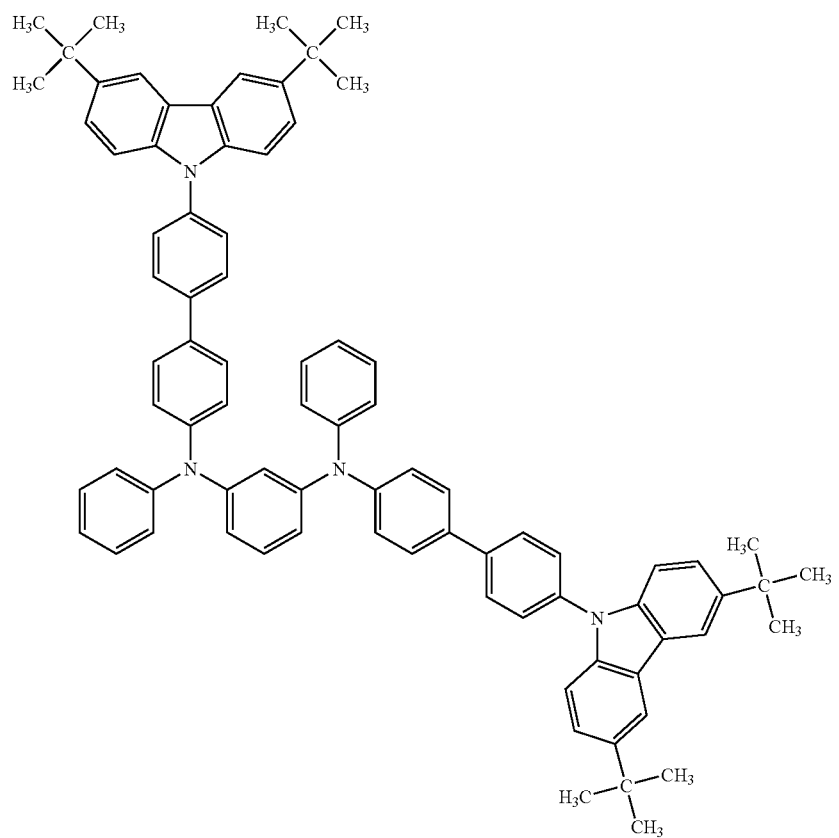
(136)
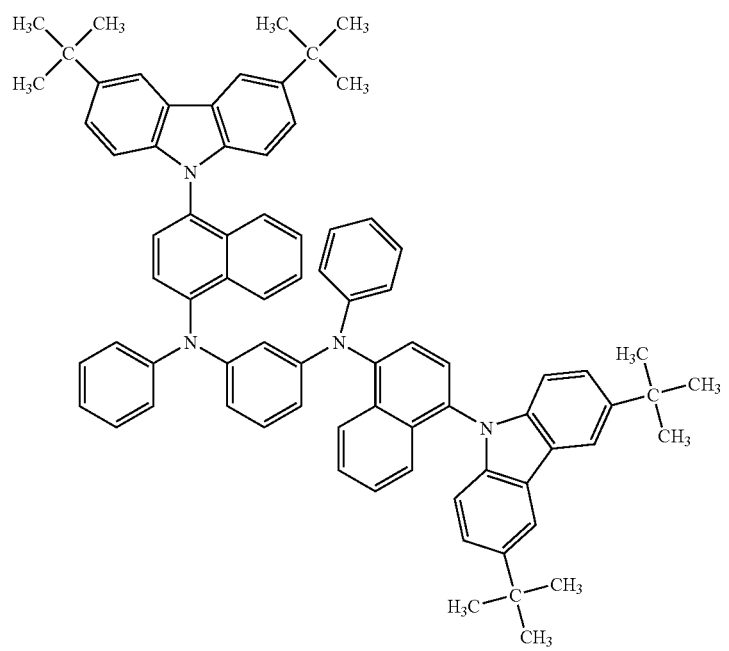
(137)

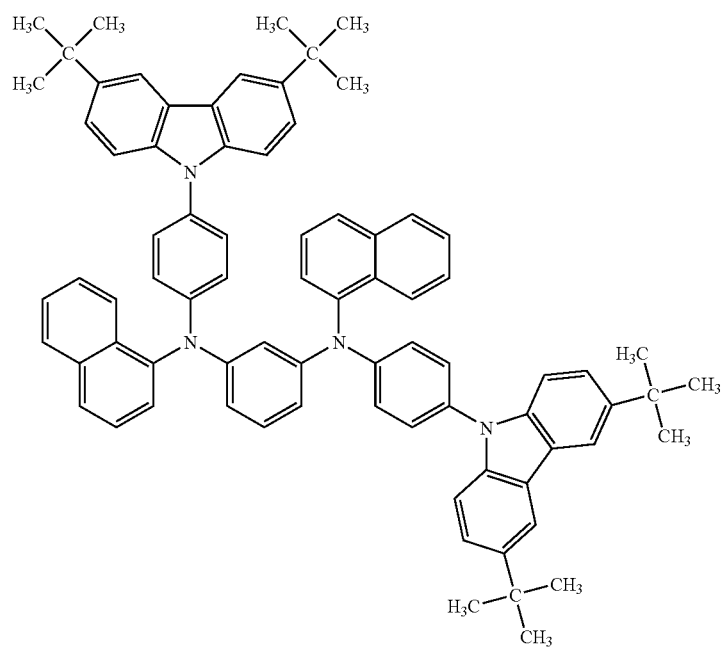
(138)
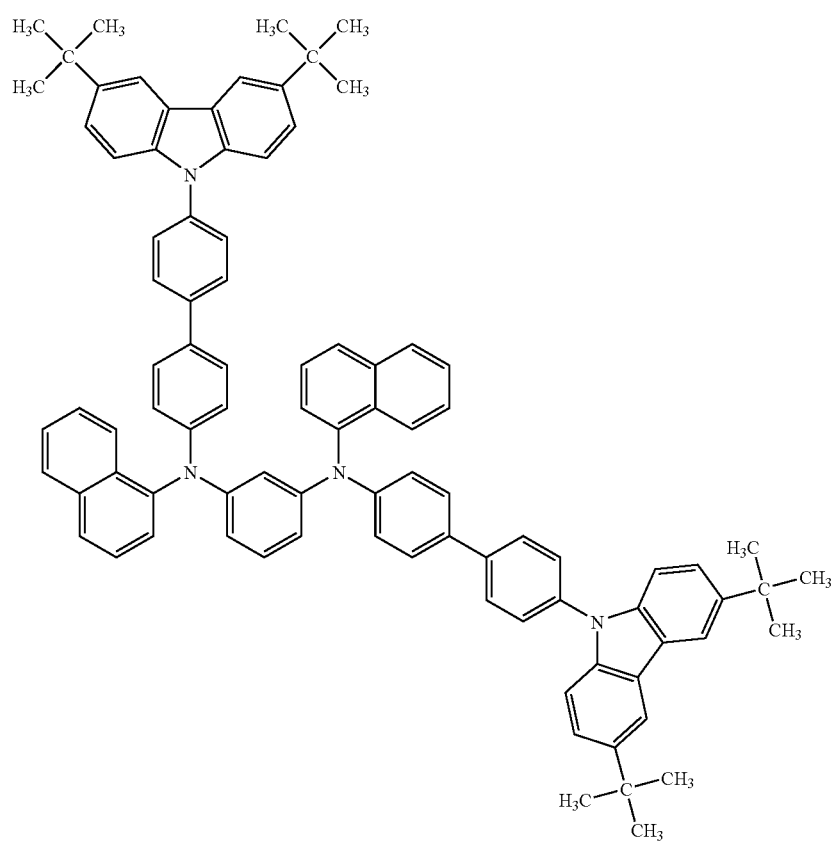
(139)

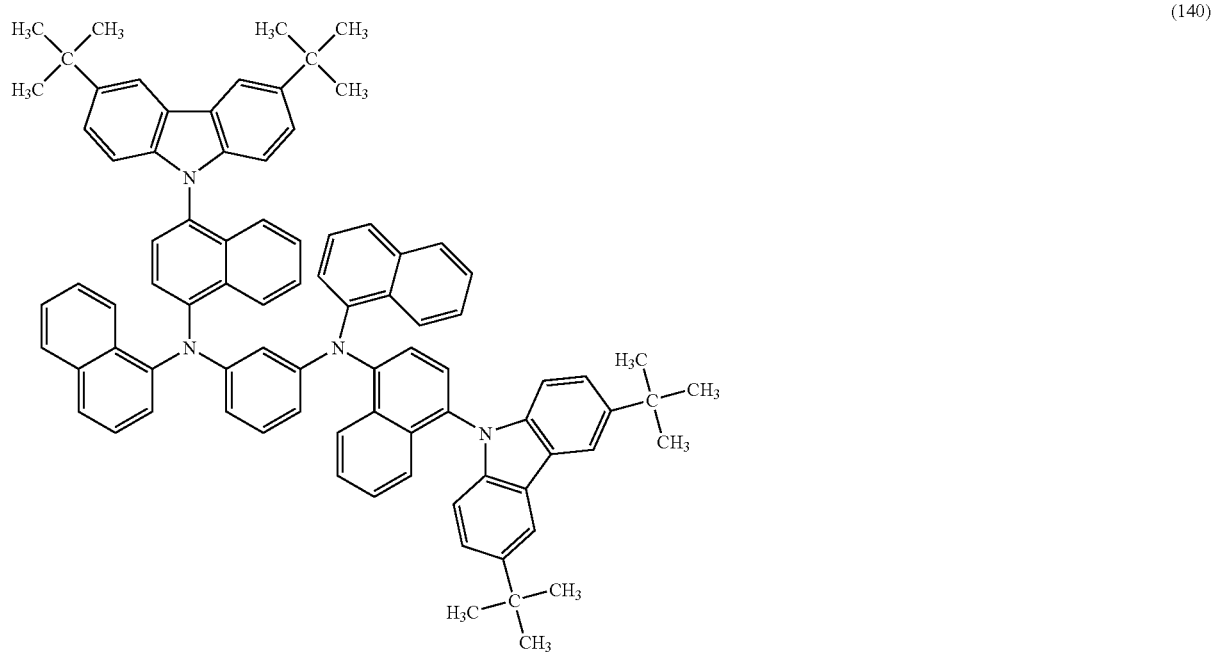

(140)

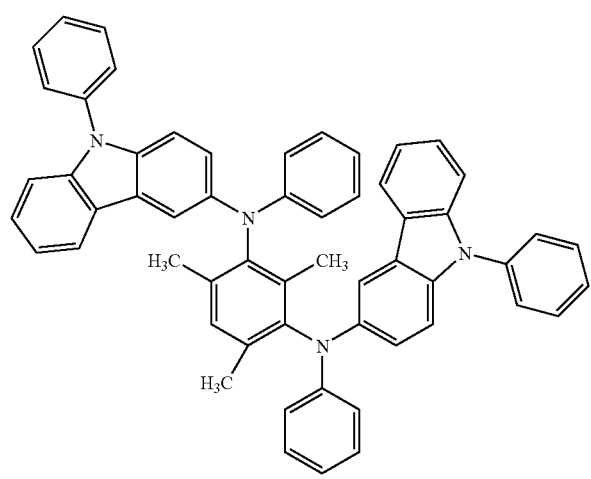

(141)

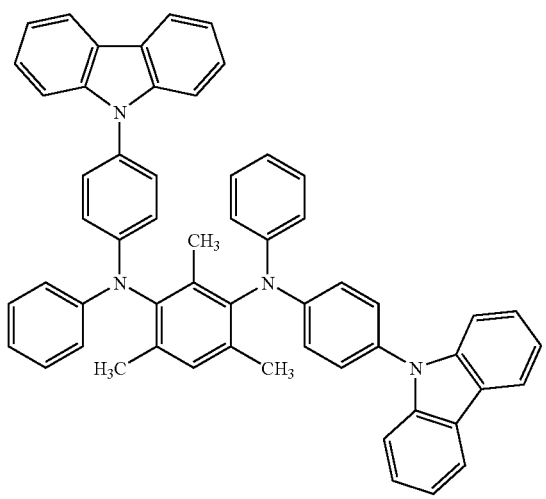

(142)

The aromatic amine compound of the present invention represented by the following General Formula (1) can be synthesized by a synthesis method shown in Synthetic Schemes (A-1) and (A-2). First, a compound including carbazole in a skeleton (Compound A) is reacted with halogen or halide such as N-bromosuccinimide (NBS), N-iodosuccinimide (NIS), bromine (Br$_2$), potassium iodide (KI), or iodine (I$_2$) to synthesize a compound including 3-bromocarbazole in a skeleton (Compound B), and then subjected to coupling reaction with a primary amine using a metal catalyst such as a palladium catalyst (Pd catalyst), thereby obtaining Compound C. By reacting obtained Compound C with 1,3,5-trihalogenated benzene using a metal catalyst such as a Pd catalyst, an aromatic amine compound of the present invention can be obtained.

(1)

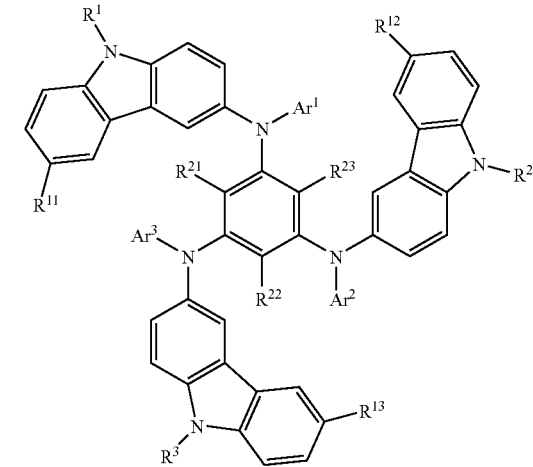

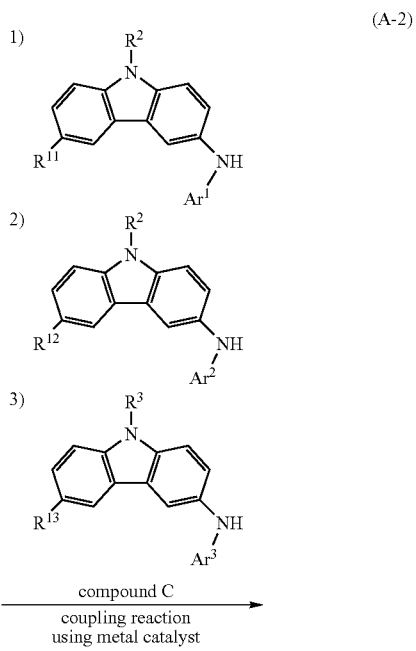

(A-1)

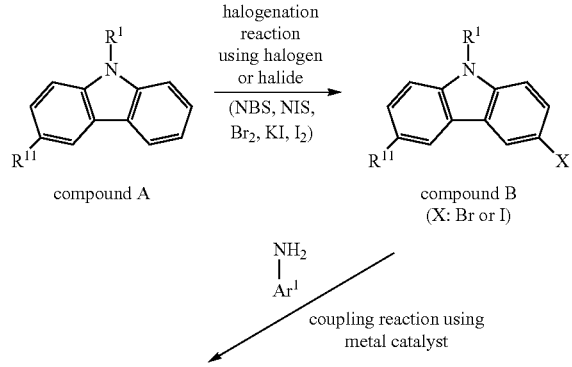

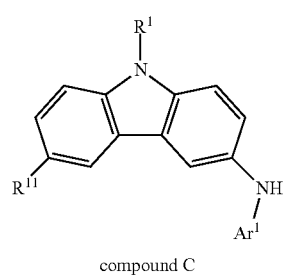

compound C

In General Formula (1) and Synthetic Schemes (A-1) and (A-2), each of $Ar^1$ to $Ar^3$ represents an aryl group having 6 to 12 carbon atoms or a heteroaromatic group having 4 to 9 carbon atoms; each of $R^1$ to $R^3$ represents an alkyl group having 1 to 4 carbon atoms or an aryl group having 6 to 25 carbon atoms; each of $R^{11}$ to $R^{13}$ represents a hydrogen atom, an alkyl group having 1 to 4 carbon atoms, or an aryl group having 6 to 25 carbon atoms; and each of $R^{21}$ to $R^{23}$ represents a hydrogen atom, a methyl group, or a methoxy group.

Note that in Synthetic Scheme (A-2), the aromatic amine compound of the present invention in General Formula (2) can be obtained through one-stage reaction by reacting 3 equivalents of one kind of Compound C with 1 equivalent of 1,3,5-trihalogenated benzene. In other words, the aromatic amine compound of the present invention in General Formula (2) is characterized by easy synthesis.

In addition, an aromatic amine compound of the present invention represented by the following General Formula (4) can be synthesized by a synthesis method shown in the above Synthetic Scheme (A-1) and the following Synthetic Scheme (A-3). The aromatic amine compound of the present invention can be obtained by reacting Compound C obtained according to Synthetic Scheme (A-1) with 1,3-dihalogenated benzene using a metal catalyst such as a Pd catalyst.

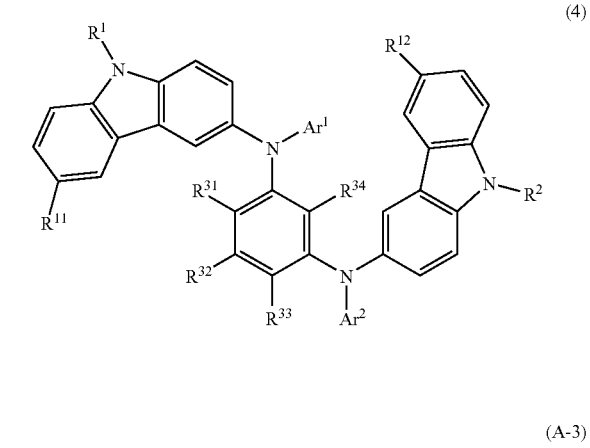

(4)

compound C

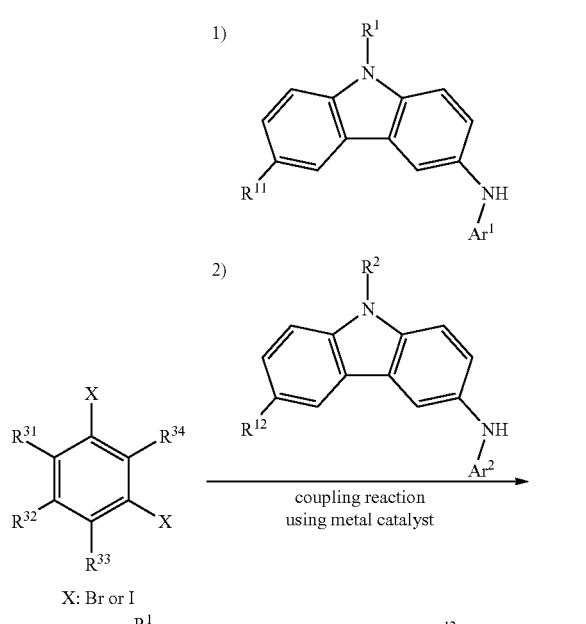

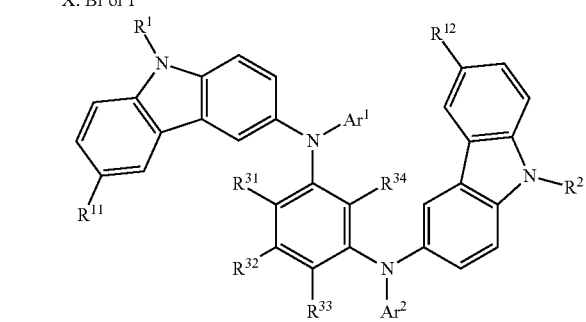

In General Formula (4) and Synthetic Scheme (A-3), each of Ar$^1$ and Ar$^2$ represents an aryl group having 6 to 12 carbon atoms or a heteroaromatic group having 4 to 9 carbon atoms; each of R$^1$ and R$^2$ represents an alkyl group having 1 to 4 carbon atoms or an aryl group having 6 to 25 carbon atoms; each of R$^{11}$ and R$^{12}$ represents a hydrogen atom, an alkyl group having 1 to 4 carbon atoms, or an aryl group having 6 to 25 carbon atoms; and each of R$^{31}$ to R$^{34}$ represents a hydrogen atom, a methyl group, or a silyl group having a substituent.

Note that in Synthetic Scheme (A-3), the aromatic amine compound of the present invention in General Formula (5) can be obtained through one-stage reaction by reacting 2 equivalents of one kind of Compound C with one equivalent of 1,3-dihalogenated benzene. In other words, the aromatic amine compound of the present invention in General Formula (5) is characterized by easy synthesis.

An aromatic amine compound of the present invention represented by the following General Formula (7) can be synthesized by synthesis method shown in Synthetic Scheme (A-4) and Synthetic Scheme (A-5). First, a compound including carbazole in a skeleton (Compound D) is reacted with dihalogenated aryl to synthesize a compound including N-halogenated arylcarbazole (Compound E), and then subjected to coupling reaction with a secondary amine using a metal catalyst such as copper iodide (CuI), thereby obtaining Compound F. By reacting Compound F obtained with 1,3,5-trihalogenated benzene using a Pd catalyst, the aromatic amine compound of the present invention can be obtained.

(7)

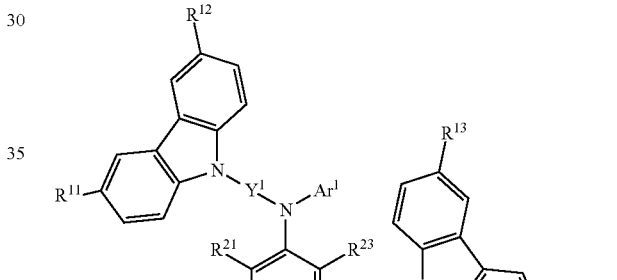

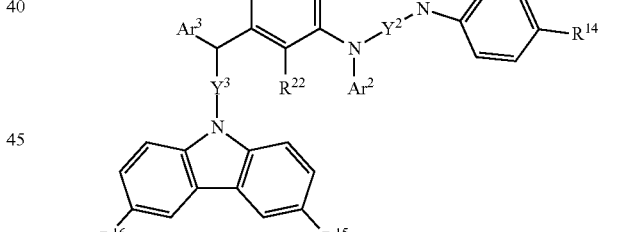

(A-4)

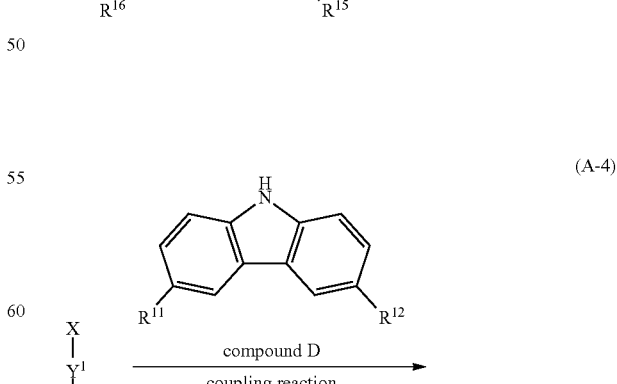

compound D
coupling reaction
using metal catalyst

X: Br or I

-continued

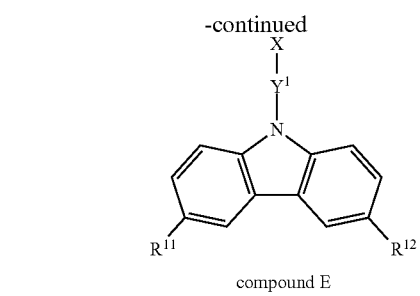
compound E

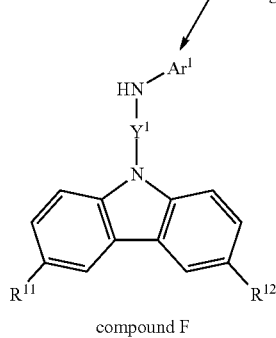
compound F compound F

1) 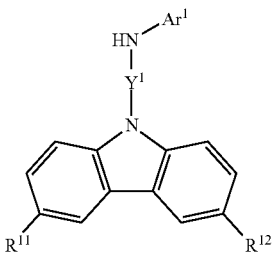

2) 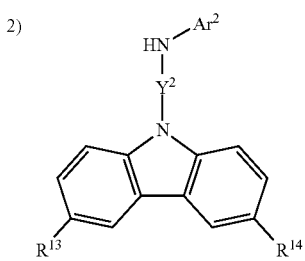

3) 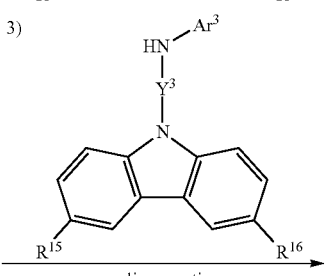

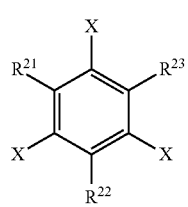
X: Br or I

-continued

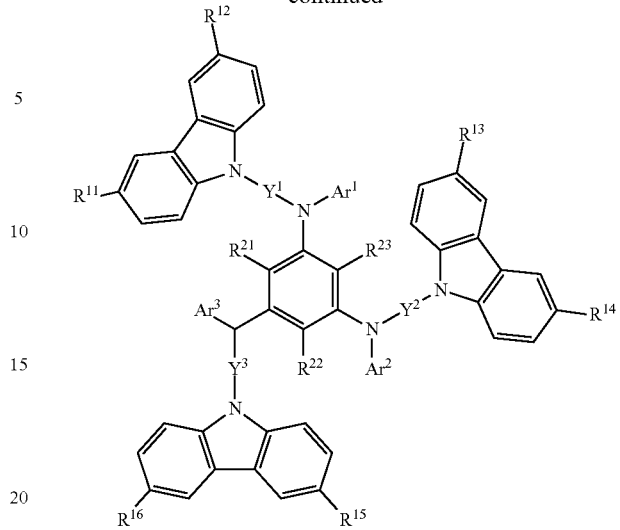

(A-5)

In General Formula (7) and Synthetic Schemes (A-4) and (A-5), each of $Ar^1$ to $Ar^3$ represents an aryl group having 6 to 12 carbon atoms or a heteroaromatic group having 4 to 9 carbon atoms; each of $Y^1$ to $Y^3$ represents an arylene group having 6 to 25 carbon atoms; each of $R^{11}$ to $R^{16}$ represents a hydrogen atom, an alkyl group having 1 to 4 carbon atoms, or an aryl group having 6 to 25 carbon atoms; and each of $R^{21}$ to $R^{23}$ represents a hydrogen atom, a methyl group, or a methoxy group.

Note that in Synthetic Scheme (A-5), the aromatic amine compound of the present invention in General Formula (8) can be obtained through one-stage reaction by reacting 3 equivalents of one kind of Compound E with one equivalent of 1,3,5-trihalogenated benzene. In other words, the aromatic amine compound of the present invention in General Formula (8) is characterized by easy synthesis.

In addition, an aromatic amine compound of the present invention represented by the following General Formula (10) can be synthesized by synthesis methods shown in the above Synthetic Scheme (A-4) and the following Synthetic Scheme (A-6). The aromatic amine compound of the present invention can be obtained by reacting Compound F obtained according to Synthetic Scheme (A-4) with 1,3-dihalogenated benzene using a metal catalyst such as a Pd catalyst.

(10)

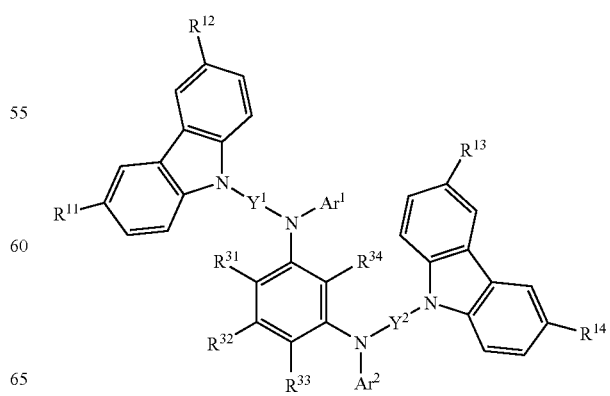

(A-6)

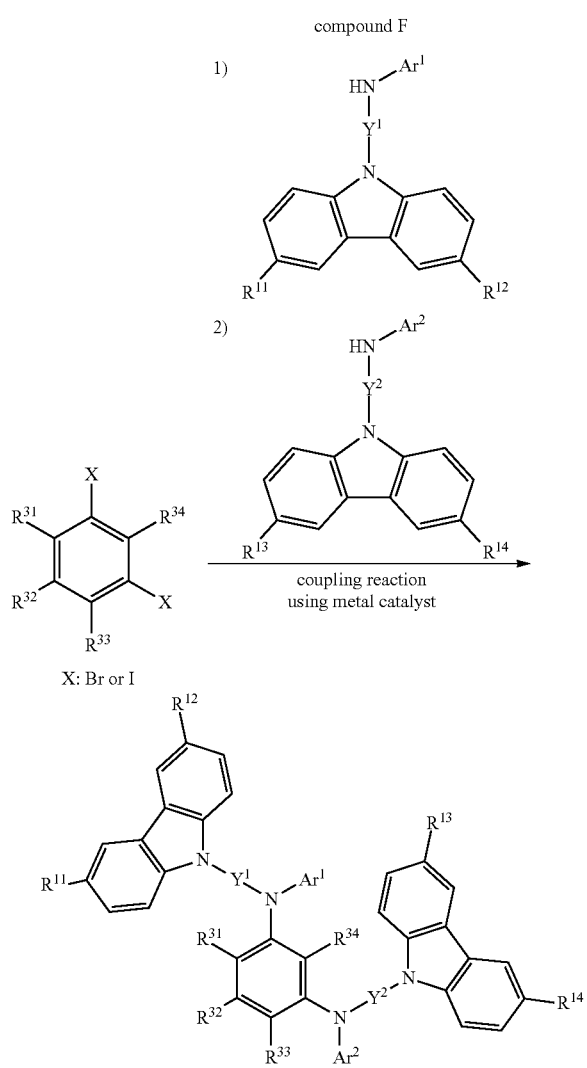

compound F

X: Br or I

In General Formula (10) and Synthetic Scheme (A-6), $Ar^1$ represents an aryl group having 6 to 12 carbon atoms or a heteroaromatic group having 4 to 9 carbon atoms; $Y^1$ represents an arylene group having 6 to 25 carbon atoms; each of $R^{11}$ and $R^{12}$ represents a hydrogen atom, an alkyl group having 1 to 4 carbon atoms, or an aryl group having 6 to 25 carbon atoms; and each of $R^{21}$ to $R^{23}$ represents a hydrogen atom, a methyl group, or a methoxy group.

Note that in Synthetic Scheme (A-6), the aromatic amine compound of the present invention in General Formula (11) can be obtained through one-stage reaction by reacting 2 equivalents of one kind of Compound E with one equivalent of 1,3-dihalogenated benzene. In other words, the aromatic amine compound of the present invention in General Formula (11) is characterized by easy synthesis.

In the above-described synthetic scheme, a Pd catalyst having tri(tert-butyl)phosphine(tert-Bu)$_3$P as a ligand can be used for the coupling reaction using a metal catalyst. For example, as the Pd catalyst, a catalyst in which (tert-Bu)$_3$P is coordinated in Pd by mixing Pd(dba)$_2$ and (tert-Bu)$_3$P can be used. Note that in place of Pd(dba)$_2$, a Pd complex in which a ligand having weaker coordination strength than (tert-Bu)$_3$P is coordinated may be used. Specifically, Pd(dba)$_2$, palladium diacetate (Pd(OAc)$_2$), or the like can be used. Preferably, Pd(dba)$_2$ is used. As the ligand, DPPF can be used in place of (tert-Bu)$_3$P. A reaction temperature is preferably in the range of a room temperature to 130° C. When heated to 130° C. or more, the Pd catalyst may be decomposed and may lose a function as a catalyst. It is more preferable to set a heating temperature in the range of 60° C. to 110° C. because it becomes easier to control the reaction and a yield is increased. Note that dba refers to trans,trans-dibenzylideneacetone. In addition, DPPF refers to 1,1-bis(diphenylphosphino)ferrocene. As a solvent, anhydrous toluene, xylene, or the like can be used. As a base, alkali metal alkoxide such as tert-BuONa can be used.

The aromatic amine compound of the present invention has an excellent hole transporting property. Therefore, a favorable electric characteristic can be obtained by using the aromatic amine compound of the present invention for an electronics device such as a light emitting element or a solar cell.

In addition, the aromatic amine compound of the present invention has a high glass transition point because it has a carbazole skeleton. In other words, since the aromatic amine compound of the present invention has excellent heat resistance, an electronics device having excellent heat resistance can be obtained by using it for an electronics device such as a light emitting element or a solar cell.

In addition, the aromatic amine compound of the present invention is stable even when oxidation reaction and subsequent reduction reaction are repeated. In other words, the aromatic amine compound of the present invention has stability in repetitive oxidation reaction. Therefore, a long-life electronics device can be obtained by using the aromatic amine compound of the present invention for an electronics device such as a light emitting element or a solar cell.

Embodiment 2

One mode of a light emitting element using the aromatic amine compound of the present invention is hereinafter explained with reference to FIG. 1A.

A light emitting element of the present invention has a plurality of layers between a pair of electrodes. The plurality of layers is a laminate of a combination of layers formed of a material having an excellent carrier injection property and a material having a high carrier transport property such that a light emitting region is formed apart from the electrodes, in other words, such that carriers are recombined in a portion apart from the electrodes.

In this embodiment, the light emitting element includes a first electrode 102, a first layer 103, a second layer 104, a third layer 105, and a fourth layer 106 which are sequentially stacked over the first electrode 102, and a second electrode 107 which is provided thereover. Note that in this embodiment, explanation is made below assuming that the first electrode 102 functions as an anode and the second electrode 107 functions as a cathode.

A substrate 101 is used as a support of the light emitting element. For the substrate 101, glass, plastic, or the like can be used, for example. Note that another material may be used as long as it functions as a support in a manufacturing process of the light emitting element.

For the first electrode 102, a metal, an alloy, a conductive compound, a mixture of them, or the like having a high work function (specifically, 4.0 eV or more) is preferably used. Specifically, indium tin oxide (ITO), indium tin oxide containing silicon, indium zinc oxide (IZO) in which indium oxide is mixed with zinc oxide (ZnO) of 2 wt % to 20 wt %, indium oxide containing tungsten oxide of 0.5 wt % to 5 wt % and zinc oxide of 0.1 wt % to 1 wt % (IWZO), or the like can be given as an example. Although these conductive metal oxide films are generally formed by sputtering, they may be formed by applying a sol-gel method or the like. In addition, gold (Au), platinum (Pt), nickel (Ni), tungsten (W), chromium (Cr), molybdenum (Mo), iron (Fe), cobalt (Co), copper (Cu), palladium (Pd), nitride of a metal material (such as titanium nitride (TiN)), or the like can be used.

The first layer 103 is a layer containing a substance having an excellent hole injection property. Molybdenum oxide ($MoO_x$), vanadium oxide ($VO_x$), ruthenium oxide ($RuO_x$), tungsten oxide ($WO_x$), manganese oxide ($MnO_x$), or the like can be used. Alternatively, the first layer 103 can be formed of phthalocyanine-based compound such as phthalocyanine (abbr.: $H_2Pc$) or copper phthalocyanine (CuPc), a high molecular compound such as poly(ethylene dioxythiophene)/poly(styrenesulfonic acid) (PEDOT/PSS), or the like.

Alternatively, a composite material formed by combining an organic compound and an inorganic compound may be used for the first layer 103. In particular, a composite material containing an organic compound and an inorganic compound having an electron accepting property with respect to the organic compound has excellent hole injection and hole transport properties because the inorganic compound accepts electrons from the organic compound and carrier density is increased. In this case, the organic compound is preferably a material having an excellent hole transport property. Specifically, an arylamine compound or a carbazole derivative can be used. Alternatively, aromatic hydrocarbon may be used as the organic compound. The inorganic compound may be any substance as long as it has an electron accepting property with respect to the organic compound, and specifically, oxide of transition metal is preferable. For example, metal oxide such as titanium oxide ($TiO_x$), vanadium oxide ($VO_x$), molybdenum oxide ($MoO_x$), tungsten oxide ($WO_x$), rhenium oxide ($ReO_x$), a ruthenium oxide ($RuO_x$), chromium oxide ($CrO_x$), zirconium oxide ($ZrO_x$), hafnium oxide ($HfO_x$), tantalum oxide ($TaO_x$), silver oxide ($AgO_x$), or manganese oxide ($MnO_x$) can be used. In the case of using the composite material formed by combining an organic compound and an inorganic compound for the first layer 103, the first layer 103 can form an ohmic contact with the first electrode 102. Therefore, a material for forming the first electrode can be selected regardless of a work function.

The second layer 104 is a layer containing a substance having an excellent hole transport property. Since the aromatic amine compound of the present invention described in Embodiment 1 has an excellent hole transport property, it can be suitably used for the second layer 104. By using the aromatic amine compound of the present invention for the second layer 104, a light emitting element with favorable characteristics can be obtained. In particular, a light emitting element with excellent heat resistance can be obtained.

The third layer 105 is layer containing a light emitting substance. As for the light emitting substance, various substances can be used without particular limitation, and a coumarin derivative such as coumarin 6 or coumarin 545T, a quinacridon derivative such as N,N'-dimethylquinacridon or N,N'-diphenylquinacridon, an acridone derivative such as N-phenylacridonoe or N-methylacridone, a condensed aromatic compound such as 2-tert-butyl-9,10-di(2-naphthyl)anthracene (abbr.: t-BuDNA), 9,10-diphenylanthracene, rubrene, periflanthene, or 2,5,8,11-tetra(tert-butyl)perylene (abbr.: TPS), a pyran derivative such as 4-dicyanomethylene-2-[p-(dimethylamino)styryl]-6-methyl-4H-pyran, an amine derivative such as 4-(2,2-diphenylvinyl)triphenylamine, or the like can be used. As a phosphorescent light emitting substance, an iridium complex such as bis{2-(p-tolyl)pyridinato}iridium(III) acetylacetonate, bis{2-(2'-benzothienyl)pyridinato}iridium(III)acetylacetonate, or bis{2-(4,6-difluorophenyl)pyridinato}iridium(III)picolinate; a platinum complex such as 2,3,7,8,12,13,17,18-octaethyl-21H,23H-porphyrin-platinum complex; a rare-earth complex such as 4,7-diphenyl-1,10-phenanthroline tris(2-thenoyltrifluoroacetonato)europium(III), or the like can be used.

Alternatively, the third layer 105 may be formed by dispersing a light emitting substance into another substance. As a material into which a light emitting substance is dispersed, various materials can be used. Specifically, a substance having a higher LUMO level and a lower HOMO level than a light emitting substance can be used. In addition, plural kinds of materials can be used as the material into which a light emitting substance is dispersed. For example, a substance which suppresses crystallization of rubrene- or the like may further be added to suppress crystallization. Moreover, 4,4'-bis[N-(1-naphthyl)-N-phenylamino]biphenyl (NPB), tris(8-quinolinolato)aluminum (Alq), or the like may further be added to efficiently transfer energy to the light emitting substance.

The fourth layer 106 is a layer formed of a substance having an excellent electron transport property, for example, a metal complex having a quinoline skeleton or a benzoquinoline skeleton such as tris(8-quinolinolato)aluminum (abbr.: Alq), tris(5-methyl-8-quinolinolato)aluminum (abbr.: $Almq_3$), bis(10-hydroxybenzo[h]quinolinato)beryllium (abbr.: $BeBq_2$), or bis(2-methyl-8-quinolinolato)(4-phenylphenolato)aluminum (abbr.: BAlq), or the like. Alternatively, a metal complex having an oxazole-based or thiazole-based ligand such as bis[2-(2-hydroxyphenyl)benzoxazolato]zinc (abbr.: $Zn(BOX)_2$) or bis[2-(2-hydmxyphenyl)benzothiazolato]zinc (abbr.: $Zn(BTZ)_2$), or the like can be used. Furthermore, besides the metal complex, 2-(4-biphenylyl)-5-(4-tert-butylphenyl)-1,3,4-oxadiazole (abbr.: PBD), 1,3-bis[5-(p-tert-butylphenyl)-1,3,4-oxadiazole-2-yl]benzene (abbr.: OXD-7), 3-(4-tert-butylphenyl)-4-phenyl-5-(4-biphenylyl)-1,2,4-triazole (abbr.: TAZ), 3-(4-tert-butylphenyl)-4-(4-ethylphenyl)-5-(4-biphenylyl)-1,2,4-triazole (abbr.: p-EtTAZ), bathophenanthroline (abbr.: BPhen), bathocuproin (abbr.: BCP), or the like can be used. The substances described here are mainly substances having electron mobility of $10^{-6}$ $cm^2/Vs$ or more. Note that a substance other than those described above may be used for the fourth layer 106 as long as the substance has a more excellent electron transport property than hole transport property. In addition, the fourth layer 106 may be not only a single layer but also stacked layers of two or more layers formed of the above substance.

As a substance for forming the second electrode 107, a metal, an alloy, a conductive compound, a mixture thereof, or the like having a low work function (specifically, 3.8 eV or less) can be used. As a specific example of such a cathode material, an element belonging to Group 1 or 2 of the Periodic Table, in other words, an alkali metal such as lithium (Li) or cesium (Cs), an alkaline earth metal such as magnesium (Mg), calcium (Ca), or strontium (Sr) or an alloy containing these (MgAg, AlLi), a rare earth metal such as europium (Eu) or ytterbium (Yb) or an alloy containing these, or the like can be given. However, by providing a layer having a function of promoting electron injection between the second electrode 107 and the fourth layer 106 so as to be stacked with the second electrode, various conductive materials such as Al, Ag, ITO, or ITO containing silicon can be used as the second electrode 107 regardless of the magnitude of the work function.

Note that, for the layer having a function of promoting electron injection, a compound of alkali metal or alkaline earth metal, such as lithium fluoride (LiF), cesium fluoride (CsF), or calcium fluoride ($CaF_2$) can be used. Alternatively, a layer formed of a substance having an electron transport property, in which alkali metal or alkaline earth metal is contained, for example, Alq in which magnesium (Mg) or lithium (Li) is contained, or the like can be used.

The first layer 103, the second layer 104, the third layer 105, and the fourth layer 106 may be formed by various methods such as an evaporation method, an ink-jet method, and a spin coating method. In addition, different methods may be separately used to form respective electrodes or layers.

In the light emitting element of the present invention having the above-described structure, current flows due to a potential difference made between the first electrode 102 and the second electrode 107; holes and electrons are recombined in the third layer 105 that is a layer containing a substance with an excellent light emitting property; and then, light is emitted. In other words, a light emitting region is formed in the third layer 105.

Figure 1B:
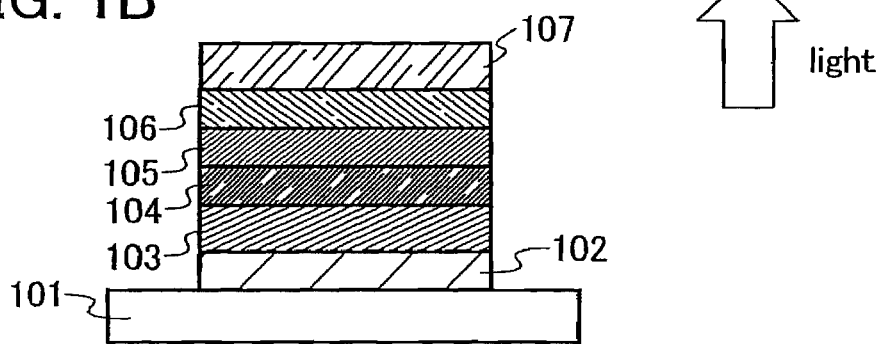
Figure 1C:
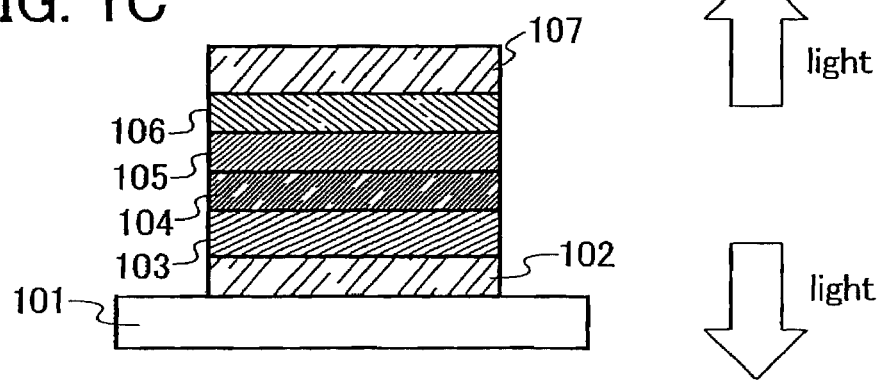

Light emission is extracted outside through either or both, the first electrode 102 and the second electrode 107. Accordingly, either or both the first electrode 102 and the second electrode 107 are formed of a light-transmitting substance. When only the first electrode 102 is formed of a light-transmitting substance, light emission is extracted from the substrate side through the first electrode 102 as shown in FIG. 1A. When only the second electrode 107 is formed of a light-transmitting substance, light emission is extracted from the side opposite to the substrate through the second electrode 107 as shown in FIG. 1B. When both the first electrode 102 and the second electrode 107 are formed of a light-transmitting substance, light emission is extracted from both the substrate side and the opposite side through the first electrode 102 and the second electrode 107 as shown in FIG. 1C.

Note that a structure of layers provided between the first electrode 102 and the second electrode 107 is not limited to the structure described above. Another structure may be employed as long as it has a structure in which a light emitting region where holes and electrons are recombined with each other is provided in a portion apart from the first electrode 102 and the second electrode 107 so as to suppress quenching caused by approach of the light emitting region and metal.

In other words, a stacking structure of the layers is not particularly limited, and the layers may be structured by freely combining layers formed of a substance having an excellent electron transport property, a substance having an excellent hole transport property, a substance having an excellent electron injection property, a substance having an excellent hole injection property, a substance having a bipolar property (a substance having an excellent electron and hole transport property), a hole blocking material, and the like with the aromatic amine compound of the present invention.

A light emitting element shown in FIG. 2 has a structure in which a first layer 303 formed of a substance having an excellent electron transport property, a second layer 304 containing a light emitting substance, a third layer 305 formed of a substance having an excellent hole transport property, a fourth layer 306 formed of a substance having an excellent hole injection property, and a second electrode 307 functioning as an anode are sequentially stacked over a first electrode 302 functioning as a cathode. Note that a reference numeral 301 denotes a substrate.

In this embodiment, the light emitting element is manufactured over a substrate formed of glass, plastic, or the like. A passive-type light emitting device can be manufactured by manufacturing a plurality of such light emitting elements over one substrate. Alternatively, for example, a thin film transistor (TFT) may be formed over a substrate formed of glass, plastic, or the like, and a light emitting element may be manufactured over an electrode which is electrically connected to the TFT. This makes it possible to manufacture an active matrix light emitting device in which the drive of the light emitting element is controlled by the TFT. Note that the structure of the TFT is not particularly limited. The TFT may be a staggered type or an inverted staggered type. Furthermore, crystallinity of a semiconductor used for the TFT is also not particularly limited, and either an amorphous semiconductor or a crystalline semiconductor may be used. Moreover, a driver circuit formed over a TFT array substrate may include either an n-type TFT or a p-type TFT, or both of them.

The aromatic amine compound of the present invention is a material having an excellent hole transport property. Therefore, when used for a light emitting element, a drive voltage of the light emitting element can be reduced, which leads to a reduction in power consumption.

In addition, the aromatic amine compound of the present invention has a high glass transition point. Therefore, when used for a light emitting element, a light emitting element having excellent heat resistance can be obtained.

Furthermore, the aromatic amine compound of the present invention is stable even when it is repeatedly subjected to oxidation reaction and subsequent reduction reaction. In other words, it has stability in repetitive oxidation reactions. Therefore, a long-life light emitting element can be obtained by using the aromatic amine compound of the present invention for a light emitting element.

Embodiment 3

In this embodiment, a light emitting element having a structure different from that described in Embodiment 2 is explained.

Since the aromatic amine compound of the present invention is a substance having an excellent hole injection property, it can be used for the first layer 103 described in Embodiment 2. By using the aromatic amine compound of the present invention for the first layer 103, a light emitting element with favorable characteristics can be obtained.

In the case of using the aromatic amine compound of the present invention for the first layer 103, various materials can be used as a substance for forming the second layer 104. For example, an aromatic amine compound (that is, a compound having a benzene ring-nitrogen bond) can be used. A widely-used material is a star-burst aromatic amine compound, for example, 4,4'-bis[N-(3-methylphenyl)-N-phenylamino]biphenyl, a derivative thereof such as 4,4'-bis[N-(1-naphthyl)-N-phenylamino]biphenyl (hereinafter referred to as NPB), 4,4',4''-tris(NX-diphenyl-amino)triphenylamine, or 4,4',4''-tris[N-(3-methylphenyl)-N-phenylamino]triphenylamine, or the like. The substances described here are mainly substances having hole mobility of $10^{-6}$ $cm^2/Vs$ or more. However, another substance may be used as long as the substance has a more excellent hole transport property than electron transport property. Note that the second layer 104 may be not only a single layer but also a mixed layer of the above substances or stacked layers of two or more layers.

In addition, the aromatic amine compound of the present invention may be used for the first layer 103 and the second layer 104.

The aromatic amine compound of the present invention is a material having an excellent hole injection property. Therefore, when used for a light emitting element, a drive voltage of the light emitting element can be reduced, which leads to a reduction in power consumption.

In addition, the aromatic amine compound of the present invention has a high glass transition point. Therefore, when used for a light emitting element, a light emitting element having excellent heat resistance can be obtained.

In addition, the aromatic amine compound of the present invention is stable even when it is repeatedly subjected to oxidation reaction and subsequent reduction reaction. In other words, it has stability in repetitive oxidation reactions. Therefore, a long-life light emitting element can be obtained by using the aromatic amine compound of the present invention for a light emitting element.

Note that the structure described in Embodiment 2 can be appropriately used except for the first layer 103.

Embodiment 4

In this embodiment, a light emitting element having a structure different from that described in Embodiment 2 is explained.

By using the aromatic amine compound of the present invention for the third layer 105 described in Embodiment 2, light emission from the aromatic amine compound of the present invention can be obtained. Since the aromatic amine compound of the present invention exhibits blue to green light emission, a light emitting element which exhibits blue to green light emission can be obtained.

The third layer 105 may be formed of only the aromatic amine compound of the present invention, or may be formed by dispersing the aromatic amine compound of the present invention into another substance. As a substance into which the aromatic amine compound of the present invention is dispersed, various materials can be used. In place of the substance having an excellent hole transport property or the substance having an excellent electron transport property described in Embodiment 2, 4,4'-di(N-carbazolyl)biphenyl (abbr.: CBP), 2,2',2"-(1,3,5-benzenetri-yl)-tris[1-phenyl-1H-benzimidazole] (abbr.: TPBI), 9,10-di(2-naphthyl)anthracene (abbr.: DNA), 2-tert-butyl-9,10-di(2-naphthyl)anthracene (abbr.: t-BuDNA), or the like can be used.

The aromatic amine compound of the present invention has a high glass transition point. Therefore, when used for a light emitting element, a light emitting element having excellent heat resistance can be obtained.

In addition, the aromatic amine compound of the present invention is stable even when it is repeatedly subjected to oxidation reaction and subsequent reduction reaction. In other words, it has stability in repetitive oxidation reactions. Therefore, a long-life light emitting element can be obtained by using the aromatic amine compound of the present invention for a light emitting element Note that the structures described in Embodiments 2 and 3 can be appropriately used except for the third layer 103.

Embodiment 5

In this embodiment, a light emitting device which is manufactured using the aromatic amine compound of the present invention is explained.

In this embodiment, a light emitting device which is manufactured using the aromatic amine compound of the present invention is explained with reference to FIGS. 3A and 3B. Note that FIG. 3A is a top view showing a light emitting device and FIG. 3B is a cross-sectional view of FIG. 3A taken along lines A-A' and B-B'. A reference numeral 601 indicated by dashed line denotes a driver circuit portion (a source side driver circuit); 602, a pixel portion; and 603, a driver circuit portion (a gate side driver circuit). A reference numeral 604 denotes a sealing substrate; 605, a sealant; and a portion surrounded by the sealant 605 is a space 607.

Note that a lead wiring 608 is a wiring for transmitting signals to be inputted to the source side driver circuit 601 and the gate side driver circuit 603 and receives a video signal, a clock signal, a start signal, a reset signal, and the like from an FPC (flexible printed circuit) 609 that is an external input terminal. Note that only the FPC is shown here; however, the FPC may be provided with a printed wiring board (PWB). The light emitting device in this specification includes not only a main body of the light emitting device but also a light emitting device with an FPC or a PWB attached.

Next, a cross-sectional structure is explained with reference to FIG. 3B. The driver circuit portion and the pixel portion are formed over an element substrate 610. Here, the source side driver circuit 601 that is the driver circuit portion and one pixel in the pixel portion 602 are shown.

Note that a CMOS circuit that is a combination of an n-channel TFT 623 and a p-channel TFT 624 is formed in the source side driver circuit 601. The driver circuit may be formed using a CMOS circuit, a PMOS circuit, or an NMOS circuit A driver integration type in which a driver circuit is formed over a substrate is described in this embodiment, but it is not necessarily required and a driver circuit can be formed not over a substrate but outside a substrate.

The pixel portion 602 has a plurality of pixels, each of which includes a switching TFT 611, a current control TFT 612, and a first electrode 613 which is electrically connected to a drain of the current control TFT 612. Note that an insulator 614 is formed to cover an end of the first electrode 613. Here, a positive type photosensitive acrylic resin film is used.

The insulator 614 is formed to have a curved surface with curvature at an upper end or a lower end thereof in order to obtain favorable coverage. For example, in the case of using positive type photosensitive acrylic as a material of the insulator 614, the insulator 614 is preferably formed to have a curved surface with a curvature radius (0.2 µm to 3 µm) only at an upper end. Either a negative type which becomes insoluble in an etchant by light irradiation or a positive type which becomes soluble in an etchant by light irradiation can be used as the insulator 614.

A layer 616 containing a light emitting substance and a second electrode 617 are formed over the first electrode 613. Here, a material having a high work function is preferably used as a material used for the first electrode 613 which functions as an anode. For example, the first electrode 613 can be formed by using a single-layer film such as an ITO film, an indium tin oxide film containing silicon, an indium oxide film containing zinc oxide of 2 wt % to 20 wt %, a titanium nitride film, a chromium film, a tungsten film, a Zn film, or a Pt film; a stacked layer of a titanium nitride film and a film containing aluminum as its main component; a three-layer structure of a titanium nitride film, a film containing aluminum as its main component, and a titanium nitride film; or the like. When the first electrode 613 has a stacked-layer structure, it can have low resistance as a wiring and form a favorable ohmic contact. Further, the first electrode can function as an anode.

The layer 616 containing a light emitting substance is formed by various methods such as an evaporation method using an evaporation mask, an ink-jet method, and a spin coating method. The layer 616 containing a light emitting substance contains the aromatic amine compound of the present invention described in Embodiment 1. Further, another material included in the layer 616 containing a light emitting substance may be a low molecular material, an intermediate molecular material (including an oligomer and a dendrimer), or a high molecular material. In addition, as a material used for the layer containing a light emitting substance, a single layer or a stacked layer of an organic compound is generally used. However, the present invention also includes a structure in which an inorganic compound is used for a part of a film formed of the organic compound.

As a material used for the second electrode 617 which is formed over the layer 616 containing a light emitting substance and functions as a cathode, a material having a low work function (Al, Mg, Li, Ca, an alloy or a compound thereof such as MgAg, MgIn, AlLi, LiF, or $CaF_2$, or the like) is preferably used. In the case where light generated in the layer 616 containing a light emitting substance is transmitted through the second electrode 617, a stacked layer of a metal thin film with a thin thickness and a transparent conductive film (of ITO, indium oxide containing zinc oxide of 2 wt % to 20 wt %, indium tin oxide containing silicon, zinc oxide (ZnO), or the like) is preferably used as the second electrode 617.

By attaching the sealing substrate 604 to the element substrate 610 with the sealant 605, a light emitting element 618 is provided in the space 607 surrounded by the element substrate 610, the sealing substrate 604, and the sealant 605. Note that the space 607 is filled with a filler, but there is also a case where the space 607 is filled with the sealant 605 or filled with an inert gas (nitrogen, argon, or the like).

Note that an epoxy-based resin is preferably used as the sealant 605. The material preferably allows as little moisture and oxygen as possible to penetrate. As the sealing substrate 604, a plastic substrate formed of FRP (Fiberglass-Reinforced Plastics), PVF (polyvinyl fluoride), Myler, polyester, acrylic, or the like can be used besides a glass substrate or a quartz substrate.

As described above, the light emitting device which is manufactured using the aromatic amine compound of the present invention can be obtained.

Since the aromatic amine compound described in Embodiment 1 is used for the light emitting device of the present invention, a light emitting device having favorable characteristics can be obtained. Specifically, a light emitting device having high heat resistance can be obtained.

In addition, since the aromatic amine compound of the present invention is a material having an excellent hole transport property, a drive voltage of the light emitting element can be reduced and power consumption of the light emitting device can be reduced.

Furthermore, the aromatic amine compound of the present invention is stable even when it is repeatedly subjected to oxidation reaction and subsequent reduction reaction. In other words, it has stability in repetitive oxidation reaction. Therefore, a long-life light emitting device can be obtained by using the aromatic amine compound of the present invention for a light emitting device.

Figure 4:
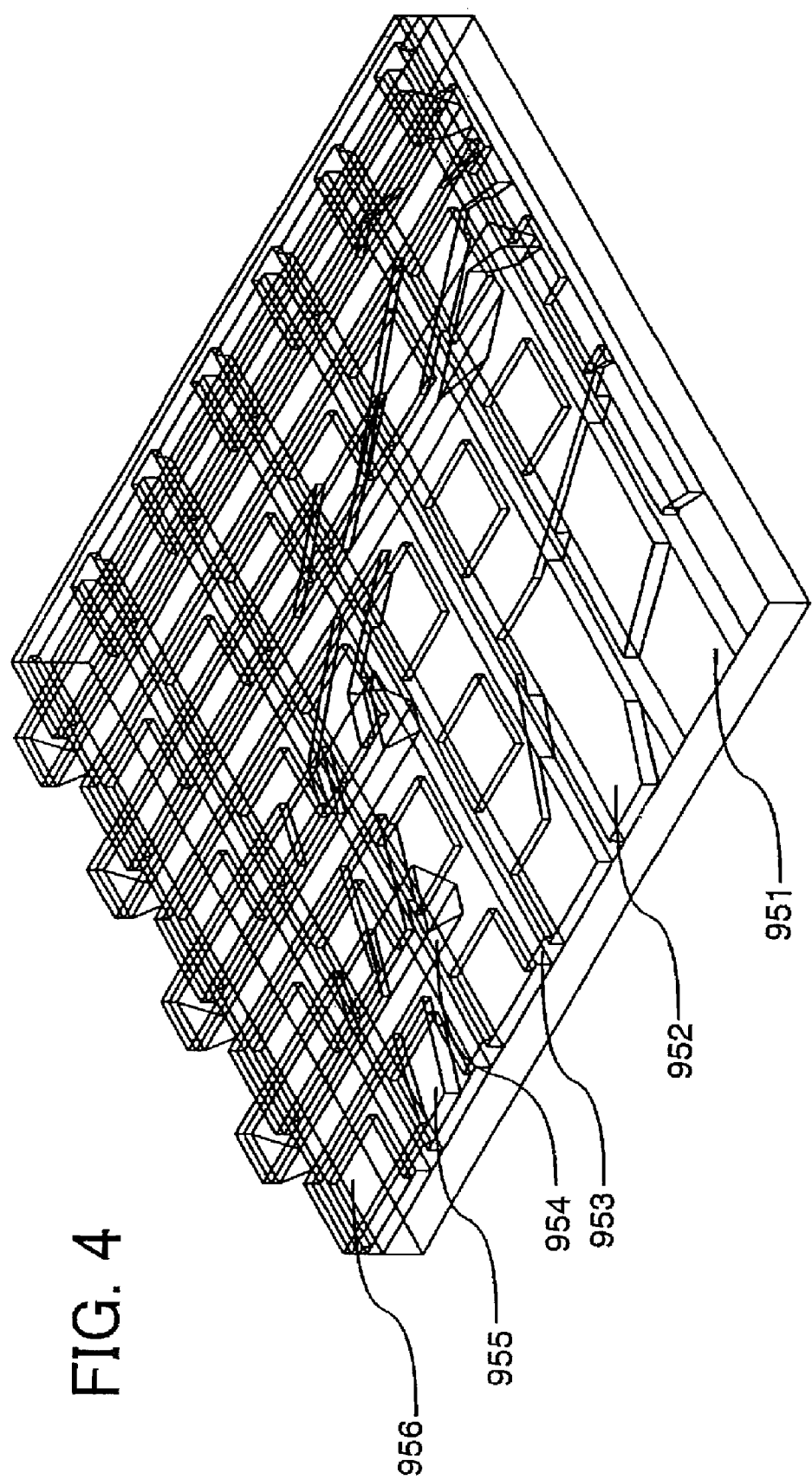
FIG. 4 is a diagram for explaining a light emitting device of the present invention.

As described above, an active-type light emitting device in which drive of a light emitting element is controlled by a transistor is explained in this embodiment. However, a passive-type light emitting device in which the light emitting element is driven without particularly providing a driver element such as a transistor may also be employed. FIG. 4 shows a perspective view of a passive-type light emitting device which is manufactured by applying the present invention. In FIG. 4, a layer 955 containing a light emitting substance is provided between an electrode 952 and an electrode 956 over a substrate 951. An end portion of the electrode 952 is covered with an insulating layer 953. A partition layer 954 is provided over the insulating layer 953. Side walls of the partition layers 954 slope so that a distance between one side wall and another side wall becomes narrow toward a substrate surface. In other words, a cross section of the partition layer 954 in the direction of a narrow side is trapezoidal, and a base (a side facing in the same direction as a plane direction of the insulating layer 953 and in contact with the insulating layer 953) is shorter than an upper side (a side facing in the same direction as the plane direction of the insulating layer 953 and not in contact with the insulating layer 953). A defect of the light emitting element due to static electricity or the like can be prevented by providing the partition layer 954 in this manner. In addition, the passive-type light emitting device can also be driven with less power consumption when it includes the light emitting element of the present invention which operates at low drive voltage.

Embodiment 6

In this embodiment, an electronic device of the present invention which includes the light emitting device described in Embodiment 5 as a component is explained. The electronic device of the present invention contains the aromatic amine compound of the present invention described in Embodiment 1 and has a display portion with high heat resistance. It also has a display portion with long life. Further, it has a display portion which consumes less power.

Examples of an electronic device having a light emitting element manufactured using the aromatic amine compound of the present invention can be given as follows: a camera such as a video camera or a digital camera, a goggle type display, a navigation system, a sound reproducing device (car audio, an audio component, or the like), a computer, a game machine, a portable information terminal (a mobile computer, a cellular phone, a portable game machine, an electronic book, or the like), an image reproducing device provided with a recording medium (specifically, a device which can reproduce a recording medium such as a digital versatile disc (DVD) and includes a display device capable of displaying images thereof), and the like. Specific examples of them are shown in FIGS. 5A to 5D.

Figure 5A:
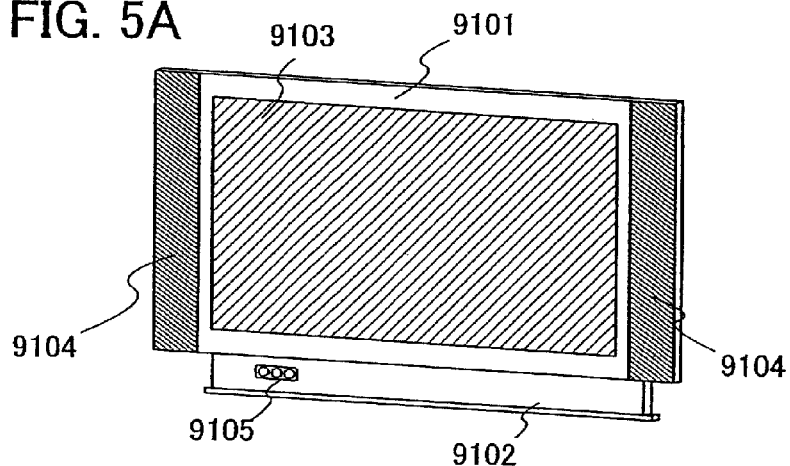
FIGS. 5A to 5D are diagrams for explaining electronic devices of the present invention.

FIG. 5A shows a television device according to the present invention, which includes a chassis 9101, a support 9102, a display portion 9103, a speaker portion 9104, a video input terminal 9105, and the like. In this television device, the display portion 9103 includes light emitting elements which are similar to those described in Embodiments 2 to 4 and arranged in matrix. The light emitting element is characterized by low voltage drive and long life. In addition, it is characterized by high heat resistance. The display portion 9103 which includes the light emitting elements also has a similar feature. Therefore, in this television device, image quality is hardly deteriorated and a reduction in power consumption is achieved. With such features, a deterioration compensation function and a power supply circuit can be significantly removed or reduced in the television device, thereby achieving reductions in size and weight of the chassis 9101 and the support 9102. Since a reduction in power consumption, an improvement in image quality, and reductions in size and weight are achieved in the television device according to the present invention, a product which is suitable for living environment can be provided.

Figure 5B:
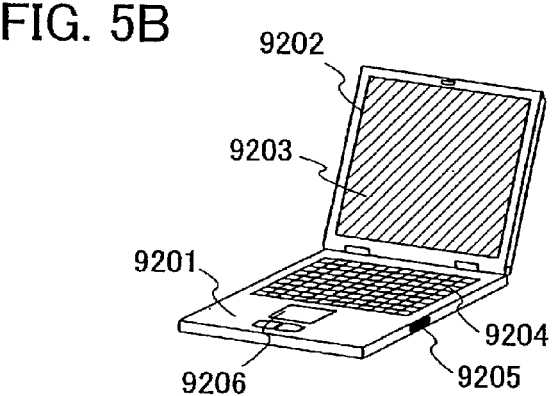

FIG. 5B shows a computer according to the present invention, which includes a main body 9201, a chassis 9202, a display portion 9203, a keyboard 9204, an external connection port 9205, a pointing mouse 9206, and the like. In this computer, the display portion 9203 includes light emitting elements which are similar to those described in Embodiments 2 to 4 and arranged in matrix. The light emitting element is characterized by low voltage drive and long life. In addition, it is characterized by high heat resistance. The display portion 9203 which includes the light emitting elements has a similar feature. Therefore, in this computer, image quality is hardly deteriorated and a reduction in power consumption is achieved. With such features, a deterioration compensation function and a power supply circuit can be significantly removed or reduced in the computer, thereby achieving reductions in size and weight of the main body 9201 and the chassis 9202. Since a reduction in power consumption, an improvement in image quality, and reductions in size and weight thereof are achieved in the computer according to the present invention, a product which is suitable for living environment can be provided.

Figure 5C:
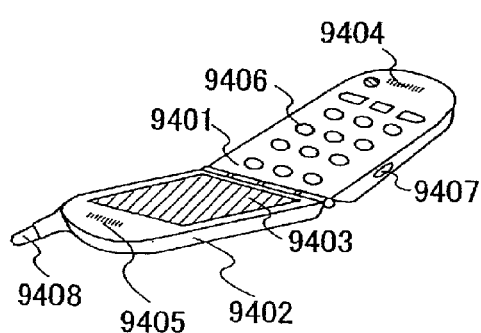

FIG. 5C shows a cellular phone according to the present invention, which includes a main body 9401, a chassis 9402, a display portion 9403, an audio input portion 9404, an audio output portion 9405, an operation key 9406, an external connection port 9407, an antenna 9408, and the like. In this cellular phone, the display portion 9403 includes light emitting elements which are similar to those described in Embodiments 2 to 4 and arranged in matrix. The light emitting element is characterized by low voltage drive and long life. It is also characterized by high heat resistance. The display portion 9403 which includes the light emitting elements also has a similar feature. Therefore, in this cellular phone, image quality is hardly deteriorated and a reduction in power consumption is achieved. With such features, a deterioration compensation function and a power supply circuit can be significantly removed or reduced in the cellular phone, thereby achieving reductions in size and weight of the main body 9401 and the chassis 9402. Since a reduction in power consumption, an improvement in image quality, and reductions in size and weight thereof are achieved in the cellular phone according to the present invention, a product which is suitable for being carried can be provided.

Figure 5D:
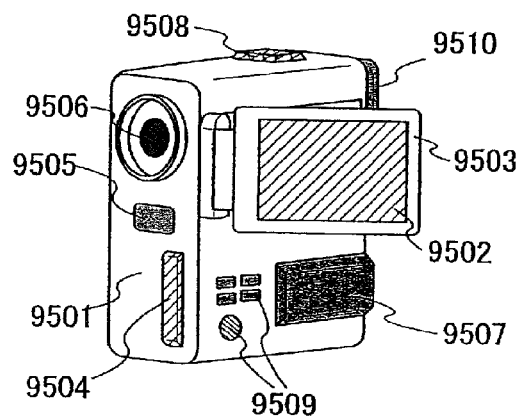

FIG. 5D shows a camera according to the present invention, which includes a main body 9501, a display portion 9502, a chassis 9503, an external connection port 9504, a remote control receiving portion 9505, an image receiving portion 9506, a battery 9507, an audio input portion 9508, an operation key 9509, an eye piece portion 9510, and the like. In this camera, the display portion 9502 includes light emitting elements which are similar to those described in Embodiments 2 to 4 and arranged in matrix. The light emitting element is characterized by low voltage drive and long life. It is also characterized by high heat resistance. The display portion 9502 which includes the light emitting elements also has similar features. Therefore, in this camera, image quality is hardly deteriorated and a reduction in power consumption is achieved. With such features, a deterioration compensation function and a power supply circuit can be significantly removed or reduced in the camera, thereby achieving reductions in size and weight of the main body 9501. Since a reduction in power consumption, an improvement in image quality, and reductions in size and weight thereof are achieved in the camera according to the present invention, a product which is suitable for being carried can be provided.

As described above, the applicable range of the light emitting device of the present invention is so wide that this light emitting device can be applied to electronic devices of various fields. By using the aromatic amine compound of the present invention, an electronic device including a display portion which consumes less power, has a long life, and has high heat resistance can be provided.

In addition, the light emitting device of the present invention can be used as a lighting system. One mode of using the light emitting element of the present invention as a lighting system is explained with reference to FIG. 6.

Figure 6:
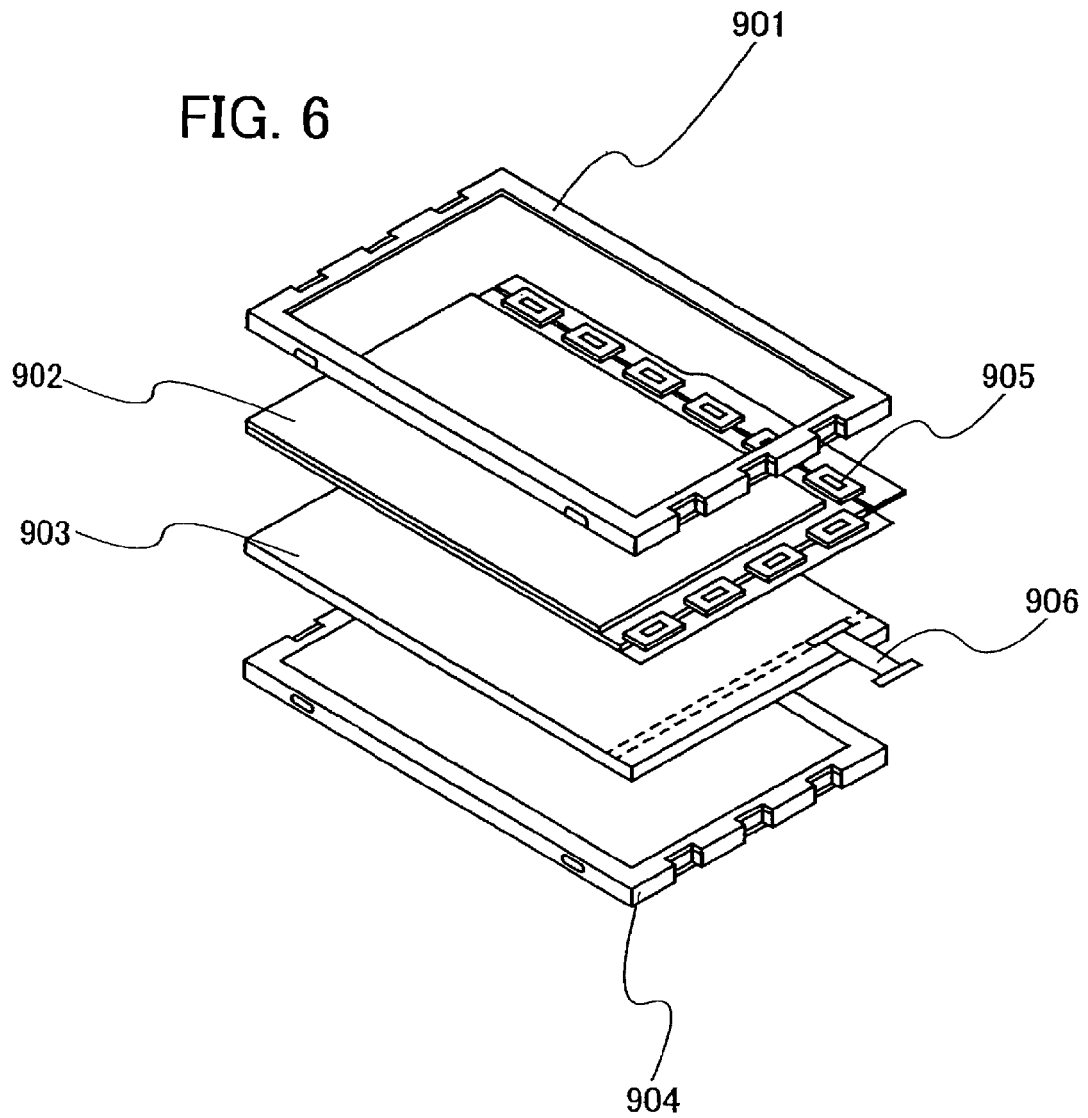
FIG. 6 is a diagram for explaining an electronic device of the present invention.

FIG. 6 shows an example of a liquid crystal display device using the light emitting device of the present invention as a backlight. The liquid crystal display device shown in FIG. 6 includes a chassis 901, a liquid crystal layer 902, a backlight 903, and a chassis 904. The liquid crystal layer 902 is connected to a driver IC 905. The light emitting device of the present invention is used as the backlight 903, to which a current is supplied through a terminal 906.

By using the light emitting device of the present invention as a backlight of a liquid crystal display device, a backlight which consumes less power can be obtained. Since the light emitting device of the present invention is a plane-emission lighting system and can be formed to have a large area, a larger-area backlight can be obtained and a larger-area liquid crystal display device can also be obtained. Furthermore, the light emitting device of the present invention is thin and consumes less power, therefore, reductions in thickness and power consumption of the display device can also be achieved. Moreover, since the light emitting device of the present invention has a long life and excellent heat resistance, a liquid crystal display device also has a long life and excellent heat resistance.

Example 1

A method for synthesizing N,N',N"-triphenyl-N,N',N"-tris (9-phenylcarbazol-3-yl)-benzene-1,3,5-triamine (abbr.: PCA3B) represented by Structural Formula (21) as an example of the aromatic amine compound of the present invention is explained.

(21)

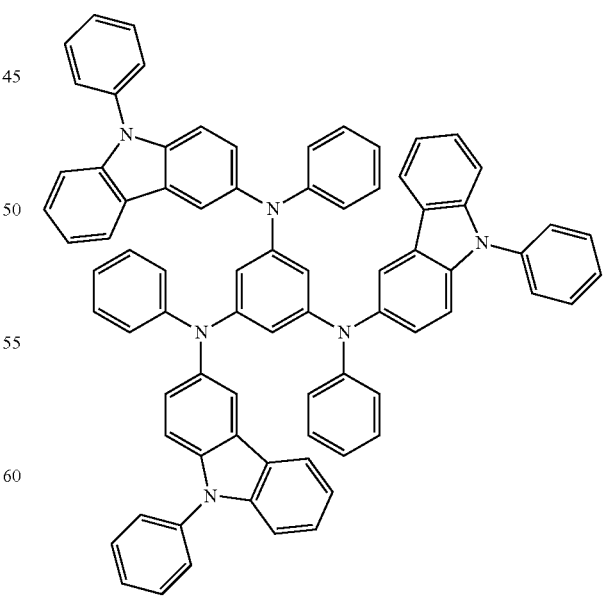

[Step 1]

First, a method for synthesizing 3-bromo-9-phenylcarbazole is explained. A synthetic scheme of 3-bromo-9-phenylcarbazole is shown in (B-1).

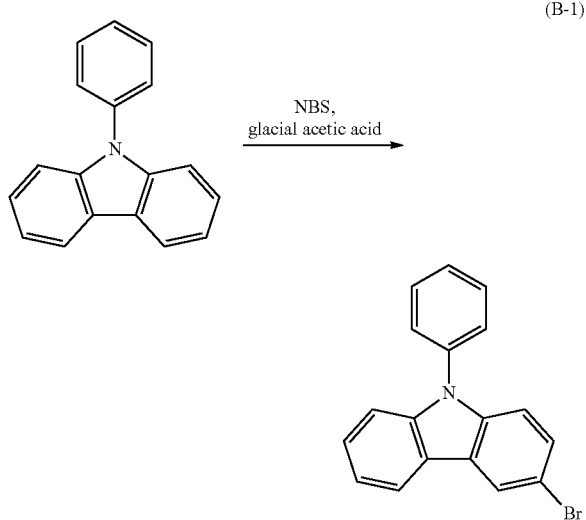

(B-1)

24.3 g (100 mmol) of 9-phenylcarbazole was dissolved in 600 mL of a glacial acetic acid, 17.8 g (100 mmol) of N-bromosuccinimide was gradually added thereto, and the mixture was stirred for approximately 20 hours at a room temperature. This glacial acetic acid solution was dropped into 1 L of ice water while stirring. The precipitated white solid was washed with water three times. This solid was dissolved in 150 mL of diethyl ether and the solution was washed with a saturated aqueous sodium hydrogen carbonate solution and water. An organic layer thereof was dried with magnesium sulfate. The organic layer was filtered, and the obtained filtrate was concentrated, where about approximately 50 mL of methanol was added and dissolved uniformly. The white solid was precipitated by leaving this solution at rest. This solid was recovered and dried, thereby obtaining 28.4 g (yield: 88%) of 3-bromo-9-phenylcarbazole as a white powder.

[Step 2]

Next, a method for synthesizing 3-(N-phenylamino)-9-phenylcarbazole (abbr.: PCA) is explained. A synthetic scheme of PCA is shown in (B-2).

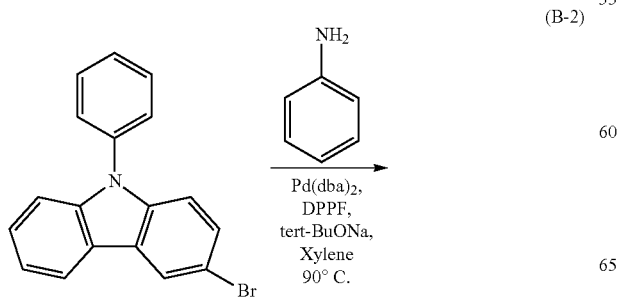

(B-2)

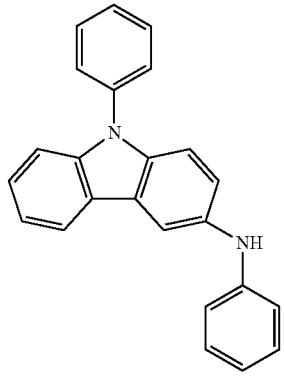

After putting 19 g (60 mmol) of 3-bromo-9-phenylcarbazole, 340 mg (0.6 mmol) of bis(dibenzylideneacetone)palladium(0), 1.6 g (3.0 mmol) of 1,1-bis(diphenylphosphino)ferrocene, and 13 g (180 mmol) of sodium tert-butoxide into a three-neck flask and replacing the air in the flask with nitrogen, 110 mL of anhydrous xylene and 7.0 g (75 mmol) of aniline were added. This was stirred for 7.5 hours while heating at 90° C. in a nitrogen atmosphere. After the reaction, about 500 mL of hot toluene was added to the suspension and the mixture was filtered through florisil, alumina, and Celite®. The obtained filtrate was concentrated and hexane-ethyl acetate was added thereto, and then the mixture was irradiated with ultrasonic waves. The obtained suspension was filtered and the residue was dried, thereby obtaining 15 g (yield: 75%) of 3-(N-phenylamino)-9-phenylcarbazole (abbr.: PCA) as a cream-colored powder.

Figure 7A:
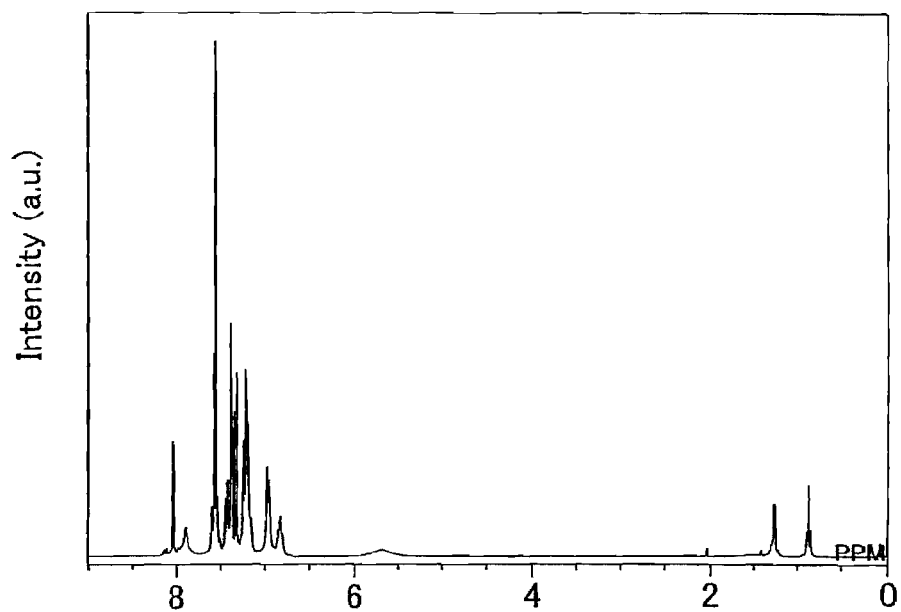
FIGS. 7A and 7B are diagrams showing $^1$H NMR charts of 3-(N-phenylamino)-9-phenylcarbazole.
Figure 7B:
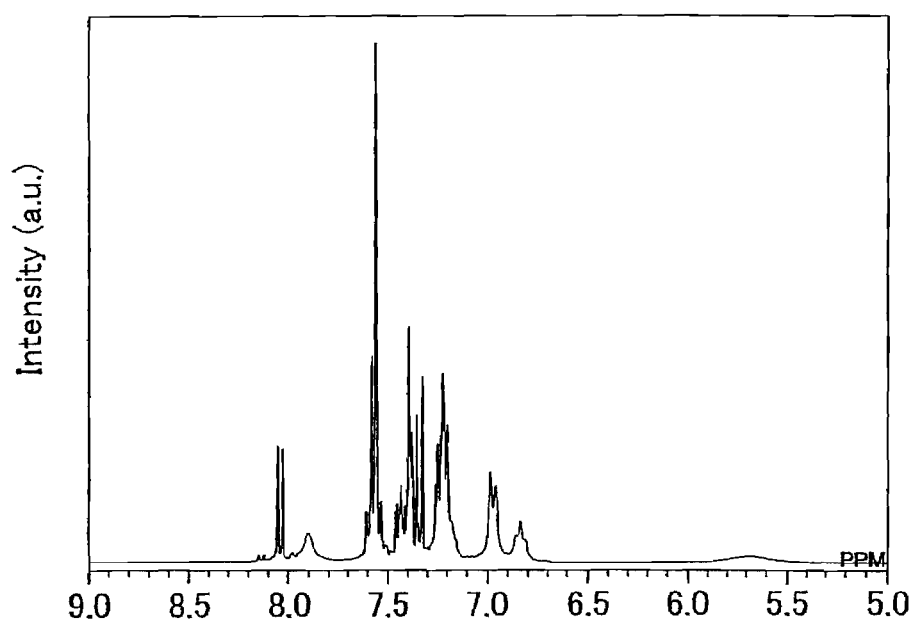

A result of proton nuclear magnetic resonance spectrometry ($^1$H NMR) analysis is as follows. $^1$H NMR (300 MHz, CDCl$_3$); δ=5.69 (s, 1H), 6.84 (t, J=6.9 Hz, 1H), 6.97 (d, J=7.8 Hz, 2H), 7.20-7.61 (m, 12H), 7.90 (s, 1H), 8.04 (d, J=7.8 Hz, 1H). FIG. 7A shows a $^1$H NMR chart, and FIG. 7B shows an enlarged view of FIG. 7A in a portion of 5.0 ppm to 9.0 ppm.

In addition, a result of nuclear magnetic resonance spectrometry analysis when using DMSO as a solvent is shown. $^1$HNMR (300 MHz, DMSO-d$_6$); δ=6.73 (t, J=7.5 Hz, 1H), 7.02 (d, J=8.1 Hz, 2H), 7.16-7.70 (m, 12H), 7.95 (s, 1H), 8.06 (s, 1H), 8.17 (d, J=7.8 Hz, 1H). $^{13}$C NMR (75.5 MHz, DMSO-d$_6$); δ=109.55, 110.30, 110.49, 114.71, 118.22, 119.70, 120.14, 120.61, 122.58, 123.35, 126.18, 126.48, 127.37, 129.15, 130.14, 135.71, 136.27, 137.11, 140.41, 145.61.

[Step 3]

Next, a method for synthesizing N,N',N''-triphenyl-N,N',N''-tris(9-phenylcarbazol-3-yl)-benzene-1,3,5-triamine (abbr.: PCA3B) represented by Structural Formula (21) is explained. A synthetic scheme of PCA3B is shown in (B-3).

(B-3)

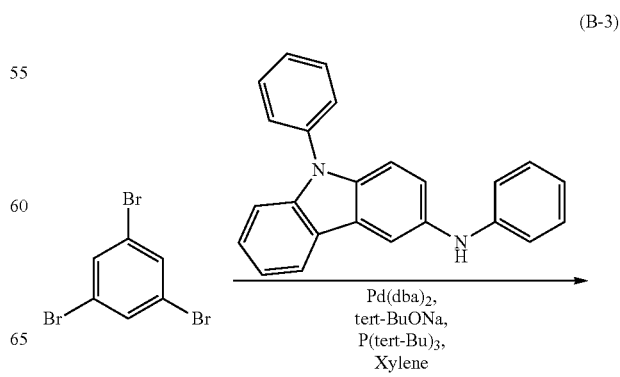

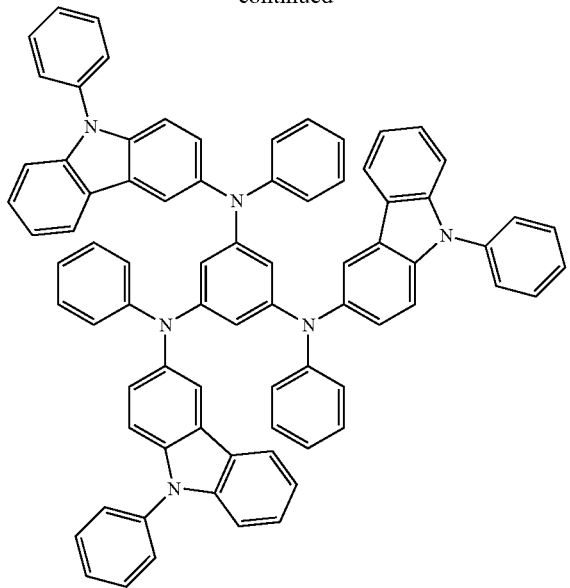

After putting L9 g (6.0 mmol) of 1,3,5-tribromobenzene, 6.4 g (19 mmol) of PCA obtained in Step 2, 580 mg (1.0 mmol) of bis(dibenzylideneacetone)palladium(0), and 4.0 g (40 mmol) of sodium tert-butoxide into a three-neck flask and replacing the air in the flask with nitrogen, 30 mL of anhydrous xylene was added and the mixture was deaerated for 3 minutes until no more bubble comes out. 6.0 mL (3.0 mmol) of tri(tert-butyl)phosphine (a 10 wt % hexane solution) was added, and the mixture was stirred in a nitrogen atmosphere while heating at 90° C. After 3.5 hours, heating was stopped and about 500 mL of toluene was added to this reaction solution, and the mixture was filtered through florisil and Celite®. The obtained filtrate was washed with water and dried by adding magnesium sulfate. This solution was filtered; the obtained filtrate was concentrated and separated by silica gel column chromatography (toluene: hexane=2:3). The obtained solution was concentrated; hexane was added; and the mixture was irradiated with ultrasonic waves. The produced solid was filtered off and dried, thereby obtaining 2.0 g (yield: 34%) of N,N',N''-triphenyl-N,N',N''-tris(9-phenylcarbazol-3-yl)-benzene-1,3,5-triamine (abbr.: PCA3B) as a light bright golden yellow powder.

Figure 8A:
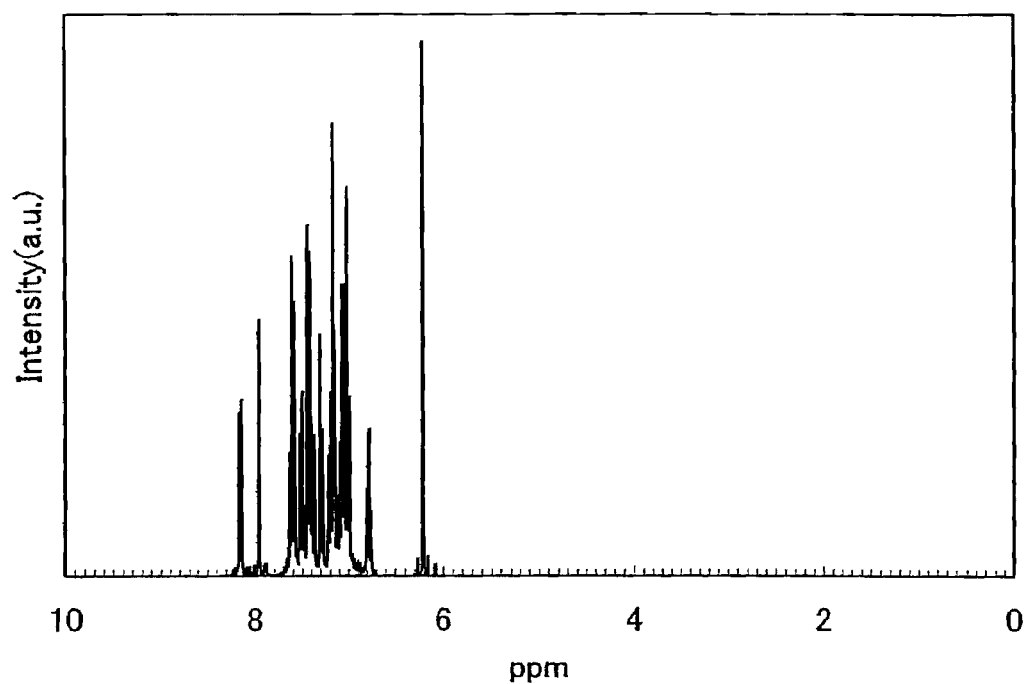
FIGS. 8A and 8B are diagrams showing $^1$H NMR charts of N,N',N''-triphenyl-N,N',N''-tris(9-phenylcarbazol-3-yl)-benzene-1,3,5-triamine that is an aromatic amine compound of the present invention.
Figure 8B:
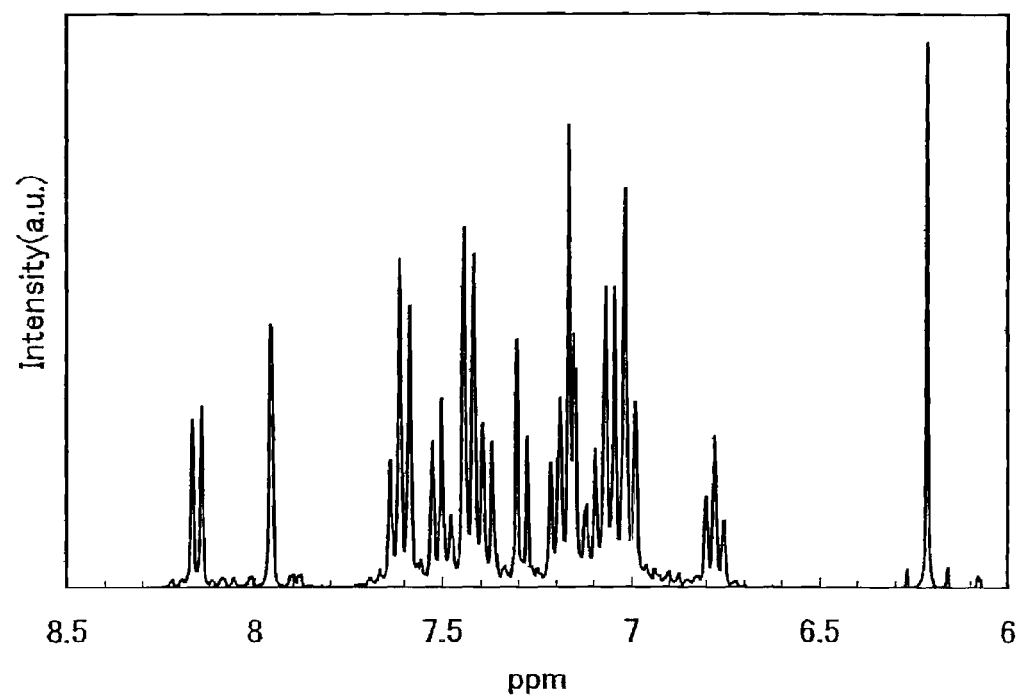

A result of proton nuclear magnetic resonance spectrometry ($^1$H NMR) analysis is as follows. $^1$H NMR (300 MHz, DMSO-$d_6$); δ=6.21 (s, 3H), 6.78 (t, J=6.9 Hz, 3H), 6.99-7.21 (m, 21H), 7.29 (d, J=8.4 Hz, 3H), 7.37-7.53 (m, 12H), 7.61 (t, J=7.8, 6H), 7.96 (d, J=1.5 Hz, 3H), 8.16 (d, J=7.5 Hz, 3H). FIG. 8A shows a $^1$H NMR chart, and FIG. 8B shows an enlarged view of FIG. 8A in a portion of 6.0 ppm to 8.5 ppm.

Figure 11:
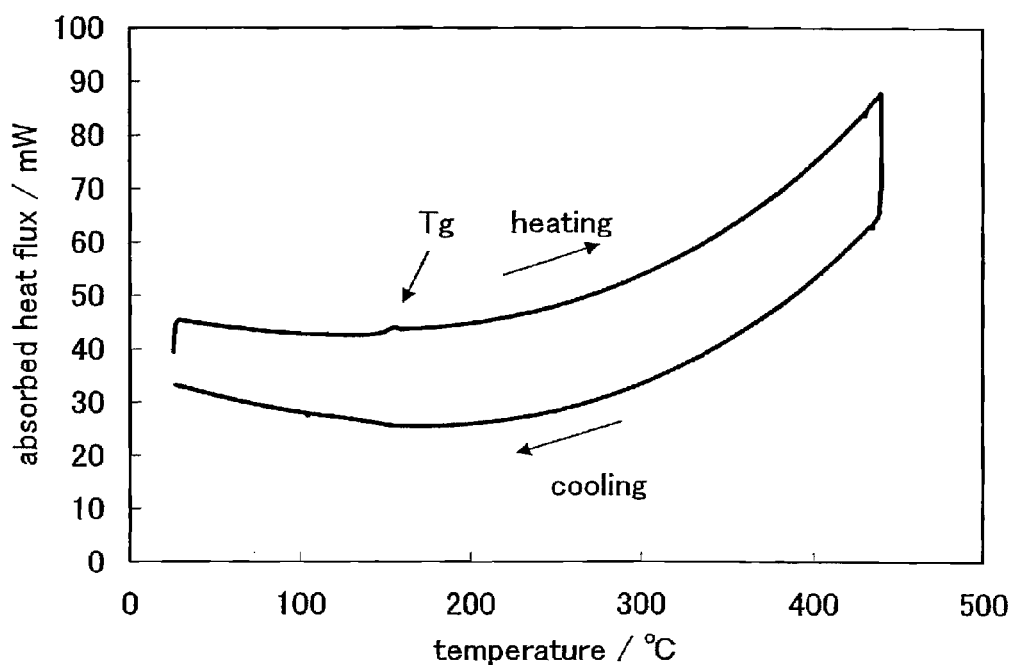
FIG. 11 is a diagram showing a DSC chart of N,N',N''-triphenyl-N,N',N''-tris(9-phenylcarbazol-3-yl)-benzene-1,3,5-triamine that is an aromatic amine compound of the present invention.

In addition, a glass transition point was measured using a differential scanning calorimeter (DSC, manufactured by Perkin Elmer Co., Ltd., Pyris 1). First, a sample was heated to 440° C. at 40° C./min and then cooled to a room temperature at 40° C./min. Subsequently, the temperature is raised to 440° C. at 10° C./min and cooled to a room temperature at 40° C./min, thereby obtaining a DSC chart of FIG. 11. This chart shows that a glass transition point (Tg) of PCA3B is 146° C. This indicates that PCA3B has a high glass transition point. Note that in this measurement, a heat absorption peak which indicates a melting point was not observed.

Figure 9:
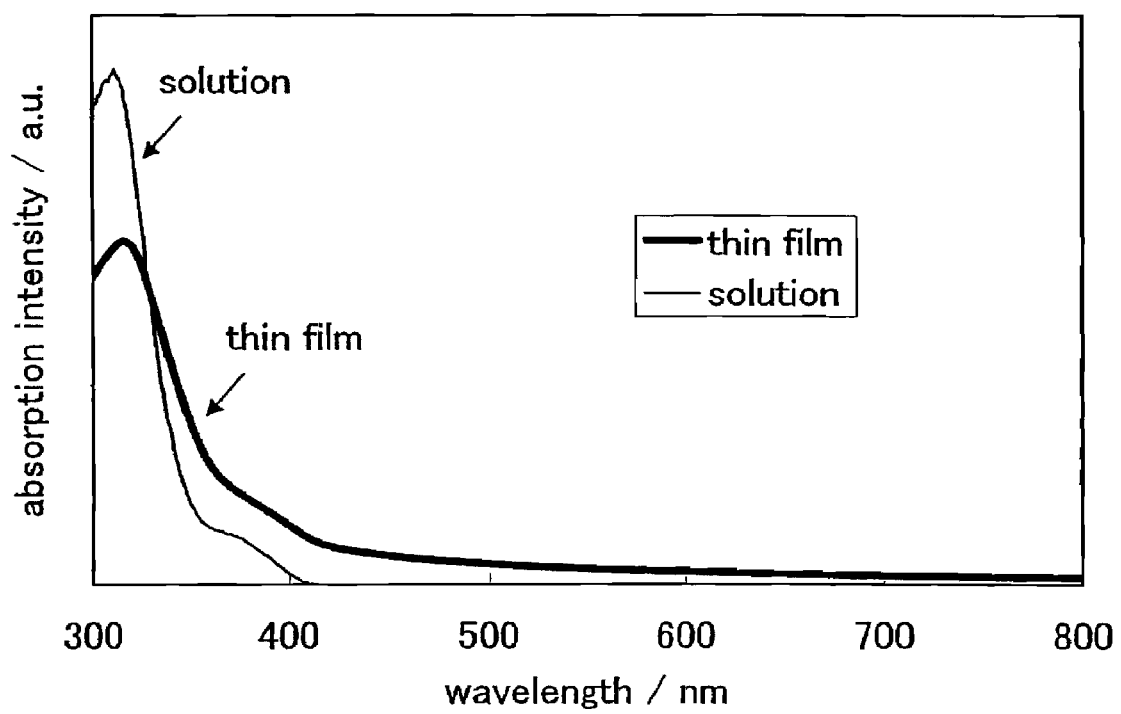
FIG. 9 is a diagram showing absorption spectra in a toluene solution and of a thin film of N,N',N''-triphenyl-N,N',N''-tris(9-phenylcarbazol-3-yl)-benzene-1,3,5-triamine that is an aromatic amine compound of the present invention.
Figure 10:
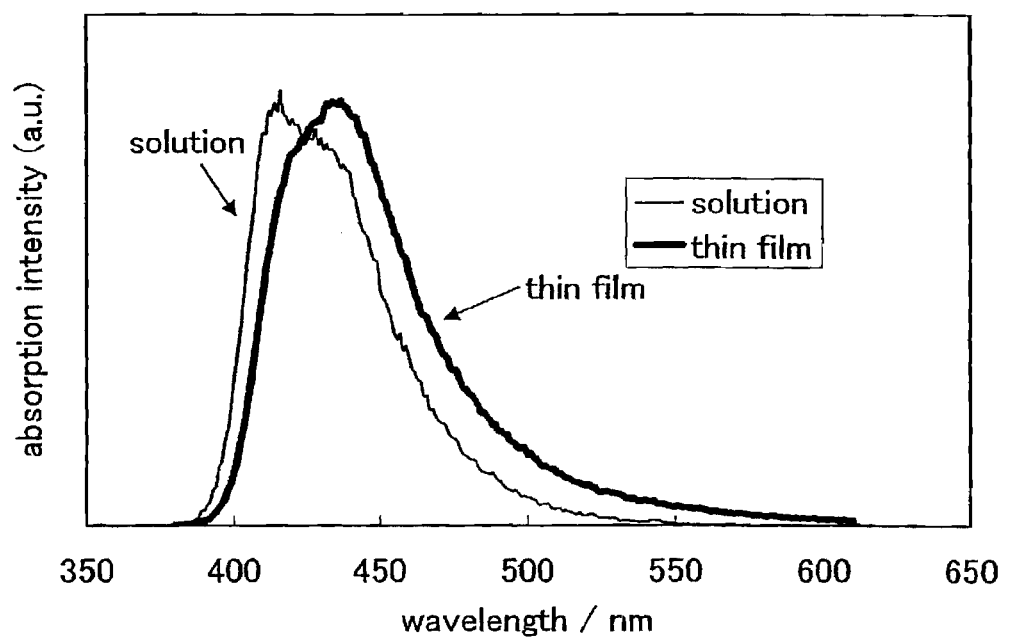
FIG. 10 is a diagram showing emission spectra in a toluene solution and of a thin film of N,N',N''-triphenyl-N,N',N''-tris(9-phenylcarbazol-3-yl)-benzene-1,3,5-triamine that is an aromatic amine compound of the present invention.

Absorption spectra of a toluene solution of PCA3B and a thin film of PCA3B are shown in FIG. 9. An ultraviolet-visible spectrophotometer (V-550, manufactured by JASCO Corporation) was used for the measurement. The solution was put in a quartz cell and the thin film was evaporated over a quartz substrate as samples, and absorption spectra of them, from which an absorption spectrum of quartz was subtracted, are shown in FIG. 9. In FIG. 9, the horizontal axis indicates wavelength (nm) and the vertical axis indicates absorption intensity (arbitrary unit). Absorption was observed at around 311 nm and 370 nm in the case of the toluene solution, and at around 316 nm and 380 nm in the case of the thin film. Emission spectra of the toluene solution (excitation wavelength: 320 nm) of PCA3B and the thin film (excitation wavelength: 311 nm) of PCA3B are shown in FIG. 10. In FIG. 10, the horizontal axis indicates wavelength (nm) and the vertical axis indicates emission intensity (arbitrary unit). The maximum emission wavelength was 416 nm (excitation wavelength: 320 nm) in the case of the toluene solution and 437 nm (excitation wavelength: 311 nm) in the case of the thin film.

As a result of measuring the HOMO level of PCA3B in a thin-film state by using a photoelectron spectrometer (AC-2, manufactured by Riken Keiki Co., Ltd.) in the atmosphere, it was −5.31 eV. Furthermore, as a result of obtaining an absorption edge from a Tauc plot using data of the absorption spectrum of the thin film of PCA3B in FIG. 9 and evaluating the absorption edge as an optical energy gap, the energy gap was 2.99 eV. Thus, the LUMO level is −2.32 eV.

In addition, an oxidation reaction characteristic of PCA3B was measured. The oxidation reaction characteristic was examined by a cyclic voltammetry (CV) measurement. Note that an electrochemical analyzer (ALS model 600A, manufactured by BAS Inc.) was used for the measurement.

As for a solution used in the CV measurement, anhydrous dimethylformamide (DMF) (manufactured by Aldrich Chemical Company, 99.8%, catalog number: 22705-6) was used as a solvent. Tetra-n-butylammonium perchlorate (n-Bu$_4$NClO$_4$) (manufactured by Tokyo Chemical Industry Co., Ltd., catalog number: T0836), which was a supporting electrolyte, was dissolved in the solvent so that the concentration of the tetra-n-butylammonium perchlorate was 100 mmol/L. Further, an object to be measured was dissolved therein so that the concentration thereof was 1 mmol/L. Thus, the solution was prepared. Further, a platinum electrode (PTE platinum electrode, manufactured by BAS Inc.) was used as a work electrode. A platinum electrode (VC-3 Pt counter electrode (5 cm), manufactured by BAS Inc.) was used as an auxiliary electrode. An Ag/Ag$^+$ electrode (RE 5 nonaqueous reference electrode, manufactured by BAS Inc.) was used as a reference electrode. Note that the measurement was carried out at a room temperature.

The oxidation reaction characteristic of PCA3B was examined as follows. A scan for changing a potential of the work electrode with respect to the reference electrode from 0.9 V to −0.04 V after changing it from −0.04 V to 0.9 V was regarded as one cycle, and measurement was performed for 100 cycles. Note that a scan rate of the CV measurement was set to be 0.1 V/s.

Figure 12:
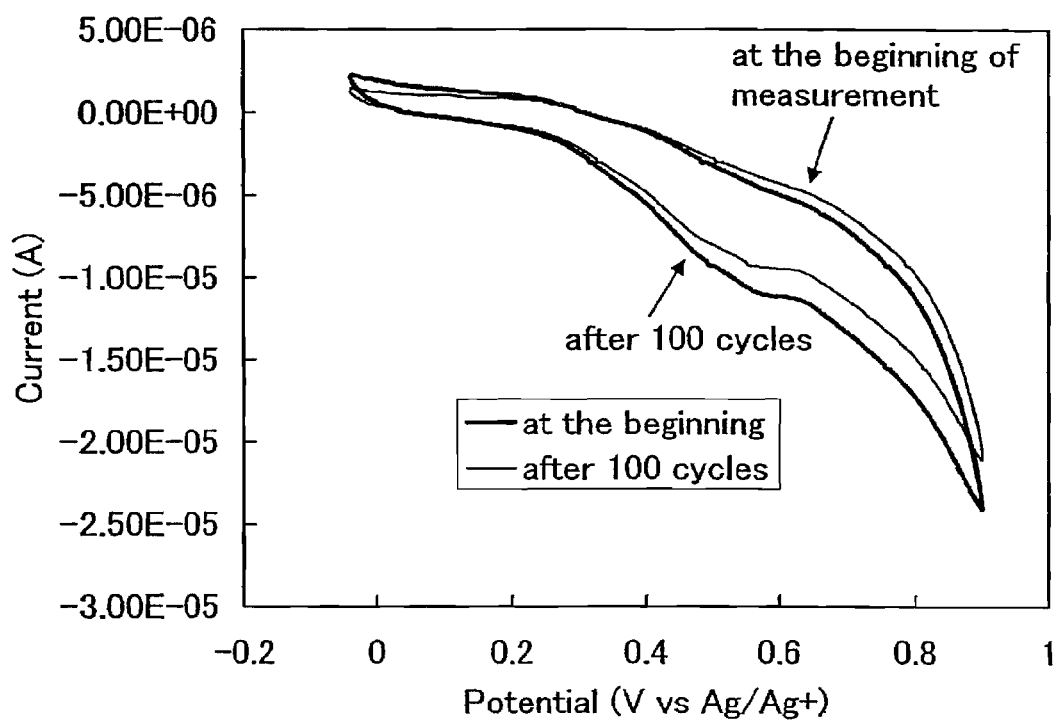
FIG. 12 is a diagram showing CV measurement results of N,N',N''-triphenyl-N,N',N''-tris(9-phenylcarbazol-3-yl)-benzene-1,3,5-triamine that is an aromatic amine compound of the present invention.

Results of examining the oxidation reaction characteristic of PCA3B are shown in FIG. 12. In FIG. 12, the horizontal axis indicates a potential (V) of the work electrode with respect to the reference electrode, whereas the vertical axis indicates the value of current flowing between the work electrode and the auxiliary electrode (1×10$^{-5}$ A).

According to FIG. 12, currents indicating oxidation were observed at around 0.4 V, 0.5 V, and 0.6 V (vs. Ag/Ag$^+$ electrode). Although the scanning was repeated for 100 cycles, changes in peak position and peak intensity of a CV curve were hardly seen in the oxidation reaction. Accordingly, it was found that the aromatic amine compound of the present invention was extremely stable with respect to oxidation reaction and subsequent reduction reaction (that is, the repetition of oxidation).

Comparative Example 1

As a comparative example, a glass transition point of 1,3,5-tris{N-(4-diphenylaminophenyl)amino}benzene described in Reference 1 was measured.

Figure 37:
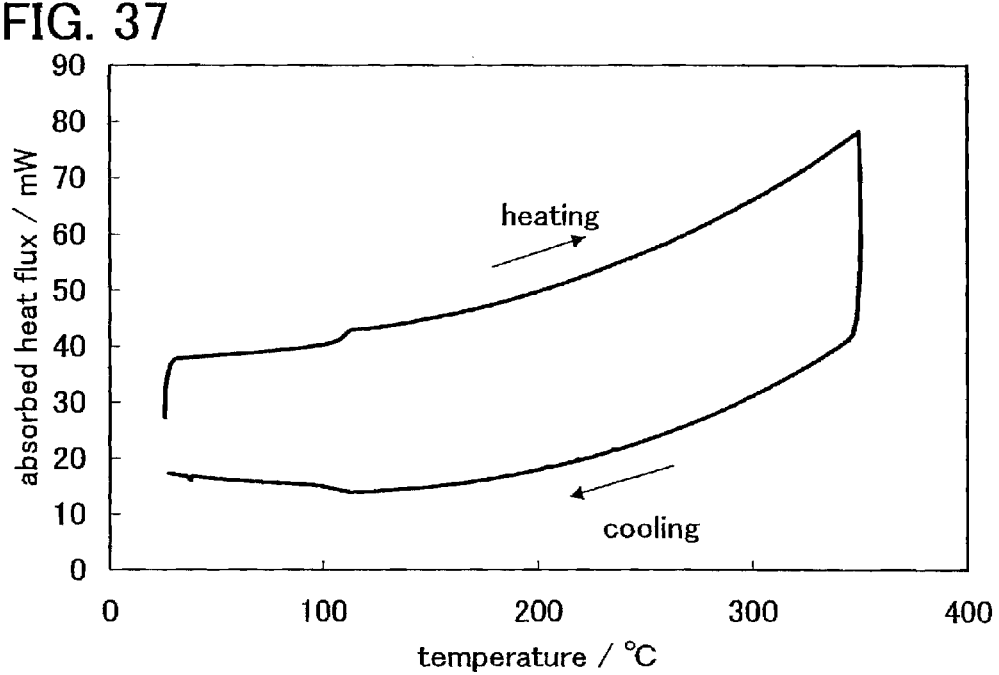
FIG. 37 is a diagram showing a DSC chart of 1,3,5-tris{N-(4-diphenylaminophenyl)amino}benzene.

The glass transition point was measured using a differential scanning calorimeter (DSC, manufactured by Perkin Elmer Co., Ltd., Pyris 1) similarly to Example 1. First, a sample was melted by being heated to 350° C. at 40° C./min and was then cooled to a room temperature at 40° C./min. Subsequently, the temperature was raised to 350° C. at 10° C./min and cooled to a room temperature at 40° C./min, thereby obtaining a DSC chart of FIG. 37. This chart shows that a glass transition point (Tg) of 1,3,5-tris{N-(4-diphenylaminophenyl)amino}benzene is 106° C. Note that in the DSC chart at the time when the sample was first melted, a heat absorption peak indicating a melting point was observed, and the melting point was 236° C. Note that it is described in Reference 1 that the glass transition point is 108° C. and the melting point is 240° C.

Accordingly, it is found that the aromatic amine compound of the present invention has a higher glass transition point than 1,3,5-tris{N-(4-diphenylaminophenyl)amino}benzene described in Reference 1 and has excellent heat resistance.

Example 2

A method for synthesizing N,N'-bis(9-phenylcarbazol-3-yl)-N,N'-diphenyl-benzene-1,3-diamine (abbr.: PCA2B) represented by Structural Formula (51) as an example of the aromatic amine compound of the present invention is explained.

(51)

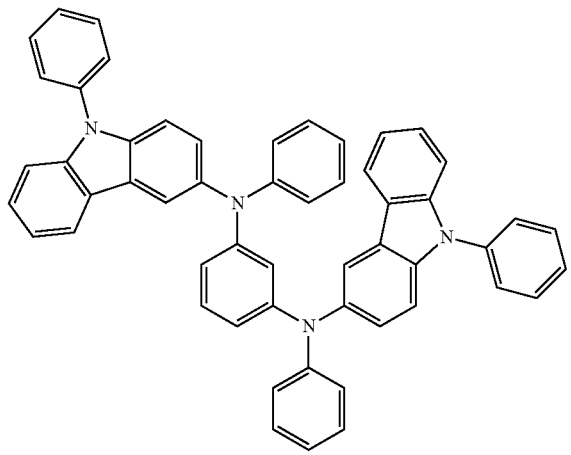

[Step 1]
A method for synthesizing PCA2B is explained. A synthetic scheme of PCA2B is shown in (B-4).

(B-4)

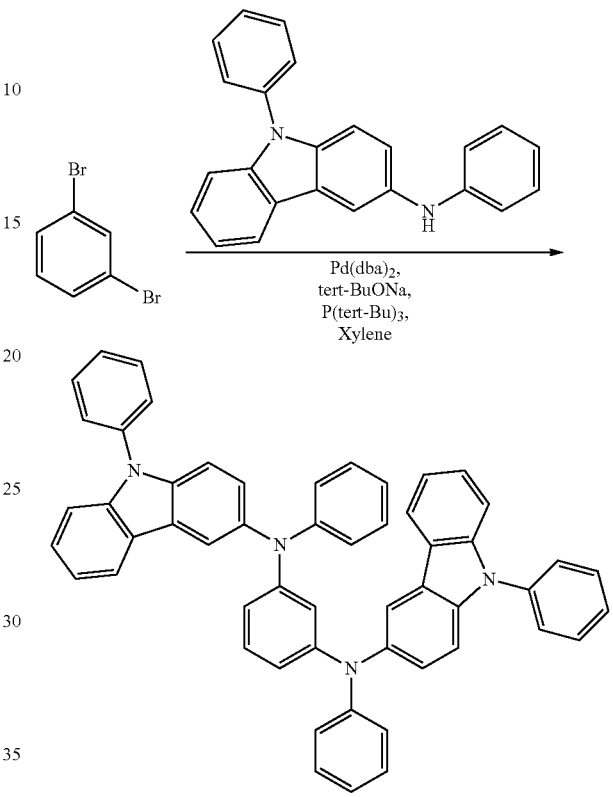

After putting 1.18 g (5.0 mmol) of 1,3-dibromobenzene, 3.3 g (10 mmol) of PCA synthesized in Step 2 of Example 1, 580 mg (1.0 mmol) of bis(dibenzylideneacetone)palladium (0), and 3.0 g (30 mmol) of sodium tert-butoxide into a three-neck flask and replacing the air in the flask with nitrogen, 20 mL of anhydrous xylene was added thereto and the mixture was deaerated for 3 minutes until no more bubble comes out. 6 mL (3 mmol) of tri(tert-butyl)phosphine (a 10 wt % hexane solution) was added, and the mixture was stirred in a nitrogen atmosphere while heating at 90° C. After 5.0 hours, heating was stopped, and about 200 mL of toluene was added to this reaction solution, and the solution was filtered through florisil and Celite®. The obtained filtrate was washed with water and dried by adding magnesium sulfate. This solution was filtered; the obtained filtrate was concentrated and separated by silica gel column chromatography (toluene: hexane=2:3). The obtained solution was concentrated; hexane was added; and the mixture was irradiated with ultrasonic waves. The produced solid was filtered off and dried, thereby obtaining 2.0 g (yield: 54%) of N,N'-bis(9-phenylcarbazol-3-yl)-N,N'-diphenyl-benzene-1,3-diamene (abbr.: PCA2B) as a light-cream-colored powder.

Figure 13A:
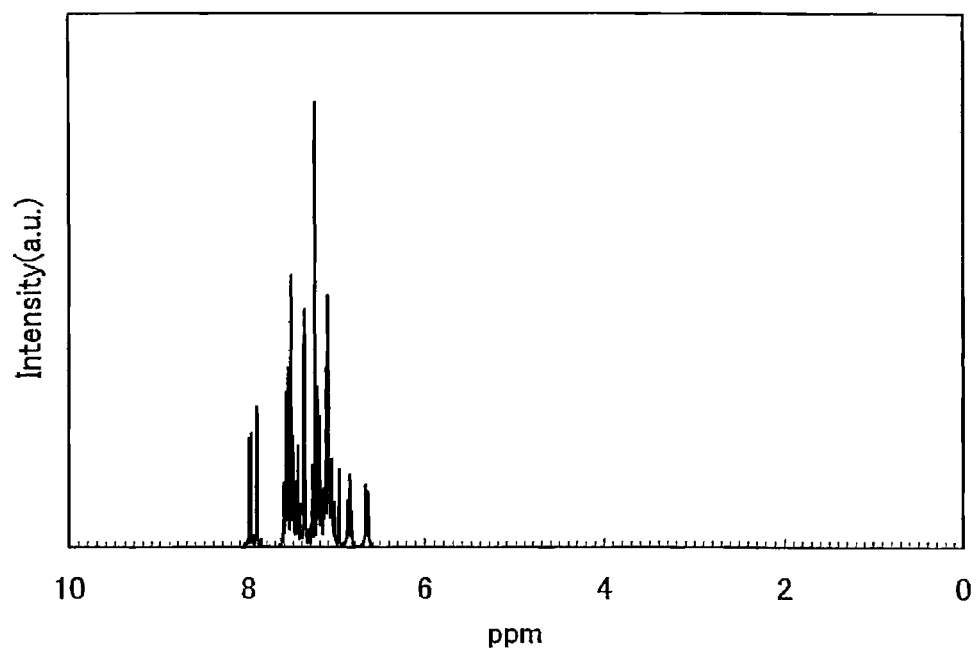
FIGS. 13A and 13B are diagrams showing $^1$H NMR charts of N,N'-bis(9-phenylcarbazol-3-yl)-N,N'-diphenyl-benzene-1,3-diamine that is an aromatic amine compound of the present invention.
Figure 13B:
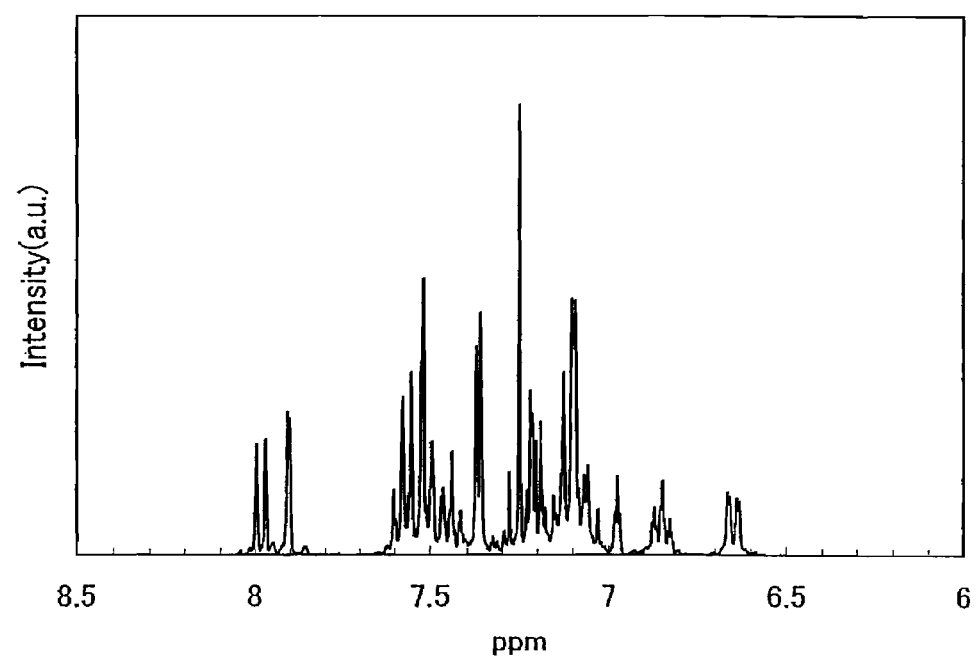

A result of proton nuclear magnetic resonance spectrometry ($^1$H NMR) analysis is as follows. $^1$H NMR (300 MHz, CDCl$_3$); δ=6.65 (dd, J=8.1 Hz, 2.1 Hz, 2H), 6.83-6.88 (m, 2H), 6.98 (t, J=2.1 Hz, 1H), 7.03-7.28 (m, 15H), 7.37 (d, J=3.3 Hz, 4H), 7.42-7.60 (m, 10H), 7.90 (d, J=2.1 Hz, 2H), 7.98 (d, J=7.8 Hz, 2H). FIG. 13A shows a $^1$H NMR chart, and FIG. 13B shows an enlarged view of FIG. 13A in a portion of 6.0 ppm to 8.5 ppm.

Figure 16:
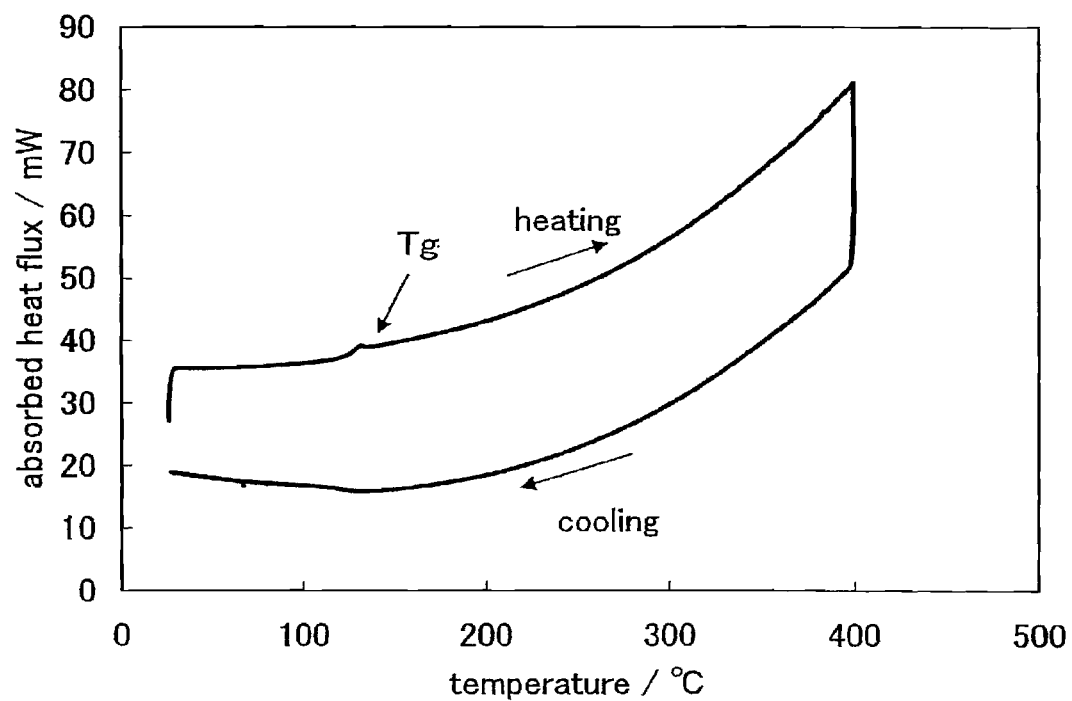
FIG. 16 is a diagram showing a DSC chart of N,N'-bis(9-phenylcarbazol-3-yl)-N,N'-diphenyl-benzene-1,3-diamine that is an aromatic amine compound of the present invention.

In addition, a glass transition point was measured using a differential scanning calorimeter (DSC, manufactured by PerkinElmer Co., Ltd., Pyris 1). First, a sample was heated to 400° C. at 40° C./min and then cooled to a room temperature at 40° C./min. Subsequently, the temperature was raised to 400° C. at 10° C./min and cooled to a room temperature at 40° C./min, thereby obtaining a DSC chart of FIG. 16. This chart shows that a glass transition point (Tg) of PCA2B is 124° C. This indicates that PCA2B has a high glass transition point. Note that in this measurement, a heat absorption peak which indicates a melting point was not observed.

Figure 14:
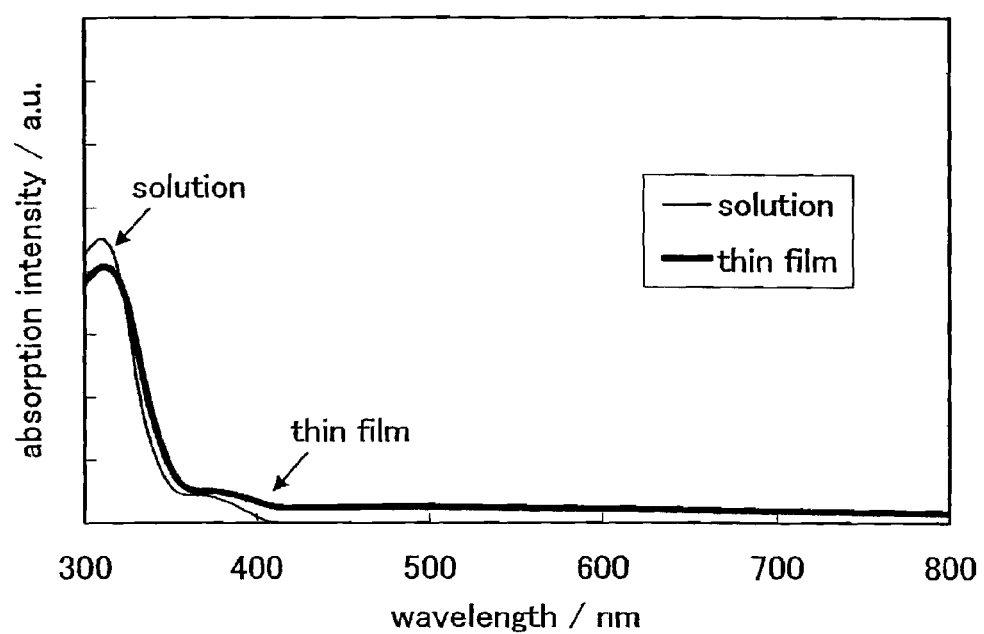
FIG. 14 is a diagram showing absorption spectra in a toluene solution and of a thin film of N,N'-bis(9-phenylcarbazol-3-yl)-N,N'-diphenyl-benzene-1,3-diamine that is an aromatic amine compound of the present invention.
Figure 15:
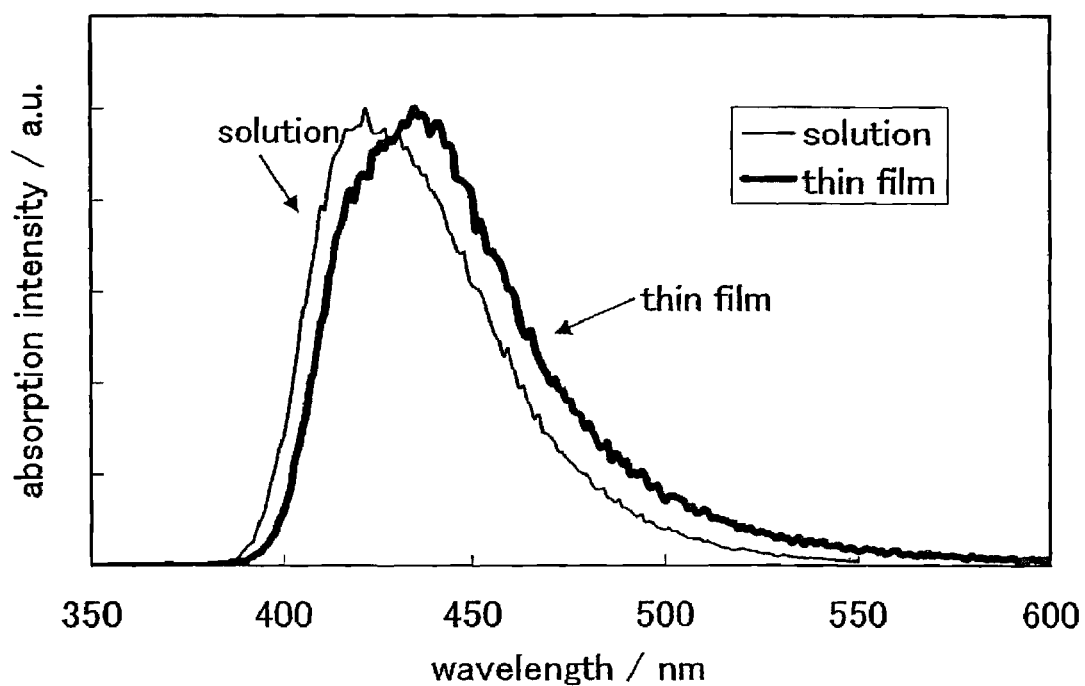
FIG. 15 is a diagram showing emission spectra in a toluene solution and of a thin film of N,N'-bis(9-phenylcarbazol-3-yl)-N,N'-diphenyl-benzene-1,3-diamine that is an aromatic amine compound of the present invention.

FIG. 14 shows absorption spectra of a toluene solution of PCA2B and a thin film of PCA2B. An ultraviolet-visible spectrophotometer (V-550, manufactured by JASCO Corporation) was used for the measurement. The solution was put in a quartz cell and the thin film was evaporated over a quartz substrate as samples, and absorption spectra of them, from which an absorption spectrum of quartz was subtracted, are shown in FIG. 14. In FIG. 14, the horizontal axis indicates wavelength (nm) and the vertical axis indicates absorption intensity (arbitrary unit). Absorption was observed at around 309 nm and 370 nm in the case of the toluene solution, and at around 311 nm and 380 nm in the case of the thin film. Emission spectra of the toluene solution (excitation wavelength: 325 nm) of PCA2B and the thin film (excitation wavelength: 311 nm) of PCA2B are shown in FIG. 15. In FIG. 15, the horizontal axis indicates wavelength (nm) and the vertical axis indicates emission intensity (arbitrary unit). The maximum emission wavelength was 422 nm (excitation wavelength: 325 nm) in the case of the toluene solution, and 435 nm (excitation wavelength: 311 nm) in the case of the thin film.

As a result of measuring the HOMO level in a thin-film state by using a photoelectron spectrometer (AC-2, manufactured by Riken Keiki Co., Ltd.) in the atmosphere, it was −5.28 eV. Furthermore, as a result of obtaining an absorption edge from a Tauc plot using data of the absorption spectrum of the thin film of PCA2B in FIG. 14 and evaluating the absorption edge as an optical energy gap, the energy gap was 2.98 eV. Thus, the LUMO level is −2.30 eV.

In addition, an oxidation reaction characteristic of PCA2B was measured. The oxidation reaction characteristic was examined by a cyclic voltammetry (CV) measurement. Note that an electrochemical analyzer (ALS model 600A, manufactured by BAS Inc.) was used for the measurement.

As for a solution used in the CV measurement, anhydrous dimethylformamide (DMF) (manufactured by Aldrich Chemical Company, 99.8%, catalog number: 22705-6) was used as a solvent. Tetra-n-butylammonium perchlorate (n-Bu$_4$NClO$_4$) (manufactured by Tokyo Chemical Industry Co., Ltd., catalog number: T0836), which was a supporting electrolyte, was dissolved in the solvent so that the concentration of the tetra-n-butylammonium perchlorate was 100 mmol/L. Further, an object to be measured was dissolved therein so that the concentration thereof was 1 mmol/L. Thus, the solution was prepared. Further, a platinum electrode (PTE platinum electrode, manufactured by BAS Inc.) was used as a work electrode. A platinum electrode (VC-3 Pt counter electrode (5 cm), manufactured by BAS Inc.) was used as an auxiliary electrode. An Ag/Ag$^+$ electrode (RE 5 nonaqueous reference electrode, manufactured by BAS Inc.) was used as a reference electrode. Note that the measurement was carried out at a room temperature.

The oxidation reaction characteristic of PCA2B was examined as follows. A scan for changing a potential of the work electrode with respect to the reference electrode from 0.7 V to 0.05 V after changing it from 0.05 V to 0.7 V, was regarded as one cycle, and measurement was performed for 100 cycles. Further, a scan rate of the CV measurement was set to be 0.1 V/s.

Figure 17:
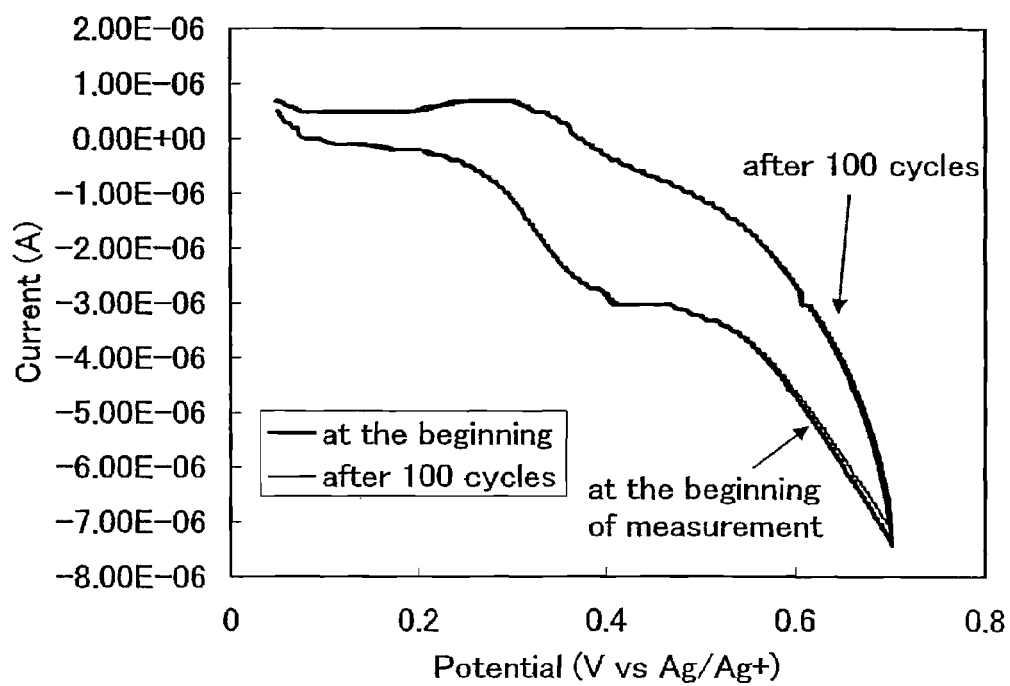
FIG. 17 is a diagram showing CV measurement results of N,N'-bis(9-phenylcarbazol-3-yl)-N,N'-diphenyl-benzene-1,3-diamine that is an aromatic amine compound of the present invention.

Results of examining the oxidation reaction characteristic of PCA2B are shown in FIG. 17. In FIG. 17, the horizontal axis indicates a potential (V) of the work electrode with respect to the reference electrode, whereas the vertical axis indicates the value of current flowing between the work electrode and the auxiliary electrode (1×10$^{-5}$ A).

According to FIG. 17, a current indicating oxidation was observed at around 0.4 V (vs. Ag/Ag$^+$ electrode). Although the scanning was repeated for 100 cycles, changes in peak position and peak intensity of a CV curve were hardly seen in the oxidation reaction. Accordingly, it was found that the aromatic amine compound of the present invention was extremely stable with respect to oxidation reaction and subsequent reduction reaction (that is, repetition of oxidation).

Example 3

Figure 30:
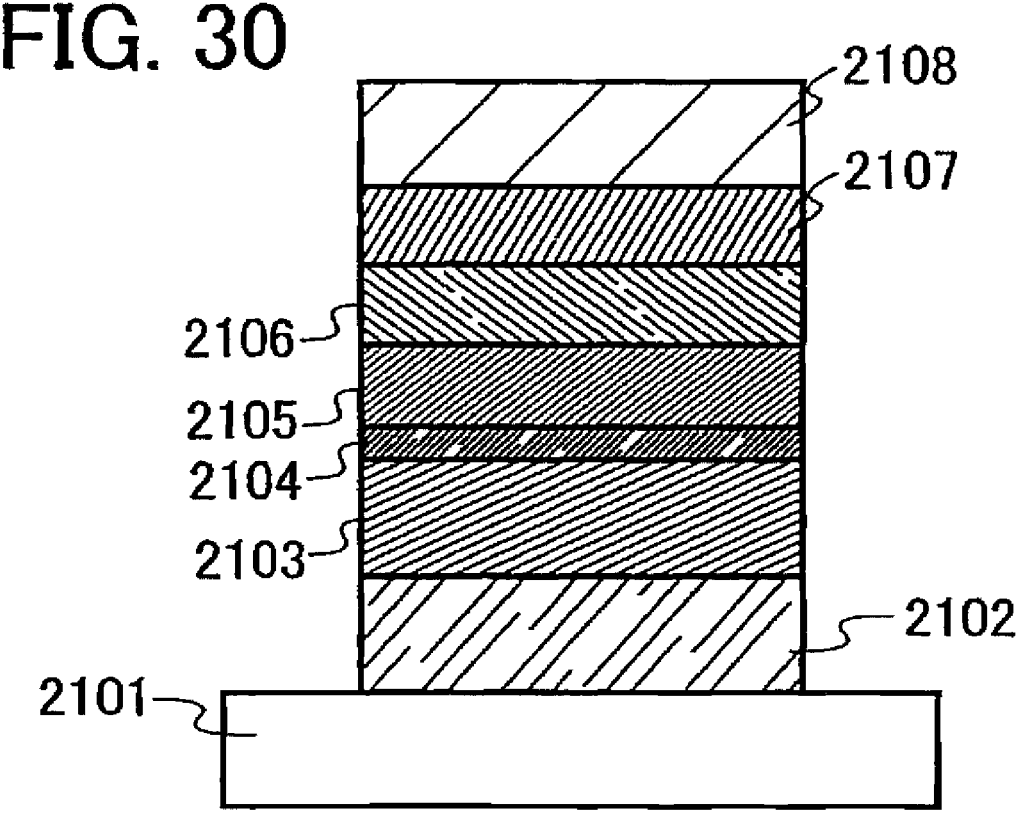
FIG. 30 is a diagram for explaining a light emitting element of the present invention.

This example explains a light emitting element of the present invention with reference to FIG. 30.

First, a film of indium tin oxide containing silicon oxide was formed over a glass substrate 2101 by a sputtering method, thereby forming a first electrode 2102. Note that a thickness thereof was 110 nm and an electrode area was 2 mm×2 mm.

Next, the substrate, over which the first electrode was formed, was fixed to a substrate holder in a vacuum evaporation apparatus so that the side, on which the first electrode was formed, faced downward. Subsequently, a layer 2103 containing a composite material of an organic compound and an inorganic compound was formed by co-evaporating NPB and molybdenum oxide (VI) over the first electrode 2102 after evacuating the vacuum evaporation apparatus and reducing a pressure to approximately 10$^{-4}$ Pa. The thickness of the first electrode 2103 was adjusted to be 50 nm and a weight ratio of NPB to molybdenum oxide (VI) was adjusted to be 4:1 (=NPB: molybdenum oxide). Note that the co-evaporation method is an evaporation method by which evaporation is performed simultaneously from a plurality of evaporation sources in one treatment chamber.

Next, the aromatic amine compound of the present invention, N,N',N''-triphenyl-N,N',N''-tris(9-phenylcarbazol-3-yl)-benzene-1,3,5-triamine (abbr.: PCA3B) represented by Structural Formula (21) was formed over the layer 2103 containing a composite material by a resistance-heating evaporation method so as to have a thickness of 10 nm, thereby forming a hole transport layer 2104.

Furthermore, a light emitting layer 2105 with a thickness of 40 nm was formed over the hole transport layer 2104 by co-evaporating Alq and coumarin 6. Here, a weight ratio of Alq to coumarin 6 was adjusted to be 1:0.01 (=Alq: coumarin 6). This caused coumarin 6 to be dispersed in the layer formed of Alq.

After that, a film of Alq was formed over the light emitting layer 2105 using a resistance-heating evaporation method so as to have a thickness of 10 nm, thereby forming an electron transporting layer 2106.

Moreover, an electron injection layer 2107 with a thickness of 20 nm was formed by co-evaporating Alq and lithium over the electron transport layer 2106. Here, a weight ratio of Alq to lithium was adjusted to be 1:0.01 (=Alq: lithium). This caused lithium to be dispersed in the layer formed of Alq.

Lastly, a film of aluminum was formed over the electron injection layer 2107 using a resistance-heating evaporation method so as to have a thickness of 200 nm, thereby forming a second electrode 2108. Thus, a light emitting element of Example 3 was manufactured.

Figure 18:
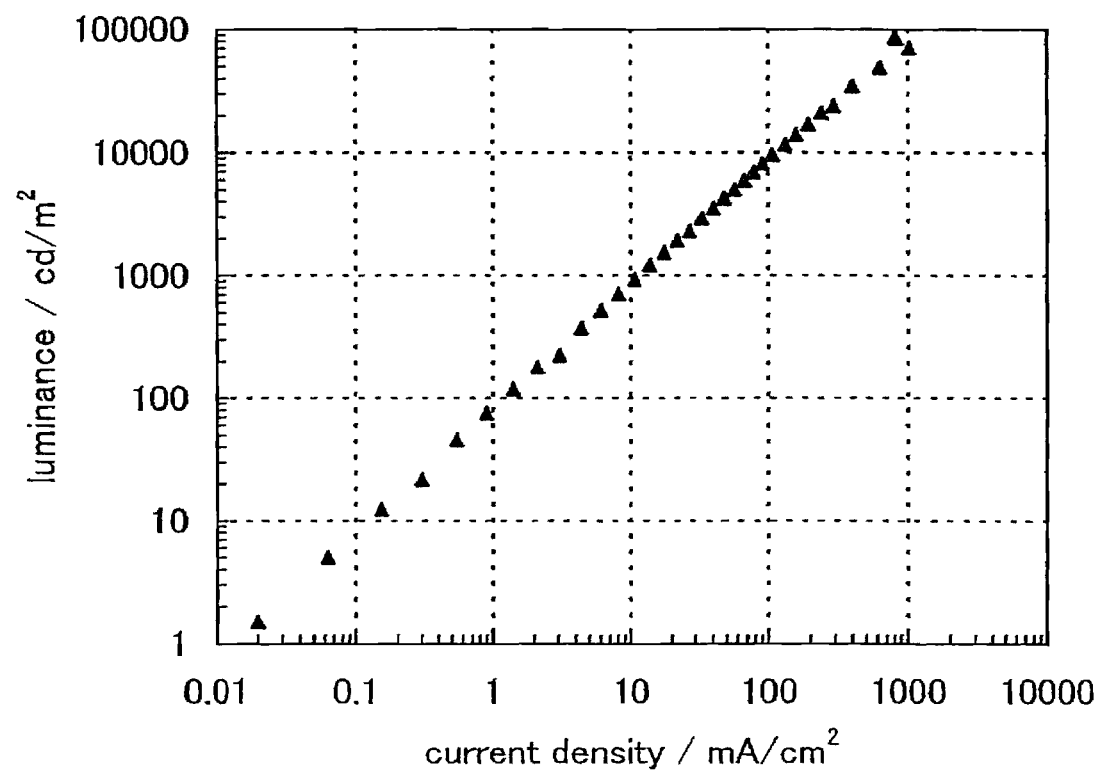
FIG. 18 is a diagram showing a current density-luminance characteristic of a light emitting element manufactured in Example 3.
Figure 19:
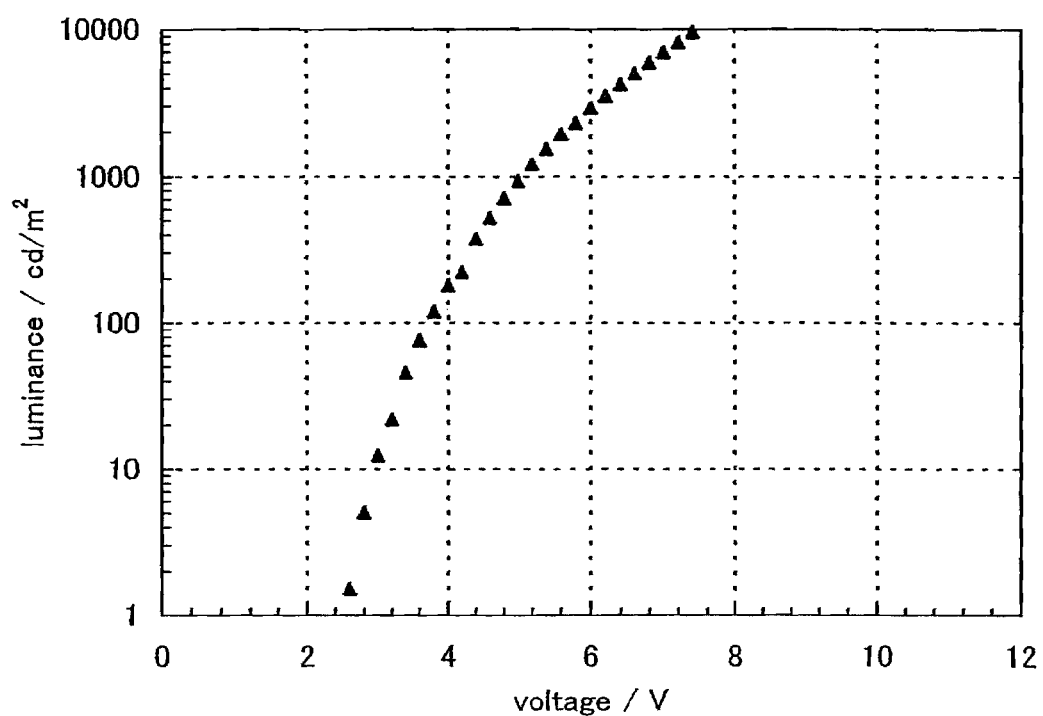
FIG. 19 is a diagram showing a voltage-luminance characteristic of a light emitting element manufactured in Example 3.
Figure 20:
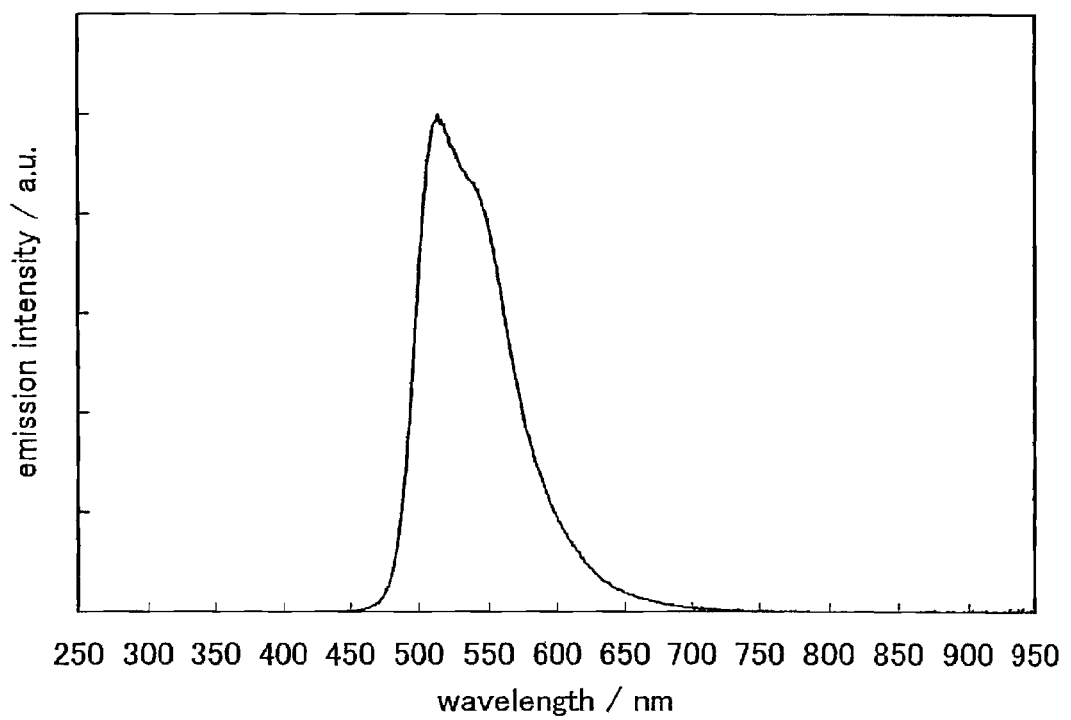
FIG. 20 is a diagram showing an emission spectrum of a light emitting element manufactured in Example 3.

FIG. 18 shows a current density-luminance characteristic of the light emitting element of Example 3. In addition, FIG. 19 shows a voltage-luminance characteristic. Further, FIG. 20 shows an emission spectrum when a current of 1 mA is applied. As for the light emitting element of Example 3, green light emission derived from coumarin 6 with CIE chromaticity coordinates (x, y)=(0.30, 0.63) was obtained with a luminance of 940 cd/m$^2$ by applying a voltage of 5.0 V.

As described above, a light emitting element with favorable characteristics was obtained by using the aromatic amine compound of the present invention for a hole transport layer.

Example 4

This example explains a light emitting element of the present invention with reference to FIG. 30.

First, a film of indium tin oxide containing silicon oxide was formed over a glass substrate 2101 by a sputtering method, thereby forming a first electrode 2102. Note that a thickness thereof was 110 nm and an electrode area was 2 mm×2 mm.

Next, the substrate, over which the first electrode was formed, was fixed to a substrate holder in a vacuum evaporation apparatus so that the side, on which the first electrode was formed, faced downward. Subsequently, a layer 2103 containing a composite material of an organic compound and an inorganic compound was formed by co-evaporating NPB and molybdenum oxide (VI) over the first electrode 2102 after evacuating the vacuum evaporation apparatus and reducing a pressure to approximately $10^{-4}$ Pa. A thickness thereof was adjusted to be 50 nm and a weight ratio of NPB to molybdenum oxide (VI) was adjusted to be 4:1 (=NPB: molybdenum oxide). Note that the co-evaporation method is an evaporation method by which evaporation is performed simultaneously from a plurality of evaporation sources in one treatment chamber.

Next, the aromatic amine compound of the present invention, N,N',N"-triphenyl-N,N',N"-tris(9-phenylcarbazol-3-yl)-benzene-1,3,5-triamine (abbr.: PCA3B) represented by Structural Formula (21) was formed over the layer 2103 containing a composite material by a resistance-heating evaporation method so as to have a thickness of 10 nm, thereby forming a hole transport layer 2104.

Furthermore, a light emitting layer 2105 with a thickness of 30 nm was formed over the hole transport layer 2104 by co-evaporating 9-[4-(N-carbazolyl)]phenyl-10-phenylanthracene (abbr.: CzPA) and 9-(4-{N-[4-(9-carbazolyl)phenyl]-N-phenylamino}phenyl)-10-phenylanthracene (abbr.: YGAPA). Here, a weight ratio of CzPA to YGAPA was adjusted to be 1:0.04 (=CzPA:YGAPA). This caused YGAPA to be dispersed in the layer formed of CzPA.

After that, a film of Alq was formed over the light emitting layer 2105 using a resistance-heating evaporation method so as to have a thickness of 10 nm, thereby forming an electron transport layer 2106.

Moreover, an electron injection layer 2107 with a thickness of 20 nm was formed by co-evaporating Alq and lithium over the electron transport layer 2106. Here, a weight ratio of Alq to lithium was adjusted to be 1:0.01 (=Alq: lithium). This caused lithium to be dispersed in the layer formed of Alq.

Lastly, a film of aluminum was formed over the electron injection layer 2107 using a resistance-heating evaporation method so as to have a thickness of 200 nm, thereby forming a second electrode 2108. Thus, a light emitting element of Example 4 was manufactured.

Figure 21:
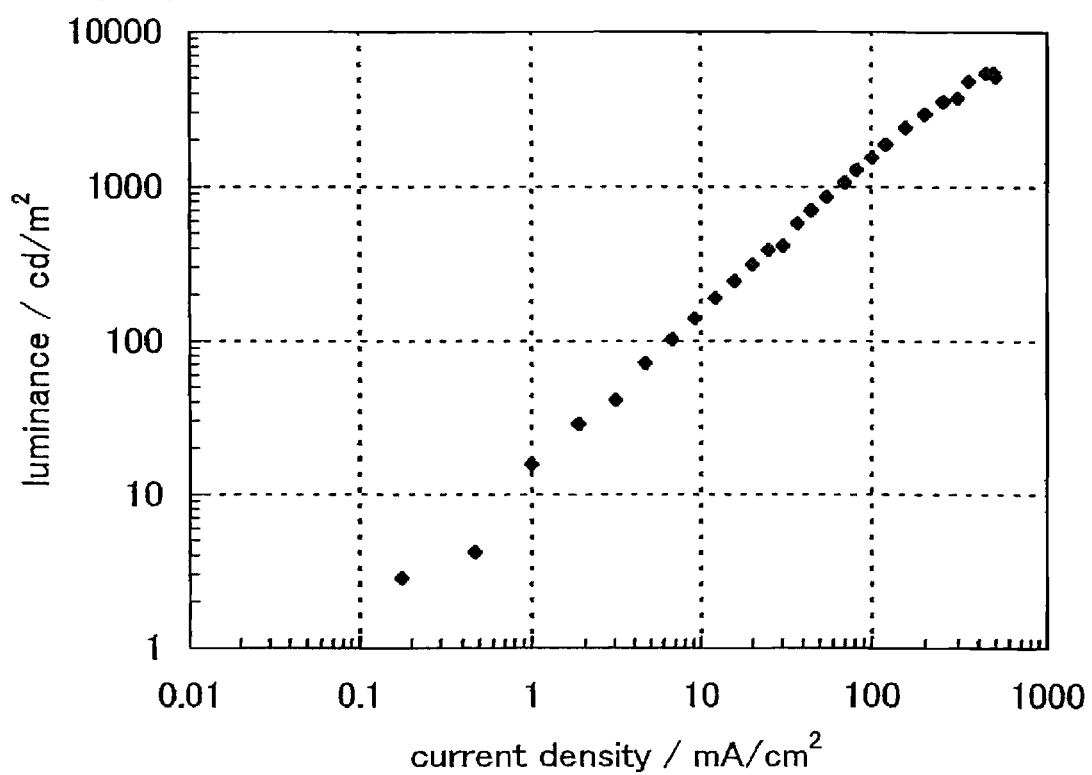
FIG. 21 is a diagram showing a current density-luminance characteristic of a light emitting element manufactured in Example 4.
Figure 22:
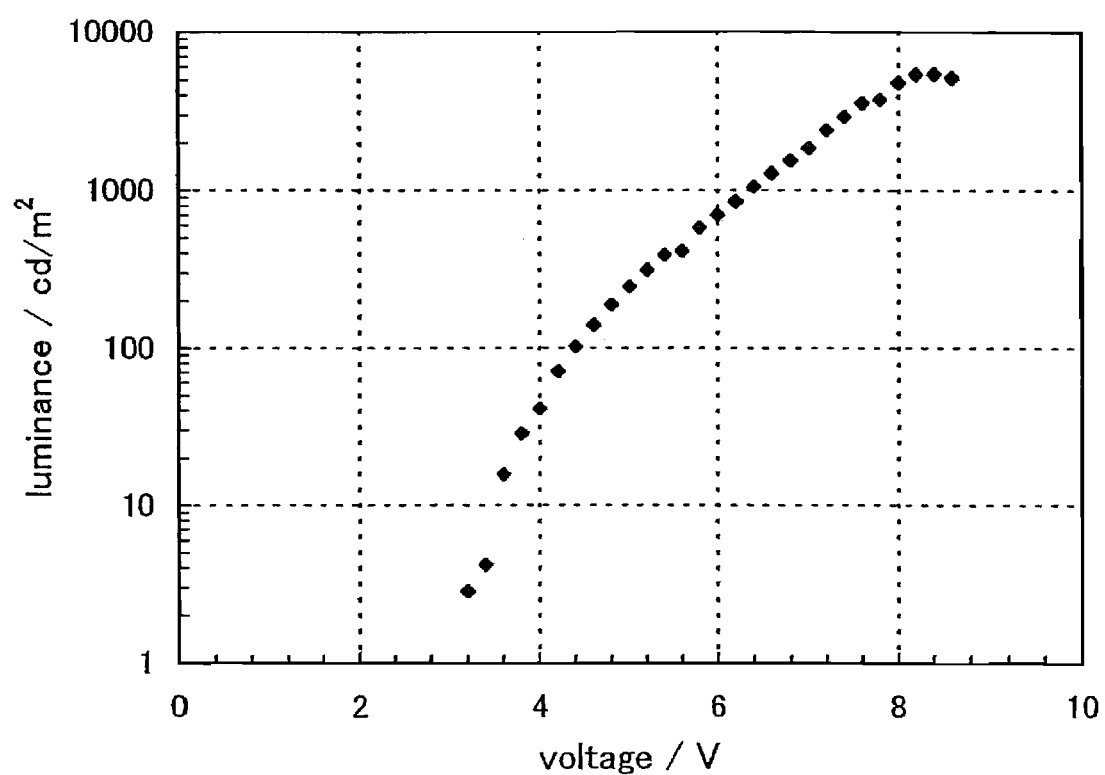
FIG. 22 is a diagram showing a voltage-luminance characteristic of a light emitting element manufactured in Example 4.
Figure 23:
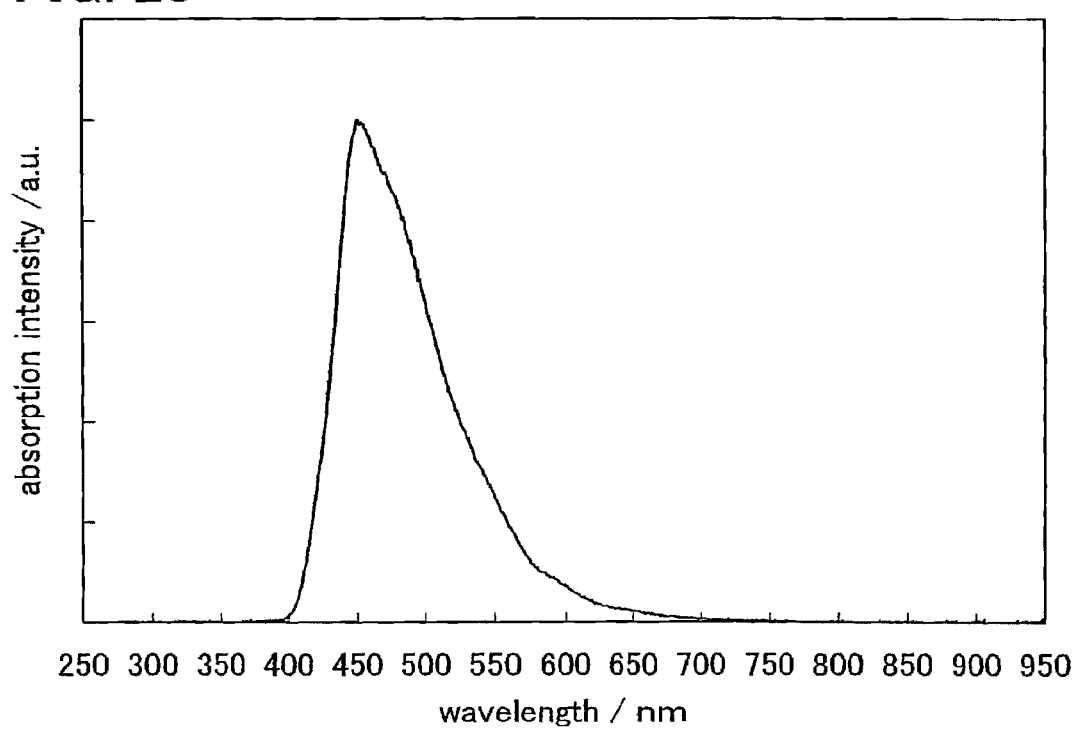
FIG. 23 is a diagram showing an emission spectrum of a light emitting element manufactured in Example 4.

FIG. 21 shows a current density-luminance characteristic of the light emitting element of Example 4. In addition, FIG. 22 shows a voltage-luminance characteristic. Further, FIG. 23 shows an emission spectrum when a current of 1 mA is applied. As for the light emitting element of Example 4, blue light emission derived from YGAPA with CIE chromaticity coordinates (x, y)=(0.17, 0.19) was obtained with a luminance of 1060 cd/m$^2$ by applying a voltage of 6.4 V.

As described above, a light emitting element with favorable characteristics was obtained by using the aromatic amine compound of the present invention for a hole transport layer.

Example 5

This example explains a light emitting element of the present invention with reference to FIG. 30.

First, a film of indium tin oxide containing silicon oxide was formed over a glass substrate 2101 by a sputtering method, thereby forming a first electrode 2102. Note that a thickness thereof was 110 nm and an electrode area was 2 mm×2 mm.

Next, the substrate, over which the first electrode was formed, was fixed to a substrate holder in a vacuum evaporation apparatus so that the side, on which the first electrode was formed, faced downward. Subsequently, a layer 2103 containing a composite material of an organic compound and an inorganic compound was formed by co-evaporating NPB and molybdenum oxide (VI) over the first electrode 2102 after evacuating the vacuum evaporation apparatus and reducing a pressure to approximately $10^{-4}$ Pa. A thickness thereof was adjusted to be 50 nm and a weight ratio of NPB to molybdenum oxide (VI) was adjusted to be 4:2 (=NPB: molybdenum oxide). Note that the co-evaporation method is an evaporation method by which evaporation is performed simultaneously from a plurality of evaporation sources in one treatment chamber.

Next, the aromatic amine compound of the present invention, N,N'-bis(9-phenylcarbazol-3-yl)-N,N'-diphenyl-benzene-1,3-diamine (abbr.: PCA2B) represented by Structural Formula (51) was formed over the layer 2103 containing a composite material by a resistance-heating evaporation method so as to have a thickness of 10 nm, thereby forming a hole transport layer 2104.

Furthermore, a light emitting layer 2105 with a thickness of 40 nm was formed over the hole transport layer 2104 by co-evaporating 9-[4-(N-carbazolyl)phenyl]-10-phenylanthracene (abbr.: CzPA) and 2,5,8,11-tetra(tert-butyl)perylene (abbr.: TBP). Here, a weight ratio of CzPA to TBP was adjusted to be 1:0.01 CzPA TBP). This caused TBP to be dispersed in the layer formed of CzPA.

After that, a film of Alq was formed over the light emitting layer 2105 using a resistance-heating evaporation method so as to have a thickness of 20 nm, thereby forming an electron transport layer 2106.

Moreover, a film of calcium fluoride was formed over the electron transport layer 2106 so as to have a thickness of 1 nm, thereby forming an electron injection layer 2107.

Lastly, a film of aluminum was formed over the electron injection layer 2107 using a resistance-heating evaporation method so as to have a thickness of 200 nm, thereby forming a second electrode 2108. Thus, a light emitting element of Example 5 was manufactured.

Figure 24:
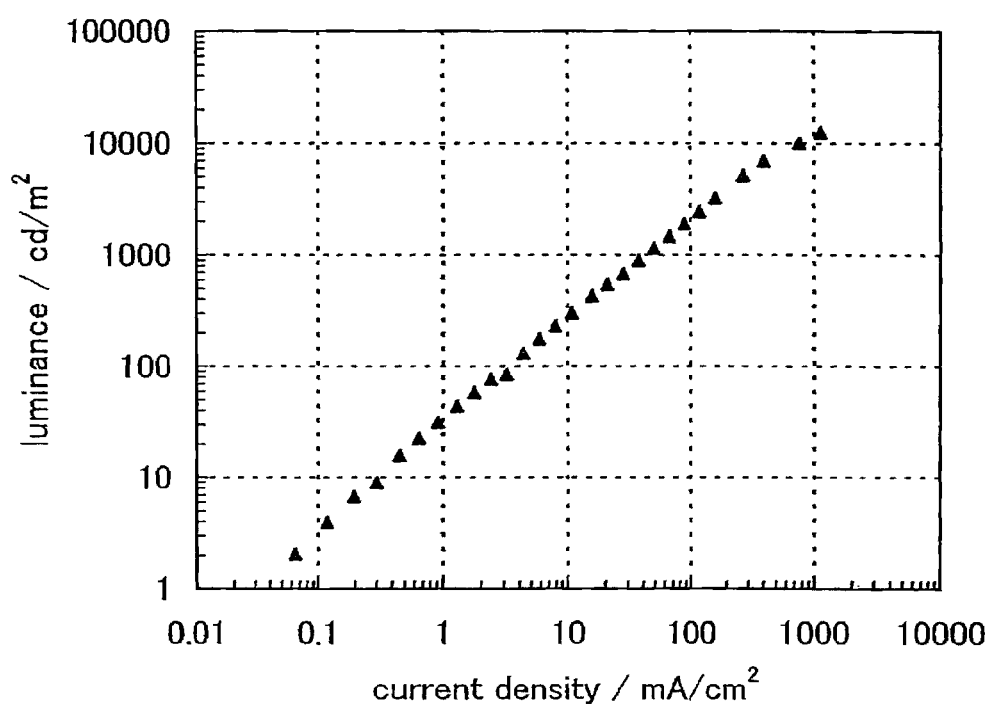
FIG. 24 is a diagram showing a current density-luminance characteristic of a light emitting element manufactured in Example 5.
Figure 25:
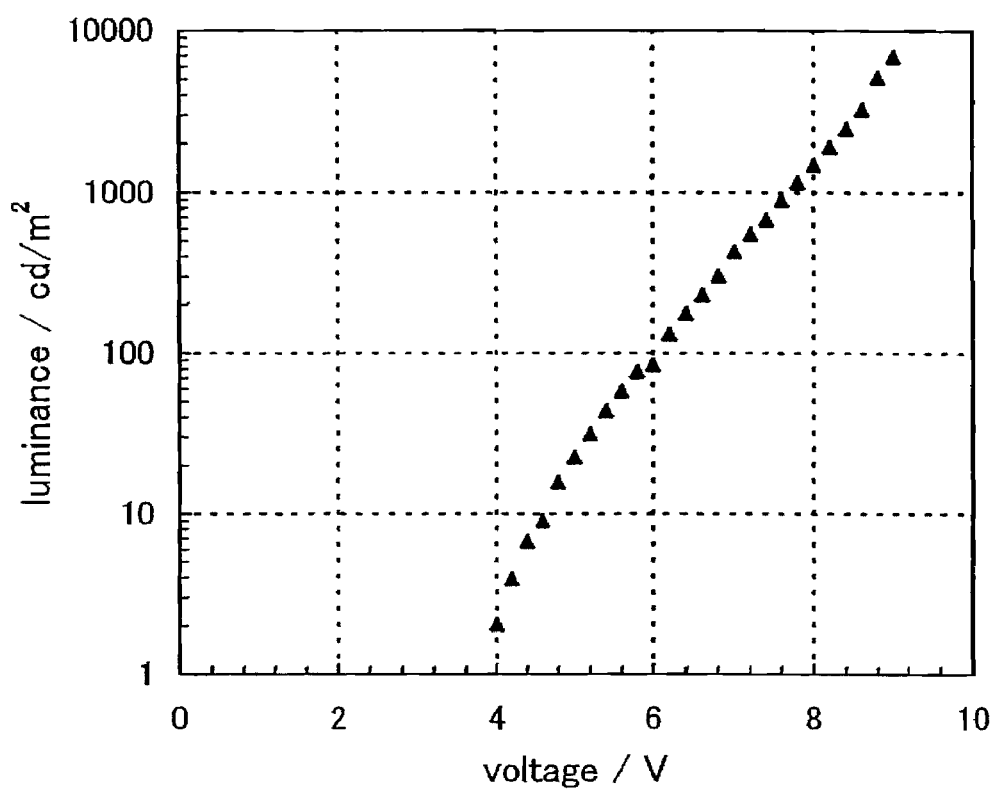
FIG. 25 is a diagram showing a voltage-luminance characteristic of a light emitting element manufactured in Example 5.
Figure 26:
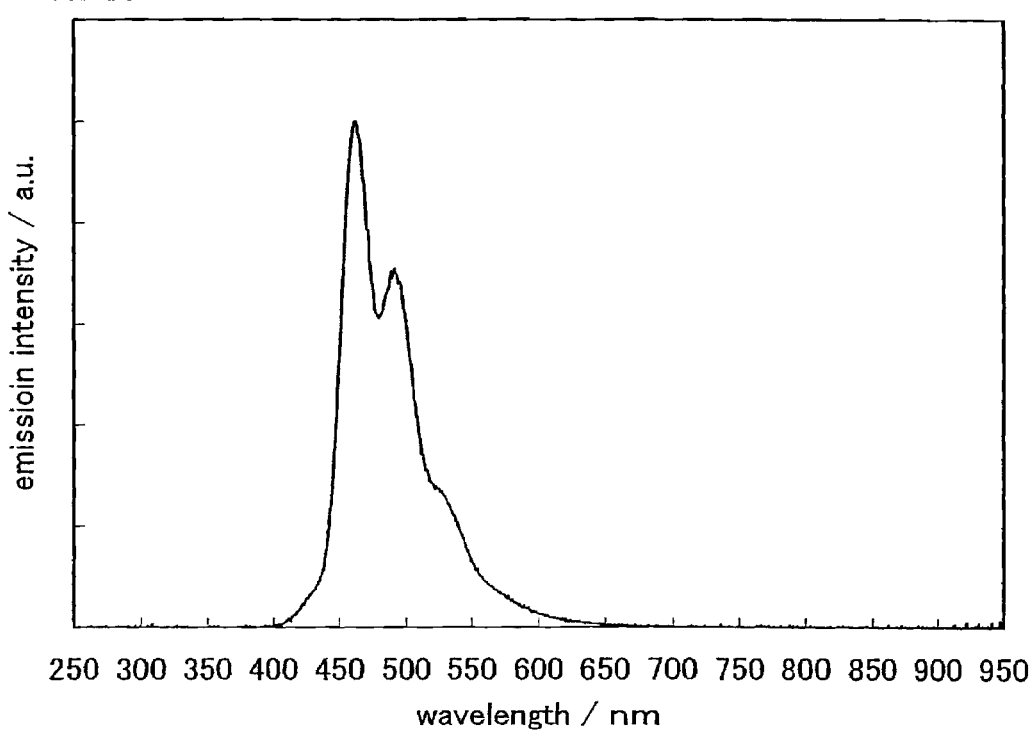
FIG. 26 is a diagram showing an emission spectrum of a light emitting element manufactured in Example 5.

FIG. 24 shows a current density-luminance characteristic of the light emitting element of Example 5. In addition, FIG. 25 shows a voltage-luminance characteristic. Further, FIG. 26 shows an emission spectrum when a current of 1 mA is applied. As for the light emitting element of Example 5, light-blue light emission derived from TBP with CIE chromaticity coordinates (x, y)=(0.16, 0.24) was obtained with a luminance of 550 cd/m² by applying a voltage of 7.2 V.

As described above, a light emitting element with favorable characteristics was obtained by using the aromatic amine compound of the present invention for a hole transport layer.

Example 6

This example explains a light emitting element of the present invention with reference to FIG. 30.

First, a film of indium tin oxide containing silicon oxide was formed over a glass substrate 2101 by a sputtering method, thereby forming a first electrode 2102. Note that a thickness thereof was 110 nm and an electrode area was 2 mm×2 mm.

Next, the substrate, over which the first electrode was formed, was fixed to a substrate holder in a vacuum evaporation apparatus so that the side, on which the first electrode was formed, faced downward. Subsequently, a layer 2103 containing a composite material of an organic compound and an inorganic compound was formed by co-evaporating NPB and molybdenum oxide (VI) over the first electrode 2102 after evacuating the vacuum evaporation apparatus and reducing a pressure to approximately $10^{-4}$ Pa. A thickness thereof was adjusted to be 50 nm and a weight ratio of NPB to molybdenum oxide (VI) was adjusted to be 4:2 (=NPB: molybdenum oxide). Note that the co-evaporation method is an evaporation method by which evaporation is performed simultaneously from a plurality of evaporation sources in one treatment chamber.

Next, a film of N,N'-bis(spiro-9,9'-bifluorene-2-yl)-N,N'-diphenylbenzidine (abbr.: BSPB) was formed over the layer 2103 containing a composite material by a resistance-heating evaporation method so as to have a thickness of 10 nm, thereby forming a hole transport layer 2104.

Furthermore, the aromatic amine compound of the present invention, N,N'-bis(9-phenylcarbazol-3-yl)-N,N'-diphenyl-benzene-1,3-diamine (abbr.: PCA2B) represented by Structural Formula (51) was formed over the hole transport layer 2104 so as to have a thickness of 30 nm, thereby forming a light emitting layer 2105.

After that, a film of BCP was formed over the light emitting layer 2105 using a resistance-heating evaporation method so as to have a thickness of 20 nm and a film of Alq is further formed so as to have a thickness of 10 nm, thereby forming an electron transport layer 2106.

Moreover, a film of calcium fluoride was formed over the electron transport layer 2106 so as to have a thickness of 1 nm, thereby forming an electron injection layer 2107.

Lastly, a film of aluminum was formed over the electron injection layer 2107 using a resistance-heating evaporation method so as to have a thickness of 200 nm, thereby forming a second electrode 2108. Thus, a light emitting element of Example 6 was manufactured.

Figure 27:
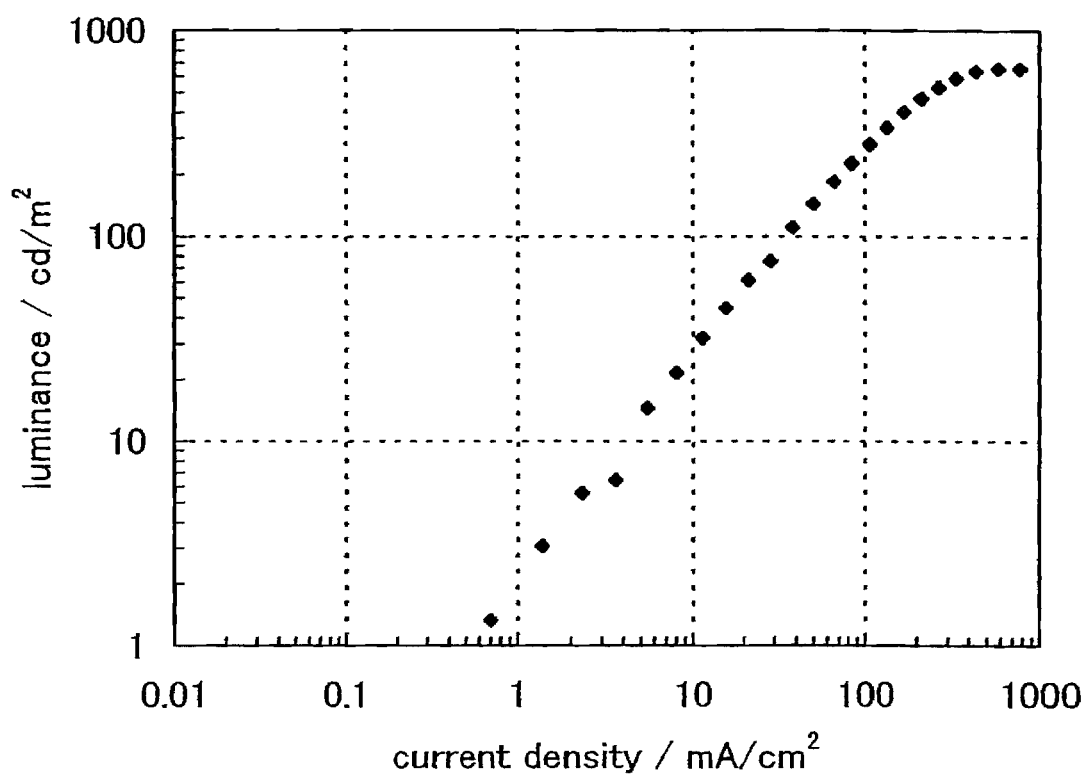
FIG. 27 is a diagram showing a current density-luminance characteristic of a light emitting element manufactured in Example 6.
Figure 28:
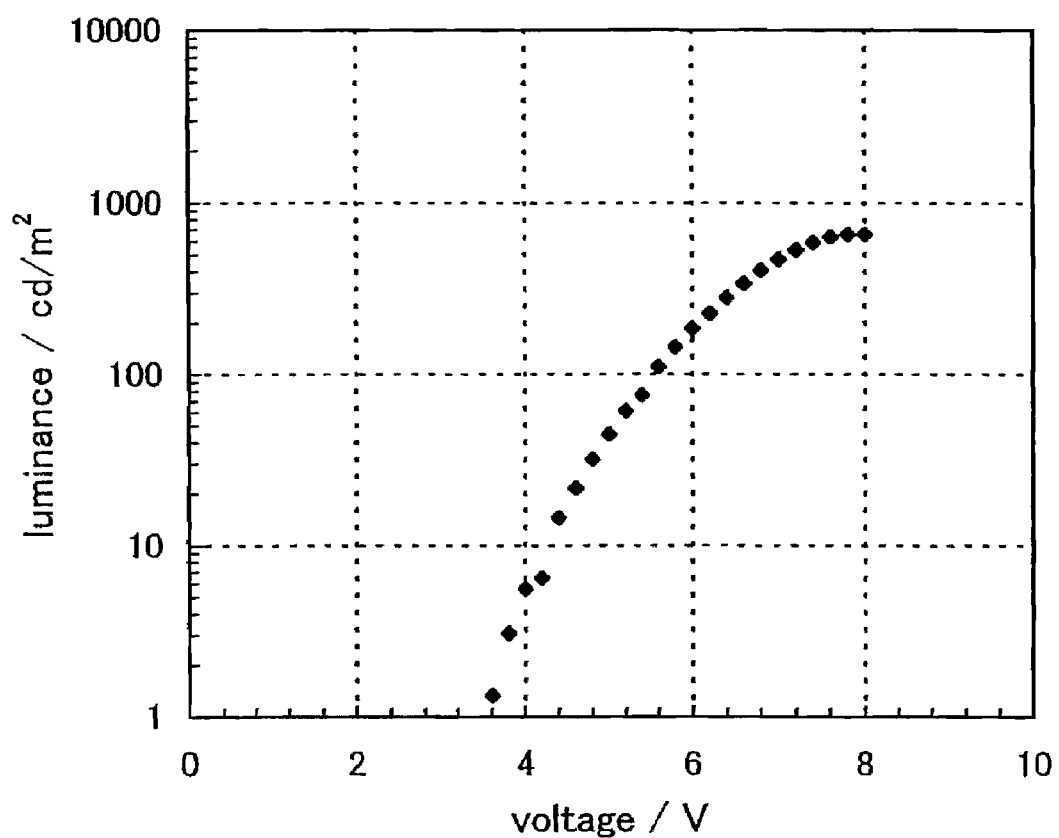
FIG. 28 is a diagram showing a voltage-luminance characteristic of a light emitting element manufactured in Example 6.
Figure 29:
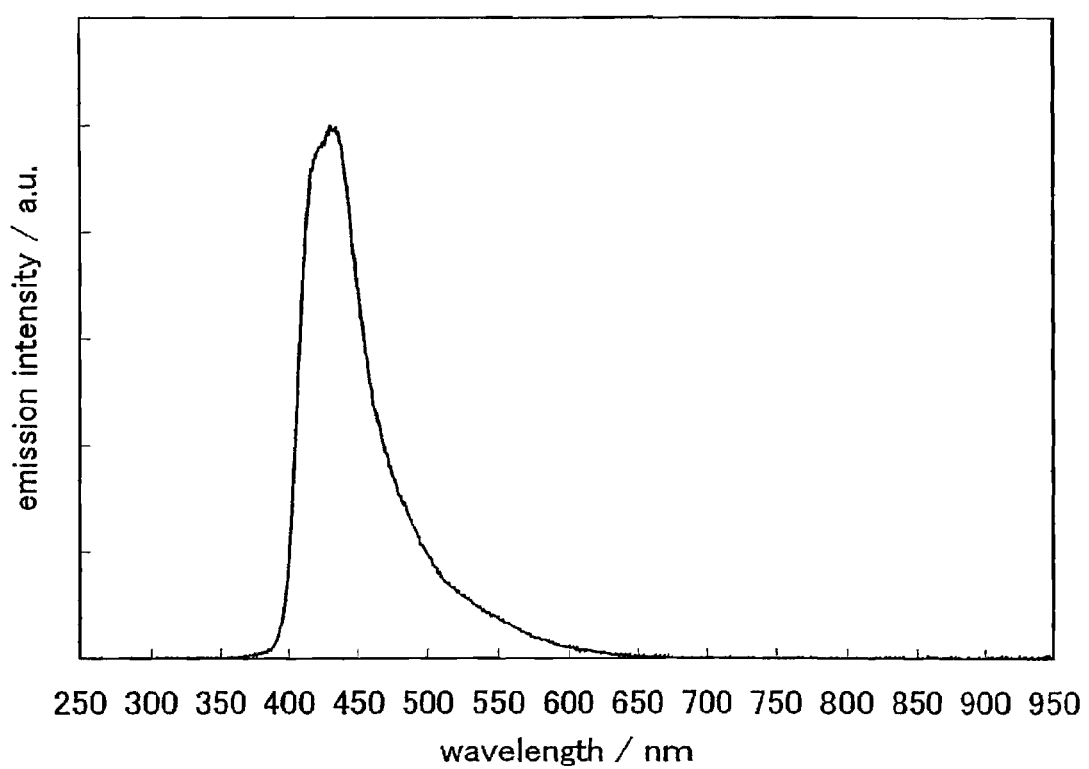
FIG. 29 is a diagram showing an emission spectrum of a light emitting element manufactured in Example 6.

FIG. 27 shows a current density-luminance characteristic of the light emitting element of Example 6. In addition, FIG. 28 shows a luminance-voltage characteristic. Further, FIG. 29 shows an emission spectrum when a current of 1 mA is applied. As for the light emitting element of Example 6, blue light emission derived from PCA2B with CIE chromaticity coordinates (x, y)=(0.17, 0.12) was obtained with a luminance of 531 cd/m² by applying a voltage of 7.2 V.

As described above, a light emitting element with favorable characteristics was obtained by using the aromatic amine compound of the present invention for a light emitting layer.

Example 7

A method for synthesizing N,N',N"-triphenyl-N,N',N"-tris[4-(carbazol-9-yl)phenyl]-benzene-1,3,5-triamine (abbr.: YGA3B) represented by Structural Formula (81) as an example of the aromatic amine compound of the present invention is explained.

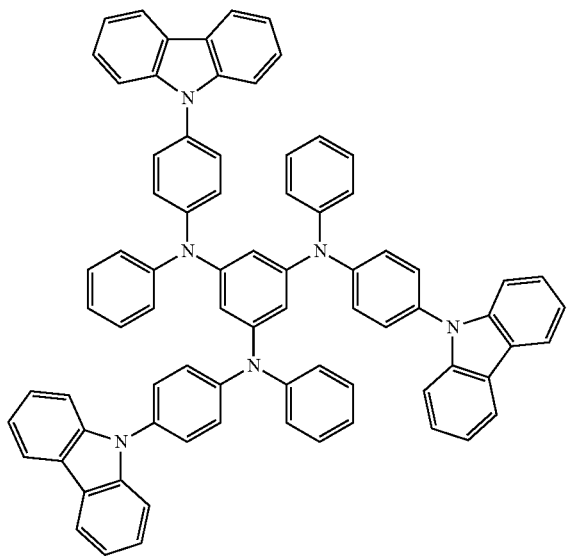

(81)

[Step 1]

A method for synthesizing 9-[4-(N-phenylamino)phenyl]carbazole (abbr.: YGA) is explained.

(i) Synthesis of N-(4-bromophenyl)carbazole

Synthetic Scheme (D-1) of N-(4-bromophenyl)carbazole is shown below

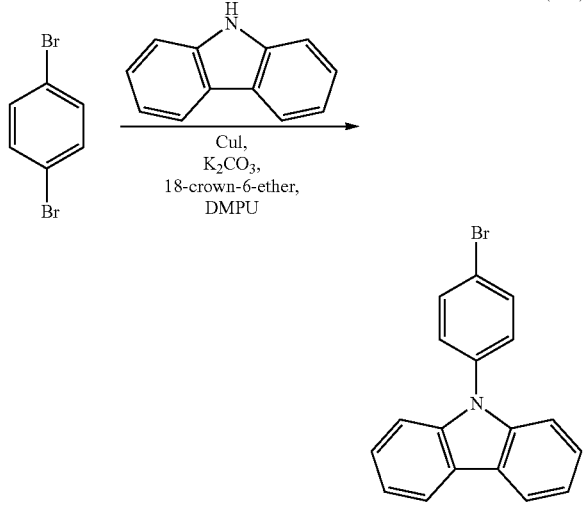

(D-1)

First, a method for synthesizing N-(4-bromophenyl)carbazole is explained. 56.3 g (0.24 mol) of 1,4-dibromobenzene, 31.3 g (0.18 mol) of carbazole, 4.6 g (0.024 mol) of copper iodide, 66.3 g (0.48 mol) of potassium carbonate, and 2.1 g (0.008 mol) of 18-crown-6-ether were put into a 300-mL three-neck flask and the air in the flask was replaced with nitrogen. Then, 8 mL of 1,3-dimethyl-3,4,5,6-tetrahydro-2 (1H)-pyrimidinone (abbr.: DMPU) was added, and the mixture was stirred for 6 hours at 180° C. After cooling the reaction mixture to a room temperature, the precipitate was removed by suction filtration. The filtrate was washed with a diluted hydrochloric acid, a saturated aqueous sodium hydrogen carbonate solution, and a saturated aqueous sodium chloride solution in this order, and then dried with magnesium sulfate. After drying, the reaction mixture was naturally filtered and concentrated, and the obtained oily substance was purified by silica gel column chromatography (hexane:ethyl acetate=9:1) and recrystallized with chloroform and hexane, thereby obtaining 20.7 g of objective N-(4-bromophenyl) carbazole as a light-brown plate crystal with a yield of 35%.

$^1$H NMR of this compound is shown below. $^1$H NMR (300 MHz, CDCl$_3$); δ=8.14 (d, J=7.8 Hz, 2H), 7.73 (d, J=8.7 Hz, 2H), 7.46 (d, J=8.4 Hz, 2H), 7.42-7.26 (m, 6H).

(ii) Synthesis of 9-[4-(N-phenylamino)phenyl]carbazole (abbr.: YGA)

Synthetic Scheme (D-2) of YGA is shown below.

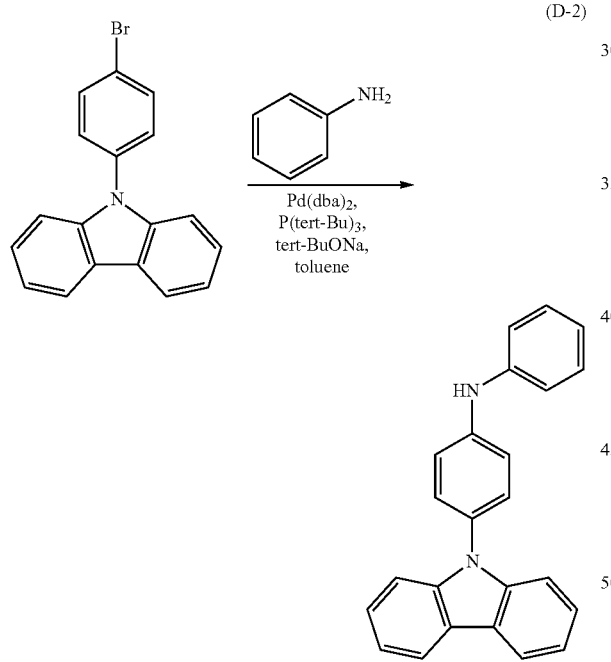

5.4 g (17.0 mmol) of N-(4-bromophenyl)carbazole obtained in (i), 1.8 mL (20.0 mmol) of aniline, 100 mg (0.17 mmol) of bis(dibenzylideneacetone)palladium(0), and 3.9 g (40 mmol) of sodium tert-butoxide were put into a 200-mL three-neck flask and the air in the flask was replaced with nitrogen. Then, 0.1 mL of tri(tert-butyl)phosphine (a 10 wt % hexane solution) and 50 mL of toluene were added, and the mixture was stirred for 6 hours at 80° C. The reaction mixture was filtered through florisil, Celite®, and alumina. The filtrate was washed with water and a saturated aqueous sodium chloride solution, and then dried with magnesium sulfate. The reaction mixture was naturally filtered and the filtrate was concentrated, and the obtained oily substance was purified by silica gel column chromatography (hexane:ethyl acetate=9:1), thereby obtaining 4.1 g of objective 9-[4-(N-phenylamino)phenyl]carbazole (abbr.: YGA) with a yield of 73%. It was confirmed by nuclear magnetic resonance method (NMR) that this compound Was 9-[4-(N-phenylamino)phenyl]carbazole (abbr.: YGA).

Figure 31A:
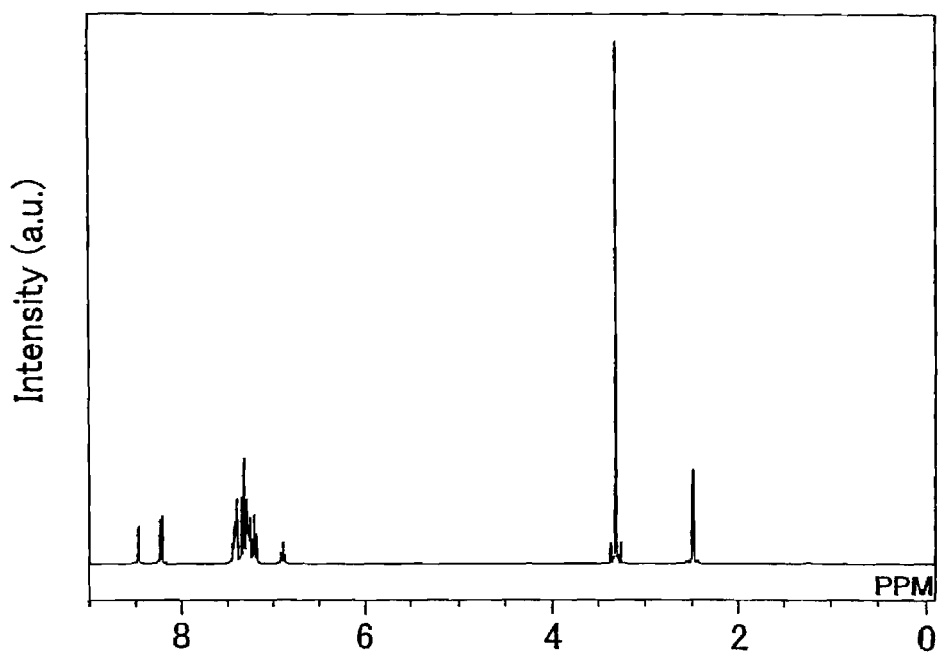
FIGS. 31A and 31B are diagrams showing $^1$H NMR charts of 9-[4-(N-phenylamino)phenyl]carbazole.
Figure 31B:
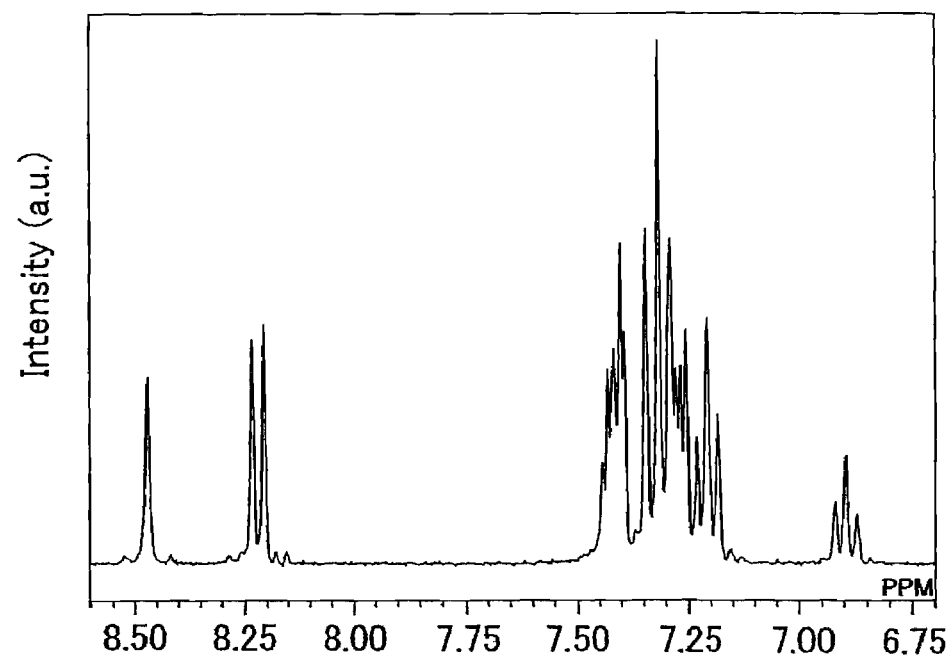

$^1$H NMR of this compound is shown below. In addition, $^1$H NMR charts are shown in FIGS. 31A and 31B. Note that FIG. 31B is an enlarged chart showing the range from 6.7 ppm to 8.6 ppm.

$^1$H NMR of this compound is shown below. $^1$H NMR (300 MHz, DMSO-d$_6$); δ=8.47 (s, 1H), 8.22 (d, J=7.8 Hz, 2H), 7.44-7.16 (m, 14H), 6.92-6.87 (m, 1H).

[Step 2]

Next, a method for synthesizing N,N',N''-triphenyl-N,N', N''-tris[4-(carbazol-9-yl)phenyl]-benzene-1,3,5-triamine (abbr.: YGA3B) represented by Structural Formula (81) is explained. A synthetic scheme of YGA3B is shown in (D-3).

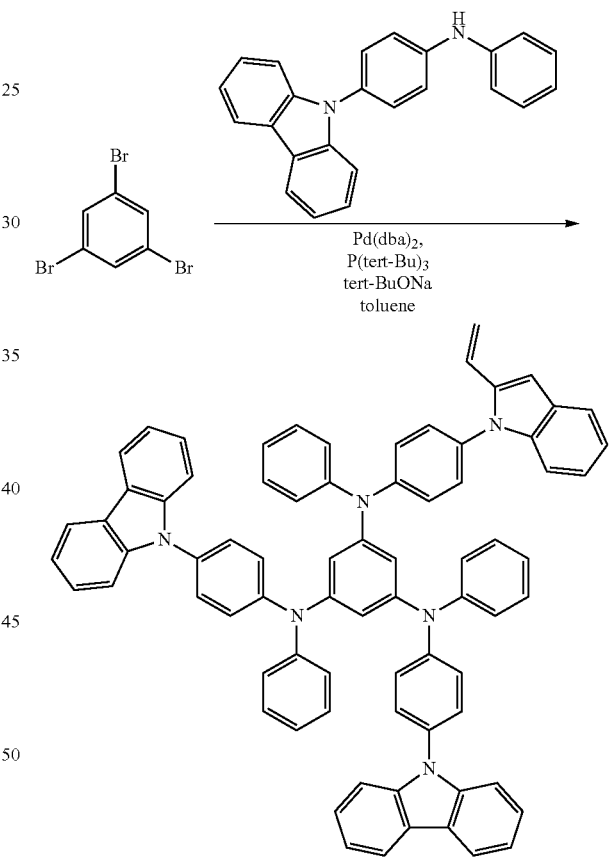

1.77 g (5.6 mmol) of 1,3,5-tribromobenzene, 5.68 g (17.0 mmol) of YGA obtained in the above Step 1, 58 mg (0.1 mol) of bis(dibenzylideneacetone)palladium(0), 0.1 mL of tri(tert-butyl)phosphine (a 10 wt % hexane solution), and 5.0 g (52 mmol) of sodium tert-butoxide were put into a 200-mL three-neck flask and the air in the flask was replaced with nitrogen. Then, 50 mL of toluene was added, and the mixture was stirred for 5 hours at 80° C. After the reaction, the reaction mixture was cooled to a room temperature and filtered through Celite®, florisil, and alumina. The filtrate was washed with water and a saturated aqueous sodium chloride solution, and an organic layer was dried with magnesium sulfate. Magnesium sulfate was removed by natural filtration, and a white solid obtained by concentrating the filtrate was purified by silica gel column chromatography (hexane:toluene=1:1) and recrystallized with chloroform and ethanol, thereby obtaining 4.6 g of objective N,N',N''-triphenyl-N,N',N''-tris[4-(carbazol-9-yl)phenyl]-benzene-1,3,5-triamine (abbr.: YGA3B) as a light-yellow powder solid with a yield of 77%.

Figure 32A:
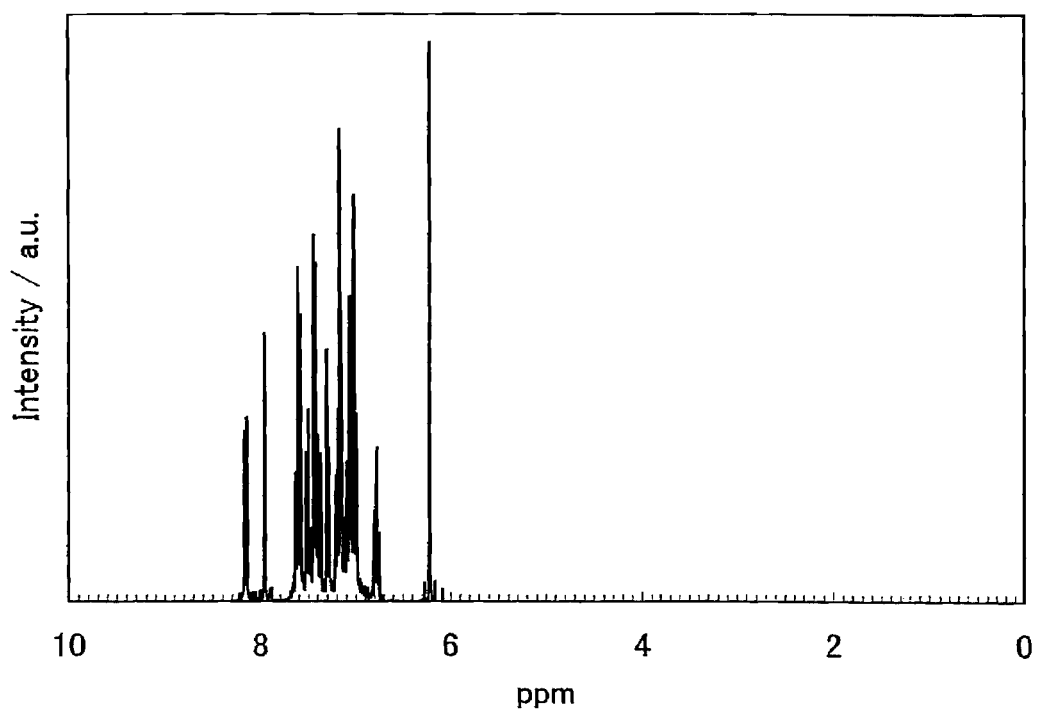
FIGS. 32A and 32B are diagrams showing $^1$H NMR charts of N,N',N''-triphenyl-N,N',N''-tris[4-(carbazol-9-yl)phenyl]-benzene-1,3,5-triamine that is an aromatic amine compound of the present invention.
Figure 32B:
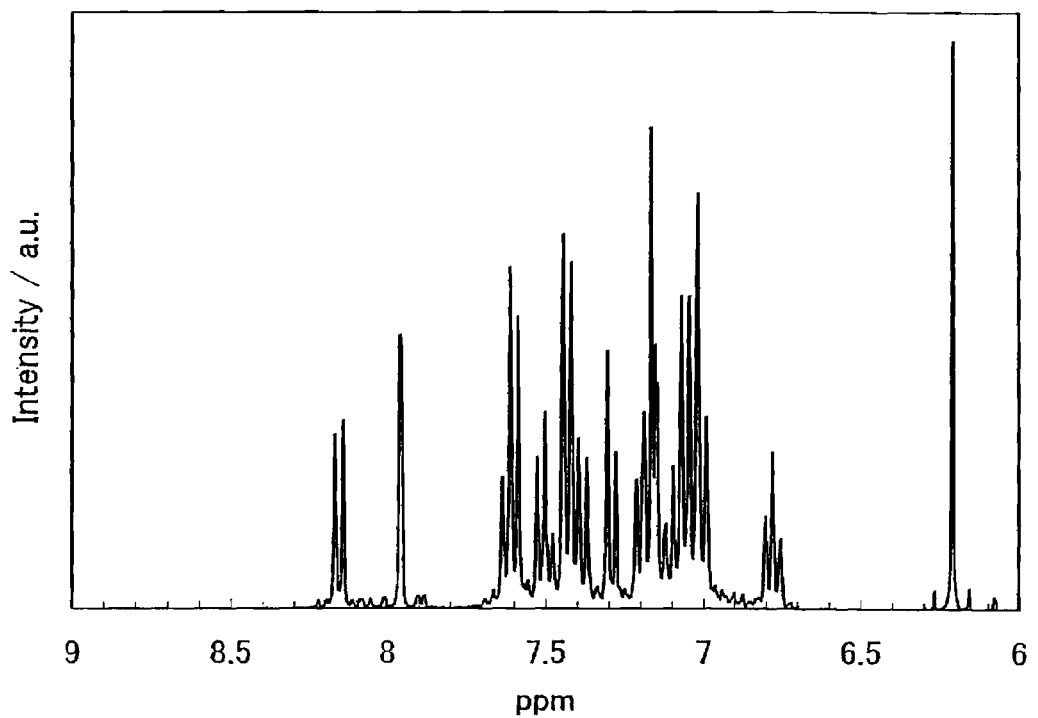

A result of proton nuclear magnetic resonance spectrometry ($^1$H NMR) analysis of this compound is as follows. $^1$H NMR (300 MHz, DMSO-$d_6$); δ=8.17 (d, J=7.20 Hz, 6H), 7.45-7.18 (m, 45H), 6.44 (s, 3H). In addition, $^1$H NMR charts are shown in FIGS. 32A and 32B. Note that FIG. 32B is an enlarged chart of FIG. 32A showing the range from 6.0 ppm to 9.0 ppm.

Example 8

A method for synthesizing N,N'-bis[4-(carbazol-9-yl)phenyl]-N,N'-diphenyl-benzene-1,3-diamine (abbr.: YGA2B) represented by Structural Formula (111) as an example of the aromatic amine compound of the present invention is explained.

(111)

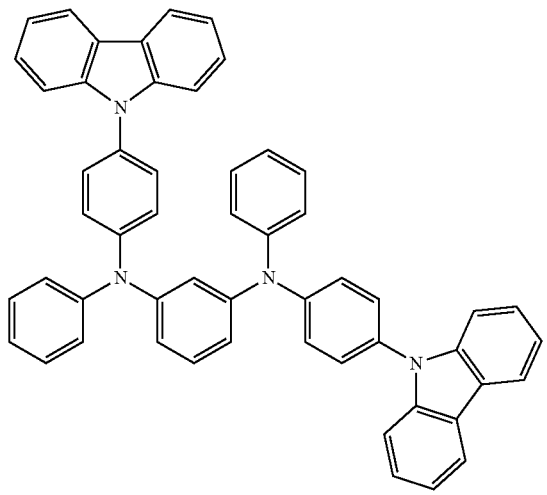

[Step 1]
A method for synthesizing YGA2B is explained. A synthetic scheme of YGA2B is shown in (D-4).

(D-4)

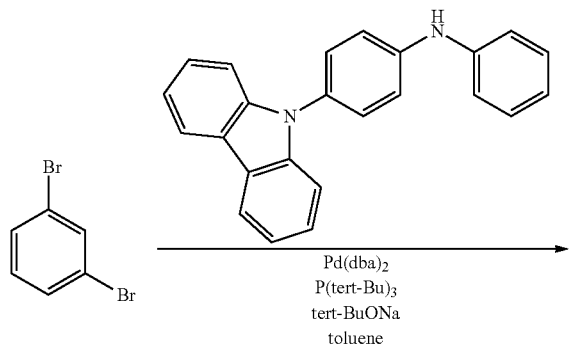

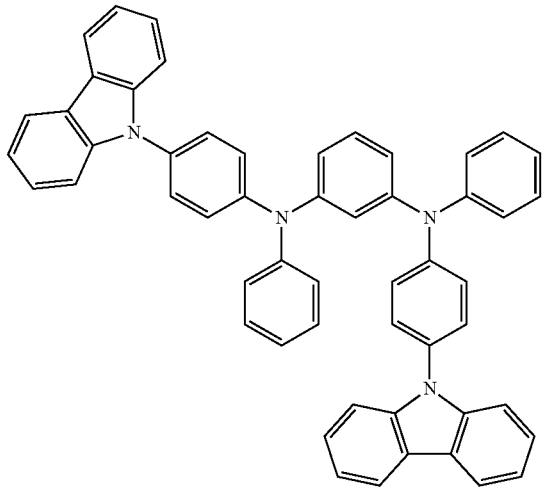

2.0 g (8.5 mmol) of 1,3-dibromobenzene, 5.68 g (17.0 mmol) of YGA obtained in Step 1 of Example 7, 58 mg (0.1 mol) of bis(dibenzylideneacetone)palladium(0), 0.1 mL of tri(tert-butyl)phosphine (a 10 wt % hexane solution), and 5.0 g (52 mmol) of sodium tert-butoxide were put into a 200-mL three-neck flask and the air in the flask was replaced with nitrogen. Then, 50 mL of toluene was added, and the mixture was stirred for 5 hours at 80° C. After the reaction, the precipitated solid was recovered by suction filtration, dissolved into toluene, and filtered through Celite®, florisil, and alumina. The filtrate was washed with water and a saturated aqueous sodium chloride solution, and an organic layer was dried with magnesium sulfate. Magnesium sulfate was removed by natural filtration, and a white solid obtained by concentrating the filtrate was recrystallized with chloroform and hexane, thereby obtaining 5.5 g of objective N,N'-bis[4-(carbazol-9-yl)phenyl]-N,N'-diphenyl-benzene-1,3-diamine (abbr.: YGA2B) as a white solid with a yield of 88%.

Figure 33A:
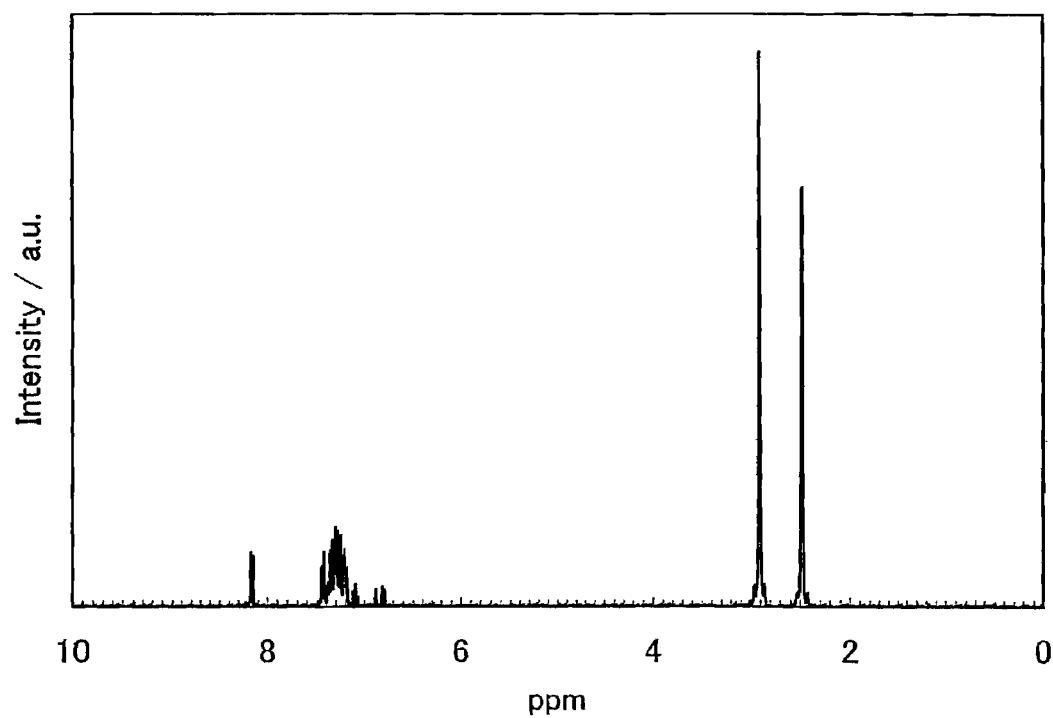
FIGS. 33A and 33B are diagrams showing $^1$H NMR charts of N,N'-bis[4-(carbazol-9-yl)phenyl]-N,N'-diphenyl-benzene-1,3-diamine that is an aromatic amine compound of the present invention.
Figure 33B:
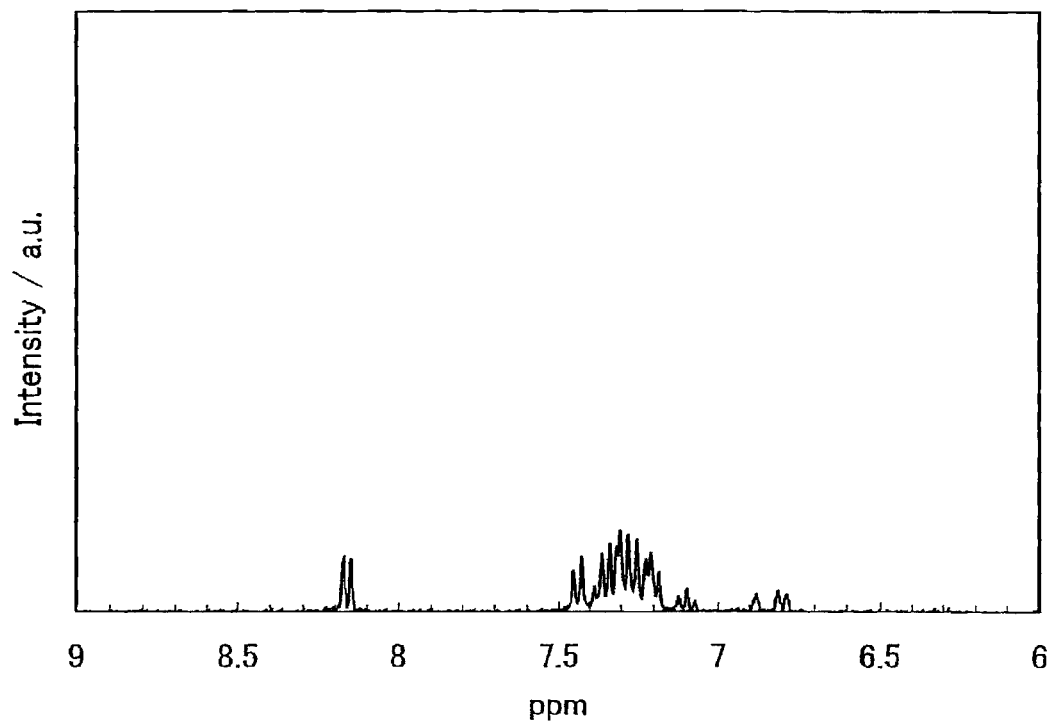

A result of proton nuclear magnetic resonance spectrometry $^1$H NMR) analysis of this compound is as follows. $^1$H NMR (300 MHz, DMSO-$d_6$); δ=8.16 (d, J=6.30 Hz, 4H), 7.45-7.07 (m, 31H), 6.88 (s, 1H), 6.80 (d, J=8.40 Hz, 2H). In addition, $^1$H NMR charts are shown in FIGS. 33A and 33B. Note that FIG. 33B is an enlarged chart of FIG. 33A showing the range from 6.0 ppm to 9.0 ppm.

Example 9

This example discloses a synthetic example of a substance used for the light emitting element manufactured in any of the other examples.

<<Synthetic Example of YGAPA>>

Hereinafter, a method for synthesizing 9-(4-{N-[4-(9-carbazolyl)phenyl)-N-phenylamino}phenyl)-10-phenylanthracene (abbr.: YGAPA) represented by Structural Formula (201) is explained.

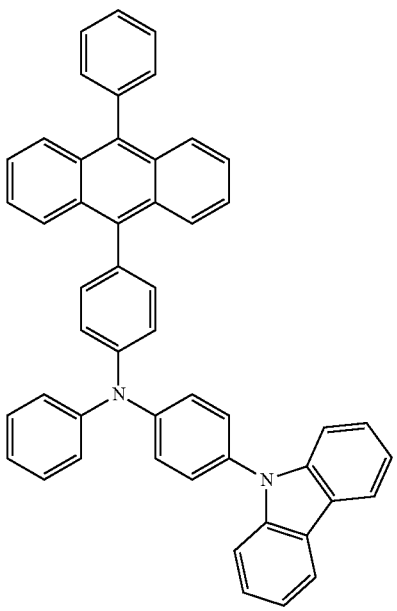

(201)

[Step 1]

A method for synthesizing 9-phenyl-10-(4-bromophenyl)anthracene (abbr.: PA) is explained.

(i) Synthesis of 9-phenylanthracene

Synthetic Scheme (f-1) of 9-phenylanthracene is shown below.

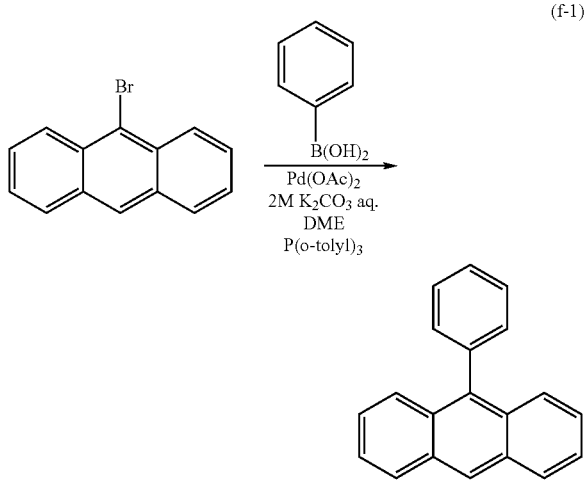

(f-1)

5.4 g (21.1 mmol) of 9-bromoanthracene, 2.6 g (21.1 mmol) of phenylboronic acid, 60 mg (0.21 mmol) of palladium acetate(II) (Pd(OAc)$_2$), 10 mL (20 mmol) of an aqueous potassium carbonate (K$_2$CO$_3$) solution (2 mol/L), 263 mg (0.84 mmol) of tri(o-tolyl)phosphine (P(o-tolyl)$_3$), and 20 mL of 1,2-dimethoxyethane (abbr.: DME) were mixed and stirred for 9 hours at 80° C. After the reaction, the precipitated solid was recovered by suction filtration, dissolved into toluene, and filtered through florisil, Celite®, and alumina. The filtrate was washed with a saturated aqueous sodium chloride solution and then dried with magnesium sulfate. After natural filtration, the filtrate was concentrated, thereby obtaining 21.5 g of objective 9-phenylanthracene as a light-brown solid with a yield of 85%.

(ii) Synthesis of 10-bromo-9-phenylanthracene

Synthetic Scheme (f-2) of 10-bromo-9-phenylanthracene is shown below.

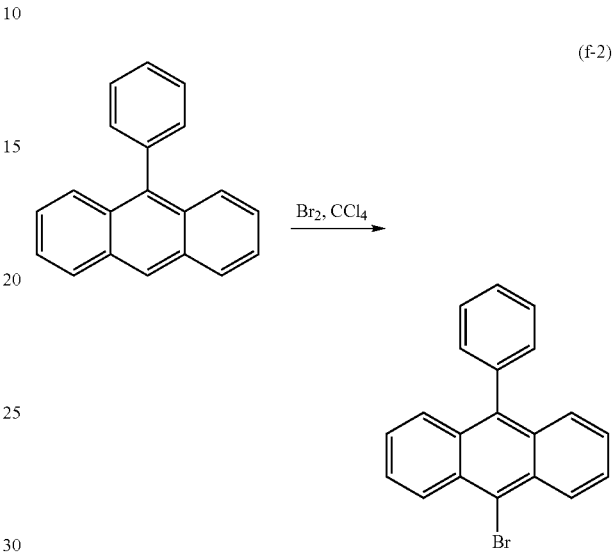

(f-2)

6.0 g (23.7 mmol) of 9-phenylanthracene was dissolved into 80 mL of carbon tetrachloride, and a solution in which 3.80 g (21.1 mmol) of bromine was dissolved in 10 mL of carbon tetrachloride was dropped into the reaction solution using a dropping funnel. After dropping, the solution was stirred for 1 hour at a room temperature. After the reaction, an aqueous sodium thiosulfate solution was added to stop the reaction. An organic layer was washed with an aqueous sodium hydroxide (NaOH) solution and a saturated sodium chloride solution and dried with magnesium sulfate. The mixture was naturally filtered, and a compound obtained by concentrating the filtrate was dissolved into toluene and filtered through florisil, Celite®, and alumina. The filtrate was concentrated and recrystallized with dichloromethane and hexane, thereby obtaining 7.0 g of objective 10-bromo-9-phenylanthracene as a light-yellow solid with a yield of 89%.

(iii) Synthesis of 9-iodo-10-phenylanthracene

Synthetic Scheme (f-3) of 9-iodo-10-phenylanthracene is shown below.

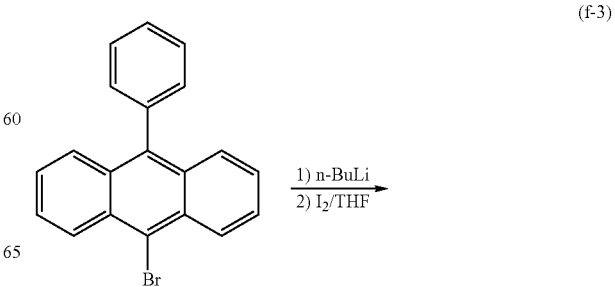

(f-3)

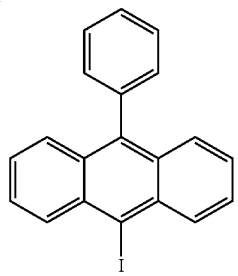

3.33 g (10 mmol) of 9-bromo-10-phenylanthracene was dissolved into 80 mL of tetrahydrofuran (abbr.: THF) and cooled to −78° C., and then 7.5 mL (12.0 mmol) of n-BuLi (1.6 mol/L) was dropped into the reaction solution using a dropping funnel and stirred for 1 hour. A solution in which 5 g (20.0 mmol) of iodine was dissolved in 20 mL of THF was dropped and further stirred for 2 hours at −78° C. After the reaction, an aqueous sodium thiosulfate solution was added to stop the reaction. An organic layer was washed with an aqueous sodium thiosulfate solution and a saturated sodium chloride solution and dried with magnesium sulfate. After natural filtration, the filtrate was concentrated, and the obtained solid was recrystallized with ethanol, thereby obtaining 3.1 g of objective 9-iodo-10-phenylanthracene as a light-yellow solid with a yield of 83%.

(iv) Synthesis of 9-phenyl-10-(4-bromophenyl)anthracene (abbr.: PA)

Synthetic Scheme (f-4) of 9-phenyl-10-(4-bromophenyl)anthracene (abbr.: PA) is shown below.

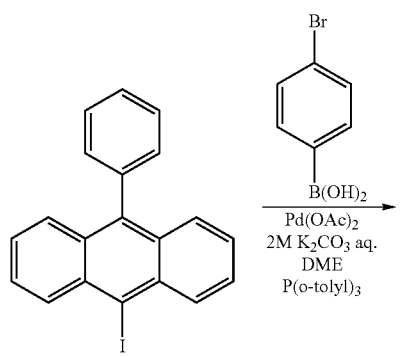

(f-4)

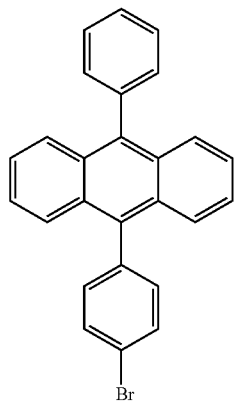

1.0 g (2.63 mmol) of 9-iodo-10-phenylanthracene, 542 mg (2.70 mmol) of p-bromophenylboronic acid, 46 mg (0.03 mmol) of tetrakis(triphenylphosphine)palladium(0) (Pd (PPh$_3$)$_4$), 3 mL (6 mmol) of an aqueous potassium carbonate (K$_2$CO$_3$) solution (2 mol/L), and 10 mL of toluene were collected, mixed, and stirred for 9 hours at 80° C. After the reaction, toluene was added and the mixture was filtered through florisil, Celite®, and alumina. The filtrate was washed with water and a saturated aqueous sodium chloride solution and then dried with magnesium sulfate. After natural filtration, the filtrate was concentrated and the obtained solid was recrystallized with chloroform and hexane, thereby obtaining 562 mg of objective 9-phenyl-10-(4-bromophenyl)anthracene as a light-brown solid with a yield of 45%.

[Step 2]

A method for synthesizing 9-(4-{N-[4-(9-carbazolyl)phenyl]-N-phenylamino}phenyl)-10-phenylanthracene (abbr.: YGAPA) is explained. Synthetic Scheme (f-5) of YGAPA is shown below.

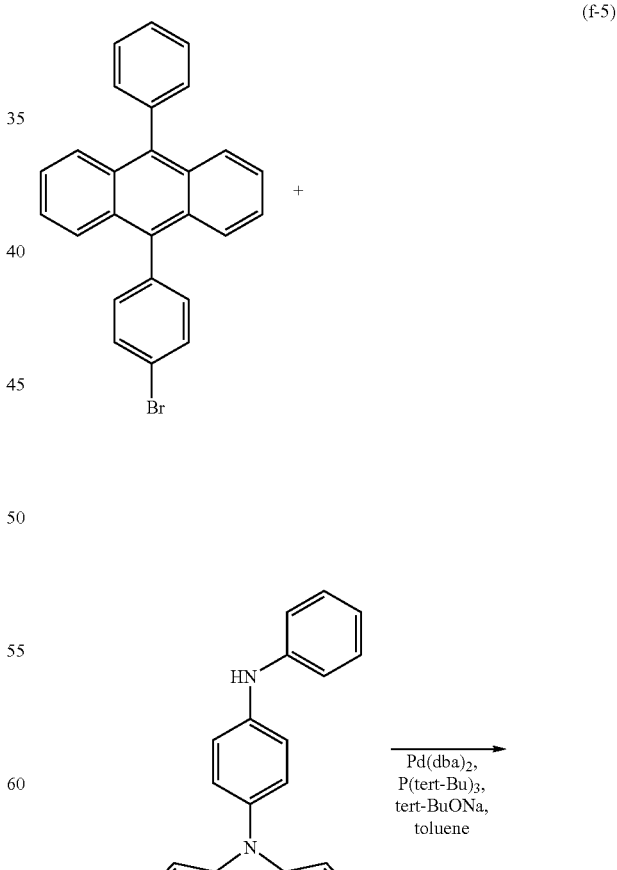

(f-5)

-continued

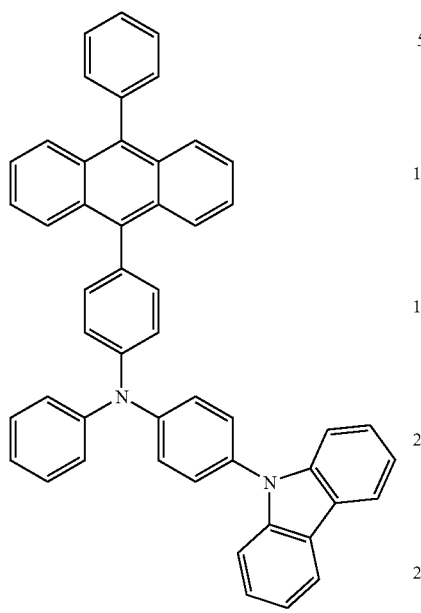

Figure 34A:
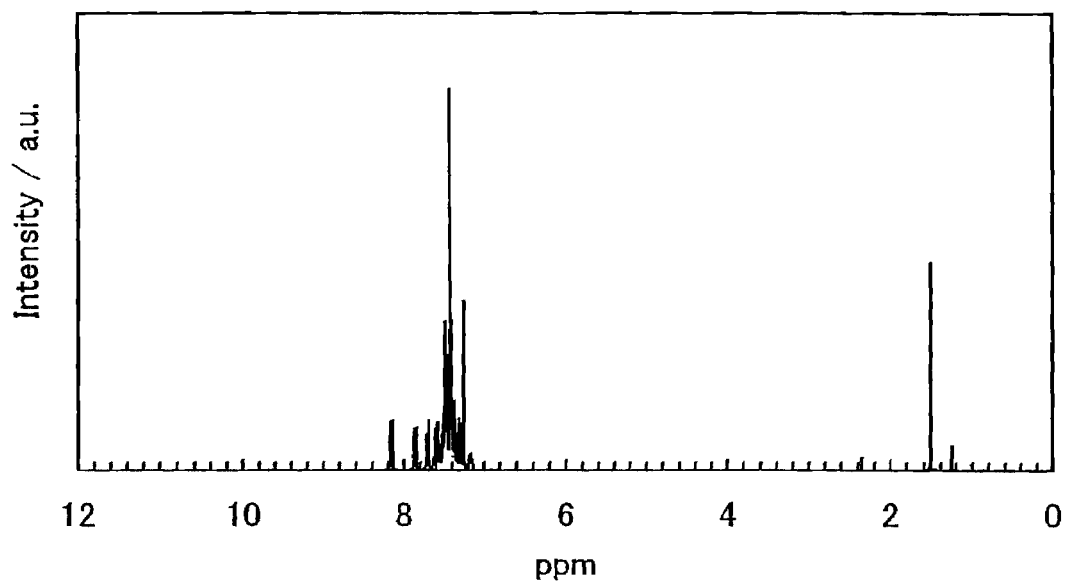
FIGS. 34A and 34B are diagrams showing $^1$H NMR charts of 9-(4-{N-[4-(9-carbazolyl)phenyl]-N-phenylamino}phenyl)-10-phenylanthracene.
Figure 34B:
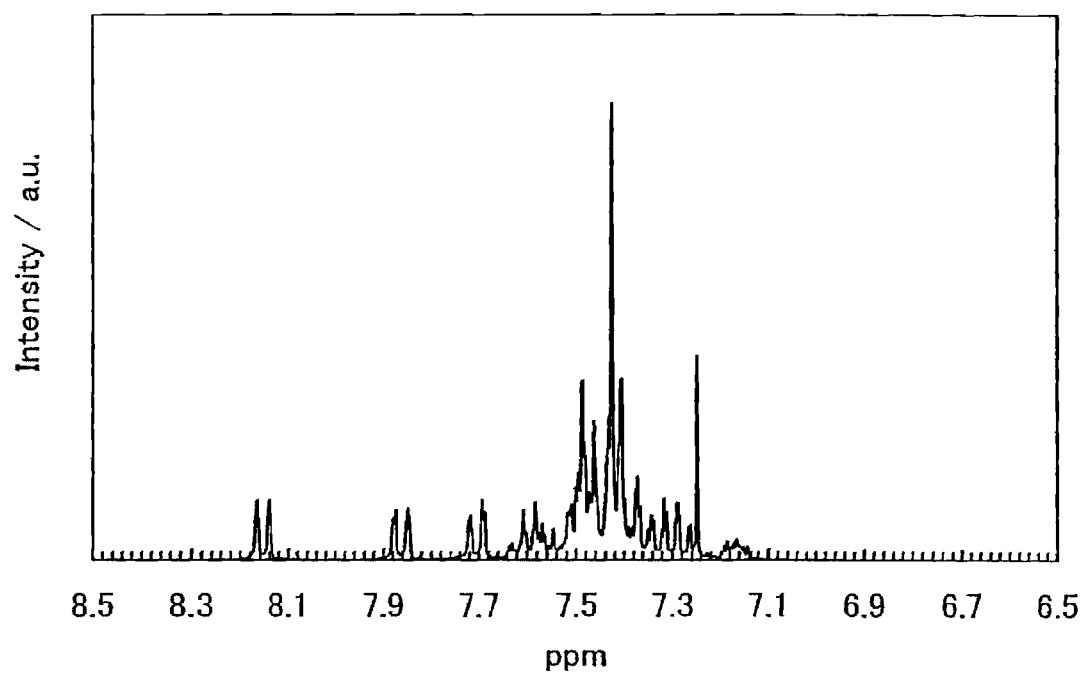

409 mg (1.0 mmol) of 9-phenyl-10-(4-bromophenyl)anthracene, 339 mg (1.0 mmol) of YGA obtained in Step 1 of Example 7, 6 mg (0.01 mmol) of bis(dibenzylideneacetone)palladium(0), 500 mg (5.2 mol) of sodium tert-butoxide, 0.1 mL of tri(tert-butyl)phosphine (a 10 wt % hexane solution), and 10 mL of toluene were collected, mixed, and stirred for 4 hours at 80° C. After the reaction, the solution was washed with water and a water layer was extracted with toluene. The water layer was washed with a saturated aqueous sodium chloride solution in conjunction with the organic layer and dried with magnesium sulfate. After natural filtration, the filtrate was concentrated and the obtained oily substance was purified by silica gel column chromatography (hexane:toluene=7:3). The obtained solid was recrystallized with dichloromethane and hexane, thereby obtaining 534 mg of objective YGAPA as a yellow powder solid with a yield of 81%. By measuring this compound by a nuclear magnetic resonance method (NMR), the compound was identified as 9-(4-{N-[4-(9-carbazolyl)phenyl]-N-phenylamino}phenyl)-10-phenylanthracene (abbr.: YGAPA). $^1$H NMR charts of YGAPA are shown in FIGS. 34A and 34B.

<<Synthetic Example of CzPA>>

Hereinafter, a method for synthesizing 9-[4-(N-carbazolyl)]phenyl-10-phenylanthracene (abbr.: CzPA) represented by Structural Formula (202) is explained.

(202)

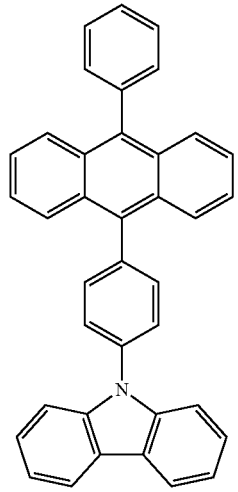

Synthetic Scheme (h-1) of 9-[4-(N-carbazolyl)]phenyl-10-phenylanthracene (abbr.: CzPA) is shown below.

(h-1)

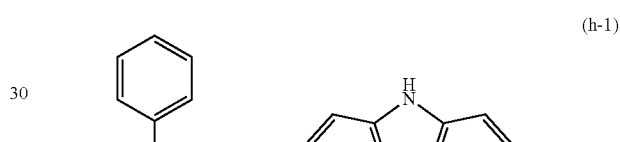

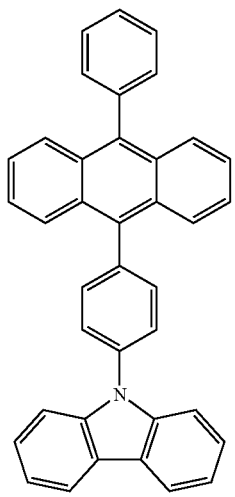

1.3 g (3.2 mmol) of 9-phenyl-10-(4-bromophenyl)anthracene, 578 mg (3.5 mmol) of carbazole, 50 mg (0.017 mmol) of bis(dibenzylideneacetone)palladium(0), 1.0 mg (0.010 mmol) of tert-butoxysodium, 0.1 mL of tri(tert-butyl) phosphine (a 10 wt % hexane solution), and 30 mL of toluene were collected, mixed, and refluxed for 10 hours while heating at 110° C. After the reaction, the solution was washed with water, and a water layer was extracted with toluene and washed with a saturated aqueous sodium chloride solution in conjunction with the organic layer. Then, the organic layer was dried with magnesium sulfate. The mixture was naturally filtered and the filtrate was concentrated. The obtained oily substance was purified by silica gel column chromatography (hexane:toluene=7:3). The obtained solid was recrystallized with dichloromethane and hexane, thereby obtaining 1.5 g of objective 9-[4-(N-carbazolyl)]phenyl-10-phenylanthracene (abbr.: CzPA) with a yield of 93%.

Figure 35A:
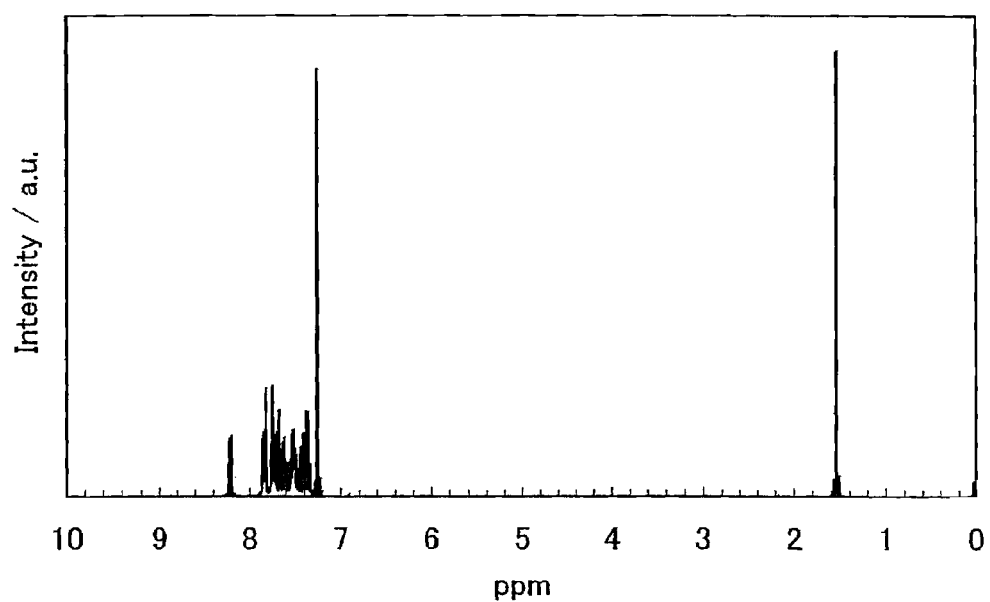
FIGS. 35A and 35B are diagrams showing $^1$H NMR charts of 9-[4-(N-carbazolyl)]phenyl-10-phenylanthracene.
Figure 35B:
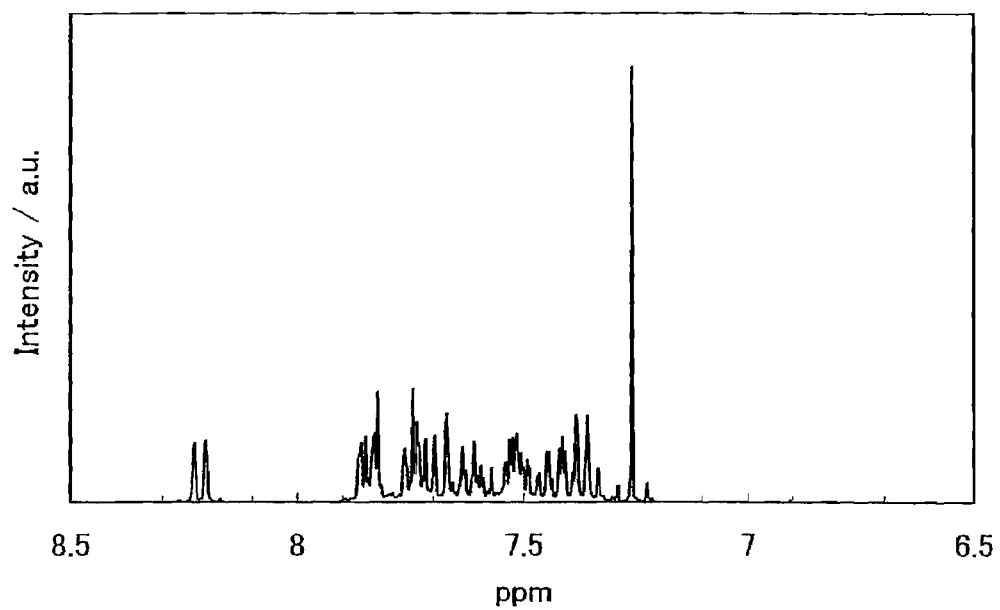

NMR data of the obtained CzPA are shown below. $^1$H NMR (300 MHz, CDCl$_3$); δ=8.22 (d, J=7.8 Hz, 2H), 7.86-7.82 (m, 3H), 7.61-736 (m, 20H). In addition, $^1$H NMR charts are shown in FIGS. 35A and 35B.

Note that 5.50 g of the obtained CzPA was purified by sublimation for 20 hours under conditions at 270° C., with an argon flow (at a flow rate of 3.0 mL/min), and under a pressure of 6.7 Pa, thereby recovering 3.98 g with a recovery rate of 72%.

<<Synthetic Example of BSPB>>

Hereinafter, a method for synthesizing N,N'-bis(spiro-9,9'-bifluorene-2-yl)-N,N'-diphenylbenzidine (abbr.: BSPB) represented by Structural Formula (203) is explained.

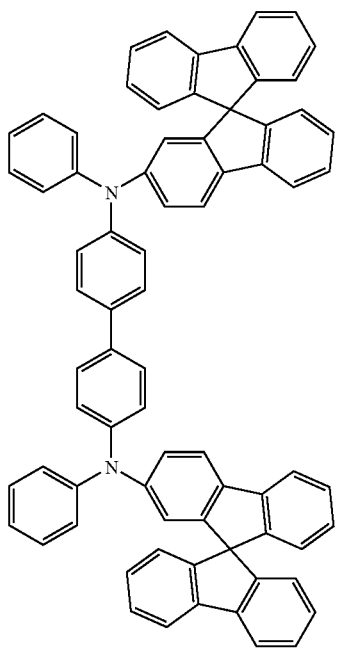

(203)

[Step 1]

First, a method for synthesizing 2-bromo-spiro-9,9'-bifluorene is explained. Synthetic Scheme (j-1) of 2-bromo-spiro-9,9'-bifluorene is shown below.

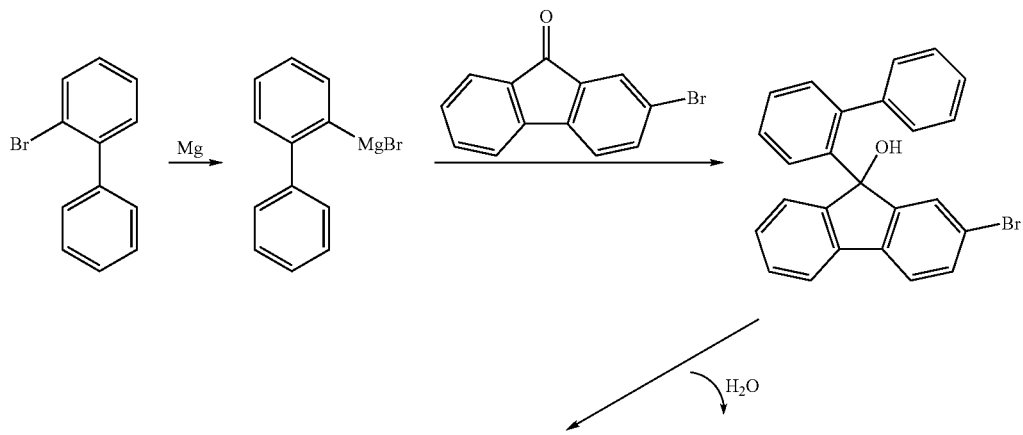

(j-1)

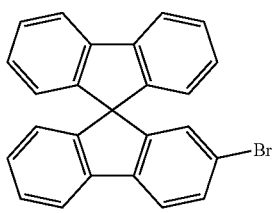

1.26 g (0.052 mol) of magnesium was put into a 100-mL three-neck flask and stirred while heating for 30 minutes and activated with a system evacuated to vacuum. After cooling to a room temperature, the system was put in a nitrogen flow. Then, 5 mL of diethyl ether and a few drops of dibromoethane were added, and 11.65 g (0.050 mol) of 2-bromobiphenyl dissolved in 15 mL of diethyl ether was gradually dropped. After dropping, the mixture was refluxed for 3 hours, thereby producing a Grignard reagent. 11.7 g (0.045 mol) of 2-bromofluorenone and 40 mL of diethyl ether were put into a 200-mL three-neck flask. The synthesized Grignard reagent was gradually dropped into this reaction solution, and the mixture was refluxed for 2 hours after the completion of dropping and stirred for about 12 hours at a room temperature. After the reaction, the reaction solution was washed with a saturated aqueous ammonia chloride solution twice. A water layer was extracted with ethyl acetate twice and washed with a saturated aqueous sodium chloride solution in conjunction with an organic layer. After drying with magnesium sulfate, the organic layer was filtered by suction and concentrated, thereby obtaining 18.76 g of 9-(2-biphenylyl)-2-bromo-9-fluorenol as a solid with a yield of 90%.

Next, 18.76 g (0.045 mol) of the synthesized 9-(2-biphenylyl)-2-bromo-9-fluorenol and 100 mL of glacial acetic acid were put into a 200-mL three-neck flask. A few drops of concentrated hydrochloric acid were added and the mixture was refluxed for 2 hours. After the reaction, the precipitate was recovered by suction filtration, and washed by filtration with a saturated aqueous sodium hydrogen carbonate solution and water. The obtained brown solid was recrystallized with ethanol, thereby obtaining 10.24 g of a light-brown powder solid with a yield of 57%. This light-brown powder solid was identified as 2-bromo-spiro-9,9'-bifluorene by a proton nuclear magnetic resonance method ($^1$H NMR).

$^1$H NMR of this compound is shown below. $^1$H NMR (300 MHz, CDCl$_3$); δ=7.86-7.79 (m, 3H), 7.70 (d, 1H, J=8.4 Hz), 7.47-7.50 (m, 1H), 7.41-7.34 (m, 3H), 7.12 (t, 3H, J=7.7 Hz), 6.85 (d, 1H, J=2.1 Hz), 6.74-6.70 (m, 3H).

[Step 2]

Next, a method for synthesizing N,N'-bis(spiro-9,9'-bifluorene-2-yl)-N,N'-diphenylbenzidine (abbr.: BSPB) is explained. Synthetic Scheme (j-2) of BSPB is shown below.

(j-2)

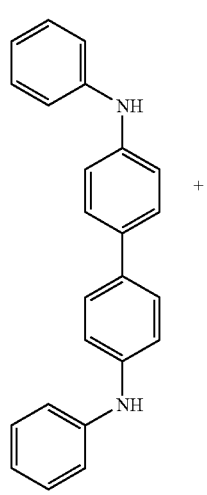

+

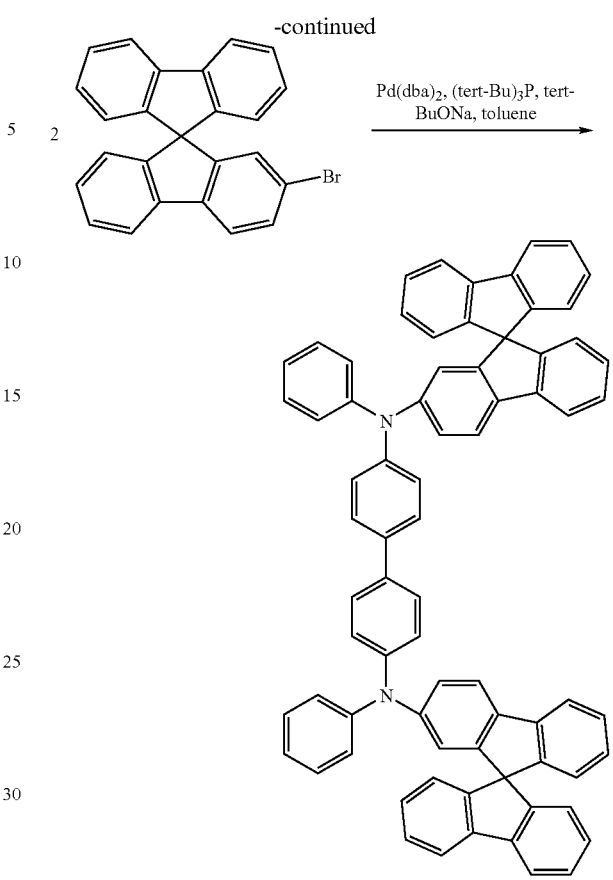

1.00 g (0.0030 mol) of N,N'-diphenylbenzidine, 2.49 g (0.0062 mol) of 2-bromo-spiro-9,9'-bifluorene synthesized in Step 1, 170 mg (0.30 mmol) of bis(dibenzylideneacetone)palladium(0), and 1.08 g (0.011 mol) of tert-butoxysodium were put into a 100-mL three-neck flask, and the system was put in a nitrogen flow. Then, 20 mL of anhydrous toluene and 0.6 mL of tri(tert-butyl)phosphine (a 10 wt % hexane solution) were added, and the mixture was stirred for 6 hours at 80° C. After the reaction, the reaction solution was cooled to a room temperature and then water was added. The precipitated solid was recovered by suction filtration and washed with dichloromethane. The obtained white solid was purified by alumina column chromatography (chloroform) and recrystallized with dichloromethane, thereby obtaining 2.66 g of white powder solid with a yield of 93%.

Figure 36:
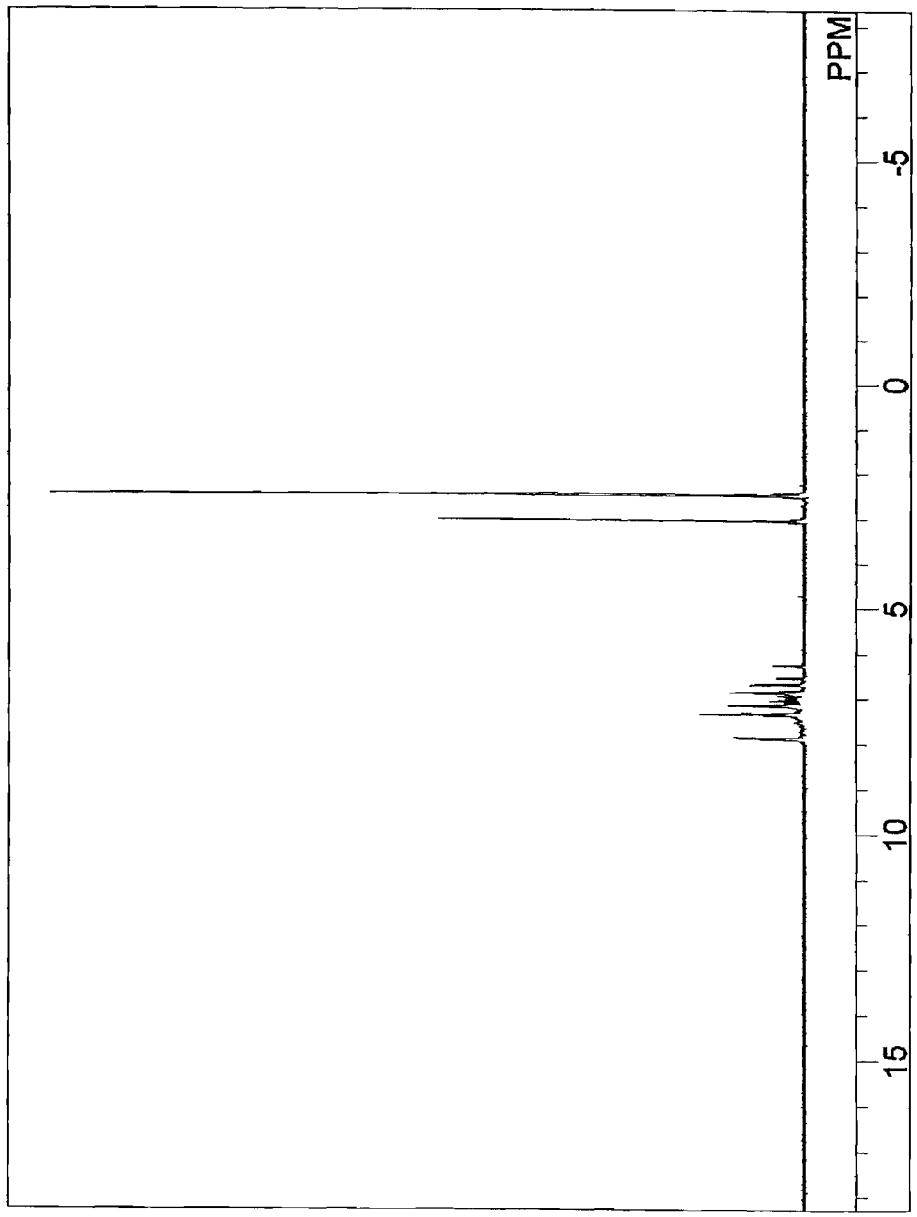
FIG. 36 is a diagram showing a $^1$H NMR chart of N,N'-bis(spiro-9,9'-bifluorene-2-yl)-N,N'-diphenylbenzidine.

The following result was obtained by analyzing the obtained white powder solid by a proton nuclear magnetic resonance method ($^1$H NMR), and the obtained white powder solid could be identified as N,N'-bis(spiro-9,9'-bifluorene-2-yl)-N,N'-diphenylbenzidine (abbr.: BSPB). In addition, a $^1$H NMR chart is shown in FIG. 36. $^1$H NMR (300 MHz, DMSO-d$_6$); δ=7.93-7.89 (m, 8H), 739-733 (m, 10H), 7.19-7.14 (m, 8H), 7.09-6.96 (m, 6H), 6.89-6.84 (m, 8H), 6.69 (d, 4H, J=7.5 Hz), 6.54 (d, 2H, J=7.8 Hz), 6.25 (d, 2H, J=2.4 Hz).

Note that 4.74 g of the obtained compound was purified by sublimation under conditions of 14 Pa and 350° C. for 24 hours, thereby recovering 3.49 g with a recovery rate of 74%.

This application is based on Japanese Patent Application serial no. 2005-302853 filed in Japan Patent Office on Oct. 18, 2005, the contents of which are hereby incorporated by reference.

What is claimed is:

1. A light emitting device comprising:

an anode;

a first layer over the anode, the first layer comprising an organic compound; and a cathode over the first layer, wherein the organic compound is represented by General Formula (1)

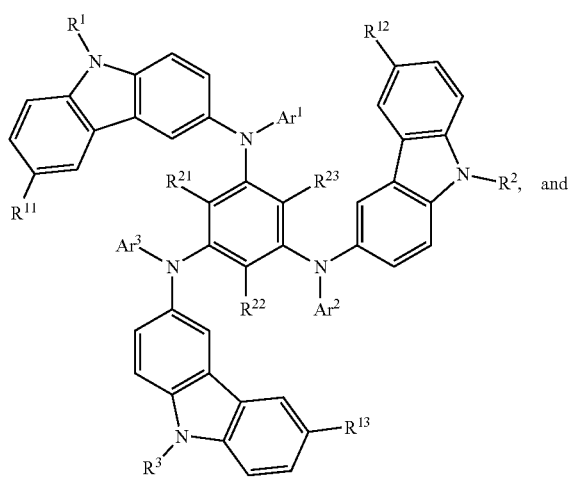

(1)

wherein:
- each of $Ar^1$ to $Ar^3$ represents an aryl group having 6 to 12 carbon atoms or a heteroaromatic group having 4 to 9 carbon atoms;
- each of $R^1$ to $R^3$ represents an alkyl group having 1 to 4 carbon atoms or an aryl group having 6 to 25 carbon atoms;
- each of $R^{11}$ to $R^{13}$ represents a hydrogen atom, an alkyl group having 1 to 4 carbon atoms, or an aryl group having 6 to 25 carbon atoms; and
- each of $R^{21}$ to $R^{23}$ represents a hydrogen atom, a methyl group, or a methoxy group.

2. The light emitting device according to claim 1, wherein:

$R^1$, $R^2$, and $R^3$ are the same;

$R^{11}$, $R^{12}$, and $R^{13}$ are the same; and $Ar^1$, $Ar^2$, and $Ar^a$ are the same.

3. The light emitting device according to claim 1, wherein each of $R^{21}$ to $R^{23}$ represents a hydrogen atom.

4. The light emitting device according to claim 1, wherein the organic compound is represented by General Formula (21)

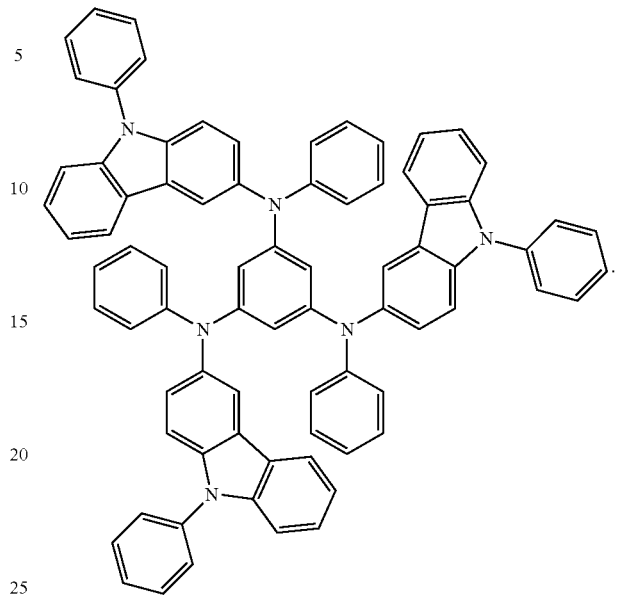

(21)

5. The light emitting device according to claim 1, further comprising a second layer between the first layer and the cathode, wherein the second layer comprises a light emitting substance.

6. The light emitting device according to claim 5, wherein the light emitting substance is dispersed in a substance in the second layer, and wherein a LUMO level of the substance is higher than a LUMO level of the light emitting substance, and wherein a HOMO level of the substance is lower than a HOMO level of the light emitting substance.

7. The light emitting device according to claim 5, wherein the light emitting substance is a phosphorescent light emitting substance.

8. The light emitting device according to claim 5, wherein the light emitting substance is an iridium complex.

9. The light emitting device according to claim 1, wherein the first layer further comprises a light emitting substance.

10. The light emitting device according to claim 9, wherein the light emitting substance is a phosphorescent light emitting substance.

11. The light emitting device according to claim 9, wherein the light emitting substance is a phosphorescent light emitting substance which emits blue light.

12. The light emitting device according to claim 9, wherein the light emitting substance is an iridium complex.

13. A lighting system comprising the light emitting device according to claim 1.

14. A light emitting device comprising:

an anode;

a light emitting layer over the anode; and a cathode over the light emitting layer, wherein an organic compound represented by General Formula (1) is dispersed in the light emitting layer;

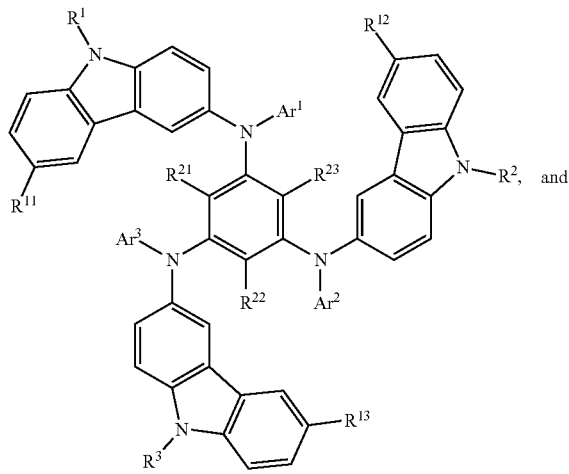
(1)

wherein:
each of $Ar^1$ to $Ar^3$ represents an aryl group having 6 to 12 carbon atoms or a heteroaromatic group having 4 to 9 carbon atoms;
each of $R^1$ to $R^3$ represents an alkyl group having 1 to 4 carbon atoms or an aryl group having 6 to 25 carbon atoms;
each of $R^{11}$ to $R^{13}$ represents a hydrogen atom, an alkyl group having 1 to 4 carbon atoms, or an aryl group having 6 to 25 carbon atoms; and
each of $R^{21}$ to $R^{23}$ represents a hydrogen atom, a methyl group, or a methoxy group.

15. The light emitting device according to claim 14, wherein:
$R^1$, $R^2$, and $R^3$ are the same;
$R^{11}$, $R^{12}$, and $R^{13}$ are the same; and
$Ar^1$, $Ar^2$, and $Ar^3$ are the same.

16. The light emitting device according to claim 14, wherein each of $R^{21}$ to $R^{23}$ represents a hydrogen atom.

17. The light emitting device according to claim 14, wherein the organic compound is represented by General Formula (21)

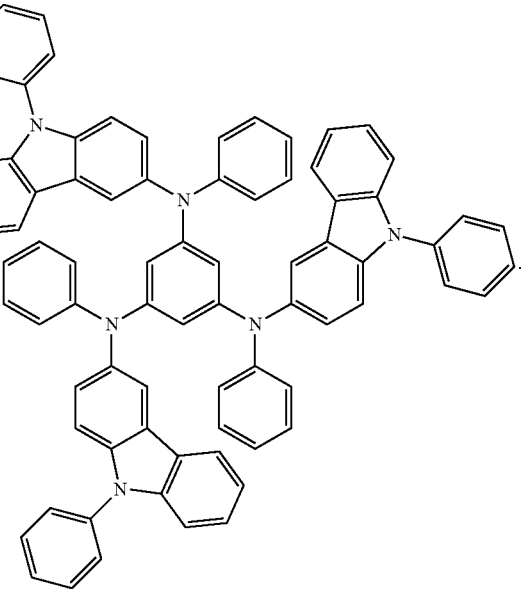
(21)

18. A lighting system comprising the light emitting device according to claim 14.

* * * * *